(12) United States Patent
Cosson et al.

(10) Patent No.: US 6,974,680 B2
(45) Date of Patent: Dec. 13, 2005

(54) VIRULENCE GENES, PROTEINS, AND THEIR USE

(75) Inventors: Pierre Cosson, Carouge (CH); Thilo Köhler, Carouge (CH); Mohammed Benghezal, Grand-Saconnex (CH); Anna Marchetti, Geneva (CH); Christian van Delden, Cologny (CH)

(73) Assignee: University of Geneva, Geneva (CH)

( * ) Notice: Subject to any disclaimer, the term of this patent is extended or adjusted under 35 U.S.C. 154(b) by 0 days.

(21) Appl. No.: 10/324,967

(22) Filed: Dec. 20, 2002

(65) Prior Publication Data

US 2004/0122212 A1 Jun. 24, 2004

(51) Int. Cl.⁷ .................................................. C12Q 1/18
(52) U.S. Cl. ............................... 435/32; 435/29; 435/4; 424/200.1
(58) Field of Search .......................... 424/200.1; 435/4, 435/32, 29

(56) References Cited

FOREIGN PATENT DOCUMENTS

| WO | WO 02/101081 A | 12/2002 |
|---|---|---|
| WO | WO 03/022881 A | 3/2003 |

OTHER PUBLICATIONS

Bronner et al., Mol. Microbiol., 14:(3) 505–19, 1994.
Clarke et al., J. Bacteriol., 177:(19) 5411–18, 1995.
Essar et al., J. Bacteriol., 172:(2) 853–66, 1990.
Essar et al., J. Bacteriol., 172:(2) 867–83, 1990.
Fani et al., Mol. Gen. Genet., 216:224–9, 1989.
Featherston et al., Mol. Microbiol., 32(2):289–99, 1999.
Kolko et al., J. Bacteriol., 183:(1) 328–35, 2001.
Leyh et al., J. Biol. Chem., 263:(5) 2409–16, 1988.
Hummerjohann et al., Microbiol., 144:1375–86, 1998.
Lobacka et al., J. Bacteriol., 176:(5) 1500–10, 1994.
Peng and Verma, J. Biol. Chem., 270:(49) 29105–10, 1995.
Neuwald et al., J. Bacteriol., 174:(2) 415–25, 1992.
Poole et al., Mol. Microbiol., 21:(21) 713–24, 1996.
Rae et al., J. Bacteriol., 179:(11) 3561–71, 1997.
Regué et al. J. Bacteriol. 183(12): 3564–73, 2001.
Reimmann et al., Microbiology, 144:3135–48, 1998.
Reimmann et al., J. Bacteriol., 183:(3) 813–20, 2001.
Rocchetta et al., Microbiol. Mol. Biol. Rev. 63:(3) 523–53, 1999.
Rombel et al., Mol. Gen. Genet., 246:519–28, 1995.
Merriman et al., J. Bacteriol., 177:252–8, 1995.
Serino et al., Mol. Gen. Genet., 249: 217–28, 1995.
Serino et al., J. Bactiol., 179:(1) 248–57, 1997.
Smith et al., Gene, 49:53–60, 1986.
Stover et al., Nature, 406: 959–964, 2000.
Tan et al., Proc. Natl. Acad. Sci. USA, 96:2408–13, 1999.
Weidner et al., J. Mol. Biol., 233:109–22, 1993.
Choi et al. *J. Bacteriol.*, 184(4):952–961 (2002).
Cosson et al. *J. Bacteriol.*, 184(11):3027–3033 (2002).
International Search Report for PCT/CH03/00836, mailed Jul. 12, 2004.

*Primary Examiner*—Jennifer E. Graser
(74) *Attorney, Agent, or Firm*—Ivor R. Elrifi; Gregory J. Sieczkiewicz; Mintz Levin

(57) ABSTRACT

A series of genes from *Pseudomonas aeruginosa* and *Klebsiella* are shown to encode products that are implicated in virulence. The identification of these genes therefore allows attenuated microorganisms to be produced. Furthermore, the genes or their encoded products can be used to identify antimicrobial drugs, diagnostic methods for the identification of a pathogen-associated disease, and in the manufacture of vaccines.

9 Claims, No Drawings

SEQUENCE LISTING

<160> NUMBER OF SEQ ID NOS: 64

<210> SEQ ID NO 1
<211> LENGTH: 1050
<212> TYPE: DNA
<213> ORGANISM: Pseudomonas aeruginosa

<400> SEQUENCE: 1

```
atggatatca agggagccct caatcgcatc gtcaaccagc tcgacctgac caccgaggaa      60
atgcaggcgg tcatgcgcca gatcatgacc gggcagtgca ccgacgcgca gatcggcgcc     120
ttcctgatgg gcatgcggat gaagagcgaa accatcgacg agatcgtcgg cgcggtggcg     180
gtgatgcgcg aactggccga cggcgtgcag ttgcctacgc tgaagcatgt ggtcgacgtg     240
gtcggcaccg gcggcgatgg cgcgaacatc ttcaacgtgt cctcggcggc gtccttcgtg     300
gtcgccgccg ctggcggcaa ggtcgccaaa cacggtaacc gcgcggtctc cggcaagagc     360
ggcagcgccg acttgctgga agccgccggc atctacctgg agctgacctc cgaacaggtg     420
gcgcgttgca tcgacaccgt cggcgtcggg ttcatgttcg cccaggtcca ccacaaggcg     480
atgaagtacg ccgccggtcc gcgccgcgag ctgggcttgc ggactctgtt caacatgctt     540
ggcccactga ccaacccggc gggagtcagg caccaggtgg tcgggtgtt cacccaggaa     600 ctgtgcaagc cgctggctga agtgctcaag cgtctcggca gcgagcatgt gctggtggtg     660
cattcgcgcg acgggctgga cgagttcagt ctggccgcgg cgacccacat tgccgagttg     720
aaggacggcg aggtacgcga gtacgaagtg cgtcccgagg acttcgggat caagagccag     780
accctgatgg ggctggaggt cgacagtccg caggcctcgc tggaactgat ccgcgacgct     840 ttgggggcggc gcaagaccga ggctgggcag aaggccgccg agctgatcgt gatgaatgcc     900
ggcccggcac tgtacgctgc cgatctgcgc accagcctgc acgagggcat tcaactggcc     960
cacgatgccc tgcacaccgg gctggcacgg gagaagatgg acgaactggt ggccttcacc    1020
gccgtttaca gagaggagaa cgcacagtga                                    1050
```

<210> SEQ ID NO 2
<211> LENGTH: 349

```
<212> TYPE: PRT
<213> ORGANISM: Pseudomonas aeruginosa

<400> SEQUENCE: 2

Met Asp Ile Lys Gly Ala Leu Asn Arg Ile Val Asn Gln Leu Asp Leu
1               5                   10                  15

Thr Thr Glu Glu Met Gln Ala Val Met Arg Gln Ile Met Thr Gly Gln
            20                  25                  30

Cys Thr Asp Ala Gln Ile Gly Ala Phe Leu Met Gly Met Arg Met Lys
        35                  40                  45

Ser Glu Thr Ile Asp Glu Ile Val Gly Ala Val Ala Val Met Arg Glu
    50                  55                  60

Leu Ala Asp Gly Val Gln Leu Pro Thr Leu Lys His Val Val Asp Val
65                  70                  75                  80

Val Gly Thr Gly Gly Asp Gly Ala Asn Ile Phe Asn Val Ser Ser Ala
                85                  90                  95

Ala Ser Phe Val Val Ala Ala Gly Gly Lys Val Ala Lys His Gly
                100                 105                 110

Asn Arg Ala Val Ser Gly Lys Ser Gly Ser Ala Asp Leu Leu Glu Ala
            115                 120                 125

Ala Gly Ile Tyr Leu Glu Leu Thr Ser Glu Gln Val Ala Arg Cys Ile
        130                 135                 140

Asp Thr Val Gly Val Gly Phe Met Phe Ala Gln Val His His Lys Ala
145                 150                 155                 160

Met Lys Tyr Ala Ala Gly Pro Arg Arg Glu Leu Gly Leu Arg Thr Leu
                165                 170                 175

Phe Asn Met Leu Gly Pro Leu Thr Asn Pro Ala Gly Val Arg His Gln
            180                 185                 190

Val Val Gly Val Phe Thr Gln Glu Leu Cys Lys Pro Leu Ala Glu Val
        195                 200                 205

Leu Lys Arg Leu Gly Ser Glu His Val Leu Val His Ser Arg Asp
210                 215                 220

Gly Leu Asp Glu Phe Ser Leu Ala Ala Ala Thr His Ile Ala Glu Leu
225                 230                 235                 240

Lys Asp Gly Glu Val Arg Glu Tyr Glu Val Arg Pro Glu Asp Phe Gly
                245                 250                 255

Ile Lys Ser Gln Thr Leu Met Gly Leu Glu Val Asp Ser Pro Gln Ala
            260                 265                 270

Ser Leu Glu Leu Ile Arg Asp Ala Leu Gly Arg Lys Thr Glu Ala
        275                 280                 285

Gly Gln Lys Ala Ala Glu Leu Ile Val Met Asn Ala Gly Pro Ala Leu
        290                 295                 300

Tyr Ala Ala Asp Leu Ala Thr Ser Leu His Glu Gly Ile Gln Leu Ala
305                 310                 315                 320

His Asp Ala Leu His Thr Gly Leu Ala Arg Glu Lys Met Asp Glu Leu
                325                 330                 335

Val Ala Phe Thr Ala Val Tyr Arg Glu Glu Asn Ala Gln
                340                 345

<210> SEQ ID NO 3
<211> LENGTH: 918
<212> TYPE: DNA
<213> ORGANISM: Pseudomonas aeruginosa

<400> SEQUENCE: 3
```

-continued

```
atggtcgaca aactgacgca cctgaaacag ctggaggcgg aaagcatcca catcatccgc      60
gaggtggccg ccgagttcga taacccggtg atgctgtact cgatcggcaa ggattccgcg     120
gtcatgctgc acctggcccg caaggccttc ttccccggca agctgccctt cccggtgatg     180
cacgtggaca cccgctggaa attccaggag atgtacaggt tccgtgatcg gatggtcgag     240
gaaatgggcc tggatctgat cacccacgtc aacccggacg gcgtcgccca gggcatcaac     300
ccgttcaccc acggcagcgc caagcacacc gacgtgatga agaccgaggg actcaagcag     360
gccctggaca gtacggtttt cgacgctgcc ttcggcggtg cgcgccgcga cgaggagaag     420
tcgcgggcca aggaacgggt ctattcgttc cgcgacagca agcaccgctg gaccccgaag     480
aaccagcgtc ccgagctgtg gaacatctac aacggcaagg tgaagaaggg cgagtcgatc     540
cgcgtcttcc cgctgtccaa ctggaccgag ctggacatct ggcaatacat ctacctggaa     600
ggcatcccga tcgtcccgct gtacttcgcc gccgagcgcg aggtcatcga agaatggc       660
acattgatca tgatcgacga cgagcgcatc ctcgagcatc tctctgacga agagaaagcc     720
cgcatcgaga gcgcatggt gcgcttccgt accctcggct gctacccgct caccggcgcg     780
gtcgagtcca cgccaccac gctgccggaa atcatccagg aaatgctcct gacgcgtact     840
tccgaacgcc agggccgggt catcgaccat gaccaggccg ttcgatgga agaaaagaaa     900
cgtcagggct atttctga                                                   918
```

<210> SEQ ID NO 4
<211> LENGTH: 305
<212> TYPE: PRT
<213> ORGANISM: Pseudomonas aeruginosa

<400> SEQUENCE: 4

```
Met Val Asp Lys Leu Thr His Leu Lys Gln Leu Glu Ala Glu Ser Ile
1               5                   10                  15

His Ile Ile Arg Glu Val Ala Ala Glu Phe Asp Asn Pro Val Met Leu
            20                  25                  30

Tyr Ser Ile Gly Lys Asp Ser Ala Val Met Leu His Leu Ala Arg Lys
        35                  40                  45

Ala Phe Phe Pro Gly Lys Leu Pro Phe Pro Val Met His Val Asp Thr
    50                  55                  60

Arg Trp Lys Phe Gln Glu Met Tyr Arg Phe Arg Asp Arg Met Val Glu
65                  70                  75                  80

Glu Met Gly Leu Asp Leu Ile Thr His Val Asn Pro Asp Gly Val Ala
                85                  90                  95

Gln Gly Ile Asn Pro Phe Thr His Gly Ser Ala Lys His Thr Asp Val
            100                 105                 110

Met Lys Thr Glu Gly Leu Lys Gln Ala Leu Asp Lys Tyr Gly Phe Asp
        115                 120                 125

Ala Ala Phe Gly Gly Ala Arg Arg Asp Glu Glu Lys Ser Arg Ala Lys
    130                 135                 140

Glu Arg Val Tyr Ser Phe Arg Asp Ser Lys His Arg Trp Asp Pro Lys
145                 150                 155                 160

Asn Gln Arg Pro Glu Leu Trp Asn Ile Tyr Asn Gly Lys Val Lys Lys
                165                 170                 175

Gly Glu Ser Ile Arg Val Phe Pro Leu Ser Asn Trp Thr Glu Leu Asp
            180                 185                 190

Ile Trp Gln Tyr Ile Tyr Leu Glu Gly Ile Pro Ile Val Pro Leu Tyr
        195                 200                 205
```

```
Phe Ala Ala Glu Arg Glu Val Ile Glu Lys Asn Gly Thr Leu Ile Met
    210                 215                 220

Ile Asp Asp Glu Arg Ile Leu Glu His Leu Ser Asp Glu Glu Lys Ala
225                 230                 235                 240

Arg Ile Glu Lys Arg Met Val Arg Phe Arg Thr Leu Gly Cys Tyr Pro
                245                 250                 255

Leu Thr Gly Ala Val Glu Ser Ser Ala Thr Thr Leu Pro Glu Ile Ile
            260                 265                 270

Gln Glu Met Leu Leu Thr Arg Thr Ser Glu Arg Gln Gly Arg Val Ile
        275                 280                 285

Asp His Asp Gln Ala Gly Ser Met Glu Glu Lys Lys Arg Gln Gly Tyr
    290                 295                 300

Phe
305

<210> SEQ ID NO 5
<211> LENGTH: 822
<212> TYPE: DNA
<213> ORGANISM: Pseudomonas aeruginosa

<400> SEQUENCE: 5
atgaggccgg tgccttgggg cgaattggtg gcgctggtgc ggcgcgccgg cgaggcgatc      60
ctgccgcact ggcgcgccga cgtggtggtg cgctcgaagg ccgacgaatc gccggtgact     120
gccgccgacc tggccgcgca ccatatattg gaggcgggat tgcgggcgct ggcgccggac     180
attccggtgc tttccgaaga ggattgcgag ataccgctga gcgagcgcgg ccactggcgg     240
cgctggtggc tggtggaccc gctggacggc accaaggagt tcatctccgg tagcgaggag     300
ttcaccgtca acgtggccct ggtcgaggat ggccgggtgc tgttcggcct ggtcggcgtg     360
ccggtgagcg gccgctgcta ctacggtggc gccggtctcg gtgcctggcg cgaggaggcc     420
gatggccgcg cgcaaccgat cagtgtgcgc ctggagcccg aggaggcctt caccgtggtg     480
gccagcaagc gccatggcag cccggcccag gagcgcctgc tggatggctt gagcgagcgc     540
ttcggcgacc tgcggcgagc cagcatcggc agttcgctga agttctgcct gctggccgag     600
ggcgctgccg actgctatcc gcgcctgacg ccaacctcgc aatgggacac ggccgccgcc     660
cagggtgtgc tggaaggcgc cggcggcgag gtgctcgacc tgcatggtgc gccattcacc     720
tacgagccgc gcgaggatta cctcaacggc tccttcctgg ccctgccgcg cgccgccgag     780
tggcgcagcg agctgatcca actggcgcgc gcgctgcact ga                        822

<210> SEQ ID NO 6
<211> LENGTH: 273
<212> TYPE: PRT
<213> ORGANISM: Pseudomonas aeruginosa

<400> SEQUENCE: 6

Met Arg Pro Val Pro Trp Gly Glu Leu Val Ala Leu Val Arg Arg Ala
1               5                   10                  15

Gly Glu Ala Ile Leu Pro His Trp Arg Ala Asp Val Val Arg Ser
            20                  25                  30

Lys Ala Asp Glu Ser Pro Val Thr Ala Ala Asp Leu Ala Ala His His
        35                  40                  45

Ile Leu Glu Ala Gly Leu Arg Ala Leu Ala Pro Asp Ile Pro Val Leu
    50                  55                  60

Ser Glu Glu Asp Cys Glu Ile Pro Leu Ser Glu Arg Gly His Trp Arg
65                  70                  75                  80
```

```
Arg Trp Trp Leu Val Asp Pro Leu Asp Gly Thr Lys Glu Phe Ile Ser
                85                  90                  95

Gly Ser Glu Glu Phe Thr Val Asn Val Ala Leu Val Glu Asp Gly Arg
            100                 105                 110

Val Leu Phe Gly Leu Val Gly Val Pro Val Ser Gly Arg Cys Tyr Tyr
        115                 120                 125

Gly Gly Ala Gly Leu Gly Ala Trp Arg Glu Ala Asp Gly Arg Ala
    130                 135                 140

Gln Pro Ile Ser Val Arg Leu Glu Pro Glu Glu Ala Phe Thr Val Val
145                 150                 155                 160

Ala Ser Lys Arg His Gly Ser Pro Ala Gln Glu Arg Leu Leu Asp Gly
                165                 170                 175

Leu Ser Glu Arg Phe Gly Asp Leu Arg Arg Ala Ser Ile Gly Ser Ser
            180                 185                 190

Leu Lys Phe Cys Leu Leu Ala Glu Gly Ala Ala Asp Cys Tyr Pro Arg
        195                 200                 205

Leu Thr Pro Thr Ser Gln Trp Asp Thr Ala Ala Gln Gly Val Leu
    210                 215                 220

Glu Gly Ala Gly Gly Glu Val Leu Asp Leu His Gly Ala Pro Phe Thr
225                 230                 235                 240

Tyr Glu Pro Arg Glu Asp Tyr Leu Asn Gly Ser Phe Leu Ala Leu Pro
                245                 250                 255

Arg Ala Ala Glu Trp Arg Ser Glu Leu Ile Gln Leu Ala Arg Ala Leu
            260                 265                 270

His
```

<210> SEQ ID NO 7
<211> LENGTH: 1299
<212> TYPE: DNA
<213> ORGANISM: Pseudomonas aeruginosa

<400> SEQUENCE: 7

```
atgcgagttc tggtccttgg cagcggtgtc atcggtaccg ccagtgcgta ttacctggcc    60
cgtgccgggt cgaggtggt ggtggtcgac cgtcaggacg tcccgcgct ggaaaccagc     120
ttcgccaacg ccggccaggt gtctcccggc tacgcttcgc cctgggcagc ccgggcatt    180
cccctgaagg ccatgaagtg gctgctggaa agcacgcgc cgctggccat caagctcacc    240
tccgatccca gccagtacgc ctggatgctg cagatgctgc gcaactgcac cgccgagcgc    300
tacgccgtga acaaggagcg catggtccgc ctgtccgagt acagccgcga ttgcctcgac    360
gaactgcgcg ccgagaccgg catcgcctac gagggccgca ccctcggcac cacccaactg    420
ttccgcaccc aggcgcagct ggacgccgcc ggcaaggaca tcgccgtgct cgagcgctcc    480
ggcgtgccct acgaggttct cgaccgcgac ggcatcgccc gcgtagagcc ggctttggcc    540
aaggtcgccg acaagctggt cggcgccttg cgcctgccca cgaccagac cggcgactgc    600
cagctgttca ccaccgcct ggcggaaatg gccaagggcc tgggcgtgga gttccgcttc    660
ggccagaaca tcgagcgcct ggacttcgcc ggcgaccgca tcaacggcgt gctggtcaac    720
ggcgaattgc tcaccgccga ccactacgtg ctggccctgg cagctactc gccgcaactg    780
ctcaagccgc tgggtatcaa ggctccggtc tatccgctga agggttattc gctgaccgtg    840
ccgatcacca accccgagat ggcgccgacc tcgaccatcc tcgacgagac ctacaaggtg    900
gcgatcaccc gcttcgacca gcgcatccgc gtcggcggca tggcggaaat cgccggcttc    960
```

-continued

```
gacctgtcgc tgaacccgcg ccgccgcgag accctggaaa tgatcaccac cgacctctat    1020
cccgagggcg gcgatatcag ccaggcgacc ttctggaccg gcctgcgccc ggcgaccccg    1080
gatggcaccc cgatcgtcgg cgccaccgc taccgcaacc tgttcctcaa taccggccac    1140
ggcaccctgg gttggaccat ggcctgcggg tcgggtcgct acctggccga cctgatggcg    1200
aagaagcgcc cgcagatcag taccgaaggc ctggatattt cccgctacag caattccccg    1260
gagaacgcca agaatgccca tccagcgcca gcacactaa                          1299
```

<210> SEQ ID NO 8
<211> LENGTH: 432
<212> TYPE: PRT
<213> ORGANISM: Pseudomonas aeruginosa

<400> SEQUENCE: 8

```
Met Arg Val Leu Val Leu Gly Ser Gly Val Ile Gly Thr Ala Ser Ala
1               5                   10                  15

Tyr Tyr Leu Ala Arg Ala Gly Phe Glu Val Val Val Asp Arg Gln
            20                  25                  30

Asp Gly Pro Ala Leu Glu Thr Ser Phe Ala Asn Ala Gly Gln Val Ser
        35                  40                  45

Pro Gly Tyr Ala Ser Pro Trp Ala Ala Pro Gly Ile Pro Leu Lys Ala
    50                  55                  60

Met Lys Trp Leu Leu Glu Lys His Ala Pro Leu Ala Ile Lys Leu Thr
65                  70                  75                  80

Ser Asp Pro Ser Gln Tyr Ala Trp Met Leu Gln Met Leu Arg Asn Cys
                85                  90                  95

Thr Ala Glu Arg Tyr Ala Val Asn Lys Glu Arg Met Val Arg Leu Ser
            100                 105                 110

Glu Tyr Ser Arg Asp Cys Leu Asp Glu Leu Arg Ala Glu Thr Gly Ile
        115                 120                 125

Ala Tyr Glu Gly Arg Thr Leu Gly Thr Thr Gln Leu Phe Arg Thr Gln
    130                 135                 140

Ala Gln Leu Asp Ala Ala Gly Lys Asp Ile Ala Val Leu Glu Arg Ser
145                 150                 155                 160

Gly Val Pro Tyr Glu Val Leu Asp Arg Asp Gly Ile Ala Arg Val Glu
                165                 170                 175

Pro Ala Leu Ala Lys Val Ala Asp Lys Leu Val Gly Ala Leu Arg Leu
            180                 185                 190

Pro Asn Asp Gln Thr Gly Asp Cys Gln Leu Phe Thr Thr Arg Leu Ala
        195                 200                 205

Glu Met Ala Lys Gly Leu Gly Val Glu Phe Arg Phe Gly Gln Asn Ile
    210                 215                 220

Glu Arg Leu Asp Phe Ala Gly Asp Arg Ile Asn Gly Val Leu Val Asn
225                 230                 235                 240

Gly Glu Leu Leu Thr Ala Asp His Tyr Val Leu Ala Leu Gly Ser Tyr
                245                 250                 255

Ser Pro Gln Leu Leu Lys Pro Leu Gly Ile Lys Ala Pro Val Tyr Pro
            260                 265                 270

Leu Lys Gly Tyr Ser Leu Thr Val Pro Ile Thr Asn Pro Glu Met Ala
        275                 280                 285

Pro Thr Ser Thr Ile Leu Asp Glu Thr Tyr Lys Val Ala Ile Thr Arg
    290                 295                 300

Phe Asp Gln Arg Ile Arg Val Gly Gly Met Ala Glu Ile Ala Gly Phe
305                 310                 315                 320
```

```
Asp Leu Ser Leu Asn Pro Arg Arg Glu Thr Leu Glu Met Ile Thr
                325                 330                 335

Thr Asp Leu Tyr Pro Glu Gly Gly Asp Ile Ser Gln Ala Thr Phe Trp
            340                 345                 350

Thr Gly Leu Arg Pro Ala Thr Pro Asp Gly Thr Pro Ile Val Gly Ala
            355                 360                 365

Thr Arg Tyr Arg Asn Leu Phe Leu Asn Thr Gly His Gly Thr Leu Gly
        370                 375                 380

Trp Thr Met Ala Cys Gly Ser Gly Arg Tyr Leu Ala Asp Leu Met Ala
385                 390                 395                 400

Lys Lys Arg Pro Gln Ile Ser Thr Glu Gly Leu Asp Ile Ser Arg Tyr
                405                 410                 415

Ser Asn Ser Pro Glu Asn Ala Lys Asn Ala His Pro Ala Pro Ala His
            420                 425                 430
```

<210> SEQ ID NO 9
<211> LENGTH: 771
<212> TYPE: DNA
<213> ORGANISM: Pseudomonas seruginosa

<400> SEQUENCE: 9

```
atggcactgg caaaacgcat catccccctgc ctcgacgtgg acaacggccg agtggtcaag      60
ggcgtcaagt tcgagaacat ccgcgacgcc ggcgacccgg tcgagatcgc tcgccgctac     120
gacgagcagg gtgccgacga gatccacttc ctcgatatca ccgccagcgt cgacgggcgc     180
gacaccaccc tgcataccgt cgagcgcatg gctagccagg tgttcattcc gctgaccgtg     240
ggcggcggcg tacgcagcgt gcaggacatc cgcaacctgt tgaatgccgg cgcggacaag     300
gtctcgatca acaccgccgc ggtgttcaac cccgagttcg tcggtgaggc cgccgaccgc     360
ttcggctcgc agtgcatcgt ggtcgccatc gacgcgaaga aggtttccgc cccgggcgag     420
gcgccgcgct gggaaatctt cacccatggc gggcgcaagc ccaccgggct ggatgccgtg     480
ctctgggcga agaagatgga agacttgggc gctggcgaga ttctcctgac cagcatggac     540
caggacggcg tgaagagcgg ttacgacctg ggcgtgaccc cgccatcag cgaggcggtg     600
aacgtgccgg tgatcgcttc cggcggcgtc ggcaacctgg agcacctggc cgccggcatc     660
ctcgagggca aggccgacgc ggtgctcgcg gcgagcatct tccacttcgg cgagtacacc     720
gtgccggaag ccaaggccta cctggccagc cgcggtatcg tggtgcgctg a               771
```

<210> SEQ ID NO 10
<211> LENGTH: 256
<212> TYPE: PRT
<213> ORGANISM: Pseudomonas aeruginosa

<400> SEQUENCE: 10

```
Met Ala Leu Ala Lys Arg Ile Ile Pro Cys Leu Asp Val Asp Asn Gly
1               5                   10                  15

Arg Val Val Lys Gly Val Lys Phe Glu Asn Ile Arg Asp Ala Gly Asp
            20                  25                  30

Pro Val Glu Ile Ala Arg Arg Tyr Asp Glu Gln Gly Ala Asp Glu Ile
        35                  40                  45

Thr Phe Leu Asp Ile Thr Ala Ser Val Asp Gly Arg Asp Thr Thr Leu
    50                  55                  60

His Thr Val Glu Arg Met Ala Ser Gln Val Phe Ile Pro Leu Thr Val
65                  70                  75                  80
```

```
Gly Gly Gly Val Arg Ser Val Gln Asp Ile Arg Asn Leu Leu Asn Ala
            85                  90                  95

Gly Ala Asp Lys Val Ser Ile Asn Thr Ala Ala Val Phe Asn Pro Glu
        100                 105                 110

Phe Val Gly Glu Ala Ala Asp Arg Phe Gly Ser Gln Cys Ile Val Val
    115                 120                 125

Ala Ile Asp Ala Lys Lys Val Ser Ala Pro Gly Glu Ala Pro Arg Trp
130                 135                 140

Glu Ile Phe Thr His Gly Gly Arg Lys Pro Thr Gly Leu Asp Ala Val
145                 150                 155                 160

Leu Trp Ala Lys Lys Met Glu Asp Leu Gly Ala Gly Glu Ile Leu Leu
                165                 170                 175

Thr Ser Met Asp Gln Asp Gly Val Lys Ser Gly Tyr Asp Leu Gly Val
            180                 185                 190

Thr Arg Ala Ile Ser Glu Ala Val Asn Val Pro Val Ile Ala Ser Gly
        195                 200                 205

Gly Val Gly Asn Leu Glu His Leu Ala Ala Gly Ile Leu Glu Gly Lys
    210                 215                 220

Ala Asp Ala Val Leu Ala Ala Ser Ile Phe His Phe Gly Glu Tyr Thr
225                 230                 235                 240

Val Pro Glu Ala Lys Ala Tyr Leu Ala Ser Arg Gly Ile Val Val Arg
                245                 250                 255
```

<210> SEQ ID NO 11
<211> LENGTH: 1035
<212> TYPE: DNA
<213> ORGANISM: Pseudomonas aeruginosa

<400> SEQUENCE: 11

```
atgatcaagg tcggcatcgt tggcggtacg ggttatacgg gcgtggaact gctgcgcctg     60
ctggcgcagc atccgcaggc ccgggtggaa gtgatcactt cgcgttccga ggcggggggtg   120
aaggtcgccg acatgtaccc gaacctgcga ggtcattatg acgacctgca gttcagcgtg   180
ccggacgcgc agcgcctcgg cgcctgcgac gtggtgttct cgccacgcc gcacggcgtg    240
gcgcacgcgc tggctggcga actgctggac gccgggaccc gggtcatcga tctgtccgct   300
gacttccgcc tggcggacgc cgaggagtgg gcgcgctggt acggccagcc gcatggcgct   360
ccggcgctgc tcgacgaggc tgtctacggc ctgccggaag tgaaccgcga agatccgc     420
caggcccgcc tgatcgccgt gccgggctgc tacccgaccg cgacccagct gggcctgatc   480
ccgctgctgg aagccggcct ggccgacgcc tcgcggctga tcgccgattg caagtccggg   540
gtcagcggtg ccgtcgggg cgccaaggtt ggctcgctgt tctgcgaggc gggcgaaagc   600
atgatggcct acgcggtcaa agggcatcgg catctcccgg aaatcagcca gggcctgcgt   660
cgggcctccg gcgcgacgt cgggctgacg ttcgtaccgc acctgacgcc aatgatccgc   720
ggtatccatg caaccctcta tgcccatgtc gcggatcgct cggtcgacct ccaggcgttg   780
ttcgagaagc gctacgccga cgaacccttc gtcgacgtga tgccggccgg cagccatccg   840
gagacccgca gcgtgcgtgg cgccaatgtc tgccgaatcg ccgtgcatcg ccccccaggc   900
ggcgacctgg tggtggtgct gtcggtgatc gacaacctgg tcaagggcgc ctcgggtcag   960
gcgctccaga acatgaacat cctgttcggg ctggacgagc gcctgggcct ctcgcatgcg  1020
gccctgctcc cctga                                                   1035
```

<210> SEQ ID NO 12

```
<211> LENGTH: 344
<212> TYPE: PRT
<213> ORGANISM: Pseudomonas aeruginosa

<400> SEQUENCE: 12

Met Ile Lys Val Gly Ile Val Gly Thr Gly Tyr Thr Gly Val Glu
1               5                   10                  15

Leu Leu Arg Leu Leu Ala Gln His Pro Gln Ala Arg Val Glu Val Ile
            20                  25                  30

Thr Ser Arg Ser Glu Ala Gly Val Lys Val Ala Asp Met Tyr Pro Asn
            35                  40                  45

Leu Arg Gly His Tyr Asp Asp Leu Gln Phe Ser Val Pro Asp Ala Gln
    50                  55                  60

Arg Leu Gly Ala Cys Asp Val Val Phe Phe Ala Thr Pro His Gly Val
65                  70                  75                  80

Ala His Ala Leu Ala Gly Glu Leu Leu Asp Ala Gly Thr Arg Val Ile
                85                  90                  95

Asp Leu Ser Ala Asp Phe Arg Leu Ala Asp Ala Glu Glu Trp Ala Arg
            100                 105                 110

Trp Tyr Gly Gln Pro His Gly Ala Pro Ala Leu Leu Asp Glu Ala Val
            115                 120                 125

Tyr Gly Leu Pro Glu Val Asn Arg Glu Lys Ile Arg Gln Ala Arg Leu
130                 135                 140

Ile Ala Val Pro Gly Cys Tyr Pro Thr Ala Thr Gln Leu Gly Leu Ile
145                 150                 155                 160

Pro Leu Leu Glu Ala Gly Leu Ala Asp Ala Ser Arg Leu Ile Ala Asp
                165                 170                 175

Cys Lys Ser Gly Val Ser Gly Ala Gly Arg Gly Ala Lys Val Gly Ser
            180                 185                 190

Leu Phe Cys Glu Ala Gly Glu Ser Met Met Ala Tyr Ala Val Lys Gly
            195                 200                 205

His Arg His Leu Pro Glu Ile Ser Gln Gly Leu Arg Arg Ala Ser Gly
    210                 215                 220

Gly Asp Val Gly Leu Thr Phe Val Pro His Leu Thr Pro Met Ile Arg
225                 230                 235                 240

Gly Ile His Ala Thr Leu Tyr Ala His Val Ala Asp Arg Ser Val Asp
                245                 250                 255

Leu Gln Ala Leu Phe Glu Lys Arg Tyr Ala Asp Glu Pro Phe Val Asp
            260                 265                 270

Val Met Pro Ala Gly Ser His Pro Glu Thr Arg Ser Val Arg Gly Ala
            275                 280                 285

Asn Val Cys Arg Ile Ala Val His Arg Pro Gln Gly Gly Asp Leu Val
    290                 295                 300

Val Val Leu Ser Val Ile Asp Asn Leu Val Lys Gly Ala Ser Gly Gln
305                 310                 315                 320

Ala Leu Gln Asn Met Asn Ile Leu Phe Gly Leu Asp Glu Arg Leu Gly
                325                 330                 335

Leu Ser His Ala Ala Leu Leu Pro
            340

<210> SEQ ID NO 13
<211> LENGTH: 1644
<212> TYPE: DNA
<213> ORGANISM: Pseudomonas aeruginosa

<400> SEQUENCE: 13
```

-continued

```
gtgagcgaac tcattcgcgt acccgacatc ggcaacggtg agggtgaagt catcgagctg      60
ctggtcaagc ccggcgacaa ggtcgaggcc gatcagagcc tgctgaccct ggaatccgac     120
aaggccagca tggaaatccc cagtcccaag gccggggtag tgaaaagcat caaggcgaag     180
gtcggcgaca ccttgaaaga aggtgacgaa atcctcgagc tggaagtgga aggcggcgaa     240
cagcctgccg aagccaaggc cgaggcagcg cccgcccaac cggaagcgcc gaaagccgaa     300
gcgcctgctc ccgccccgag cgagagcaag ccggccgccc cgccgcgggc cagcgtccag     360
gacatcaagg tcccggacat cggctcggcc ggcaaggcca acgtcatcga agtgatggtc     420
aaggccggcg acacggtcga ggccgaccag tcgctgatca ccctggaatc cgacaaggcc     480
agcatggaga tccctcgcc ggcctccggg gtggtggaaa gcgtctcgat caaggtcggt     540
gacgaagtcg gcaccggcga cctgatcctc aagctgaagg tggaaggcgc cgctccggca     600
gccgaagagc aaccggcagc cgctccggcc caggccgcgg cgcccgccgc cgagcagaag     660
cccgccgcgg cggcccctgc gccagccaag gccgataccc cggctccggt cggcgcaccc     720
agccgcgacg cgccaaggt ccacgccggc ccggcggtgc gcatgctggc gcgcgagttc     780
ggcgtcgagc tgagcgaagt gaaagccagc ggtcccaagg gtcgcatcct caaggaagac     840
gtccaggtct tcgtcaagga gcaactgcag cgcgccaagt ccggcggtgc cggcgccacc     900
ggcggagccg gcatcccgcc gatcccggaa gtcgacttca gcaagttcgg cgaagtggaa     960
gaagtggcga tgacccgcct gatgcaggtc ggcgccgcca acctgcatcg cagctggctg    1020
aacgtgccgc acgtgaccca gttcgaccag tcggacatca ccgacatgga agccttccgc    1080
gttgcccaga aggccgcggc ggagaaggcc ggggtcaagc tgaccgtact gccgatcctg    1140
ctcaaggcct gcgcccacct gctcaaggaa ctgccggact tcaacagttc gctggccccc    1200
agcggcaagg cgctgatccg caagaagtac gtacacatcg gcttcgccgt ggacactccg    1260
gacggcctgc tggtcccggt gatccgcgat gtcgaccgga gagcctcct gcaactggcc    1320
gccgaggccg ccgacctggc cgacaaggcc cgcaacaaga gctctcggc cgatgccatg    1380
cagggcgcct gcttcaccat ctccagtctc ggccacatcg gcggcaccgg cttcacgccg    1440
atcgtcaacg cgccggaagt ggcgatcctc ggtgtgtcca aggcgaccat gcagccggta    1500
tgggacggca aggccttcca gccgcgcctg atgctgccgc tgtcgctgtc ctacgaccat    1560
cgcgtgatca acggtgccgc cgcggcgcgc ttcaccaagc gcctgggcga gctgctggcg    1620
gacatccgca ccctgctcct gtaa                                           1644
```

<210> SEQ ID NO 14
<211> LENGTH: 547
<212> TYPE: PRT
<213> ORGANISM: Pseudomonas aeruginosa

<400> SEQUENCE: 14

```
Met Ser Glu Leu Ile Arg Val Pro Asp Ile Gly Asn Gly Glu Gly Glu
1               5                   10                  15

Val Ile Glu Leu Leu Val Lys Pro Gly Asp Lys Val Glu Ala Asp Gln
            20                  25                  30

Ser Leu Leu Thr Leu Glu Ser Asp Lys Ala Ser Met Glu Ile Pro Ser
        35                  40                  45

Pro Lys Ala Gly Val Val Lys Ser Ile Lys Ala Lys Val Gly Asp Thr
    50                  55                  60

Leu Lys Glu Gly Asp Glu Ile Leu Glu Leu Glu Val Glu Gly Gly Glu
65                  70                  75                  80
```

```
Gln Pro Ala Glu Ala Lys Ala Glu Ala Ala Pro Ala Gln Pro Glu Ala
                85                  90                  95

Pro Lys Ala Glu Ala Pro Ala Pro Ala Pro Ser Glu Ser Lys Pro Ala
            100                 105                 110

Ala Pro Ala Ala Ala Ser Val Gln Asp Ile Lys Val Pro Asp Ile Gly
        115                 120                 125

Ser Ala Gly Lys Ala Asn Val Ile Glu Val Met Val Lys Ala Gly Asp
    130                 135                 140

Thr Val Glu Ala Asp Gln Ser Leu Ile Thr Leu Glu Ser Asp Lys Ala
145                 150                 155                 160

Ser Met Glu Ile Pro Ser Pro Ala Ser Gly Val Val Glu Ser Val Ser
                165                 170                 175

Ile Lys Val Gly Asp Glu Val Gly Thr Gly Asp Leu Ile Leu Lys Leu
            180                 185                 190

Lys Val Glu Gly Ala Ala Pro Ala Ala Glu Glu Gln Pro Ala Ala Ala
        195                 200                 205

Pro Ala Gln Ala Ala Ala Pro Ala Ala Glu Gln Lys Pro Ala Ala Ala
    210                 215                 220

Ala Pro Ala Pro Ala Lys Ala Asp Thr Pro Ala Pro Val Gly Ala Pro
225                 230                 235                 240

Ser Arg Asp Gly Ala Lys Val His Ala Gly Pro Ala Val Arg Met Leu
                245                 250                 255

Ala Arg Glu Phe Gly Val Glu Leu Ser Glu Val Lys Ala Ser Gly Pro
            260                 265                 270

Lys Gly Arg Ile Leu Lys Glu Asp Val Gln Val Phe Val Lys Glu Gln
        275                 280                 285

Leu Gln Arg Ala Lys Ser Gly Ala Gly Ala Thr Gly Gly Ala Gly
    290                 295                 300

Ile Pro Pro Ile Pro Glu Val Asp Phe Ser Lys Phe Gly Glu Val Glu
305                 310                 315                 320

Glu Val Ala Met Thr Arg Leu Met Gln Val Gly Ala Ala Asn Leu His
                325                 330                 335

Arg Ser Trp Leu Asn Val Pro His Val Thr Gln Phe Asp Gln Ser Asp
            340                 345                 350

Ile Thr Asp Met Glu Ala Phe Arg Val Ala Gln Lys Ala Ala Ala Glu
        355                 360                 365

Lys Ala Gly Val Lys Leu Thr Val Leu Pro Ile Leu Leu Lys Ala Cys
    370                 375                 380

Ala His Leu Leu Lys Glu Leu Pro Asp Phe Asn Ser Ser Leu Ala Pro
385                 390                 395                 400

Ser Gly Lys Ala Leu Ile Arg Lys Lys Tyr Val His Ile Gly Phe Ala
                405                 410                 415

Val Asp Thr Pro Asp Gly Leu Leu Val Pro Val Ile Arg Asp Val Asp
            420                 425                 430

Arg Lys Ser Leu Leu Gln Leu Ala Ala Glu Ala Ala Asp Leu Ala Asp
        435                 440                 445

Lys Ala Arg Asn Lys Lys Leu Ser Ala Asp Ala Met Gln Gly Ala Cys
    450                 455                 460

Phe Thr Ile Ser Ser Leu Gly His Ile Gly Gly Thr Gly Phe Thr Pro
465                 470                 475                 480

Ile Val Asn Ala Pro Glu Val Ala Ile Leu Gly Val Ser Lys Ala Thr
                485                 490                 495
```

Met Gln Pro Val Trp Asp Gly Lys Ala Phe Gln Pro Arg Leu Met Leu
            500                 505                 510

Pro Leu Ser Leu Ser Tyr Asp His Arg Val Ile Asn Gly Ala Ala Ala
        515                 520                 525

Ala Arg Phe Thr Lys Arg Leu Gly Glu Leu Leu Ala Asp Ile Arg Thr
    530                 535                 540

Leu Leu Leu
545

<210> SEQ ID NO 15
<211> LENGTH: 996
<212> TYPE: DNA
<213> ORGANISM: Pseudomonas aeruginosa

<400> SEQUENCE: 15

```
atgagttggc tgactcccgc tctggtcacc atcatcctca ccgtggtcaa ggccatcgtg      60
gtgctgctcg ccgtggtcat ctgcggcgcc ctgctaagct gggtcgagcg ccgcctgctc     120
ggcctctggc aggaccgcta cggccccaac cgggtcggtc cgttcggtgc gttccagctc     180
ggcgcggaca tggtcaagat gttcttcaag gaggactgga ccccgccgtt cgccgacaag     240
atgatcttca ccctggcccc ggtaatcgcg atgggcgccc tgctcgtcgc cttcgccatc     300
gtgccgatca cccccacctg ggcgtggcg gacctgaaca tcggcatcct gttcttcttc     360
gccatggccg gcctgacggt gtacgccgtg ctgttcgccg gctggtcgag caacaacaag     420
ttcgccctgc tcggcagcct gcgcgcctcg gcccagacca tctcctacga ggtgttcctg     480
gccctgtcgc tgatgggcat cgtcgcccag gtcggctcgt tcaacatgcg cgacatcgtc     540
cagtaccaga tcgacaacgt ctggttcatc attccgcagt tcttcggctt ctgcaccttc     600
atcatcgccg gcgtcgccgt gacccaccgt cacccgttcg accagccgga agcggagcag     660
gaactggcgg acggctacca catcgagtac gccgggatga atggggcat gttcttcgtc     720
ggcgagtaca tcggcatcgt actggtctcg gcgctgctgg cgaccctgtt cttcggcggc     780
tggcacggtc cgttcctgga cacctgccc tggctgtcgt tcttctactt cgccgccaag     840
accggcttct tcatcatgct cttcatcctg atccgcgcct cgctgccgcg tccgcgctat     900
gaccaggtga tggcgttcag ctggaaggtg tgcctgccgc tgaccctgat caacctgctg     960
gtgaccggcg cgctcgtgct ggccgcggcc cagtaa                               996
```

<210> SEQ ID NO 16
<211> LENGTH: 331
<212> TYPE: PRT
<213> ORGANISM: Pseudomonas aeruginosa

<400> SEQUENCE: 16

Met Ser Trp Leu Thr Pro Ala Leu Val Thr Ile Ile Leu Thr Val Val
1               5                   10                  15

Lys Ala Ile Val Val Leu Leu Ala Val Val Ile Cys Gly Ala Leu Leu
            20                  25                  30

Ser Trp Val Glu Arg Arg Leu Leu Gly Leu Trp Gln Asp Arg Tyr Gly
        35                  40                  45

Pro Asn Arg Val Gly Pro Phe Gly Ala Phe Gln Leu Gly Ala Asp Met
    50                  55                  60

Val Lys Met Phe Phe Lys Glu Asp Trp Thr Pro Pro Phe Ala Asp Lys
65                  70                  75                  80

Met Ile Phe Thr Leu Ala Pro Val Ile Ala Met Gly Ala Leu Leu Val
                85                  90                  95

-continued

```
Ala Phe Ala Ile Val Pro Ile Thr Pro Thr Trp Gly Val Ala Asp Leu
                100                 105                 110

Asn Ile Gly Ile Leu Phe Phe Ala Met Ala Gly Leu Thr Val Tyr
        115                 120                 125

Ala Val Leu Phe Ala Gly Trp Ser Ser Asn Asn Lys Phe Ala Leu Leu
    130                 135                 140

Gly Ser Leu Arg Ala Ser Ala Gln Thr Ile Ser Tyr Glu Val Phe Leu
145                 150                 155                 160

Ala Leu Ser Leu Met Gly Ile Val Ala Gln Val Gly Ser Phe Asn Met
                165                 170                 175

Arg Asp Ile Val Gln Tyr Gln Ile Asp Asn Val Trp Phe Ile Ile Pro
            180                 185                 190

Gln Phe Phe Gly Phe Cys Thr Phe Ile Ile Ala Gly Val Ala Val Thr
        195                 200                 205

His Arg His Pro Phe Asp Gln Pro Glu Ala Glu Gln Glu Leu Ala Asp
    210                 215                 220

Gly Tyr His Ile Glu Tyr Ala Gly Met Lys Trp Gly Met Phe Phe Val
225                 230                 235                 240

Gly Glu Tyr Ile Gly Ile Val Leu Val Ser Ala Leu Leu Ala Thr Leu
                245                 250                 255

Phe Phe Gly Gly Trp His Gly Pro Phe Leu Asp Thr Leu Pro Trp Leu
            260                 265                 270

Ser Phe Phe Tyr Phe Ala Ala Lys Thr Gly Phe Phe Ile Met Leu Phe
        275                 280                 285

Ile Leu Ile Arg Ala Ser Leu Pro Arg Pro Arg Tyr Asp Gln Val Met
    290                 295                 300

Ala Phe Ser Trp Lys Val Cys Leu Pro Leu Thr Leu Ile Asn Leu Leu
305                 310                 315                 320

Val Thr Gly Ala Leu Val Leu Ala Ala Gln
                325                 330

<210> SEQ ID NO 17
<211> LENGTH: 7347
<212> TYPE: DNA
<213> ORGANISM: Pseudomonas aeruginosa

<400> SEQUENCE: 17
gtgcaagcac tcatagagaa ggtgggctcc ctttcccccc aggaaaggaa ggcattggct      60
gtcctgctca agcagcaagg tgtcaatctc ttcgagatcg cgccagtgtt caagcgccag     120
gacggcgagc ccctgcggct ctcctatgcc caggagcgac agtggtttct ctggcaactg     180
gagccggaaa gcgcggccta ccatatcccg agtgtcttgc gtctacgtgg gcggctggac     240
ctggatgccc tgcaacgcag cttcgacagc ctggttgcgc ggcacgagac cctacgcacc     300
cgttttcgcc tcgacggcga cgaggcgcgc aggagatcg ccgcatccat ggcattgccg     360
ttggatatcg tcgcgttggg gccgctcgag gagggcgccc tcgctcggca ggtcgagacg     420
acgatcgcgc ggccgttcga cctggagcgt gggccgctgc tgcgggtgag cctgttgcgg     480
ctggccgagg acgaccatgt gctggtgctg gtccagcatc acatcgtgtc gacggttgg      540 tcgatgcagg tgatggtcga ggaactggtc cagctctatg ccgcctatag tcgagggctc     600
gaggtagcgc tgccggcttt gccgatccag tacgcggact acgccctgtg cagcgcagc      660 tggatggagg ccgggggaaaa ggagcgccag ttggcgtact ggaccggcct gctgggcggc    720
gagcagccgg tgctggagtt gccgttcgac cggccgcgcc cggttcggca aagccatcgt    780
```

```
ggtgcccagt tcatcctgga actggatatt gatctgtccc aggcgctcag gcgcgtggcc      840
cagcaggagg gggctactgc cttcgccctg ttgctggctt cgttccaggc gctgctgtat      900
cgctacagcg ggcaggcgga tatccgtgtc ggcgtgccga tcgccaatcg caaccgcgtg      960
gagaccgagc ggctgatcgg cttcttcgtc aacacccagg tgctcaaggc cgacctggac     1020
ggtcggatgg gcttcgacga gctgctggcc caggcccgcc aacgcgcgct ggaggcccag     1080
gcgcaccagg acctgccgtt cgagcaactg gtggaggcct gcagccggga gcgcagtctt     1140
agccacaacc cgctgttcca ggtgctgttc aactaccaga gcgaagcccg tgcaacggc      1200
caggcattcc gcttcgacga gttacagatg aaaagcgtgc agttcgacag ccggacggcg     1260
cagttcgact tgacgttgga cctgacggac gaagagcagc gttttttgcgc cgttttcgac     1320
tacgccaccg acctgttcga cgcctccacc gtggaacgcc tggccggcca ttggcgcaac     1380
ctgttgcgcg gcatcgtcgc caacccacga cagcggctcg gcgagttgcc gctgctggat     1440
gcgccggagc gccggcagac cctctccgaa tggaacccgg cccagcgcga gtgcgcggtg     1500
cagggcaccct tgcagcagcg tttcgaggaa caggcgcggc aacggccaca ggcggttgcg     1560
ctgatcctcg acgaacaacg gttgagctac ggcgaactga atgcgcgggc caatcgcctg     1620
gcgcactgcc tgatcgcccg tggcgttggc gcggacgtgc cggtcgggct ggcgctggag     1680
cgttcgctgg acatgctggt cggcttgctg gcgatcctca aggccggcgg cgcctacctg     1740
ccgttggacc cggcggcgcc agaggagcgc ctggcgcata tcctcgacga cagtggggta     1800
cggctgctgc tgacccaggg gcatctgctc gagcgcctgc cacggcaggc gggggtggag     1860
gtgctggcca tcgacggact ggtgctggag ggctacgccg agagcgatcc gctcccgacg     1920
ctatcggcga caacctggc ctacgtgatc tatacctcgg gctcgaccgg caagcccaag     1980
ggcacattgc tcacccaccg caacgcgctg cgcctgttca gcgccaccga ggcctggttc     2040
ggcttcgacg agcgggacgt gtggacattg ttccattcct acgccttcga tttctcggtc     2100
tgggaaatct tcggcgcgct gctctatggc gggtgcctgg tgattgtgcc gcaatgggtg     2160
agccgttcgc cggaagactt ctaccgtctg ctgtgccgcg aaggcgtgac ggtgctcaac     2220
cagacgccgt cggcgttcaa gcaactgatg gcggtggcct gttccgccga catggcgacg     2280
cagcagccgc cgctgcgcta cgtgatcttc ggtggcgagg cgctggatct gcagagcctg     2340
cggccgtggt tccagcgctt cggcgatcgc cagccgcaac tggtgaacat gtacggcatc     2400
accgagacca cggtgcacgt aacctaccgt ccggtgagcg aggccgacct ggaaggtggc     2460
ctggtcagtc cgattggcgg gaccatcccg gacctgtcct ggtacatcct cgaccgtgac     2520
ctgaacccgg tgccgcgcgg cgcggtgggc gagctgtaca tcggtcgcgc cgggctggcg     2580
cgcggctacc tgaggcggcc cgggttgagt gccacccgct tcgtgccgaa cccgttcccc     2640
ggcggcgccg cgagcggct gtaccgtacc ggcgacctgg cacggttcca ggcggatggc     2700
aatatcgagt acatcgggcg tatcgaccac caggtgaagg ttcgcggctt ccgtatcgaa     2760
ctgggcgaga tcgaagcggc gctcgccggt ctggccgggg tacgcgatgc cgtggtgctg     2820
gcccatgacg gagtcggcgg cacgcaactg gtgggatacg tggtggcgga ctcggcggag     2880
gatgccgagc gtctgcggga gtcgctgcgg gagtcgctga gcggcacct gccggactac     2940
atggtgccgg cgcacctgat gctgctggag cggatgccgc tgacggtcaa tggcaagctc     3000
gaccggcagg cgttgccgca accggatgcg agcctgtcgc aacaggccta tcgagcgccc     3060
ggtagcgagc tggagcagcg catcgcagcg atctggtcgg agatcctggg agtggaacgg     3120
```

-continued

```
gtcggcctgg acgacaactt cttcgaactg ggcggtcatt cgttgctggc tacccgggtg    3180
atttctcggg ttcgccagga gcagcagttg gacgcaagcc tgaaggcgtt gttcgagcgg    3240
ccggttctgg aagcgttcgc ccagggattg aacgcacga cggatgcggt ctcgacgata    3300
ccgcttgccg atcggcagca accgttggca ctgtccttcg ctcaggagcg tcagtggttc    3360
ctctggcaac tggagccgga aagcgcggcc taccatattc cgagtgcctt gcgcctacgc    3420
gggcggctgg acgtggatgc cttgcaacgc agcttcgaca gcctggtcgc gcggcatgaa    3480
accttgcgta cccgcttccg gctggaggga gggcgttcgt accagcaggt acaacctgcg    3540
gttagcgttt ccatcgagcg ggaacagttc ggtgaagaag gcctgatcga acggatacag    3600
gccatcgttg tgcagccatt cgacctggaa cggggccgc tgctgcgggt gaacctgttg    3660
caactggccg aggacgacca tgtactggtg ctggtccagc accacatcgt gtccgatggt    3720
tggtcgatgc aggtgatggt cgaggaactg gtccagctct atgccgccta tagccaaggg    3780
ctcgacgtgt tgttgccagc cctgccgatc cagtacgcgg actacgccct gtggcagcgc    3840
agctggatgg aggcggggga aaaggagcgc cagttggcgt actggaccgg cctgctgggc    3900
ggcgagcagc cggtgctgga gttgccgttc gatcggccgc gtccggcccg gcagagccat    3960
cgtggcgcgc agtttgggttt cgagctatcg cgggaactgg tcgaggccgt gagagccttg    4020
gcccagcgta aggcgccag tagtttcatg ctgttgctgg cctcgttcca ggcgctgttg    4080
tatcgctaca gcgggcaggc ggatatccgt gtcggtgtgc cgatcgccaa tcgcaaccgc    4140
gtggagaccg agcggctgat cggcttcttc gtcaacaccc aggtgctcaa ggccgacctg    4200
gacggtcgga tgggcttcga cgagctgctg gcccaggccc gccaacgcgc gctggaggcc    4260
caggcgcacc aggacctgcc gttcgagcaa ctggtggaag ccttgcagcc ggagcgcaat    4320
gccagccaca acccactgtt ccaggtgctg ttcaaccatc agagcgagat acgtcggtg    4380
acgcccgagg ttcagttgga ggacctgcgt ctggaaggcc tggcctggga cggccagact    4440
gcgcagttcg acctgacgct ggatattcag gaagacgaaa acggcatctg gcctccttc    4500
gactatgcca ccgatctgtt cgacgcctcc accgtggaac gcctggccgg ccattggcgc    4560
aacctgttgc gcggcatcgt cgccaaccca cgacagcggc tcggcgagtt gccgctgctg    4620
gatgcgccgg agcgccggca gaccctctcc gaatggaacc cggcccagcg cgagtgcgcg    4680
gtgcagggca ccttgcagca gcgttcgag gagcaggcgc ggcaacggcc acaggcggtt    4740
gcgctgatcc tcgacgaaca acggttgagc tacggcgaac tgaatgcgcg ggccaatcgc    4800
ctggcgcact gcctgatcgc tcgcggcgtt ggcgcggacg tgccggtcgg gctggcgctg    4860
gagcgttcgc tggacatgct ggtcggcttg ctggcgatcc tcaaggccgg cggcgcctac    4920
ctgccgttgg acccggcggc gccagaggag cgcctggcgc atatcctcga cgacagtggg    4980
gtacggctgc tgctgacccg ggggcatctg ctcgagcgcc tgccgcggca ggcgggggtg    5040
gaggtgctgg ccatcgacgg actggtgctg gacggctacg ccgagagcga tccgctcccg    5100
acgctatcgg cggacaacct ggcctacgtg atctatacct cgggctcgac cggcaagccc    5160
aagggcacgt tgctcaccca ccgcaacgcg ctgcgcctgt tcagcgccac cgaggcctgg    5220
ttcggcttcg acgagcggga cgtgtggacg ttgttccatt cctacgcctt cgatttctcg    5280
gtctgggaaa tcttcggcgc gctgctctat ggcgggcgcc tggtgatcgt gccgcaatgg    5340
gtgagccgtt cgccggaaga cttctaccgt ctgctgtgcc gcgaaggcgt gacggtgctc    5400
aaccagacgc cgtcgcgtt caagcaactg atggcggtgg cctgttccgc cgacatggcg    5460
acgcagcagc cggcgctgcg ctacgtgatc ttcggtggcg aggcgctgga tctgcagagc    5520
```

```
ctgcggccgt ggttccagcg ctttggcgat cgccagccgc aactggtgaa catgtacggc    5580
atcaccgaga ccacggtaca cgtaacctac cgtccggtga gcgaagccga cctgaagggt    5640
ggcctggtca gtccgatcgg cgggaccatc ccggacctgt cctggtacat cctcgaccgt    5700
gacctgaacc cggtgccgcg cggcgcggtg ggcgagctgt acatcggtcg cgccggtctg    5760 gcgcgcgggct acctgaggcg gcccggggttg agtgccaccc gcttcgtgcc gaacccgttc    5820
cccggcggtg ccggcgagcg gctgtaccgt accggcgacc tggcacggtt ccaggcggat    5880
ggcaatatcg agtacatcgg gcgtatcgac caccaggtga aggttcgcgg cttccgtatc    5940
gaactgggtg agatcgaagc ggcgctcgcc ggtctggccg gggtacgcga tgccgtggtg    6000
ctggcccatg acgggtcgg cggcacgcaa ctggtgggat acgtggtggc ggactcggcg    6060
gaggatgccg agcgtctgcg ggagtcgctg cgggagtcgc tgaagcggca cctgccggac    6120
tacatggtgc cggcgcacct gatgctgctg agcggatgc cgctgacggt caatggcaag    6180
ctcgaccggc aggcgttgcc gcaaccggat gcgagcttgt cgcagcaggc ctatcgagcg    6240
cccggtagcg agctggagca gcgcatcgca gcgatctggg cggagatcct gggagtggaa    6300
cgggtcggcc tggacgacaa cttcttcgaa ctgggcggtc actcattgtt gctgctgatg    6360
ctcaaggagc ggatcggcga tacctgccag gctacgctga gcatcagcca actgatgacc    6420
catgccagcg tcgcggaaca ggcggcatgc atcgaggggc aggcgcgtga gtcgttgctg    6480
gtgccgctca acggcaggcg cgaaggttcg ccgctgttca tgttccatcc gagtttcggc    6540
tctgtgcact gttacaagac cctcgccatg gcgctgcggg atcgtcatcc ggtcaagggt    6600
gttgtctgcc gtgccctgct gggcgctggt cgcgaggtgc cggagtggga cgatatggtt    6660
gcggaatacg ccgagcaatt gctgcaggag caccccgaag gggttttcaa cctggcggga    6720
tggtcgctcg cggcaacct ggcgatggat gtcgcggccc ggctggagca gcgtgggcgg    6780
caggtggctt tcgtcggctg gatcgatgca ccggcaccgg tcagggtcga agcgttctgg    6840
aacgagatcg ggccgacgcc ggaggcagtc ccgaacctat ccgtgggcga gatgcgggtg    6900
gaactgctcg gtgtcatgtt tccggagcgg gccgagcata tcgaacgggc ctggtcatcg    6960
atctgctccg ccacgacgga cgatgagcag cgctggacga ggatgagcga ctgggcggaa    7020
gcggagatcg cgccgagtt cgcgacactg cgcagcgaaa tcgcacagag caacgaactg    7080
gaagtgtcct gggagttgaa acagatcctc gacgagcgcc tgaaagcgat ggattacccg    7140
cgtctgacgg cgaaggtcag cctctggtgg gccgcgcgca gcaccaatgc catccagcgg    7200
agcgcggtgg agcgctcgat ggccgaggcg atcgggctg agcgtgtcga accggtgcgg    7260
gtgctggata cccggcacga caagatcatc gaccaccctg agtttgtgca gagcttccgg    7320
gccgccctgg agcgtgccgg gcgctga                                         7347
```

<210> SEQ ID NO 18
<211> LENGTH: 2448
<212> TYPE: PRT
<213> ORGANISM: Pseudomonas aeruginosa

<400> SEQUENCE: 18

Met Gln Ala Leu Ile Glu Lys Val Gly Ser Leu Ser Pro Gln Glu Arg
1               5                   10                  15

Lys Ala Leu Ala Val Leu Leu Lys Gln Gln Gly Val Asn Leu Phe Glu
            20                  25                  30

Ile Ala Pro Val Phe Lys Arg Gln Asp Gly Glu Pro Leu Arg Leu Ser
        35                  40                  45

```
Tyr Ala Gln Glu Arg Gln Trp Phe Leu Trp Gln Leu Glu Pro Glu Ser
            50                  55                  60

Ala Ala Tyr His Ile Pro Ser Val Leu Arg Leu Arg Gly Arg Leu Asp
65                  70                  75                  80

Leu Asp Ala Leu Gln Arg Ser Phe Asp Ser Leu Val Ala Arg His Glu
                85                  90                  95

Thr Leu Arg Thr Arg Phe Arg Leu Asp Gly Asp Glu Ala Arg Gln Glu
                100                 105                 110

Ile Ala Ala Ser Met Ala Leu Pro Leu Asp Ile Val Ala Leu Gly Pro
                115                 120                 125

Leu Glu Glu Gly Ala Leu Ala Arg Gln Val Glu Thr Thr Ile Ala Arg
    130                 135                 140

Pro Phe Asp Leu Glu Arg Gly Pro Leu Leu Arg Val Ser Leu Leu Arg
145                 150                 155                 160

Leu Ala Glu Asp Asp His Val Leu Val Leu Val Gln His His Ile Val
                165                 170                 175

Ser Asp Gly Trp Ser Met Gln Val Met Val Glu Glu Leu Val Gln Leu
                180                 185                 190

Tyr Ala Ala Tyr Ser Arg Gly Leu Glu Val Ala Leu Pro Ala Leu Pro
                195                 200                 205

Ile Gln Tyr Ala Asp Tyr Ala Leu Trp Gln Arg Ser Trp Met Glu Ala
    210                 215                 220

Gly Glu Lys Glu Arg Gln Leu Ala Tyr Trp Thr Gly Leu Leu Gly Gly
225                 230                 235                 240

Glu Gln Pro Val Leu Glu Leu Pro Phe Asp Arg Pro Arg Pro Val Arg
                245                 250                 255

Gln Ser His Arg Gly Ala Gln Phe Ile Leu Glu Leu Asp Ile Asp Leu
                260                 265                 270

Ser Gln Ala Leu Arg Arg Val Ala Gln Gln Glu Gly Ala Thr Ala Phe
    275                 280                 285

Ala Leu Leu Leu Ala Ser Phe Gln Ala Leu Leu Tyr Arg Tyr Ser Gly
    290                 295                 300

Gln Ala Asp Ile Arg Val Gly Val Pro Ile Ala Asn Arg Asn Arg Val
305                 310                 315                 320

Glu Thr Glu Arg Leu Ile Gly Phe Phe Val Asn Thr Gln Val Leu Lys
                325                 330                 335

Ala Asp Leu Asp Gly Arg Met Gly Phe Asp Glu Leu Leu Ala Gln Ala
                340                 345                 350

Arg Gln Arg Ala Leu Glu Ala Gln Ala His Gln Asp Leu Pro Phe Glu
                355                 360                 365

Gln Leu Val Glu Ala Leu Gln Pro Glu Arg Ser Leu Ser His Asn Pro
    370                 375                 380

Leu Phe Gln Val Leu Phe Asn Tyr Gln Ser Glu Ala Arg Gly Asn Gly
385                 390                 395                 400

Gln Ala Phe Arg Phe Asp Glu Leu Gln Met Glu Ser Val Gln Phe Asp
                405                 410                 415

Ser Arg Thr Ala Gln Phe Asp Leu Thr Leu Asp Leu Thr Asp Glu Glu
                420                 425                 430

Gln Arg Phe Cys Ala Val Phe Asp Tyr Ala Thr Asp Leu Phe Asp Ala
                435                 440                 445

Ser Thr Val Glu Arg Leu Ala Gly His Trp Arg Asn Leu Leu Arg Gly
450                 455                 460
```

```
Ile Val Ala Asn Pro Arg Gln Arg Leu Gly Glu Leu Pro Leu Leu Asp
465                 470                 475                 480

Ala Pro Glu Arg Arg Gln Thr Leu Ser Glu Trp Asn Pro Ala Gln Arg
                485                 490                 495

Glu Cys Ala Val Gln Gly Thr Leu Gln Gln Arg Phe Glu Glu Gln Ala
            500                 505                 510

Arg Gln Arg Pro Gln Ala Val Ala Leu Ile Leu Asp Glu Gln Arg Leu
            515                 520                 525

Ser Tyr Gly Glu Leu Asn Ala Arg Ala Asn Arg Leu Ala His Cys Leu
        530                 535                 540

Ile Ala Arg Gly Val Gly Ala Asp Val Pro Val Gly Leu Ala Leu Glu
545                 550                 555                 560

Arg Ser Leu Asp Met Leu Val Gly Leu Leu Ala Ile Leu Lys Ala Gly
                565                 570                 575

Gly Ala Tyr Leu Pro Leu Asp Pro Ala Ala Pro Glu Glu Arg Leu Ala
            580                 585                 590

His Ile Leu Asp Asp Ser Gly Val Arg Leu Leu Thr Gln Gly His
        595                 600                 605

Leu Leu Glu Arg Leu Pro Arg Gln Ala Gly Val Glu Val Leu Ala Ile
    610                 615                 620

Asp Gly Leu Val Leu Asp Gly Tyr Ala Glu Ser Asp Pro Leu Pro Thr
625                 630                 635                 640

Leu Ser Ala Asp Asn Leu Ala Tyr Val Ile Tyr Thr Ser Gly Ser Thr
                645                 650                 655

Gly Lys Pro Lys Gly Thr Leu Leu Thr His Arg Asn Ala Leu Arg Leu
            660                 665                 670

Phe Ser Ala Thr Glu Ala Trp Phe Gly Phe Asp Glu Arg Asp Val Trp
        675                 680                 685

Thr Leu Phe His Ser Tyr Ala Phe Asp Phe Ser Val Trp Glu Ile Phe
    690                 695                 700

Gly Ala Leu Leu Tyr Gly Gly Cys Leu Val Ile Val Pro Gln Trp Val
705                 710                 715                 720

Ser Arg Ser Pro Glu Asp Phe Tyr Arg Leu Leu Cys Arg Glu Gly Val
                725                 730                 735

Thr Val Leu Asn Gln Thr Pro Ser Ala Phe Lys Gln Leu Met Ala Val
            740                 745                 750

Ala Cys Ser Ala Asp Met Ala Thr Gln Gln Pro Ala Leu Arg Tyr Val
        755                 760                 765

Ile Phe Gly Gly Glu Ala Leu Asp Leu Gln Ser Leu Arg Pro Trp Phe
    770                 775                 780

Gln Arg Phe Gly Asp Arg Gln Pro Gln Leu Val Asn Met Tyr Gly Ile
785                 790                 795                 800

Thr Glu Thr Thr Val His Val Thr Tyr Arg Pro Val Ser Glu Ala Asp
                805                 810                 815

Leu Glu Gly Gly Leu Val Ser Pro Ile Gly Thr Ile Pro Asp Leu
            820                 825                 830

Ser Trp Tyr Ile Leu Asp Arg Asp Leu Asn Pro Val Pro Arg Gly Ala
        835                 840                 845

Val Gly Glu Leu Tyr Ile Gly Arg Ala Gly Leu Ala Arg Gly Tyr Leu
    850                 855                 860

Arg Arg Pro Gly Leu Ser Ala Thr Arg Phe Val Pro Asn Pro Phe Pro
865                 870                 875                 880

Gly Gly Ala Gly Glu Arg Leu Tyr Arg Thr Gly Asp Leu Ala Arg Phe
```

-continued

```
            885                 890                 895
Gln Ala Asp Gly Asn Ile Glu Tyr Ile Gly Arg Ile Asp His Gln Val
            900                 905                 910
Lys Val Arg Gly Phe Arg Ile Glu Leu Gly Glu Ile Glu Ala Ala Leu
            915                 920                 925
Ala Gly Leu Ala Gly Val Arg Asp Ala Val Val Leu Ala His Asp Gly
            930                 935                 940
Val Gly Gly Thr Gln Leu Val Gly Tyr Val Val Ala Asp Ser Ala Glu
945                 950                 955                 960
Asp Ala Glu Arg Leu Arg Glu Ser Leu Arg Glu Ser Leu Lys Arg His
            965                 970                 975
Leu Pro Asp Tyr Met Val Pro Ala His Leu Met Leu Leu Glu Arg Met
            980                 985                 990
Pro Leu Thr Val Asn Gly Lys Leu Asp Arg Gln Ala Leu Pro Gln Pro
            995                 1000                1005
Asp Ala Ser Leu Ser Gln Gln Ala Tyr Arg Ala Pro Gly Ser Glu
            1010                1015                1020
Leu Glu Gln Arg Ile Ala Ala Ile Trp Ser Glu Ile Leu Gly Val
            1025                1030                1035
Glu Arg Val Gly Leu Asp Asp Asn Phe Phe Glu Leu Gly Gly His
            1040                1045                1050
Ser Leu Leu Ala Thr Arg Val Ile Ser Arg Val Arg Gln Glu Gln
            1055                1060                1065
Gln Leu Asp Ala Ser Leu Lys Ala Leu Phe Glu Arg Pro Val Leu
            1070                1075                1080
Glu Ala Phe Ala Gln Gly Leu Glu Arg Thr Thr Asp Ala Val Ser
            1085                1090                1095
Thr Ile Pro Leu Ala Asp Arg Gln Gln Pro Leu Ala Leu Ser Phe
            1100                1105                1110
Ala Gln Glu Arg Gln Trp Phe Leu Trp Gln Leu Glu Pro Glu Ser
            1115                1120                1125
Ala Ala Tyr His Ile Pro Ser Ala Leu Arg Leu Arg Gly Arg Leu
            1130                1135                1140
Asp Val Asp Ala Leu Gln Arg Ser Phe Asp Ser Leu Val Ala Arg
            1145                1150                1155
His Glu Thr Leu Arg Thr Arg Phe Arg Leu Glu Gly Gly Arg Ser
            1160                1165                1170
Tyr Gln Gln Val Gln Pro Ala Val Ser Val Ser Ile Glu Arg Glu
            1175                1180                1185
Gln Phe Gly Glu Gly Leu Ile Glu Arg Ile Gln Ala Ile Val
            1190                1195                1200
Val Gln Pro Phe Asp Leu Glu Arg Gly Pro Leu Leu Arg Val Asn
            1205                1210                1215
Leu Leu Gln Leu Ala Glu Asp Asp His Val Leu Val Leu Val Gln
            1220                1225                1230
His His Ile Val Ser Asp Gly Trp Ser Met Gln Val Met Val Glu
            1235                1240                1245
Glu Leu Val Gln Leu Tyr Ala Ala Tyr Ser Gln Gly Leu Asp Val
            1250                1255                1260
Val Leu Pro Ala Leu Pro Ile Gln Tyr Ala Asp Tyr Ala Leu Trp
            1265                1270                1275
Gln Arg Ser Trp Met Glu Ala Gly Glu Lys Glu Arg Gln Leu Ala
            1280                1285                1290
```

-continued

```
Tyr Trp Thr Gly Leu Leu Gly Gly Glu Gln Pro Val Leu Glu Leu
    1295                1300                1305

Pro Phe Asp Arg Pro Arg Pro Ala Arg Gln Ser His Arg Gly Ala
    1310                1315                1320

Gln Leu Gly Phe Glu Leu Ser Arg Glu Leu Val Glu Ala Val Arg
    1325                1330                1335

Ala Leu Ala Gln Arg Glu Gly Ala Ser Ser Phe Met Leu Leu Leu
    1340                1345                1350

Ala Ser Phe Gln Ala Leu Leu Tyr Arg Tyr Ser Gly Gln Ala Asp
    1355                1360                1365

Ile Arg Val Gly Val Pro Ile Ala Asn Arg Asn Arg Val Glu Thr
    1370                1375                1380

Glu Arg Leu Ile Gly Phe Phe Val Asn Thr Gln Val Leu Lys Ala
    1385                1390                1395

Asp Leu Asp Gly Arg Met Gly Phe Asp Glu Leu Leu Ala Gln Ala
    1400                1405                1410

Arg Gln Arg Ala Leu Glu Ala Gln Ala His Gln Asp Leu Pro Phe
    1415                1420                1425

Glu Gln Leu Val Glu Ala Leu Gln Pro Glu Arg Asn Ala Ser His
    1430                1435                1440

Asn Pro Leu Phe Gln Val Leu Phe Asn His Gln Ser Glu Ile Arg
    1445                1450                1455

Ser Val Thr Pro Glu Val Gln Leu Glu Asp Leu Arg Leu Glu Gly
    1460                1465                1470

Leu Ala Trp Asp Gly Gln Thr Ala Gln Phe Asp Leu Thr Leu Asp
    1475                1480                1485

Ile Gln Glu Asp Glu Asn Gly Ile Trp Ala Ser Phe Asp Tyr Ala
    1490                1495                1500

Thr Asp Leu Phe Asp Ala Ser Thr Val Glu Arg Leu Ala Gly His
    1505                1510                1515

Trp Arg Asn Leu Leu Arg Gly Ile Val Ala Asn Pro Arg Gln Arg
    1520                1525                1530

Leu Gly Glu Leu Pro Leu Leu Asp Ala Pro Glu Arg Arg Gln Thr
    1535                1540                1545

Leu Ser Glu Trp Asn Pro Ala Gln Arg Glu Cys Ala Val Gln Gly
    1550                1555                1560

Thr Leu Gln Gln Arg Phe Glu Glu Gln Ala Arg Gln Arg Pro Gln
    1565                1570                1575

Ala Val Ala Leu Ile Leu Asp Glu Gln Arg Leu Ser Tyr Gly Glu
    1580                1585                1590

Leu Asn Ala Arg Ala Asn Arg Leu Ala His Cys Leu Ile Ala Arg
    1595                1600                1605

Gly Val Gly Ala Asp Val Pro Val Gly Leu Ala Leu Glu Arg Ser
    1610                1615                1620

Leu Asp Met Leu Val Gly Leu Leu Ala Ile Leu Lys Ala Gly Gly
    1625                1630                1635

Ala Tyr Leu Pro Leu Asp Pro Ala Ala Pro Glu Glu Arg Leu Ala
    1640                1645                1650

His Ile Leu Asp Asp Ser Gly Val Arg Leu Leu Leu Thr Gln Gly
    1655                1660                1665

His Leu Leu Glu Arg Leu Pro Arg Gln Ala Gly Val Glu Val Leu
    1670                1675                1680
```

-continued

```
Ala Ile Asp Gly Leu Val Leu Asp Gly Tyr Ala Glu Ser Asp Pro
1685                1690                1695

Leu Pro Thr Leu Ser Ala Asp Asn Leu Ala Tyr Val Ile Tyr Thr
1700                1705                1710

Ser Gly Ser Thr Gly Lys Pro Lys Gly Thr Leu Leu Thr His Arg
1715                1720                1725

Asn Ala Leu Arg Leu Phe Ser Ala Thr Glu Ala Trp Phe Gly Phe
1730                1735                1740

Asp Glu Arg Asp Val Trp Thr Leu Phe His Ser Tyr Ala Phe Asp
1745                1750                1755

Phe Ser Val Trp Glu Ile Phe Gly Ala Leu Leu Tyr Gly Gly Arg
1760                1765                1770

Leu Val Ile Val Pro Gln Trp Val Ser Arg Ser Pro Glu Asp Phe
1775                1780                1785

Tyr Arg Leu Leu Cys Arg Glu Gly Val Thr Val Leu Asn Gln Thr
1790                1795                1800

Pro Ser Ala Phe Lys Gln Leu Met Ala Val Ala Cys Ser Ala Asp
1805                1810                1815

Met Ala Thr Gln Gln Pro Ala Leu Arg Tyr Val Ile Phe Gly Gly
1820                1825                1830

Glu Ala Leu Asp Leu Gln Ser Leu Arg Pro Trp Phe Gln Arg Phe
1835                1840                1845

Gly Asp Arg Gln Pro Gln Leu Val Asn Met Tyr Gly Ile Thr Glu
1850                1855                1860

Thr Thr Val His Val Thr Tyr Arg Pro Val Ser Glu Ala Asp Leu
1865                1870                1875

Lys Gly Gly Leu Val Ser Pro Ile Gly Gly Thr Ile Pro Asp Leu
1880                1885                1890

Ser Trp Tyr Ile Leu Asp Arg Asp Leu Asn Pro Val Pro Arg Gly
1895                1900                1905

Ala Val Gly Glu Leu Tyr Ile Gly Arg Ala Gly Leu Ala Arg Gly
1910                1915                1920

Tyr Leu Arg Arg Pro Gly Leu Ser Ala Thr Arg Phe Val Pro Asn
1925                1930                1935

Pro Phe Pro Gly Gly Ala Gly Glu Arg Leu Tyr Arg Thr Gly Asp
1940                1945                1950

Leu Ala Arg Phe Gln Ala Asp Gly Asn Ile Glu Tyr Ile Gly Arg
1955                1960                1965

Ile Asp His Gln Val Lys Val Arg Gly Phe Arg Ile Glu Leu Gly
1970                1975                1980

Glu Ile Glu Ala Ala Leu Ala Gly Leu Ala Gly Val Arg Asp Ala
1985                1990                1995

Val Val Leu Ala His Asp Gly Val Gly Gly Thr Gln Leu Val Gly
2000                2005                2010

Tyr Val Val Ala Asp Ser Ala Glu Asp Ala Glu Arg Leu Arg Glu
2015                2020                2025

Ser Leu Arg Glu Ser Leu Lys Arg His Leu Pro Asp Tyr Met Val
2030                2035                2040

Pro Ala His Leu Met Leu Leu Glu Arg Met Pro Leu Thr Val Asn
2045                2050                2055

Gly Lys Leu Asp Arg Gln Ala Leu Pro Gln Pro Asp Ala Ser Leu
2060                2065                2070

Ser Gln Gln Ala Tyr Arg Ala Pro Gly Ser Glu Leu Glu Gln Arg
```

-continued

```
              2075                2080                2085
Ile Ala  Ala Ile Trp Ala Glu  Ile Leu Gly Val Glu  Arg Val Gly
    2090                2095                2100

Leu Asp  Asp Asn Phe Phe Glu  Leu Gly Gly His Ser  Leu Leu Leu
    2105                2110                2115

Leu Met  Leu Lys Glu Arg Ile  Gly Asp Thr Cys Gln  Ala Thr Leu
    2120                2125                2130

Ser Ile  Ser Gln Leu Met Thr  His Ala Ser Val Ala  Glu Gln Ala
    2135                2140                2145

Ala Cys  Ile Glu Gly Gln Ala  Arg Glu Ser Leu Leu  Val Pro Leu
    2150                2155                2160

Asn Gly  Arg Arg Glu Gly Ser  Pro Leu Phe Met Phe  His Pro Ser
    2165                2170                2175

Phe Gly  Ser Val His Cys Tyr  Lys Thr Leu Ala Met  Ala Leu Arg
    2180                2185                2190

Asp Arg  His Pro Val Lys Gly  Val Val Cys Arg Ala  Leu Leu Gly
    2195                2200                2205

Ala Gly  Arg Glu Val Pro Glu  Trp Asp Asp Met Val  Ala Glu Tyr
    2210                2215                2220

Ala Glu  Gln Leu Leu Gln Glu  His Pro Glu Gly Val  Phe Asn Leu
    2225                2230                2235

Ala Gly  Trp Ser Leu Gly Gly  Asn Leu Ala Met Asp  Val Ala Ala
    2240                2245                2250

Arg Leu  Glu Gln Arg Gly Arg  Gln Val Ala Phe Val  Gly Trp Ile
    2255                2260                2265

Asp Ala  Pro Ala Pro Val Arg  Val Glu Ala Phe Trp  Asn Glu Ile
    2270                2275                2280

Gly Pro  Thr Pro Glu Ala Val  Pro Asn Leu Ser Val  Gly Glu Met
    2285                2290                2295

Arg Val  Glu Leu Leu Gly Val  Met Phe Pro Glu Arg  Ala Glu His
    2300                2305                2310

Ile Glu  Arg Ala Trp Ser Ser  Ile Cys Ser Ala Thr  Thr Asp Asp
    2315                2320                2325

Glu Gln  Arg Trp Thr Arg Met  Ser Asp Trp Ala Glu  Ala Glu Ile
    2330                2335                2340

Gly Ala  Glu Phe Ala Thr Leu  Arg Ser Glu Ile Ala  Gln Ser Asn
    2345                2350                2355

Glu Leu  Glu Val Ser Trp Glu  Leu Lys Gln Ile Leu  Asp Glu Arg
    2360                2365                2370

Leu Lys  Ala Met Asp Tyr Pro  Arg Leu Thr Ala Lys  Val Ser Leu
    2375                2380                2385

Trp Trp  Ala Ala Arg Ser Thr  Asn Ala Ile Gln Arg  Ser Ala Val
    2390                2395                2400

Glu Arg  Ser Met Ala Glu Ala  Ile Gly Ala Glu Arg  Val Glu Pro
    2405                2410                2415

Val Arg  Val Leu Asp Thr Arg  His Asp Lys Ile Ile  Asp His Pro
    2420                2425                2430

Glu Phe  Val Gln Ser Phe Arg  Ala Ala Leu Glu Arg  Ala Gly Arg
    2435                2440                2445

<210> SEQ ID NO 19
<211> LENGTH: 3132
<212> TYPE: DNA
<213> ORGANISM: Pseudomonas aeruginosa
```

<400> SEQUENCE: 19

```
atgtccgaat tcttcatcaa gcggccgaac ttcgcctggg tggtggccct gttcatctcc      60
ctggccggcc tgctggtcat ttccaaattg ccggtagcgc agtacccaa tgtcgcgccg      120
ccacagatca ccatcaccgc cacctatccc ggcgcctcgg cgaaggtgct ggtggactcc      180
gtcaccagtg tgctcgagga gtcgctgaac ggcgccaagg gcctgctcta cttcgagtcg      240
accaacaact ccaacggcac cgccgagatc gtcgtcacct tcgagccggg caccgatccg      300
gacctggccc aggtggacgt gcagaaccgc ctgaagaaag ccgaggcgcg catgccgcag      360
gcggtgctga cccagggcct gcaggtcgag cagaccagcg ccggtttcct gctgatctat      420
gcgctcagct acaaggaagg cgctcagcgc agcgacacca ccgccctcgg cgactacgcc      480
gcgcgcaata tcaacaacga gctgcggcgc ctgccgggcg tcggcaagct gcaattcttc      540
tcttccgagg cggccatgcg ggtctggatc gatccgcaga agctggtggg cttcggcctc      600
tccatcgacg acgtgagcaa tgccatccgc gggcagaacg tgcaggtgcc ggccggcgcc      660
ttcggcagcg caccgggcag ttccgcgcag gagctgacgg cgaccctggc ggtgaagggc      720
accctggacg atccgcagga gttcggccag gtagtgctgc gcgccaacga ggacggctcg      780
ctggtccggc tcgccgatgt cgcgcgcctg gaactcggca aggagagcta caacatttcc      840
tcgcgactga acggcacgcc caccgtgggc ggggctatcc agctgtcgcc cggggccaac      900
gcgatccaga ccgctaccct ggtgaaacag cgtctcgccg aactgtcggc gttcttcccc      960
gaggacatgc agtacagcgt gccctacgac acctcgcgct cgtcgacgt ggccatcgag      1020
aaggtgatcc acaccctgat cgaagcgatg gtcctggtgt cctggtgat gttcctgttc      1080
ctgcagaacg tccgctacac cctgatcccg tccatcgtgg tgccggtgtg cctgctgggt      1140
acgctgatgg tgatgtacct gctggggttc tcggtgaaca tgatgaccat gttcggcatg      1200
gtcctggcga tcggcatcct ggtggacgac gccatcgtgg tggtggagaa cgtcgagcgg      1260
atcatggcgg aggaggggat tccccggcc gaggccacgg tcaaggcgat gaagcaggta      1320
tccggcgcca tcgtcggcat caccctggtg ctctcggcgg tgttcctgcc gctggctttc      1380
atggccggtt cggtgggggt gatctaccag cagttctcgg tgtcgctggc ggtctcgatc      1440
ctgttctccg gcttcctcgc cctgaccttc accccgcgc tgtgcgccac gctgctcaag      1500
cccattcccg aagggcacca cgagaagcgc ggcttcttcg gcgccttcaa ccgtggcttc      1560
gcccgcgtca ccgagcgcta ttcgctgctc aactcgaagc tggtgcgcg cgccggacgc      1620
ttcatgctgg tgtacgccgg cctggtggcc atgctcggct acttctacct gcgcctgccg      1680
gaagccttcg tgccggcgga agacctcggc tacatggtgg tcgacgtgca actgccgcct      1740
ggcgcttcgc gcgtgcgcac cgatgccacc ggcgaggagc tcgagcgctt cctcaagtcc      1800
cgcgaggcg tggcttcggt gttcctgatc tcgggcttca gcttctccgg ccagggcgac      1860
aatgccgcgc tggccttccc aaccttcaag gactggtccg agcgaggcgc cgagcagtcg      1920
gccgccgccg agatcgccgc gctgaacgag catttcgcgc tgcccgacga tggcacggtc      1980
atggccgtgt cgccgccacc gatcaacggt ctgggtaact ccggcggctt cgcattgcgc      2040
ctgatggacc gtagcggggt cggccgcgaa gcgctgctgc aggctcgcga tactcttctt      2100
ggcgagatcc agaccaaccc gaaattcctt tacgcgatga tggaaggact ggccgaagcg      2160
ccgcaactgc gcctgttgat cgaccggag aaggcccgtg ccctgggggt gagcttcgag      2220
accatcagcg gcacgctgtc cgctgccttc ggctcggagg tgatcaacga cttcaccaat      2280
```

-continued

```
gcggggcgcc aacagcgggt ggtgatccag gccgaacagg gcaaccggat gaccccggaa    2340
agcgtgctcg agctatacgt gcctaacgct gctggcaacc tggtaccgct cagcgccttc    2400
gtcagcgtga atgggaaga gggaccggtg caattggtgc gctataacgg ctacccgtcg    2460
atccgcatcg tcggtgacgc cgcgcccggc ttcagtaccg cgaagccat ggcggaaatg    2520 gagcgcctgg cctcgcagct gccggccggc atcggctacg agtggaccgg cctgtcctat    2580
caggagaagg tctccgccgg gcaggccacc agcctgttcg ccctcgccat cctggtggtg    2640
ttcctgttgc tggtggcgct ctacgagagc tggtcgatcc cgctgtcggt gatgctgatc    2700
gtgccgatcg cgccatcgg cgcggtgctc cggtgatgg tcagcggtat gtccaacgac    2760
gtgtatttca aggtcggcct gatcaccatc atcggtcttt cggcgaagaa cgcgatcctc    2820
atcgtcgagt tcgccaagga actctgggag caggggcata gctgcgcga cgccgccatc    2880 gaggccgcgc gcctgcgctt ccggccgatc atcatgactt ccatggcgtt catcctcggc    2940 gtgataccc tggccctggc cagcggtgcc ggcgcggcga ccagcgtgc catcggcacc    3000 ggagtgatcg gcgggatgct cagcgccacc ttcctcggcg tgctgttcgt acctatctgt    3060
ttcgtctggc tgctgtcgct gctgcgcagc aagccggcac ccatcgaaca ggccgcttcg    3120
gccggggagt ga                                                       3132
```

```
<210> SEQ ID NO 20
<211> LENGTH: 1043
<212> TYPE: PRT
<213> ORGANISM: Pseudomonas aeruginosa

<400> SEQUENCE: 20
```

```
Met Ser Glu Phe Phe Ile Lys Arg Pro Asn Phe Ala Trp Val Val Ala
1               5                   10                  15

Leu Phe Ile Ser Leu Ala Gly Leu Leu Val Ile Ser Lys Leu Pro Val
            20                  25                  30

Ala Gln Tyr Pro Asn Val Ala Pro Gln Ile Thr Ile Thr Ala Thr
        35                  40                  45

Tyr Pro Gly Ala Ser Ala Lys Val Leu Val Asp Ser Val Thr Ser Val
    50                  55                  60

Leu Glu Glu Ser Leu Asn Gly Ala Lys Gly Leu Leu Tyr Phe Glu Ser
65                  70                  75                  80

Thr Asn Asn Ser Asn Gly Thr Ala Glu Ile Val Thr Phe Glu Pro
                85                  90                  95

Gly Thr Asp Pro Asp Leu Ala Gln Val Asp Val Gln Asn Arg Leu Lys
            100                 105                 110

Lys Ala Glu Ala Arg Met Pro Gln Ala Val Leu Thr Gln Gly Leu Gln
        115                 120                 125

Val Glu Gln Thr Ser Ala Gly Phe Leu Leu Ile Tyr Ala Leu Ser Tyr
    130                 135                 140

Lys Glu Gly Ala Gln Arg Ser Asp Thr Thr Ala Leu Gly Asp Tyr Ala
145                 150                 155                 160

Ala Arg Asn Ile Asn Asn Glu Leu Arg Arg Leu Pro Gly Val Gly Lys
                165                 170                 175

Leu Gln Phe Phe Ser Ser Glu Ala Ala Met Arg Val Trp Ile Asp Pro
            180                 185                 190

Gln Lys Leu Val Gly Phe Gly Leu Ser Ile Asp Asp Val Ser Asn Ala
        195                 200                 205

Ile Arg Gly Gln Asn Val Gln Val Pro Ala Gly Ala Phe Gly Ser Ala
    210                 215                 220
```

```
Pro Gly Ser Ser Ala Gln Glu Leu Thr Ala Thr Leu Ala Val Lys Gly
225                 230                 235                 240

Thr Leu Asp Asp Pro Gln Glu Phe Gly Gln Val Val Leu Arg Ala Asn
            245                 250                 255

Glu Asp Gly Ser Leu Val Arg Leu Ala Asp Val Ala Arg Leu Glu Leu
                260                 265                 270

Gly Lys Glu Ser Tyr Asn Ile Ser Ser Arg Leu Asn Gly Thr Pro Thr
            275                 280                 285

Val Gly Gly Ala Ile Gln Leu Ser Pro Gly Ala Asn Ala Ile Gln Thr
    290                 295                 300

Ala Thr Leu Val Lys Gln Arg Leu Ala Glu Leu Ser Ala Phe Phe Pro
305                 310                 315                 320

Glu Asp Met Gln Tyr Ser Val Pro Tyr Asp Thr Ser Arg Phe Val Asp
                325                 330                 335

Val Ala Ile Glu Lys Val Ile His Thr Leu Ile Glu Ala Met Val Leu
                340                 345                 350

Val Phe Leu Val Met Phe Leu Phe Leu Gln Asn Val Arg Tyr Thr Leu
            355                 360                 365

Ile Pro Ser Ile Val Val Pro Val Cys Leu Leu Gly Thr Leu Met Val
370                 375                 380

Met Tyr Leu Leu Gly Phe Ser Val Asn Met Met Thr Met Phe Gly Met
385                 390                 395                 400

Val Leu Ala Ile Gly Ile Leu Val Asp Asp Ala Ile Val Val Val Glu
            405                 410                 415

Asn Val Glu Arg Ile Met Ala Glu Glu Gly Ile Ser Pro Ala Glu Ala
            420                 425                 430

Thr Val Lys Ala Met Lys Gln Val Ser Gly Ala Ile Val Gly Ile Thr
            435                 440                 445

Leu Val Leu Ser Ala Val Phe Leu Pro Leu Ala Phe Met Ala Gly Ser
450                 455                 460

Val Gly Val Ile Tyr Gln Gln Phe Ser Val Ser Leu Ala Val Ser Ile
465                 470                 475                 480

Leu Phe Ser Gly Phe Leu Ala Leu Thr Phe Thr Pro Ala Leu Cys Ala
            485                 490                 495

Thr Leu Leu Lys Pro Ile Pro Glu Gly His His Glu Lys Arg Gly Phe
            500                 505                 510

Phe Gly Ala Phe Asn Arg Gly Phe Ala Arg Val Thr Glu Arg Tyr Ser
            515                 520                 525

Leu Leu Asn Ser Lys Leu Val Ala Arg Ala Gly Arg Phe Met Leu Val
            530                 535                 540

Tyr Ala Gly Leu Val Ala Met Leu Gly Tyr Phe Tyr Leu Arg Leu Pro
545                 550                 555                 560

Glu Ala Phe Val Pro Ala Glu Asp Leu Gly Tyr Met Val Val Asp Val
                565                 570                 575

Gln Leu Pro Pro Gly Ala Ser Arg Val Arg Thr Asp Ala Thr Gly Glu
            580                 585                 590

Glu Leu Glu Arg Phe Leu Lys Ser Arg Glu Ala Val Ala Ser Val Phe
            595                 600                 605

Leu Ile Ser Gly Phe Ser Phe Ser Gly Gln Gly Asp Asn Ala Ala Leu
610                 615                 620

Ala Phe Pro Thr Phe Lys Asp Trp Ser Glu Arg Gly Ala Glu Gln Ser
625                 630                 635                 640
```

-continued

```
Ala Ala Ala Glu Ile Ala Ala Leu Asn Glu His Phe Ala Leu Pro Asp
            645                 650                 655

Asp Gly Thr Val Met Ala Val Ser Pro Pro Ile Asn Gly Leu Gly
            660                 665                 670

Asn Ser Gly Gly Phe Ala Leu Arg Leu Met Asp Arg Ser Gly Val Gly
            675                 680                 685

Arg Glu Ala Leu Leu Gln Ala Arg Asp Thr Leu Leu Gly Glu Ile Gln
        690                 695                 700

Thr Asn Pro Lys Phe Leu Tyr Ala Met Met Glu Gly Leu Ala Glu Ala
705                 710                 715                 720

Pro Gln Leu Arg Leu Leu Ile Asp Arg Glu Lys Ala Arg Ala Leu Gly
                725                 730                 735

Val Ser Phe Glu Thr Ile Ser Gly Thr Leu Ser Ala Ala Phe Gly Ser
            740                 745                 750

Glu Val Ile Asn Asp Phe Thr Asn Ala Gly Arg Gln Gln Arg Val Val
            755                 760                 765

Ile Gln Ala Glu Gln Gly Asn Arg Met Thr Pro Glu Ser Val Leu Glu
770                 775                 780

Leu Tyr Val Pro Asn Ala Ala Gly Asn Leu Val Pro Leu Ser Ala Phe
785                 790                 795                 800

Val Ser Val Lys Trp Glu Gly Pro Val Gln Leu Val Arg Tyr Asn
                805                 810                 815

Gly Tyr Pro Ser Ile Arg Ile Val Gly Asp Ala Ala Pro Gly Phe Ser
                820                 825                 830

Thr Gly Glu Ala Met Ala Glu Met Glu Arg Leu Ala Ser Gln Leu Pro
            835                 840                 845

Ala Gly Ile Gly Tyr Glu Trp Thr Gly Leu Ser Tyr Gln Glu Lys Val
            850                 855                 860

Ser Ala Gly Gln Ala Thr Ser Leu Phe Ala Leu Ala Ile Leu Val Val
865                 870                 875                 880

Phe Leu Leu Leu Val Ala Leu Tyr Glu Ser Trp Ser Ile Pro Leu Ser
                885                 890                 895

Val Met Leu Ile Val Pro Ile Gly Ala Ile Gly Ala Val Leu Ala Val
                900                 905                 910

Met Val Ser Gly Met Ser Asn Asp Val Tyr Phe Lys Val Gly Leu Ile
            915                 920                 925

Thr Ile Ile Gly Leu Ser Ala Lys Asn Ala Ile Leu Ile Val Glu Phe
930                 935                 940

Ala Lys Glu Leu Trp Glu Gln Gly His Ser Leu Arg Asp Ala Ala Ile
945                 950                 955                 960

Glu Ala Ala Arg Leu Arg Phe Arg Pro Ile Ile Met Thr Ser Met Ala
                965                 970                 975

Phe Ile Leu Gly Val Ile Pro Leu Ala Leu Ala Ser Gly Ala Gly Ala
                980                 985                 990

Ala Ser Gln Arg Ala Ile Gly Thr Gly Val Ile Gly Gly Met Leu Ser
            995                 1000                 1005

Ala Thr Phe Leu Gly Val Leu Phe Val Pro Ile Cys Phe Val Trp
            1010                1015                1020

Leu Leu Ser Leu Leu Arg Ser Lys Pro Ala Pro Ile Glu Gln Ala
            1025                1030                1035

Ala Ser Ala Gly Glu
            1040
```

-continued

<210> SEQ ID NO 21
<211> LENGTH: 642
<212> TYPE: DNA
<213> ORGANISM: Pseudomonas aeruginosa

<400> SEQUENCE: 21

```
atgaacgatg cttctccccg tctgaccgaa cgcggcaggc aacgccgccg cgccatgctc    60
gacgccgcta cccaggcctt tctcgaacac ggtttcgaag caccaccct ggacatggtg    120
atagaacggg ccggtggttc acgggggacc ctgtacagct ccttcggcgg caaggagggc    180
ctgttcgccg cggtgatcgc ccacatgatc ggggaaatct tcgacgacag cgccgatcag    240
ccgcgccccg ccgccacgct gagcgccacc ctcgagcatt tcggccggcg ctttctcacc    300
agcctgctcg atcccgctg ccagagcctc tatcgcctgg tggtggcgga atccccgcgg    360
tttccggcga tcggcaagtc cttctacgag caggggccgc agcagagcta tctgctgctc    420
agcgagcgac tggccgcggt cgctcctcac atggacgagg aaacgctcta cgcggtggcc    480
tgccagtttc tcgagatgct caaggccgac ctgttcctca aggccctcag cgtggccgac    540
ttccagccga ccatggcgct gctggaaacc cgcctcaagc tgtcggtgga catcatcgcc    600
tgctacctgg aacacctgtc gcagagcccc gcgcagggct ga                      642
```

<210> SEQ ID NO 22
<211> LENGTH: 213
<212> TYPE: PRT
<213> ORGANISM: Pseudomonas aeruginosa

<400> SEQUENCE: 22

```
Met Asn Asp Ala Ser Pro Arg Leu Thr Glu Arg Gly Arg Gln Arg Arg
1               5                   10                  15

Arg Ala Met Leu Asp Ala Ala Thr Gln Ala Phe Leu Glu His Gly Phe
            20                  25                  30

Glu Gly Thr Thr Leu Asp Met Val Ile Glu Arg Ala Gly Gly Ser Arg
        35                  40                  45

Gly Thr Leu Tyr Ser Ser Phe Gly Gly Lys Glu Gly Leu Phe Ala Ala
    50                  55                  60

Val Ile Ala His Met Ile Gly Glu Ile Phe Asp Asp Ser Ala Asp Gln
65                  70                  75                  80

Pro Arg Pro Ala Ala Thr Leu Ser Ala Thr Leu Glu His Phe Gly Arg
                85                  90                  95

Arg Phe Leu Thr Ser Leu Leu Asp Pro Arg Cys Gln Ser Leu Tyr Arg
            100                 105                 110

Leu Val Val Ala Glu Ser Pro Arg Phe Pro Ala Ile Gly Lys Ser Phe
        115                 120                 125

Tyr Glu Gln Gly Pro Gln Gln Ser Tyr Leu Leu Ser Glu Arg Leu
    130                 135                 140

Ala Ala Val Ala Pro His Met Asp Glu Glu Thr Leu Tyr Ala Val Ala
145                 150                 155                 160

Cys Gln Phe Leu Glu Met Leu Lys Ala Asp Leu Phe Leu Lys Ala Leu
                165                 170                 175

Ser Val Ala Asp Phe Gln Pro Thr Met Ala Leu Leu Glu Thr Arg Leu
            180                 185                 190

Lys Leu Ser Val Asp Ile Ile Ala Cys Tyr Leu Glu His Leu Ser Gln
        195                 200                 205

Ser Pro Ala Gln Gly
    210
```

<210> SEQ ID NO 23
<211> LENGTH: 1017
<212> TYPE: DNA
<213> ORGANISM: Pseudomonas aeruginosa

<400> SEQUENCE: 23

```
atgtctgatg atgcccgttt ccagcagctg aattgctggt tggactcttg tttgcccgag      60
ttgttcgttg ccgaaggttg gggggaagtg ccccccgccg aactgatccc ggccagtagc     120
gacgccagct tccgtcgtta tttccgctgg cagggagggg accgcagcct ggtggtgatg     180
gacgcgccgc cgcccagga agactgccga ccgttcgtca aggtcgccgg actgctcgcc     240
ggagccggcg tgcatgtgcc gaggattctc gcccaggacc tggagaacgg tttcctgctg     300
ctcagtgacc tgggccggca gacctacctc gacgtgcttc atcccgggaa tgccgacgag     360
ctgttcgaac cggccctgga tgcgctgatc gccttccaga aggtcgatgt cgccggtgtc     420
ctgcctgcct acgacgaagc ggtgctgcgc gcgagctgc agctgttccc cgactggtac      480
ctggcccgcc acctcggcgt ggagctggag ggcgagacgc tggcccgctg gaaacggatc     540
tgcgacctgc tggtacgcag cgcgctggag caaccgcggg tgttcgtcca tcgcgactat     600
atgccgcgca atctgatgct cagcgagccc aacccgggcg tcctcgactt ccaggacgcc     660
ctgcacggcc cggtcaccta cgatgtcacc tgcctgtaca aggacgcctt cgtcagttgg     720
ccggagccgc gcgtgcatgc cgcgctgaac cgttactgga gaaggcgac ctgggccggc      780
atcccgctgc cgccaagctt cgaagacttc ctccgtgcca cgacctgat gggcgtgcag     840
cgccacctga aggtgattgg catcttcgcc cgtatctgtc accgcgacgg caagccgcgc     900
tacctgggtg acgtgccgcg cttcttccgt tatctggaaa ccgccgtggc gcgccgtccc     960
gagctggccg aactgggcga gctgctggcc tcgctgccgc agggagccga ggcatga      1017
```

<210> SEQ ID NO 24
<211> LENGTH: 338
<212> TYPE: PRT
<213> ORGANISM: Pseudomonas aeruginosa

<400> SEQUENCE: 24

Met Ser Asp Asp Ala Arg Phe Gln Gln Leu Asn Cys Trp Leu Asp Ser
1               5                   10                  15

Cys Leu Pro Glu Leu Phe Val Ala Glu Gly Trp Gly Glu Val Pro Pro
            20                  25                  30

Ala Glu Leu Ile Pro Ala Ser Ser Asp Ala Ser Phe Arg Arg Tyr Phe
        35                  40                  45

Arg Trp Gln Gly Gly Asp Arg Ser Leu Val Val Met Asp Ala Pro Pro
    50                  55                  60

Pro Gln Glu Asp Cys Arg Pro Phe Val Lys Val Ala Gly Leu Leu Ala
65                  70                  75                  80

Gly Ala Gly Val His Val Pro Arg Ile Leu Ala Gln Asp Leu Glu Asn
                85                  90                  95

Gly Phe Leu Leu Leu Ser Asp Leu Gly Arg Gln Thr Tyr Leu Asp Val
            100                 105                 110

Leu His Pro Gly Asn Ala Asp Glu Leu Phe Glu Pro Ala Leu Asp Ala
        115                 120                 125

Leu Ile Ala Phe Gln Lys Val Asp Val Ala Gly Val Leu Pro Ala Tyr
    130                 135                 140

Asp Glu Ala Val Leu Arg Arg Glu Leu Gln Leu Phe Pro Asp Trp Tyr
145                 150                 155                 160

```
Leu Ala Arg His Leu Gly Val Glu Leu Glu Gly Glu Thr Leu Ala Arg
                165                 170                 175
Trp Lys Arg Ile Cys Asp Leu Leu Val Arg Ser Ala Leu Glu Gln Pro
            180                 185                 190
Arg Val Phe Val His Arg Asp Tyr Met Pro Arg Asn Leu Met Leu Ser
        195                 200                 205
Glu Pro Asn Pro Gly Val Leu Asp Phe Gln Asp Ala Leu His Gly Pro
    210                 215                 220
Val Thr Tyr Asp Val Thr Cys Leu Tyr Lys Asp Ala Phe Val Ser Trp
225                 230                 235                 240
Pro Glu Pro Arg Val His Ala Ala Leu Asn Arg Tyr Trp Lys Lys Ala
                245                 250                 255
Thr Trp Ala Gly Ile Pro Leu Pro Pro Ser Phe Glu Asp Phe Leu Arg
            260                 265                 270
Ala Ser Asp Leu Met Gly Val Gln Arg His Leu Lys Val Ile Gly Ile
        275                 280                 285
Phe Ala Arg Ile Cys His Arg Asp Gly Lys Pro Arg Tyr Leu Gly Asp
    290                 295                 300
Val Pro Arg Phe Phe Arg Tyr Leu Glu Thr Ala Val Ala Arg Arg Pro
305                 310                 315                 320
Glu Leu Ala Glu Leu Gly Glu Leu Leu Ala Ser Leu Pro Gln Gly Ala
                325                 330                 335
Glu Ala
```

<210> SEQ ID NO 25
<211> LENGTH: 3270
<212> TYPE: DNA
<213> ORGANISM: Pseudomonas aeruginosa

<400> SEQUENCE: 25

```
atgagcggat tccaggacca gagtatcgac gaaggcgtgc gcaagcgcac cgcctaccag      60
aacgatcggc gtgcacgact ggcattgaac gtcgagcgac aggacggcgg tatcctgcag     120
attccggtgg ccagcgatat gctcggccat gaggagcacg agcgtatcca gcagaacacc     180
ttcctggctg tgatgccgct ggtccgcctg ccaacgctgg gcaaggccgg ttatggcgac     240
cagctgcccg ccggcgcgct accgcgggcg ggacggatct acctgttcca ggacggcaag     300
ttgtggcgcg aactggaatg tgatggcaag ggcaacctgt cgaagtcga tctcctgcag      360
gggcgcagcc agcgtgcgga caagcgtccg gccttaggca agacacaagc gctgatcctg     420
gtgccggtgc tggtcaaggg gcagttcgtg atcccacgct acaccatggc ctatagcgaa     480
actccctggc cttggtcgta catcgactgg ctggaggagg accgcagcg gtcaaccgg       540
cgctgccagc agatggcgtc cgcttggaac gcctcggtgg ccaaccagca ctggaaagcc     600
tccatccatc aacccgcgct ggtcattgat catcacgccc agggtttgcg acctcgcgac     660
ttcaacgtcg agagcgcgct ggaagacccg gcggaattca cacctgagtt cgccgccttt     720
cgcgaagagt cgctggtgtg ccagttgcag cgacgccagc aggaattggc gccctgctg      780
aagcaggctc cgccctctgc gctacctact ctggaagccg agaggacgt actggaaacc      840
ctcaagctgc gtggccatcc aacctcatc gggctgatgc tcgacgactc gctgttcgcc      900
ttgcgccacg ctgcggcgca ggcgcgccac tgcgccgcct acttgcgcag cctcaatgca     960
ctgctgccgc accgtcccaa cggacgctat gcacaggtgc tgagcaacat gctcgacggc    1020
ccgctcgcca agctcagggg cgaggtcgat caggccgaac tggacgaggc gatcttcgcc    1080
```

-continued

```
gaggagcgac agtcttgccg aatccacctg acgcagcagg tcgagcatct ggttgccctg    1140
ctggaaggcc ccttgcaccc ggtgttgcag gactggaccc accagtgcga cgaagccctg    1200
ctggagccct acagcctgat gagcgaggca ctggctgcgc tgaaccagct tcccgaccgc    1260
tgcgacgcac tgtacagcgg taccgcctac cgggcgctgg cggcacatgt cgagcgggtg    1320
gtcagcacgg ttctgcaggc aagccacccg cttggcgcca tgctcctggc caaggacgaa    1380
ggacaacttc ccgagccggt tcggcgcctg caggcgctgc gcgatagccc gcggacgccg    1440
gaccccgatg caatgggcct cagcacgctg atgctgggag ccagtctgct gggcgaggtc    1500
gaccagccca gcgccggcaa gagcctcgcc tacttcctcg gcgacctgct ggacgtgttc    1560
ggcgccagcg tagtcgagca actcggccgg ctgtcccagg cgccacccca gatccagctc    1620
gaccgcttgt tcgcaccgac cttcaatact ctgagcgccc tctcggtgaa gatgaaaggt    1680
atccgcctgc tgcccgacag tcaggtgccg ctcgacatgg ttgtcgtcgg cgtgcgcgga    1740
gccggcctgc gcaacggtct gaccgaggtc gagcgccagg agctgaggcg caagagctat    1800
cggcgcgcca tcgttcagga cggtgccggc aatcccctgg ccggcaccag tccccgcgac    1860
accggcatga gtcgcgccaa cctgcgcaac gtcatggtgg tggcggtacc caaggatcac    1920
ccggacctgc ttgcctacac gaaattccgt acgcagttag gcacgttgac ccaggtgatg    1980
gagaacactc gcatcgtgcc gacgatgatg ctggggtttg cgatttataa cttgaatgtg    2040
caggtgcagg catacagtgg cttgtagac agtggagaaa agcacagagg acgatcggg    2100 gctgtcggtg cagtaatcga tttaacagcc gctggaggaa gccatgcaaa gctgcttttc    2160
ggaccatcta ctgcaaagta tctagaaacc ccacgtatat cggtagccca aatatcccct    2220
cgatgggcca ggaatctaga agttcaaaca ggcagcccta agttagggtt gctacgtggg    2280
cttggtggcg cagccacact attcggtgca ggcatcagtg tatgggatgg ctaccgagct    2340
ttgaggcagg agatagcga tgcggctgcg gcctacggtg tggccgcagt gggtgggggc    2400 cttttggggtg cctacgtcct aggatggata gtaaacccct atgctttgct ggctggtgcg    2460
gttttggcga tcggaggcac tgtggtcgct aatctactga ctgacagcga tgcggaaacc    2520
atcgtaaaga aaggcccctt cggccggcaa ttcgccgagg ctggcctgct cgattcgctg    2580
atgggccagg accagcgctt cgcccatctg aaagacccgc aaacggccta tcgccaattg    2640 ctggagtcc tcggccatcc gcgggtcttt gtccatcgcc tggaagactg cgcaaattg    2700 gcgccggcgc cgcatcgatc tgtcttgcag gaagcggaac ggggtcgcca agcggtcagc    2760
cgcactgcgc tatcctgcat cgaccccaag ttgcaggcgc tggaggcaaa cgattgggcc    2820
gtggtgctga gttccccgct cctggccatg ttcgagaatg gccagaaggc gttccgcctg    2880
gtggcccagg agtttctcag cagcttgccg atcgatccgg gcaccctgtt cggcgtcaag    2940
cgctaccatc gggtccccgc ggggccccgcc aagctcgaag ccttgccgtt ggatgctgcc    3000
agcgtgctct atgtgctgcc ggccagcctg ccgattccgc agttgtctcc tcgggcccgc    3060
tatagcatgc gcatgaccca gggtttgaag atcagcgcac agttcgaact caatgccgac    3120
cagcctgagc agcggcttgt cctgcctcaa cccagcccga gagttggag tgcattcaca    3180 tccgccaatc ggtaccttcc cccggacgac ttgggccccc atgctgcgcc accttattgg    3240
ttgatagaga acagtgagtt caacgtatga                                    3270
```

<210> SEQ ID NO 26
<211> LENGTH: 1089
<212> TYPE: PRT

<213> ORGANISM: Pseudomonas aeruginosa

<400> SEQUENCE: 26

```
Met Ser Gly Phe Gln Asp Gln Ser Ile Asp Glu Gly Val Arg Lys Arg
1               5                   10                  15

Thr Ala Tyr Gln Asn Asp Arg Arg Ala Arg Leu Ala Leu Asn Val Glu
            20                  25                  30

Arg Gln Asp Gly Gly Ile Leu Gln Ile Pro Val Ala Ser Asp Met Leu
        35                  40                  45

Gly His Glu Glu His Glu Arg Ile Gln Gln Asn Thr Phe Leu Ala Val
    50                  55                  60

Met Pro Leu Val Arg Leu Pro Thr Leu Gly Lys Ala Gly Tyr Gly Asp
65                  70                  75                  80

Gln Leu Pro Ala Gly Ala Leu Pro Arg Ala Gly Arg Ile Tyr Leu Phe
                85                  90                  95

Gln Asp Gly Lys Leu Trp Arg Glu Leu Glu Cys Asp Gly Lys Gly Asn
            100                 105                 110

Leu Phe Glu Val Asp Leu Leu Gln Gly Arg Ser Gln Arg Ala Asp Lys
        115                 120                 125

Arg Pro Ala Leu Gly Lys Thr Gln Ala Leu Ile Leu Val Pro Val Leu
    130                 135                 140

Val Lys Gly Gln Phe Val Ile Pro Arg Tyr Thr Met Ala Tyr Ser Glu
145                 150                 155                 160

Thr Pro Trp Pro Trp Ser Tyr Ile Asp Trp Leu Glu Glu Asp Pro Gln
                165                 170                 175

Arg Val Asn Arg Arg Cys Gln Gln Met Ala Ser Ala Trp Asn Ala Ser
            180                 185                 190

Val Ala Asn Gln His Trp Lys Ala Ser Ile His Gln Pro Ala Leu Val
        195                 200                 205

Ile Asp His His Ala Gln Gly Leu Arg Pro Arg Asp Phe Asn Val Glu
    210                 215                 220

Ser Ala Leu Glu Asp Pro Ala Glu Phe Thr Pro Glu Phe Ala Ala Phe
225                 230                 235                 240

Arg Glu Glu Ser Leu Val Cys Gln Leu Gln Arg Arg Gln Gln Glu Leu
                245                 250                 255

Ala Pro Leu Leu Lys Gln Ala Pro Pro Ser Ala Leu Pro Thr Leu Glu
            260                 265                 270

Ala Gly Glu Asp Val Leu Glu Thr Leu Lys Leu Arg Gly His Pro Asn
        275                 280                 285

Leu Ile Gly Leu Met Leu Asp Asp Ser Leu Phe Ala Leu Arg His Ala
    290                 295                 300

Ala Ala Gln Ala Arg His Cys Ala Ala Tyr Leu Arg Ser Leu Asn Ala
305                 310                 315                 320

Leu Leu Pro His Arg Pro Asn Gly Arg Tyr Ala Gln Val Leu Ser Asn
                325                 330                 335

Met Leu Asp Gly Pro Leu Ala Lys Leu Arg Gly Glu Val Asp Gln Ala
            340                 345                 350

Glu Leu Asp Glu Ala Ile Phe Ala Glu Glu Arg Gln Ser Cys Arg Ile
        355                 360                 365

His Leu Thr Gln Gln Val Glu His Leu Val Ala Leu Leu Glu Gly Pro
    370                 375                 380

Leu His Pro Val Leu Gln Asp Trp Thr His Gln Cys Asp Glu Ala Leu
385                 390                 395                 400
```

-continued

```
Leu Glu Pro Tyr Ser Leu Met Ser Glu Ala Leu Ala Ala Leu Asn Gln
                405                 410                 415

Leu Pro Asp Arg Cys Asp Ala Leu Tyr Ser Gly Thr Ala Tyr Arg Ala
            420                 425                 430

Leu Ala Ala His Val Glu Arg Val Val Ser Thr Val Leu Gln Ala Ser
        435                 440                 445

His Pro Leu Gly Ala Met Leu Leu Ala Lys Asp Glu Gly Gln Leu Pro
    450                 455                 460

Glu Pro Val Arg Arg Leu Gln Ala Leu Arg Asp Ser Pro Arg Thr Pro
465                 470                 475                 480

Asp Pro Asp Ala Met Gly Leu Ser Thr Leu Met Leu Gly Ala Ser Leu
                485                 490                 495

Leu Gly Glu Val Asp Gln Pro Ser Ala Gly Lys Ser Leu Ala Tyr Phe
            500                 505                 510

Leu Gly Asp Leu Leu Asp Val Phe Gly Ala Ser Val Val Glu Gln Leu
        515                 520                 525

Gly Arg Leu Ser Gln Gly Ala Thr Gln Ile Gln Leu Asp Arg Leu Phe
    530                 535                 540

Ala Pro Thr Phe Asn Thr Leu Ser Ala Leu Ser Val Lys Met Lys Gly
545                 550                 555                 560

Ile Arg Leu Leu Pro Asp Ser Gln Val Pro Leu Asp Met Val Val Val
                565                 570                 575

Gly Val Arg Gly Ala Gly Leu Arg Asn Gly Leu Thr Glu Val Glu Arg
            580                 585                 590

Gln Glu Leu Arg Arg Lys Ser Tyr Arg Arg Ala Ile Val Gln Asp Gly
        595                 600                 605

Ala Gly Asn Pro Leu Ala Gly Thr Ser Pro Arg Asp Thr Gly Met Ser
    610                 615                 620

Arg Ala Asn Leu Arg Asn Val Met Val Ala Val Pro Lys Asp His
625                 630                 635                 640

Pro Asp Leu Leu Ala Tyr Thr Lys Phe Arg Thr Gln Leu Gly Thr Leu
                645                 650                 655

Thr Gln Val Met Glu Asn Thr Arg Ile Val Pro Thr Met Met Leu Gly
            660                 665                 670

Phe Ala Ile Tyr Asn Leu Asn Val Gln Val Gln Ala Tyr Ser Gly Phe
        675                 680                 685

Val Asp Ser Gly Glu Lys His Arg Gly Thr Ile Gly Ala Val Gly Ala
    690                 695                 700

Val Ile Asp Leu Thr Ala Ala Gly Gly Ser His Ala Lys Leu Leu Phe
705                 710                 715                 720

Gly Pro Ser Thr Ala Lys Tyr Leu Glu Thr Pro Arg Ile Ser Val Ala
                725                 730                 735

Gln Ile Ser Pro Arg Trp Ala Arg Asn Leu Glu Val Gln Thr Gly Ser
            740                 745                 750

Pro Lys Leu Gly Leu Leu Arg Gly Leu Gly Ala Ala Thr Leu Phe
        755                 760                 765

Gly Ala Gly Ile Ser Val Trp Asp Gly Tyr Arg Ala Leu Arg Gln Gly
    770                 775                 780

Asp Ser Asp Ala Ala Ala Tyr Gly Val Ala Ala Val Gly Gly Gly
785                 790                 795                 800

Leu Trp Gly Ala Tyr Val Leu Gly Trp Ile Val Asn Pro Tyr Ala Leu
                805                 810                 815

Leu Ala Gly Ala Val Leu Ala Ile Gly Gly Thr Val Val Ala Asn Leu
```

-continued

```
                  820             825             830
Leu Thr Asp Ser Asp Ala Glu Thr Ile Val Lys Lys Gly Pro Phe Gly
        835                 840                 845
Arg Gln Phe Ala Glu Ala Gly Leu Leu Asp Ser Leu Met Gly Gln Asp
    850                 855                 860
Gln Arg Phe Ala His Leu Lys Asp Pro Gln Thr Ala Tyr Arg Gln Leu
865                 870                 875                 880
Leu Gly Val Leu Gly His Pro Arg Val Phe Val His Arg Leu Glu Asp
                885                 890                 895
Trp Arg Lys Leu Ala Pro Ala Ala His Arg Ser Val Leu Gln Glu Ala
            900                 905                 910
Glu Arg Gly Arg Gln Ala Val Ser Arg Thr Ala Leu Ser Cys Ile Asp
        915                 920                 925
Pro Lys Leu Gln Ala Leu Glu Ala Asn Asp Trp Ala Val Val Leu Ser
    930                 935                 940
Ser Pro Leu Leu Ala Met Phe Glu Asn Gly Gln Lys Ala Phe Arg Leu
945                 950                 955                 960
Val Ala Gln Glu Phe Leu Ser Ser Leu Pro Ile Asp Pro Gly Thr Leu
                965                 970                 975
Phe Gly Val Lys Arg Tyr His Arg Val Pro Ala Gly Pro Ala Lys Leu
            980                 985                 990
Glu Ala Leu Pro Leu Asp Ala Ala  Ser Val Leu Tyr Val  Leu Pro Ala
        995                 1000                1005
Ser Leu  Pro Ile Pro Gln Leu  Ser Pro Arg Ala Arg  Tyr Ser Met
    1010                1015                1020
Arg Met  Thr Gln Gly Leu Lys  Ile Ser Ala Gln Phe  Glu Leu Asn
    1025                1030                1035
Ala Asp  Gln Pro Glu Gln Arg  Leu Val Leu Pro Gln  Pro Ser Pro
    1040                1045                1050
Lys Ser  Trp Ser Ala Phe Thr  Ser Ala Asn Arg Tyr  Leu Pro Pro
    1055                1060                1065
Asp Asp  Leu Gly Pro His Ala  Ala Pro Pro Tyr Trp  Leu Ile Glu
    1070                1075                1080
Asn Ser  Glu Phe Asn Val
    1085
```

<210> SEQ ID NO 27
<211> LENGTH: 756
<212> TYPE: DNA
<213> ORGANISM: Pseudomonas aeruginosa

<400> SEQUENCE: 27

```
atgagcgccg cctgggtccg gccgttccgc ctgacgccga tgccgcgcct gcgcctggcc      60
tgcttccccc atgcaggcgg cagcgccagc ttcttccgta gctggagcga acgcctgccg     120
ccagacatcg acctgcttgc cctgcagtac ccgggtcgcg aggaccgctt caacgaggcg     180
ccggccaccc gcctggagga cctcgccgac ggcgccgccc tcgccctgcg cgatttcgcc     240
gacgcgcccc tggcgctgtt cggccacagt ctcggcgcgg cgctggccta cgaaaccgcc     300
ctgcgcctgg aaagcgccgg cgcgccgctg cgccacctgt tcgtctccgc ccatccggca     360
ccgcaccggg aacgcggcgg cgcgttgcac gcgcggcgac aggcggcgct gctggaggac     420
gtccgccgcc aggtggcgc cagcgagcta ctcgaggacg ccgacctgcg cgcgctgttc     480
ctgccgatcc tgcgcgccga ctaccaggcg atcgagacct accgacgggc gcagcccatc     540
```

```
gccctggcct gcgccctcga cgtcctcctc ggcgagcacg acgaggaagt cagcgccgcc      600
gaggcgcagg cctggagcga cgccagccgg actcccgcca ggctgcggcg ctttcctggc      660
ggccacttct acctgagcga ggggcgcgac gcggtgatcg agcacctgct gcgccgcctc      720
gcacatcccg acgcccttte ccgagaggtt gcatga                               756
```

<210> SEQ ID NO 28
<211> LENGTH: 251
<212> TYPE: PRT
<213> ORGANISM: Pseudomonas aeruginosa

<400> SEQUENCE: 28

```
Met Ser Ala Ala Trp Val Arg Pro Phe Arg Leu Thr Pro Met Pro Arg
1               5                   10                  15

Leu Arg Leu Ala Cys Phe Pro His Ala Gly Gly Ser Ala Ser Phe Phe
            20                  25                  30

Arg Ser Trp Ser Glu Arg Leu Pro Pro Asp Ile Asp Leu Leu Ala Leu
        35                  40                  45

Gln Tyr Pro Gly Arg Glu Asp Arg Phe Asn Glu Ala Pro Ala Thr Arg
    50                  55                  60

Leu Glu Asp Leu Ala Asp Gly Ala Ala Leu Ala Leu Arg Asp Phe Ala
65                  70                  75                  80

Asp Ala Pro Leu Ala Leu Phe Gly His Ser Leu Gly Ala Ala Leu Ala
                85                  90                  95

Tyr Glu Thr Ala Leu Arg Leu Glu Ser Ala Gly Ala Pro Leu Arg His
            100                 105                 110

Leu Phe Val Ser Ala His Pro Ala Pro His Arg Gln Arg Gly Gly Ala
        115                 120                 125

Leu His Arg Gly Asp Glu Ala Ala Leu Leu Glu Asp Val Arg Arg Gln
    130                 135                 140

Gly Gly Ala Ser Glu Leu Leu Glu Asp Ala Asp Leu Arg Ala Leu Phe
145                 150                 155                 160

Leu Pro Ile Leu Arg Ala Asp Tyr Gln Ala Ile Glu Thr Tyr Arg Arg
                165                 170                 175

Ala Gln Pro Ile Ala Leu Ala Cys Ala Leu Asp Val Leu Leu Gly Glu
            180                 185                 190

His Asp Glu Glu Val Ser Ala Ala Glu Ala Gln Ala Trp Ser Asp Ala
        195                 200                 205

Ser Arg Thr Pro Ala Arg Leu Arg Arg Phe Pro Gly Gly His Phe Tyr
    210                 215                 220

Leu Ser Glu Gly Arg Asp Ala Val Ile Glu His Leu Leu Arg Arg Leu
225                 230                 235                 240

Ala His Pro Asp Ala Leu Ser Arg Glu Val Ala
                245                 250
```

<210> SEQ ID NO 29
<211> LENGTH: 4317
<212> TYPE: DNA
<213> ORGANISM: Pseudomonas aeruginosa

<400> SEQUENCE: 29

```
atggatctgc ccccgattc ccgtaccgcc ctgcgcgact ggctgaccga gcagctcgcc       60
gacctgctcg gcgaaccgct tgctgacgtg cgcgccctgg cggacgacga cgacctgctg     120
ggctgcggcc tcgactcgat ccgcctgatg tacctgcagg aacgcctgcg cgcgcgtggc     180
tcgacgctgg acttcgccca gttggcgcag cgccctgcc tggggcctg gctcgacctg      240
```

-continued

```
ctggcctgcg cggaccggct gtccgccccg gcaacggtcg cgctgccgac ggcgcaggat    300
cgcgatcagc cgttcgagct gtcttccgtg cagcaggcct actggctggg acgtggcgcc    360
ggcgaggtgc tgggcaacgt cagctgccat gcctttctgg aattccgcac gcgggatgtc    420
gaccccgcag cgcctggccg cggcggcgag tgcgtgcgtc aacgccaccc gatgttgcgg    480
gcgcgcttcc tcgacggtcg ccagcagatc cttccgacgc cgccgctgtc ctgcttcgac    540
ctgcaggact ggcgcacctt acaggtggac gaggccgagc gcgactggca ggcgctgcgc    600
gactggcgcg cccatgaatg cctggcgtg gagcgcggcc aggtgttcct gctcgggctg     660
gtgcgcatgc cgggcggcga ggatcgcctc tggctgagtc tcgacctgct tgccgccgat    720
gtcgaaagcc tgcgcctgct gctggccgaa ctgggcgttg cctacctggc gccggagcgc    780
ctggcggagc cgccggcgct gcatttcgcc gactacctgg cgcaccgtgc ggcgcaacgc    840
gccgaggccg cggcgcgggc ccgcgactac tggctggaac gcctgccgcg cttgccggac    900
gcgccggccc tgccgttggc ctgcgcgccg gaaagcatcc gccagccgcg cacccggcgc    960
ctggcattcc agctttccgc cggcgagagc cggcgcctgg agcgtcttgc cgcgcagcat   1020
ggcgtgacct tgtccagcgt gttcggctgc gccttcgcgc tggtcctggc gcgctggagc   1080
gaaagcgcgg aatttctcct caacgtgccg ttgttcgatc ggcatgccga cgacccgcgt   1140
atcggcgagg tgatcgccga cttcaccacc ctgttgctgc tggagtgccg gatgcaggcc   1200
ggggtgtcct cgccgaggc ggtgaagagc ttccagcgca acctccacgg agccatcgac    1260
cacgccgcat tccccgccct ggaggtgctc cgcgaggcgc cgcggcaggg ccagccacgc   1320
tcggcgccgg tggtgttcgc cagcaacctg ggcgaggagg gcttcgtccc ggcggccttc   1380
cgcgacgctt tcgcgatctc ccacgacatg ctctcgcaga ccccgcaggt ctggctcgac   1440
caccagctct accgggtggg cgacggtatc ctgctggcct gggatagcgt cgtcggcctg   1500
ttccccgaag gtctgccgga aaccatgttc gaagcctacg tggggctgct ccagcgtctc   1560
tgcgacagcg cctgggggca gcccgccgat ctgccgttgc cctgggcgca gcaggcgcgc   1620
cgggccctgc tcaacggcca gccggcatgc gccacggcgc gcaccctgca tcgcgacttc   1680
ttccttcgcg ccgccgaggc gccggatgcc gacgcgctgc tctatcgcga ccaacgtgtc   1740
acccgcggcg aactggccga gcgtgcgctg cgcatcgccg gcggcctgcg cgaagccggg   1800
gtgcgccctg gcgacgcggt cgaggtcagc ctgccgcgcg gaccgcagca ggtcgcggcg   1860
gtattcggcg tgctcgccgc aggcgcctgc tacgtgccgc tggacatcga ccagccgcc    1920
gcacggcggc gcctgatcga agaggccgcc ggggtatgcc tggcgatcac cgaggaggac   1980
gatccgcagg ccttgccgcc gcgcctggat gtccagcgcc tgctgcgcgg cccggcgctg   2040
gccgcccccg tgccgctggc gccgcaggcg agtgcctatg tgatctacac ctcgggctcc   2100
accgggtgc caagggcgt cgaggtcagc cacgcggcgg cgatcaatac catcgacgcg    2160
ctgctcgacc tgctgcgggt gaacgcatcg gatcgcttgc tggcggtctc cgcgctggac   2220
ttcgatctgt cggtcttcga cctgttcggc ggcctcggcg ccggtgccag cctggtcctg   2280
ccggcccagg aacaggcgcg cgatgccgct gcctgggcgg aggctatcca gcggcatgcg   2340
gtgagcctgt ggaactcggc gccggccttg ctggagatgg ccctcagcct gccggcgagc   2400
caggccgact atcgcagtct gcgggcggtg ctgctgtccg cgactgggt ggccctggac    2460
ctgccggcc gcctgcgccc acgttgtgcc gaaggctgcc gcctgcatgt gctgggtggc    2520
gctaccgaag cgggcatctg gtcgaacctg cagagcgtcg atacggtgcc gccgcactgg   2580
```

```
cgttcgattc cctacggccg gccattgccg ggacaggcct accgggtggt cgacacccac   2640
gggcgcgacg tgccggacct ggtggtcggc gagctgtgga tcggcggcgc cagcctggcc   2700
cgcggctatc gcaacgatcc cgaactcagc gcccggcgtt tcgtccacga tgcccagggc   2760
cgctggtatc gcaccggcga tcgcggtcgc tactggggcg acggtaccct ggaattcctc   2820
ggtcgggtcg accagcaggt gaaagtgcgc ggccagcgca tcgagttggg cgaggtggag   2880
gccgcgctgt gcgcccaggc tggcgtggag agcgcctgcg cggcggtgct cggcggtggc   2940
gtggcgagcc tcggcgcggt gctggtaccg cgcctggcgc acgggccga aggctccatg   3000
gatctaccgg ccgcacagcc cttcgccggc ctggcagagg ccgaggcggt actcacccgg   3060
gaaatcctcg gcgcgctgct ggaggcgccg ctggagctag acgacggttt cgccggcgc   3120
tggctggact ggctagcgga ctccgccgcc agcgcgctgc cgtcgctcga cgaggcgttg   3180
cgccggctcg gctggcaggc cgcggggctg accgcgatgg caacgctct gcgcggcctg   3240
ctcgccggca acaggcgcc ggccgcgctg ctcctcgatc cctggctggc gccgcaggcg   3300
gtggccgcgc gcctgccgga cggccgcgag gccctggcgc gcctgctcga agcgctgccg   3360
acgccggctg ccggcgaacg cctgcgggtg cggtgctgg ataccgcgc cgggctctgg   3420
ctcgaccagg gcatggcctc gctgttgcgc ccagggctgg aactgaccct cttcgaacgc   3480
agccgcgtcc tcctcgacgc cgccgccacc cgcttgccgg aacggatcgt ggtgcaggcg   3540
ctggacgacg gcctgctacc tgccgagcac ctcggtcgct acaccgggt gatcagcttc   3600
gccgcgctgc acgcctacga ggccagccgc gaaggcctgg cgctggcggc ggcgctgctg   3660
cgcccgcagg gccgcctgtt gctggtggac ctgctatgcg agtcgccact ggcgctgctc   3720
ggtgcggcct tgctcgacga ccggccgctg cgcctggcgg agctgccgag cctgttggcc   3780
gatctcgccg ctgcgggact ggcgccgcgt tgcctgtggc gcagcgagcg gatcgccctg   3840
gtcgaggcgc tggcaccggg actcgggctc gacgccgccg cgctccaggc cggcctggag   3900
caacgcctgc cccaggcgat gcggcccgaa cgcctgtggt gcctgccaag cctgccgttg   3960
aacggcaatg gcaaggtcga tcgtcgccgc ctggccgaga gcatgacccg cgcactcggc   4020
gagtgtcgtc acgagccctc ggcggaggag ccgctggaag cccatgagca agcgctggcc   4080
gagtgctggg aagcggttct caaacgcccg gtgcgtcgtc gcgaggcgag cttcttcagc   4140
ctcggcggcg acagcctgct ggcgacccgc ctgctggccg catacgtga gcgtttcggc   4200
gtacgcctgg gcatggccga cttctatcgc cagccgaccc tggccggtct tgcccgccac   4260
ttgcaggtgc agaccgtcga aatcgaggaa acccaactgg aagagggcgt gctatga     4317
```

<210> SEQ ID NO 30
<211> LENGTH: 1438
<212> TYPE: PRT
<213> ORGANISM: Pseudomonas aeruginosa

<400> SEQUENCE: 30

```
Met Asp Leu Pro Pro Asp Ser Arg Thr Ala Leu Arg Asp Trp Leu Thr
 1               5                  10                  15

Glu Gln Leu Ala Asp Leu Leu Gly Glu Pro Leu Ala Asp Val Arg Ala
            20                  25                  30

Leu Ala Asp Asp Asp Leu Leu Gly Cys Gly Leu Asp Ser Ile Arg
        35                  40                  45

Leu Met Tyr Leu Gln Glu Arg Leu Arg Ala Arg Gly Ser Thr Leu Asp
    50                  55                  60

Phe Ala Gln Leu Ala Gln Arg Pro Cys Leu Gly Ala Trp Leu Asp Leu
```

```
                65                  70                  75                  80
Leu Ala Cys Ala Asp Arg Leu Ser Ala Pro Ala Thr Val Ala Leu Pro
                    85                  90                  95
Thr Ala Gln Asp Arg Asp Gln Pro Phe Glu Leu Ser Ser Val Gln Gln
                    100                 105                 110
Ala Tyr Trp Leu Gly Arg Gly Ala Gly Glu Val Leu Gly Asn Val Ser
                    115                 120                 125
Cys His Ala Phe Leu Glu Phe Arg Thr Arg Asp Val Asp Pro Gln Arg
                    130                 135                 140
Leu Ala Ala Ala Ala Glu Cys Val Arg Gln Arg His Pro Met Leu Arg
145                 150                 155                 160
Ala Arg Phe Leu Asp Gly Arg Gln Gln Ile Leu Pro Thr Pro Pro Leu
                    165                 170                 175
Ser Cys Phe Asp Leu Gln Asp Trp Arg Thr Leu Gln Val Asp Glu Ala
                    180                 185                 190
Glu Arg Asp Trp Gln Ala Leu Arg Asp Trp Arg Ala His Glu Cys Leu
                    195                 200                 205
Ala Val Glu Arg Gly Gln Val Phe Leu Leu Gly Leu Val Arg Met Pro
                    210                 215                 220
Gly Gly Glu Asp Arg Leu Trp Leu Ser Leu Asp Leu Leu Ala Ala Asp
225                 230                 235                 240
Val Glu Ser Leu Arg Leu Leu Leu Ala Glu Leu Gly Val Ala Tyr Leu
                    245                 250                 255
Ala Pro Glu Arg Leu Ala Glu Pro Pro Ala Leu His Phe Ala Asp Tyr
                    260                 265                 270
Leu Ala His Arg Ala Ala Gln Arg Ala Glu Ala Ala Arg Ala Arg
                    275                 280                 285
Asp Tyr Trp Leu Glu Arg Leu Pro Arg Leu Pro Asp Ala Pro Ala Leu
                    290                 295                 300
Pro Leu Ala Cys Ala Pro Glu Ser Ile Arg Gln Pro Arg Thr Arg Arg
305                 310                 315                 320
Leu Ala Phe Gln Leu Ser Ala Gly Glu Ser Arg Arg Leu Glu Arg Leu
                    325                 330                 335
Ala Ala Gln His Gly Val Thr Leu Ser Ser Val Phe Gly Cys Ala Phe
                    340                 345                 350
Ala Leu Val Leu Ala Arg Trp Ser Glu Ser Ala Glu Phe Leu Leu Asn
                    355                 360                 365
Val Pro Leu Phe Asp Arg His Ala Asp Asp Pro Arg Ile Gly Glu Val
                    370                 375                 380
Ile Ala Asp Phe Thr Thr Leu Leu Leu Leu Glu Cys Arg Met Gln Ala
385                 390                 395                 400
Gly Val Ser Phe Ala Glu Ala Val Lys Ser Phe Gln Arg Asn Leu His
                    405                 410                 415
Gly Ala Ile Asp His Ala Ala Phe Pro Ala Leu Glu Val Leu Arg Glu
                    420                 425                 430
Ala Arg Arg Gln Gly Gln Pro Arg Ser Ala Pro Val Val Phe Ala Ser
                    435                 440                 445
Asn Leu Gly Glu Glu Gly Phe Val Pro Ala Ala Phe Arg Asp Ala Phe
                    450                 455                 460
Gly Asp Leu His Asp Met Leu Ser Gln Thr Pro Gln Val Trp Leu Asp
465                 470                 475                 480
His Gln Leu Tyr Arg Val Gly Asp Gly Ile Leu Leu Ala Trp Asp Ser
                    485                 490                 495
```

```
Val Val Gly Leu Phe Pro Glu Gly Leu Pro Glu Thr Met Phe Glu Ala
            500                 505                 510
Tyr Val Gly Leu Leu Gln Arg Leu Cys Asp Ser Ala Trp Gly Gln Pro
        515                 520                 525
Ala Asp Leu Pro Leu Pro Trp Ala Gln Gln Ala Arg Arg Ala Leu Leu
    530                 535                 540
Asn Gly Gln Pro Ala Cys Ala Thr Ala Arg Thr Leu His Arg Asp Phe
545                 550                 555                 560
Phe Leu Arg Ala Ala Glu Ala Pro Asp Ala Asp Ala Leu Leu Tyr Arg
                565                 570                 575
Asp Gln Arg Val Thr Arg Gly Glu Leu Ala Glu Arg Ala Leu Arg Ile
            580                 585                 590
Ala Gly Gly Leu Arg Glu Ala Gly Val Arg Pro Gly Asp Ala Val Glu
        595                 600                 605
Val Ser Leu Pro Arg Gly Pro Gln Gln Val Ala Val Phe Gly Val
    610                 615                 620
Leu Ala Ala Gly Ala Cys Tyr Val Pro Leu Asp Ile Asp Gln Pro Pro
625                 630                 635                 640
Ala Arg Arg Arg Leu Ile Glu Glu Ala Gly Val Cys Leu Ala Ile
                645                 650                 655
Thr Glu Glu Asp Asp Pro Gln Ala Leu Pro Pro Arg Leu Asp Val Gln
            660                 665                 670
Arg Leu Leu Arg Gly Pro Ala Leu Ala Pro Val Pro Leu Ala Pro
        675                 680                 685
Gln Ala Ser Ala Tyr Val Ile Tyr Thr Ser Gly Ser Thr Gly Val Pro
    690                 695                 700
Lys Gly Val Glu Val Ser His Ala Ala Ala Ile Asn Thr Ile Asp Ala
705                 710                 715                 720
Leu Leu Asp Leu Leu Arg Val Asn Ala Ser Asp Arg Leu Leu Ala Val
                725                 730                 735
Ser Ala Leu Asp Phe Asp Leu Ser Val Phe Asp Leu Phe Gly Gly Leu
            740                 745                 750
Gly Ala Gly Ala Ser Leu Val Leu Pro Ala Gln Glu Gln Ala Arg Asp
        755                 760                 765
Ala Ala Ala Trp Ala Glu Ala Ile Gln Arg His Ala Val Ser Leu Trp
    770                 775                 780
Asn Ser Ala Pro Ala Leu Leu Glu Met Ala Leu Ser Leu Pro Ala Ser
785                 790                 795                 800
Gln Ala Asp Tyr Arg Ser Leu Arg Ala Val Leu Leu Ser Gly Asp Trp
                805                 810                 815
Val Ala Leu Asp Leu Pro Gly Arg Leu Arg Pro Arg Cys Ala Glu Gly
            820                 825                 830
Cys Arg Leu His Val Leu Gly Gly Ala Thr Glu Ala Gly Ile Trp Ser
        835                 840                 845
Asn Leu Gln Ser Val Asp Thr Val Pro Pro His Trp Arg Ser Ile Pro
    850                 855                 860
Tyr Gly Arg Pro Leu Pro Gly Gln Ala Tyr Arg Val Val Asp Thr His
865                 870                 875                 880
Gly Arg Asp Val Pro Asp Leu Val Val Gly Glu Leu Trp Ile Gly Gly
                885                 890                 895
Ala Ser Leu Ala Arg Gly Tyr Arg Asn Asp Pro Glu Leu Ser Ala Arg
            900                 905                 910
```

-continued

```
Arg Phe Val His Asp Ala Gln Gly Arg Trp Tyr Arg Thr Gly Asp Arg
        915                 920                 925

Gly Arg Tyr Trp Gly Asp Gly Thr Leu Glu Phe Leu Gly Arg Val Asp
        930                 935                 940

Gln Gln Val Lys Val Arg Gly Gln Arg Ile Glu Leu Gly Glu Val Glu
945                 950                 955                 960

Ala Ala Leu Cys Ala Gln Ala Gly Val Glu Ser Ala Cys Ala Ala Val
                965                 970                 975

Leu Gly Gly Gly Val Ala Ser Leu Gly Ala Val Leu Val Pro Arg Leu
                980                 985                 990

Ala Pro Arg Ala Glu Gly Ser Met Asp Leu Pro Ala Ala Gln Pro Phe
            995                 1000                1005

Ala Gly Leu Ala Glu Ala Glu Ala Val Leu Thr Arg Glu Ile Leu
    1010                1015                1020

Gly Ala Leu Leu Glu Ala Pro Leu Glu Leu Asp Asp Gly Leu Arg
    1025                1030                1035

Arg Arg Trp Leu Asp Trp Leu Ala Asp Ser Ala Ala Ser Ala Leu
    1040                1045                1050

Pro Ser Leu Asp Glu Ala Leu Arg Arg Leu Gly Trp Gln Ala Ala
    1055                1060                1065

Gly Leu Thr Ala Met Gly Asn Ala Leu Arg Gly Leu Leu Ala Gly
    1070                1075                1080

Glu Gln Ala Pro Ala Ala Leu Leu Leu Asp Pro Trp Leu Ala Pro
    1085                1090                1095

Gln Ala Val Ala Ala Arg Leu Pro Asp Gly Arg Glu Ala Leu Ala
    1100                1105                1110

Arg Leu Leu Glu Ala Leu Pro Thr Pro Ala Ala Gly Glu Arg Leu
    1115                1120                1125

Arg Val Ala Val Leu Asp Thr Arg Ala Gly Leu Trp Leu Asp Gln
    1130                1135                1140

Gly Met Ala Ser Leu Leu Arg Pro Gly Leu Glu Leu Thr Leu Phe
    1145                1150                1155

Glu Arg Ser Arg Val Leu Leu Asp Ala Ala Ala Thr Arg Leu Pro
    1160                1165                1170

Glu Arg Ile Val Val Gln Ala Leu Asp Asp Gly Leu Leu Pro Ala
    1175                1180                1185

Glu His Leu Gly Arg Tyr Asp Arg Val Ile Ser Phe Ala Ala Leu
    1190                1195                1200

His Ala Tyr Glu Ala Ser Arg Glu Gly Leu Ala Leu Ala Ala Ala
    1205                1210                1215

Leu Leu Arg Pro Gln Gly Arg Leu Leu Leu Val Asp Leu Leu Cys
    1220                1225                1230

Glu Ser Pro Leu Ala Leu Leu Gly Ala Ala Leu Leu Asp Asp Arg
    1235                1240                1245

Pro Leu Arg Leu Ala Glu Leu Pro Ser Leu Leu Ala Asp Leu Ala
    1250                1255                1260

Ala Ala Gly Leu Ala Pro Arg Cys Leu Trp Arg Ser Glu Arg Ile
    1265                1270                1275

Ala Leu Val Glu Ala Leu Ala Pro Gly Leu Gly Leu Asp Ala Ala
    1280                1285                1290

Ala Leu Gln Ala Gly Leu Glu Gln Arg Leu Pro Gln Ala Met Arg
    1295                1300                1305

Pro Glu Arg Leu Trp Cys Leu Pro Ser Leu Pro Leu Asn Gly Asn
```

-continued

```
                    1310                1315                1320
Gly Lys Val Asp Arg Arg Leu Ala Glu Ser Met Thr Arg Ala
    1325                1330                1335

Leu Gly Glu Cys Arg His Glu Pro Ser Ala Glu Pro Leu Glu
    1340                1345                1350

Ala His Glu Gln Ala Leu Ala Glu Cys Trp Glu Ala Val Leu Lys
    1355                1360                1365

Arg Pro Val Arg Arg Glu Ala Ser Phe Phe Ser Leu Gly Gly
    1370                1375                1380

Asp Ser Leu Leu Ala Thr Arg Leu Leu Ala Gly Ile Arg Glu Arg
    1385                1390                1395

Phe Gly Val Arg Leu Gly Met Ala Asp Phe Tyr Arg Gln Pro Thr
    1400                1405                1410

Leu Ala Gly Leu Ala Arg His Leu Gln Val Gln Thr Val Glu Ile
    1415                1420                1425

Glu Glu Thr Gln Leu Glu Glu Gly Val Leu
    1430                1435
```

<210> SEQ ID NO 31
<211> LENGTH: 5430
<212> TYPE: DNA
<213> ORGANISM: Pseudomonas aeruginosa

<400> SEQUENCE: 31

```
atgagcctcg gcgaactgct ggaaacctgc cgcagccggc gcatcgaact ctggagcgag      60
gcgggccgcc tgcgctatcg cgcccccag ggtgccctcg acgccggcct cgccgagcgc     120
ctgcgggccg agcgcgaggc cctgctggaa cacctggaag gcggccctgg ctggcgcgcc     180
gaacccgaca tggcccacca gcgcttcccg ctgacccgg tgcaggccgc ctacgtgctg      240
ggccgccagg cggccttcga ctacggcggt aacgcctgcc agctgtacgc cgagtacgac     300
tggccggccg acaccgatcc ggcgcgcctg gaggcggcct ggaacgccat ggtcgagcgc     360
cacccgatgc tgcgcgcggt gatcgaggac aacgcctggc agcgcgtgct gcccgaggtg     420
ccctggcagc ggctgaccgt gcatgcctgc gcggggctcg acgaggccgc tttccaggcg     480
cacctggagc gggtccgcga acgcctcgac cacgcctgcg cggcgctcga ccagtggccg     540
gtcctgcgcc ccgagctgag tatcggccgg gatgcctgcg tactgcactg ctcggtggat     600
ttcaccctgg tcgactacgc cagcctgcaa ttgctgcttg cgaatggcg ccgccgctat      660
ctcgatccgc aatggacggc ggaaccgctg gaggcgacct tccgcgacta tgtcggcgtc     720
gagcagcgcc gacgccagtc gccagcctgg cagcgcgacc gcgactggtg gctggcgcgt     780
ctcgacgcgc taccggggcg tcccgacctg ccgctgcggg tgcagccgga cacccggtcc     840
acgcgcttcc ggcacttcca gcgcgcctc gacgaggccg cctggcaggc gctcggcgcg     900
cgcgccggcg aacacggcct gagcgctgcc ggcgtggcct tggcggcctt cgccgagacc     960
atcggtcgct ggagccaggc accggcgttc tgtctcaacc tgacggtact caaccggccg    1020
ccgctgcatc gcagctggc gcaggtgctc ggtgacttca ccgcgctcag cctgctggca    1080
gtggacagcc gccacggcga cagtttcgtc gagcgtgccc gacgcatcgg cgagcagatg    1140
ttcgacgacc tgaccaccc gaccttcagc ggcgtcgacc tgctgcgcga actggcgcgc    1200
cggcgtggtc gcggcgccga tctgatgccg gtggtgttca ccagtggcat cggcagcgtg    1260
cagcgcctgc tcgcgatgg cgaggcgccg cgcgccac gctacatgat cagccagacc    1320
ccgcaggtct ggctggactg ccaggtcacc gaccagttcg gcggcctgga gatcggctgg    1380
```

-continued

```
gacgtacgcc tcgggttgtt ccccgagggc caggcggaag ccatgttcga cgacttcgtc   1440
gggctgctcc ggcgcctggc gcagagcccg cgcgcctgga ccgacggcga tgccacggaa   1500
cccgtcgagg cgccgccgca ggcgttgccc ggtagtgccc ggagcatcgc cgccggtttc   1560
gccgagcgtg ccctgctgac ccccgacgcc acggcgatcc acgatgccgc cggcagctac   1620
agctaccgcc aggtcgccca gcacgccagc gccctgcgcc cgtcctgga agcgcacggc    1680
gcgggccgtg gccggcgggt cgcggtgatg ctgccgaaaa cgccgcgca attggtcgcg    1740
gtgatcggca tcctccaggc cggcgccgcc tatgtgccgg tggacatccg ccagcctccg   1800
ctgcggcgcc aggcgatcct cgccagcgcc gaagtggtcg cgctggtctg cctggaaagc   1860
gatgtcccgg acgtcggctg cgcctgcgtg gccatcgacc ggctggccgc cgacagcgcc   1920
tggccgccac cgcccgcggc ggaggtggcg gcggacgacc tcgcctacgt gatctacacc   1980
tccggctcca ccggcacgcc aaagggcgtg atgctcagcc atgcggcggt gagcaacacg   2040
ctgctcgaca tcaaccagcg ctacggcgtc gacgccaacg accgcgtcct cggcctcgcc   2100
gagctgagct tcgacctctc ggtctacgac ttcttcggcg ccaccgcggc gggggcccag   2160
gtggtcctcc cggacccggc gcgcggcagc gatccatcgc actgggcgga actgctggaa   2220
cgccacgcca tcaccctgtg gaactcggtg ccggcccaag gccagatgct catcgattac   2280
ctggagagcg agccgcaacg tcacctgccg gaccgcgct gcgtgctctg gtccggtgac   2340
tggattccgg tcagcctgcc gacccgctgg tggcggcgct ggccggacag cgcgctgttc   2400
agcctgggcg gcgccaccga ggcggcgatc tggtcgatcg agcagccgat ccgcccgcag   2460
cacaccgagc tggccagcat cccttatggc cgtgccctgc gcgggcagag cgtggaagtc   2520
ctggatgccc gcgggcggcg ctgccgcgcc ggcgtgcgcg gcgagatcca tatcggcggg   2580
gtgggcctgg cgctcggcta cgccggcgat ccgcagcgca ccgccgaacg cttcgtccgt   2640
caccccgatg gccgtcgcct gtatcgcacc ggcgacctcg gccgctacct ggccgacggc   2700
agcatcgagt tcctcggccg cgaggacgac caggtgaaga ttcgcggcca ccgcatcgaa   2760
ctggccgaac tggacgccgc gctgtgcgct catccgcagg tcaacctggc ggccaccgtg   2820
gtgctcggcg agacccacga gcgcagcctg ccagcttcg tcaccctgca tgcgccggtg    2880
gaggctggcg aggatccgcg tacgcgctc gacgcggtgc gccagcgggc ggcccaggcc    2940
ttgcgccgcg actggggcag cgaggagggc atcgccgcgg cggtggccgc actcgaccgt   3000
gcctgcctcg cctcgttggc cgcctggctg ccggcagcg gtctgttcgc cagtgcgacg    3060
ccgctggact tagccacct gtgccagcgc ctgggtatcg ccgaggcgcg ccagcgcctg    3120
ctgcgccact ggttgcgcca actggaggag ggcggctacc tgcgcgccga gggcgagggc   3180
tggctgggct gcgccgagcg tcccgcgcag agtccggagg acgcctggac ggcgttcgcc   3240
ggctgcgcgc cggcggcgct ctggccggcc gagctggtcg cctacctgcg tgacagcgcg   3300
caatccctcg gcgagcaact ggccgggcgg atcagcccgg cggcgctgat gttcccgcag   3360
ggctcggcgc gcatcgccga ggccatgtac agccagggcc tgcatgccca ggcgctgcac   3420
gaggccatgg ccgaggccat cgccgccatc gtcgagcgcc agccgcaacg gcgctggcgc   3480
ctgctggagc ttggcgccgg caccgccgcc gccagccgca cggtgatcgc ccggttggcg   3540
ccgctggtgc agcgaggggc ggaggtggac tacctgttca ccgacgtttc cagctacttc   3600
ctcgccgccg cccgcgagcg cttcgccgac cagccgtggg tacgcttcgg ccgcttcgac   3660
atgaacggcg atcttctcga ccagggcgtg gcgccgcact cggtggatat cctgctcagc   3720
```

```
tccggggcct tgaacaacgc gctggacacc ccggcgctgc tggccggcct gcgcgagttg    3780
ctgagcgccg acgcctggct ggtgatccag gaactgacgc gcgagcacaa cgagatcagc    3840
gtcagccaga gcctgatgat ggaaaacccg cgcgacctcc gcgacgagcg ccgccaactg    3900
ttcgtccaca ccgggcaatg gctggagtgg ctggcggcac agggtggcga cctggcttgt    3960
ggggtggtgc cgccgggcag cgctctcgac ctgcttggct acgatgtcct gctggctcgc    4020
tgcaagaccg accgcgcccg cctggagccg gccgagctgc tggccttcgt cgaagcgcgg    4080
gtgccgcgct acatgctccc ggcgcagttg cgcgtgctcg aacgcctgcc ggtcaccggc    4140
aacggcaaga tcgaccgcaa ggccctgacc ggctttgccc gccagcccca gcggaccttt    4200
cggcatggcg tcgcgcaggc accggccgac gaactggaga atgcgctgct ggcactctgg    4260
cgggaggtgc tggacaaccc gtcgctgggc gtcgagcaag acttcttcgg ggccggcggc    4320
gactcgctgt tgatcgccca gttgatcgcc cgtttgcgcg aacgactgga aagcgcccgt    4380
cggcatccgt tcgatcgcct gctacgctgg gcgctcagcc agccgacgcc gcgcggcctg    4440
gccgaacgcc tgcgcagcgc gccggaagag ggccgtgggc cagccctggc cgcggcgcgc    4500
ggcgtcgccc cggcgccggc cggcatgtcg cgcgcaccgc tcgccgaggg cgcggtggcg    4560
ctcgacccgc tggtgcgcct ggtgcccggc gagggcgtgc cgcgggtgct ggtccacgaa    4620
ggcctcggca cgctactgcc gtaccgcccg ctgcttcgcg ccctgggtga ggggcggccg    4680
ttgctggggc tggccgtgca tgacagcgac gcctacctgg cgatccccgc cgagcatctc    4740
aacgcctgcc tcggccgccg ctacgccgag gcgctccatc gcgccgggct acgcgaggtc    4800
gacctgctcg gctactgctc cggcgggctg gtcgccctgg agaccgccaa gtccctggtc    4860
cagcgcgggg tgcgcgtgcg ccaactggat atcgtctcca gctaccggat tccctaccgg    4920
gtggacgacg agcgcctgct gttgttcagc ttcgccgcga ccctcggcct ggataccgcg    4980
gcgctcggct tccccgcgcc ggaacgtctc ggccaggcgg tgcaggcggc gctcgcgcag    5040
acaccggagc gcctggtcgc cgaggcgctg gcggggctgc cgggcctggc cgatctcgtc    5100
gccctgcgcg gccgcgtgct acaggcggcc agcggtagcg ccgacgccgt cagcgtcgaa    5160
cgcgacaccc tctaccggct gttctgtcac tcggtgcgtg ccagccaggc cgaggcgccg    5220
gagccctacg tcggcgcgct gcggctgttc gtgccggacg ccggcaaccc attggtgccg    5280
cgctacgccg aggctctgga gacccaatgg cgggccgccg cgcttggcgc gtgcggcatc    5340
cacgaggtgc ccggcgggca cttcgactgc ctgggcgaag ccctggcgca atccttgtcg    5400
aaacccatgc cagaggaggc gagccgatga                                      5430
```

<210> SEQ ID NO 32
<211> LENGTH: 1809
<212> TYPE: PRT
<213> ORGANISM: Pseudomonas aeruginosa

<400> SEQUENCE: 32

```
Met Ser Leu Gly Glu Leu Leu Glu Thr Cys Arg Ser Arg Arg Ile Glu
1               5                   10                  15

Leu Trp Ser Glu Ala Gly Arg Leu Arg Tyr Arg Ala Pro Gln Gly Ala
            20                  25                  30

Leu Asp Ala Gly Leu Ala Glu Arg Leu Arg Ala Glu Arg Glu Ala Leu
        35                  40                  45

Leu Glu His Leu Glu Gly Gly Pro Gly Trp Arg Ala Glu Pro Asp Met
    50                  55                  60

Ala His Gln Arg Phe Pro Leu Thr Pro Val Gln Ala Ala Tyr Val Leu
```

-continued

```
             65                  70                  75                  80
Gly Arg Gln Ala Ala Phe Asp Tyr Gly Gly Asn Ala Cys Gln Leu Tyr
                    85                  90                  95
Ala Glu Tyr Asp Trp Pro Ala Asp Thr Asp Pro Ala Arg Leu Glu Ala
                100                 105                 110
Ala Trp Asn Ala Met Val Glu Arg His Pro Met Leu Arg Ala Val Ile
                115                 120                 125
Glu Asp Asn Ala Trp Gln Arg Val Leu Pro Glu Val Pro Trp Gln Arg
            130                 135                 140
Leu Thr Val His Ala Cys Ala Gly Leu Asp Glu Ala Ala Phe Gln Ala
145                 150                 155                 160
His Leu Glu Arg Val Arg Glu Arg Leu Asp His Ala Cys Ala Ala Leu
                165                 170                 175
Asp Gln Trp Pro Val Leu Arg Pro Glu Leu Ser Ile Gly Arg Asp Ala
                180                 185                 190
Cys Val Leu His Cys Ser Val Asp Phe Thr Leu Val Asp Tyr Ala Ser
                195                 200                 205
Leu Gln Leu Leu Leu Gly Glu Trp Arg Arg Tyr Leu Asp Pro Gln
            210                 215                 220
Trp Thr Ala Glu Pro Leu Glu Ala Thr Phe Arg Asp Tyr Val Gly Val
225                 230                 235                 240
Glu Gln Arg Arg Arg Gln Ser Pro Ala Trp Gln Arg Asp Arg Asp Trp
                245                 250                 255
Trp Leu Ala Arg Leu Asp Ala Leu Pro Gly Arg Pro Asp Leu Pro Leu
                260                 265                 270
Arg Val Gln Pro Asp Thr Arg Ser Thr Arg Phe Arg His Phe His Ala
                275                 280                 285
Arg Leu Asp Glu Ala Ala Trp Gln Ala Leu Gly Ala Arg Ala Gly Glu
            290                 295                 300
His Gly Leu Ser Ala Ala Gly Val Ala Leu Ala Ala Phe Ala Glu Thr
305                 310                 315                 320
Ile Gly Arg Trp Ser Gln Ala Pro Ala Phe Cys Leu Asn Leu Thr Val
                325                 330                 335
Leu Asn Arg Pro Pro Leu His Pro Gln Leu Ala Gln Val Leu Gly Asp
                340                 345                 350
Phe Thr Ala Leu Ser Leu Leu Ala Val Asp Ser Arg His Gly Asp Ser
                355                 360                 365
Phe Val Glu Arg Ala Arg Arg Ile Gly Glu Gln Met Phe Asp Asp Leu
                370                 375                 380
Asp His Pro Thr Phe Ser Gly Val Asp Leu Leu Arg Glu Leu Ala Arg
385                 390                 395                 400
Arg Arg Gly Arg Gly Ala Asp Leu Met Pro Val Val Phe Thr Ser Gly
                405                 410                 415
Ile Gly Ser Val Gln Arg Leu Leu Gly Asp Gly Glu Ala Pro Arg Ala
                420                 425                 430
Pro Arg Tyr Met Ile Ser Gln Thr Pro Gln Val Trp Leu Asp Cys Gln
                435                 440                 445
Val Thr Asp Gln Phe Gly Gly Leu Glu Ile Gly Trp Asp Val Arg Leu
                450                 455                 460
Gly Leu Phe Pro Glu Gly Gln Ala Glu Ala Met Phe Asp Asp Phe Val
465                 470                 475                 480
Gly Leu Leu Arg Arg Leu Ala Gln Ser Pro Arg Ala Trp Thr Asp Gly
                485                 490                 495
```

```
Asp Ala Thr Glu Pro Val Glu Ala Pro Pro Gln Ala Leu Pro Gly Ser
            500                 505                 510

Ala Arg Ser Ile Ala Ala Gly Phe Ala Glu Arg Ala Leu Leu Thr Pro
        515                 520                 525

Asp Ala Thr Ala Ile His Asp Ala Ala Gly Ser Tyr Ser Tyr Arg Gln
        530                 535                 540

Val Ala Gln His Ala Ser Ala Leu Arg Arg Val Leu Glu Ala His Gly
545                 550                 555                 560

Ala Gly Arg Gly Arg Arg Val Ala Val Met Leu Pro Lys Ser Ala Ala
                565                 570                 575

Gln Leu Val Ala Val Ile Gly Ile Leu Gln Ala Gly Ala Ala Tyr Val
            580                 585                 590

Pro Val Asp Ile Arg Gln Pro Pro Leu Arg Arg Gln Ala Ile Leu Ala
        595                 600                 605

Ser Ala Glu Val Val Ala Leu Val Cys Leu Glu Ser Asp Val Pro Asp
        610                 615                 620

Val Gly Cys Ala Cys Val Ala Ile Asp Arg Leu Ala Ala Asp Ser Ala
625                 630                 635                 640

Trp Pro Pro Pro Ala Ala Glu Val Ala Ala Asp Asp Leu Ala Tyr
                645                 650                 655

Val Ile Tyr Thr Ser Gly Ser Thr Gly Thr Pro Lys Gly Val Met Leu
            660                 665                 670

Ser His Ala Ala Val Ser Asn Thr Leu Leu Asp Ile Asn Gln Arg Tyr
        675                 680                 685

Gly Val Asp Ala Asn Asp Arg Val Leu Gly Leu Ala Glu Leu Ser Phe
        690                 695                 700

Asp Leu Ser Val Tyr Asp Phe Phe Gly Ala Thr Ala Ala Gly Ala Gln
705                 710                 715                 720

Val Val Leu Pro Asp Pro Ala Arg Gly Ser Asp Pro Ser His Trp Ala
                725                 730                 735

Glu Leu Leu Glu Arg His Ala Ile Thr Leu Trp Asn Ser Val Pro Ala
            740                 745                 750

Gln Gly Gln Met Leu Ile Asp Tyr Leu Glu Ser Glu Pro Gln Arg His
        755                 760                 765

Leu Pro Gly Pro Arg Cys Val Leu Trp Ser Gly Asp Trp Ile Pro Val
        770                 775                 780

Ser Leu Pro Thr Arg Trp Trp Arg Arg Trp Pro Asp Ser Ala Leu Phe
785                 790                 795                 800

Ser Leu Gly Gly Ala Thr Glu Ala Ala Ile Trp Ser Ile Glu Gln Pro
                805                 810                 815

Ile Arg Pro Gln His Thr Glu Leu Ala Ser Ile Pro Tyr Gly Arg Ala
            820                 825                 830

Leu Arg Gly Gln Ser Val Glu Val Leu Asp Ala Arg Gly Arg Arg Cys
        835                 840                 845

Pro Pro Gly Val Arg Gly Glu Ile His Ile Gly Gly Val Gly Leu Ala
        850                 855                 860

Leu Gly Tyr Ala Gly Asp Pro Gln Arg Thr Ala Glu Arg Phe Val Arg
865                 870                 875                 880

His Pro Asp Gly Arg Arg Leu Tyr Arg Thr Gly Asp Leu Gly Arg Tyr
                885                 890                 895

Leu Ala Asp Gly Ser Ile Glu Phe Leu Gly Arg Glu Asp Asp Gln Val
            900                 905                 910
```

-continued

```
Lys Ile Arg Gly His Arg Ile Glu Leu Ala Glu Leu Asp Ala Ala Leu
        915                 920                 925

Cys Ala His Pro Gln Val Asn Leu Ala Ala Thr Val Val Leu Gly Glu
    930                 935                 940

Thr His Glu Arg Ser Leu Ala Ser Phe Val Thr Leu His Ala Pro Val
945                 950                 955                 960

Glu Ala Gly Glu Asp Pro Arg Thr Ala Leu Asp Ala Val Arg Gln Arg
                965                 970                 975

Ala Ala Gln Ala Leu Arg Arg Asp Trp Gly Ser Glu Glu Gly Ile Ala
            980                 985                 990

Ala Ala Val Ala Ala Leu Asp Arg Ala Cys Leu Ala Ser Leu Ala Ala
        995                1000                1005

Trp Leu Ala Gly Ser Gly Leu Phe Ala Ser Ala Thr Pro Leu Asp
    1010                1015                1020

Leu Ala Thr Leu Cys Gln Arg Leu Gly Ile Ala Glu Ala Arg Gln
    1025                1030                1035

Arg Leu Leu Arg His Trp Leu Arg Gln Leu Glu Glu Gly Gly Tyr
    1040                1045                1050

Leu Arg Ala Glu Gly Glu Gly Trp Leu Gly Cys Ala Glu Arg Pro
    1055                1060                1065

Ala Gln Ser Pro Glu Asp Ala Trp Thr Ala Phe Ala Gly Cys Ala
    1070                1075                1080

Pro Ala Ala Leu Trp Pro Ala Glu Leu Val Ala Tyr Leu Arg Asp
    1085                1090                1095

Ser Ala Gln Ser Leu Gly Glu Gln Leu Ala Gly Arg Ile Ser Pro
    1100                1105                1110

Ala Ala Leu Met Phe Pro Gln Gly Ser Ala Arg Ile Ala Glu Ala
    1115                1120                1125

Met Tyr Ser Gln Gly Leu His Ala Gln Ala Leu His Glu Ala Met
    1130                1135                1140

Ala Glu Ala Ile Ala Ala Ile Val Glu Arg Gln Pro Gln Arg Arg
    1145                1150                1155

Trp Arg Leu Leu Glu Leu Gly Ala Gly Thr Ala Ala Ala Ser Arg
    1160                1165                1170

Thr Val Ile Ala Arg Leu Ala Pro Leu Val Gln Arg Gly Ala Glu
    1175                1180                1185

Val Asp Tyr Leu Phe Thr Asp Val Ser Ser Tyr Phe Leu Ala Ala
    1190                1195                1200

Ala Arg Glu Arg Phe Ala Asp Gln Pro Trp Val Arg Phe Gly Arg
    1205                1210                1215

Phe Asp Met Asn Gly Asp Leu Leu Asp Gln Gly Val Ala Pro His
    1220                1225                1230

Ser Val Asp Ile Leu Leu Ser Ser Gly Ala Leu Asn Asn Ala Leu
    1235                1240                1245

Asp Thr Pro Ala Leu Leu Ala Gly Leu Arg Glu Leu Leu Ser Ala
    1250                1255                1260

Asp Ala Trp Leu Val Ile Gln Glu Leu Thr Arg Glu His Asn Glu
    1265                1270                1275

Ile Ser Val Ser Gln Ser Leu Met Met Glu Asn Pro Arg Asp Leu
    1280                1285                1290

Arg Asp Glu Arg Arg Gln Leu Phe Val His Thr Gly Gln Trp Leu
    1295                1300                1305

Glu Trp Leu Ala Ala Gln Gly Gly Asp Leu Ala Cys Gly Val Val
```

-continued

```
            1310                1315                1320
Pro Pro Gly Ser Ala Leu Asp Leu Leu Gly Tyr Asp Val Leu Leu
    1325                1330                1335
Ala Arg Cys Lys Thr Asp Arg Ala Arg Leu Glu Pro Ala Glu Leu
    1340                1345                1350
Leu Ala Phe Val Glu Ala Arg Val Pro Arg Tyr Met Leu Pro Ala
    1355                1360                1365
Gln Leu Arg Val Leu Glu Arg Leu Pro Val Thr Gly Asn Gly Lys
    1370                1375                1380
Ile Asp Arg Lys Ala Leu Thr Gly Phe Ala Arg Gln Pro Gln Ala
    1385                1390                1395
Asp Leu Arg His Gly Val Ala Gln Ala Pro Ala Asp Glu Leu Glu
    1400                1405                1410
Asn Ala Leu Leu Ala Leu Trp Arg Glu Val Leu Asp Asn Pro Ser
    1415                1420                1425
Leu Gly Val Glu Gln Asp Phe Phe Gly Ala Gly Gly Asp Ser Leu
    1430                1435                1440
Leu Ile Ala Gln Leu Ile Ala Arg Leu Arg Glu Arg Leu Glu Ser
    1445                1450                1455
Ala Arg Arg His Pro Phe Asp Arg Leu Leu Arg Trp Ala Leu Ser
    1460                1465                1470
Gln Pro Thr Pro Arg Gly Leu Ala Glu Arg Leu Arg Ser Ala Pro
    1475                1480                1485
Glu Glu Gly Arg Gly Pro Ala Leu Ala Ala Ala Arg Gly Val Ala
    1490                1495                1500
Pro Ala Pro Ala Gly Met Ser Arg Ala Pro Leu Ala Glu Gly Ala
    1505                1510                1515
Val Ala Leu Asp Pro Leu Val Arg Leu Val Pro Gly Glu Gly Val
    1520                1525                1530
Pro Arg Val Leu Val His Glu Gly Leu Gly Thr Leu Leu Pro Tyr
    1535                1540                1545
Arg Pro Leu Leu Arg Ala Leu Gly Glu Gly Arg Pro Leu Leu Gly
    1550                1555                1560
Leu Ala Val His Asp Ser Asp Ala Tyr Leu Ala Ile Pro Ala Glu
    1565                1570                1575
His Leu Asn Ala Cys Leu Gly Arg Arg Tyr Ala Glu Ala Leu His
    1580                1585                1590
Arg Ala Gly Leu Arg Glu Val Asp Leu Leu Gly Tyr Cys Ser Gly
    1595                1600                1605
Gly Leu Val Ala Leu Glu Thr Ala Lys Ser Leu Val Gln Arg Gly
    1610                1615                1620
Val Arg Val Arg Gln Leu Asp Ile Val Ser Ser Tyr Arg Ile Pro
    1625                1630                1635
Tyr Arg Val Asp Asp Glu Arg Leu Leu Leu Phe Ser Phe Ala Ala
    1640                1645                1650
Thr Leu Gly Leu Asp Thr Ala Ala Leu Gly Phe Pro Ala Pro Glu
    1655                1660                1665
Arg Leu Gly Gln Ala Val Gln Ala Ala Leu Ala Gln Thr Pro Glu
    1670                1675                1680
Arg Leu Val Ala Glu Ala Leu Ala Gly Leu Pro Gly Leu Ala Asp
    1685                1690                1695
Leu Val Ala Leu Arg Gly Arg Val Leu Gln Ala Ala Ser Gly Ser
    1700                1705                1710
```

-continued

```
Ala Asp Ala Val Ser Val Glu Arg Asp Thr Leu Tyr Arg Leu Phe
    1715                1720                1725

Cys His Ser Val Arg Ala Ser Gln Ala Glu Ala Pro Glu Pro Tyr
    1730                1735                1740

Val Gly Ala Leu Arg Leu Phe Val Pro Asp Ala Gly Asn Pro Leu
    1745                1750                1755

Val Pro Arg Tyr Ala Glu Ala Leu Glu Thr Gln Trp Arg Ala Ala
    1760                1765                1770

Ala Leu Gly Ala Cys Gly Ile His Glu Val Pro Gly Gly His Phe
    1775                1780                1785

Asp Cys Leu Gly Glu Ala Leu Ala Gln Ser Leu Ser Lys Pro Met
    1790                1795                1800

Pro Glu Glu Ala Ser Arg
    1805
```

<210> SEQ ID NO 33
<211> LENGTH: 1713
<212> TYPE: DNA
<213> ORGANISM: Pseudomonas aeruginosa

<400> SEQUENCE: 33

```
gtgaccccgg tgctgtggcg cctgctgcgc acctatcgct ggcggctggc ggcggccatg      60
gggttgcagg ccctggccgg gctctgctcg ctgttgccct ggatgcttct cgcctggctc     120
gccgagccgc tggcgcgcgg ccaggcgcag ccggccctgc tggccctggt gctgctggcg     180
gtgctggcct ggctgggctg ccaggcgctg gccgcgcacc tggcccaccg ggtcgacgcg     240
gacctctgca cgacctgcg cctgcgcctg ctggcgcacc tgcaacggct gccgctggac     300
tggttcggtc gccagggccc ggacggcgtg gcgcgcctcg tggagcagga cgtgcgggcc     360
ctgcaccaac tgatcgcgca cgctcccaac gatctcagca acctgttggt ggtgccgctc     420
gtcgcgttgc tctggctggc ctggctgcac ccctggctgc tgctgttctg cctgctgccg     480
ctggtgctgg ccgccgccgg cttcctgctg ctgcgctcgg cgcgctaccg cgacctggtg     540
ctgcggcgca acgccgcgct ggaaaggctc tcggcggact atggcgaatt cgcccacaac     600
ctgctgctgg cccgacagta ccccggcgcc ggcatacaac agggcgccga ggcgtcggcg     660
gcggccttcg gcgaagcgtt cggcgcctgg gtgaagcggg tcggccacct cgccgcgctg     720
gtctacgtgc agttgtcgac gccctggctg ctggcctggg tcctgctcgg cgcgctggcc     780
ctggatgccc tcggcgtgcc gctggcgctc ggccaggcct gtgccttcct gctcctgctg     840
cgggccttgg ctgccccggt gcaggcgctc ggccacggcg gcgacgcgct gctgggcgcg     900
cgcgccgccg ccgagcgcct gcagcaggtg ttcgaccagg cgccgctggc cgagggccgc     960
tcgacccgcg agccggtcga tggcgcggtg gcgctgcacg gcctgggcca tgcctatgaa    1020
ggcgtggagg tcctggccga tatcgatctg gagctggagg atggcagcct ggtggccctg    1080
gtcggtccct cgggctccgg caagagcacc ctgctgcacc tgctggcgcg ctacatggac    1140
gcgcagcgcg cgaactgga ggttggcggc ctggcactga aggacatgcc tgatgccgtg    1200
cgccatcggc atatcgcgct ggtcggccag caggcggcgg cgctggagat ccctggcc     1260
gacaacattg ccctgttccg ccccgatgcc gatctcagg agattcgcca ggcggcccgt     1320
gacgcctgcc tcgacgagcg catcatggcc ctgccgcgtg ctacgacag cgtgccggga    1380
cgcgacctgc aactgtccgg cggcgaactg caacgactgg ccctggcccg tgcgctgcta    1440
tcgccggcga gcctgttgct gctcgacgag ccaacctcgg cgctggatcc gcagaccgcc    1500
```

-continued

```
cggcaggtcc tgcgcaacct gcgcgaacgc ggcggtggcc ggacccgggt gatcgtcgcc   1560
catcgtctgg ccgaagtcag cgatgccgac ctgatcctgg tgctggtcgc tggccgtctg   1620
gtcgaacgcg gcgagcacgc ggcgctgttg gcggcggacg gcgcctatgc gcgcttgtgg   1680
cgtgaacaga acggcgcgga ggtggcggca tga                                1713
```

<210> SEQ ID NO 34
<211> LENGTH: 570
<212> TYPE: PRT
<213> ORGANISM: Pseudomonas aeruginosa

<400> SEQUENCE: 34

```
Met Thr Pro Val Leu Trp Arg Leu Leu Arg Thr Tyr Arg Trp Arg Leu
1               5                   10                  15

Ala Ala Ala Met Gly Leu Gln Ala Leu Ala Gly Leu Cys Ser Leu Leu
            20                  25                  30

Pro Trp Met Leu Leu Ala Trp Leu Ala Glu Pro Leu Ala Arg Gly Gln
        35                  40                  45

Ala Gln Pro Ala Leu Leu Ala Leu Val Leu Leu Ala Val Leu Ala Trp
    50                  55                  60

Leu Gly Cys Gln Ala Leu Ala His Leu Ala His Arg Val Asp Ala
65                  70                  75                  80

Asp Leu Cys Asn Asp Leu Arg Leu Arg Leu Leu Ala His Leu Gln Arg
                85                  90                  95

Leu Pro Leu Asp Trp Phe Gly Arg Gln Gly Pro Asp Gly Val Ala Arg
            100                 105                 110

Leu Val Glu Gln Asp Val Arg Ala Leu His Gln Leu Ile Ala His Ala
        115                 120                 125

Pro Asn Asp Leu Ser Asn Leu Leu Val Val Pro Leu Val Ala Leu Leu
    130                 135                 140

Trp Leu Ala Trp Leu His Pro Trp Leu Leu Leu Phe Cys Leu Leu Pro
145                 150                 155                 160

Leu Val Leu Ala Ala Ala Gly Phe Leu Leu Leu Arg Ser Ala Arg Tyr
                165                 170                 175

Arg Asp Leu Val Leu Arg Arg Asn Ala Ala Leu Glu Arg Leu Ser Ala
            180                 185                 190

Asp Tyr Gly Glu Phe Ala His Asn Leu Leu Leu Ala Arg Gln Tyr Pro
        195                 200                 205

Gly Ala Gly Ile Gln Gln Gly Ala Glu Ala Ser Ala Ala Ala Phe Gly
    210                 215                 220

Glu Ala Phe Gly Ala Trp Val Lys Arg Val Gly His Leu Ala Ala Leu
225                 230                 235                 240

Val Tyr Val Gln Leu Ser Thr Pro Trp Leu Leu Ala Trp Val Leu Leu
                245                 250                 255

Gly Ala Leu Ala Leu Asp Ala Leu Gly Val Pro Leu Ala Leu Gly Gln
            260                 265                 270

Ala Cys Ala Phe Leu Leu Leu Leu Arg Ala Leu Ala Ala Pro Val Gln
        275                 280                 285

Ala Leu Gly His Gly Gly Asp Ala Leu Leu Gly Ala Arg Ala Ala Ala
    290                 295                 300

Glu Arg Leu Gln Gln Val Phe Asp Gln Ala Pro Leu Ala Glu Gly Arg
305                 310                 315                 320

Ser Thr Arg Glu Pro Val Asp Gly Ala Val Ala Leu His Gly Leu Gly
                325                 330                 335
```

His Ala Tyr Glu Gly Val Glu Val Leu Ala Asp Ile Asp Leu Glu Leu
            340                 345                 350
Glu Asp Gly Ser Leu Val Ala Leu Val Gly Pro Ser Gly Ser Gly Lys
        355                 360                 365
Ser Thr Leu Leu His Leu Leu Ala Arg Tyr Met Asp Ala Gln Arg Gly
    370                 375                 380
Glu Leu Glu Val Gly Gly Leu Ala Leu Lys Asp Met Pro Asp Ala Val
385                 390                 395                 400
Arg His Arg His Ile Ala Leu Val Gly Gln Gln Ala Ala Ala Leu Glu
                405                 410                 415
Ile Ser Leu Ala Asp Asn Ile Ala Leu Phe Arg Pro Asp Ala Asp Leu
            420                 425                 430
Gln Glu Ile Arg Gln Ala Ala Arg Asp Ala Cys Leu Asp Glu Arg Ile
        435                 440                 445
Met Ala Leu Pro Arg Gly Tyr Asp Ser Val Pro Gly Arg Asp Leu Gln
    450                 455                 460
Leu Ser Gly Gly Glu Leu Gln Arg Leu Ala Leu Ala Arg Ala Leu Leu
465                 470                 475                 480
Ser Pro Ala Ser Leu Leu Leu Asp Glu Pro Thr Ser Ala Leu Asp
                485                 490                 495
Pro Gln Thr Ala Arg Gln Val Leu Arg Asn Leu Arg Glu Arg Gly Gly
            500                 505                 510
Gly Arg Thr Arg Val Ile Val Ala His Arg Leu Ala Glu Val Ser Asp
        515                 520                 525
Ala Asp Leu Ile Leu Val Leu Val Ala Gly Arg Leu Val Glu Arg Gly
    530                 535                 540
Glu His Ala Ala Leu Leu Ala Ala Asp Gly Ala Tyr Ala Arg Leu Trp
545                 550                 555                 560
Arg Glu Gln Asn Gly Ala Glu Val Ala Ala
                565                 570

<210> SEQ ID NO 35
<211> LENGTH: 1725
<212> TYPE: DNA
<213> ORGANISM: Pseudomonas aeruginosa

<400> SEQUENCE: 35

| | | | | | |
|---|---|---|---|---|---|
| atgaccctgt | tcgaacgaat | gcgtgcgctg | cccgaagact | gccgtgccgc | gttgcgccgg | 60 |
| gcgagcgcct | gggcggtcct | gcggcgctg | ctggacgccg | cttgcggcgt | attgctggtg | 120 |
| ccgttggtcg | aggcctggtt | cgccgaaggc | gcgttgccct | ggcgctgggt | cgccgcgttg | 180 |
| ctcggcttga | gctggcgca | ggcgctgttg | cagtacctgg | ccctgcgtcg | cggtttcgcc | 240 |
| gccggcggct | cgctggcggc | tggactggtg | cgcagcctgg | tggcgcgctt | gccgcgcctg | 300 |
| gcgccgccgg | cgctgcgccg | ggtcgcgccg | gccgaaggcc | tgctgcgcgg | cccggtgatg | 360 |
| caggcgatgg | gcattccggc | gcacctgctg | gggccgctga | tcgccgcgtt | ggtgacgccg | 420 |
| ctcggggtga | tcctcgggct | gttcctgatc | gacccgtcca | tcgccctcgg | cctgctcctt | 480 |
| gctggtgcct | tcctcgccgc | gctgttgcgc | tggagcgggc | ggcgcaatct | ggcggcggag | 540 |
| gatgcccggc | tggccgccga | gcgcgacgcc | gcacggcagt | gcaggcgtt | cgccgaacgc | 600 |
| cagccactgc | tgcgcgcggc | gcagcgcgaa | agcgtcgccc | gccagggct | ggaagaggcc | 660 |
| ttgcgcagtc | tccaccgcag | cacccctggat | ctgttgcggc | gcagcctgcc | cagcggcctc | 720 |
| ggcttcgccc | tggcggtgca | ggcggcgttc | gccttcgccc | tgctcggcgg | cgcctgggcg | 780 |

-continued

```
gtggagcggc aatggctgga cggcgctcgg ctggtggccg tgctggtgct gctggtgcgc      840
ttcatcgagc cgctggccca gctcacccat ctcgaccagg cgttgcgcgg cgcctggcag      900
gcgctggata ccctgctgcg ggttttcgcc ctggctccgc tgcgcagccc cgagccgggc      960
gagcggccgc acgacgccag cctggcggcc gaggccgtgg aattgcgcct ggaagatggc     1020
cgcgccttgc tcgaggacat tccctgagg ctggagccgg gttcgctgaa cgtcctcgtc     1080
ggaccctccg gggccggcaa gagcagcctg ctggcgctgc tcgggcggct ctacgacgtc     1140
gatgccgggc gtgtcctgct gggtggcgtg gatatccgcc ggttgagcga acgaccctc     1200 gccgccagtc gtaacctggt gttccaggac aacggcctgt tccgcggcag cgttgcctgg     1260
aacctgcgca tggcgcgagc ggacgccgat ctcgaagcgc tgcgcgaggc ggcgcgggcg     1320
gttggcctgc tggaagagat cgaggcctgg ccgcagggct gggacagcga cgtcggtccc     1380
ggcggcgcgc tgctgtccgg cggccagcgg caacgcctgt gcctggctcg cgggctgctc     1440
tcgacggcgc cgttgctgct gctcgacgag cccaccgcca gcctcgacgc cgccagcgag     1500
gcgcaggtgc tgcgcagcct gctcgggttg cgcggccggc gcaccctgct ggtagtgacc     1560
caccgcccgg cgctggcgcg tcaggccgac caggtactgc tgctggagga ggggcgcctg     1620
cgcctcagcg gacttcacgc cgatctgctc gtccgggacg actggtatgc cggtttcgtc     1680
gggctggcgg gcgaggaaag ttccgcgacg gtcgtggatc gatag                     1725
```

<210> SEQ ID NO 36
<211> LENGTH: 574
<212> TYPE: PRT
<213> ORGANISM: Pseudomonas aeruginosa

<400> SEQUENCE: 36

```
Met Thr Leu Phe Glu Arg Met Arg Ala Leu Pro Glu Asp Cys Arg Ala
 1               5                  10                  15

Ala Leu Arg Arg Ala Ser Ala Trp Ala Val Leu Ala Ala Leu Leu Asp
             20                  25                  30

Ala Ala Cys Gly Val Leu Leu Val Pro Leu Val Glu Ala Trp Phe Ala
         35                  40                  45

Glu Gly Ala Leu Pro Trp Arg Trp Val Ala Ala Leu Gly Leu Ser
     50                  55                  60

Leu Ala Gln Ala Leu Leu Gln Tyr Leu Ala Leu Arg Arg Gly Phe Ala
 65                  70                  75                  80

Ala Gly Gly Ser Leu Ala Ala Gly Leu Val Arg Ser Leu Val Ala Arg
                 85                  90                  95

Leu Pro Arg Leu Ala Pro Pro Ala Leu Arg Arg Val Ala Pro Ala Glu
            100                 105                 110

Gly Leu Leu Arg Gly Pro Val Met Gln Ala Met Gly Ile Pro Ala His
        115                 120                 125

Leu Leu Gly Pro Leu Ile Ala Ala Leu Val Thr Pro Leu Gly Val Ile
    130                 135                 140

Leu Gly Leu Phe Leu Ile Asp Pro Ser Ile Ala Leu Gly Leu Leu
145                 150                 155                 160

Ala Gly Ala Phe Leu Ala Ala Leu Leu Arg Trp Ser Gly Arg Arg Asn
                165                 170                 175

Leu Ala Ala Glu Asp Ala Arg Leu Ala Ala Glu Arg Asp Ala Ala Arg
            180                 185                 190

Gln Leu Gln Ala Phe Ala Glu Arg Gln Pro Leu Leu Arg Ala Ala Gln
        195                 200                 205
```

```
Arg Glu Ser Val Ala Arg Gln Gly Leu Glu Ala Leu Arg Ser Leu
    210                 215                 220

His Arg Ser Thr Leu Asp Leu Leu Arg Arg Ser Leu Pro Ser Gly Leu
225                 230                 235                 240

Gly Phe Ala Leu Ala Val Gln Ala Ala Phe Ala Phe Ala Leu Leu Gly
                245                 250                 255

Gly Ala Trp Ala Val Glu Arg Gln Trp Leu Asp Gly Ala Arg Leu Val
                260                 265                 270

Ala Val Leu Val Leu Leu Val Arg Phe Ile Glu Pro Leu Ala Gln Leu
            275                 280                 285

Thr His Leu Asp Gln Ala Leu Arg Gly Ala Trp Gln Ala Leu Asp Thr
            290                 295                 300

Leu Leu Arg Val Phe Ala Leu Ala Pro Leu Arg Ser Pro Glu Pro Gly
305                 310                 315                 320

Glu Arg Pro His Asp Ala Ser Leu Ala Ala Glu Ala Val Glu Leu Arg
                325                 330                 335

Leu Glu Asp Gly Arg Ala Leu Leu Glu Asp Ile Ser Leu Arg Leu Glu
                340                 345                 350

Pro Gly Ser Leu Asn Val Leu Val Gly Pro Ser Gly Ala Gly Lys Ser
            355                 360                 365

Ser Leu Leu Ala Leu Leu Gly Arg Leu Tyr Asp Val Asp Ala Gly Arg
370                 375                 380

Val Leu Gly Gly Val Asp Ile Arg Arg Leu Ser Glu Thr Thr Leu
385                 390                 395                 400

Ala Ala Ser Arg Asn Leu Val Phe Gln Asp Asn Gly Leu Phe Arg Gly
                405                 410                 415

Ser Val Ala Trp Asn Leu Arg Met Ala Arg Ala Asp Ala Asp Leu Glu
                420                 425                 430

Ala Leu Arg Glu Ala Ala Arg Ala Val Gly Leu Leu Glu Glu Ile Glu
            435                 440                 445

Ala Trp Pro Gln Gly Trp Asp Ser Asp Val Gly Pro Gly Gly Ala Leu
450                 455                 460

Leu Ser Gly Gly Gln Arg Gln Arg Leu Cys Leu Ala Arg Gly Leu Leu
465                 470                 475                 480

Ser Thr Ala Pro Leu Leu Leu Leu Asp Glu Pro Thr Ala Ser Leu Asp
                485                 490                 495

Ala Ala Ser Glu Ala Gln Val Leu Arg Ser Leu Leu Gly Leu Arg Gly
                500                 505                 510

Arg Arg Thr Leu Leu Val Val Thr His Arg Pro Ala Leu Ala Arg Gln
            515                 520                 525

Ala Asp Gln Val Leu Leu Glu Glu Gly Arg Leu Arg Leu Ser Gly
            530                 535                 540

Leu His Ala Asp Leu Leu Val Arg Asp Asp Trp Tyr Ala Gly Phe Val
545                 550                 555                 560

Gly Leu Ala Gly Glu Glu Ser Ser Ala Thr Val Val Asp Arg
                565                 570

<210> SEQ ID NO 37
<211> LENGTH: 558
<212> TYPE: DNA
<213> ORGANISM: Pseudomonas aeruginosa
<220> FEATURE:
<221> NAME/KEY: misc_feature
<222> LOCATION: (85)..(85)
<223> OTHER INFORMATION: n is a, c, g, or t
```

```
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (174)..(175)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t

<400> SEQUENCE: 37
ctctttcagc cgcacgcggc gcacctcgtg tgtgatcagt gagtggtttg caactgcggg    60
tcaaggatct ggatttccct cacangtncg atcatcgtgc gggagggcaa gggctccaag   120
gatcgggcct tgatgttacc cgagagcttg cacccagcc tgcgcgagca gggnnaattg   180
atccggtgga tgaccttttg aatgaccttt aatagattat attactaatt aattggggac   240
cctanaggtc ccctttttta ttttaaaaat tttttcacaa aacggtttat ttncataaag   300
cttgctcaat caatcaccnt atccncggga attcggccta gcggccaga tctgatcaag   360 agacagacct ccagctttgc atccggagcg accacacgag cgaggtcagt cactttcatc   420
gaaggaattt tcttgacata gatctcacca ccttccatgt cctcaaaggc atgccacact   480
aactcgacgc cctcctccaa agaaatcatg aaccgggtca tccgctcatc agtgataggc   540
aagacgccct tgtccttg                                                 558

<210> SEQ ID NO 38
<211> LENGTH: 479
<212> TYPE: DNA
<213> ORGANISM: Klebsiella sp.

<400> SEQUENCE: 38
acgcaggata tcttcttcat caaattgtcg atgcccgcct tcgctacgct gcggtttcag    60
tagaccgtaa cgacgctgcc aggcgcgcag tgtgaccgga ttgattccgc aacgttcggc   120
gacttcaccg atactgtaaa acgccatagc agcctcacat caacctgata ccttaatacc   180
taaactaacg aattcaggca tcctgtacaa ctctattttc ttgtacagat aaagatatca   240
ggttgcggct cacagcgccc gggaaaaaag atgaaaaaat gtttagctga tttcgcggtg   300
gttcattttt tctccggcca tgcgacggcg ggtaggcccc ccaggcgcgc gctggcgaac   360
aaattgccct gaaactgtga ataccggct gattccagcc acatccactc ttcagcacgc    420
tcaacgccga cggctgagac cgcaatctcc agagaagtac agcatttgat aatcgcctg    479

<210> SEQ ID NO 39
<211> LENGTH: 516
<212> TYPE: DNA
<213> ORGANISM: Klebsiella sp.

<400> SEQUENCE: 39
```

```
gaccatgtgc tgatgaccaa taccgcctat gagccaagcc aggacttttg taccaaaatt    60
ctcgccaaac tcggcgtcac caccagctgg ttcgatccct taatcggcgc cgatatcgcc   120
cgtctggttc gccctgagac ccgcgtggtg ttcctcgaat cgcccggctc gatcaccatg   180
gaagtgcacg atgtgccggc gatagtcgcc gccgtgcgtc aggtcgcccc ggaagcgatt   240
atcatgatcg ataacacctg ggcggcgggg atcctgttta agccctgga ttttggcatt   300 gatatttcca ttcaggcagg caccaaatac ctgatcggcc attccgacgc catggtgggc   360
accgcggtgg cgaacgcgcg ctgctggccg cagctgcgtg aaaatgccta cctgatgggg   420
caaatgctgg acgccgatac tgcctatatg accagccgcg gcctgcgaac cctgggcgtg   480
cgcctgcgtc agcatcatga aagcagcctg cgcatc                             516

<210> SEQ ID NO 40
<211> LENGTH: 377
<212> TYPE: DNA
<213> ORGANISM: Klebsiella sp.

<400> SEQUENCE: 40
cttttggccc cttttttgtc tttattctgg agaacttatt atggcgaaag aatttggtcg    60
cccgcagcgt gtggcccagg agatgcaaaa agagattgcc atcatcctgc agcgtgaaat   120
taaagatccg cgtctgggca tgatgaccac cgtttccggt gtggaaatgt cccgtgacct   180
ggcctatgcc aaggtgtatg tcaccttcct taacgacaaa gatgaagccg cggtgaaagc   240
gggcatcaaa gcgctgcagg aagcttctgg ctttatccgc tctctgctgg ggaaagcgat   300
gcgtctgcgc atcgtaccgg aactgacttt cttctacgac aactcactgg tggaagggat   360
gcgtatgtcc aacctgg                                                 377

<210> SEQ ID NO 41
<211> LENGTH: 625
<212> TYPE: DNA
<213> ORGANISM: Klebsiella sp.

<400> SEQUENCE: 41
gcccagcccg ctttcccgct tgcccagtta aaagccttcg tggagcagga atttgctcag    60
attaagcatg ttctgcacgg catcagcctg ctgggtcagt gcccggacag cgtcaatgcc   120
gcgctgatct gccgcggcga aaagctctcc atcgccatca tggcgggtct gctggaagcc   180
cgtggacaca aagtcagtgt cattaacccg gtcgaaaaac tgctcgccgt gggtcactat   240
ctggaatcca ccgtcgatat cgccgaatcc accgccgcca ttgccgccag ccagatcccg   300
gcagaccata tgatcctgat ggccgggttt accgccggca atgagaaagg cgagctggtg   360
gtgctggggc gtaacggctc cgactactcg gctgcgtac tggccgcctg cctgcgcgct   420
gactgctgcg aaatctggac cgatgtcgac ggagtgtaca cctgcgatcc gcgtcaggtg   480
ccggatgcgc gcctgctgaa atcgatgtct tatcaggagg cgatggagct ctcctacttt   540
ggcgcgaaag tgctgcaccc gcgcaccatt gccctatcg cccagttcca atcccatgc   600 ctgattaaaa ataccggcaa ccccc                                         625

<210> SEQ ID NO 42
<211> LENGTH: 355
<212> TYPE: DNA
<213> ORGANISM: Klebsiella sp.

<400> SEQUENCE: 42
ggcgcagcgt ctgctcgtca ccgtcaagct cgaagcttaa cattgcgcca aaaccttttt    60
```

```
gctgacgcgc cgcaatttca tgccctggt tttccggcag cgatggatga tacagcttt    120 tcaccagcgg ctgggttttc agatactcaa cgatcgccag ggcatttcgc tgcgccactt   180
ccatccgtgg agacagcgtc cgcagcccgc gcaacagcag atagctgtcg aaggcgctgc   240
cggtgacgcc aatattattc gcccaccatg ccagttcggt gacagttgcc ggatctttgg   300
caatcaccac cccggccacc acatcggagt gaccattgag gtatttggta cagga         355

<210> SEQ ID NO 43
<211> LENGTH: 500
<212> TYPE: DNA
<213> ORGANISM: Klebsiella sp.

<400> SEQUENCE: 43
gttgcgtccc aggcgggtaa acgcatcctg caggtagtca atttcgtcgt cggccagcgc    60
cagacccaga cggaggttgg cgtcaatcag cgcctgacgc ccttcgccca gcaggtcgac   120
gctggtgacc ggcgtcggct gatggtgagc gaacagcttc tcgcccgctt ccagctcgtc   180
gaagacgctc tccatcatgc ggtcatgcag ctccgccgcc accgcggccc actgcgcttc   240
ggtcagggtt gaggcttcaa cgtaatacgc cacgccgcgc tcaagacgca caacctgcgc   300
cagaccgcag ttgtgagcga tatcggtagc tttagaagac cagggagaga tggtgccagg   360 gcgagggtc acgagcagta atttaccggt cggggtatgg ctgcttaagc tcgggccata   420
ctgaagcagt cgcgccaggc gctcgcgatc gtcagcgctc agcggggcgt tcagatcggc   480
aaaatgaata tattcggcat                                              500

<210> SEQ ID NO 44
<211> LENGTH: 439
<212> TYPE: DNA
<213> ORGANISM: Klebsiella sp.

<400> SEQUENCE: 44
gtattggcat cgtactcctg ggctggccgg tgacaaaggc gatgcgctta tctttgctgg    60
cgaacaaata cgcatcgccc tcttccgtct ccgcgaggat ctcgagatcg gtatagtcgc   120
gaataagtcc ggccggaaaa tcagcatagc gtgagtgcgg ggccaggaaa gagtcgtcga   180
aaccgcgggt cagtaaggcg tgcggatgaa gaatatggtg ttcatagacg ccggaaatct   240
tttcggcgcg ggtctgcttg ggaatgccgt acagaatgtt cagcgcggcc tgaaccgccc   300
aacagacgaa cagcgtcgaa gtgacgtgat ccttggccca ctccagcacc tgtttgatct   360
gcggccagta agcaacatcg ttaaactcaa ccaggcctaa aggagcgccg gtaacaatca   420
ggccgtcaaa gttctgatc                                               439

<210> SEQ ID NO 45
<211> LENGTH: 297
<212> TYPE: DNA
<213> ORGANISM: Klebsiella sp.

<400> SEQUENCE: 45
gaggttcata tgtccgtact cgatctaaac gcgcttaatg cattgccgaa agtggaacgc    60
attctggcac tcgcggaaac caacgcccaa ctggaaaagc ttgacgccga agggcgtgtg   120
gcgtgggcgc tggaaaatct gccgggaaac tatgtgctgt cgtcgagctt tggcattcag   180
gcggcggtaa gtttgcatct ggtgaatcag atccgcccgg acattccggt gatcctcacc   240
gataccggct acctgttccc ggaaacctat cagtttattg acgagctgac ggacaag      297
```

<210> SEQ ID NO 46
<211> LENGTH: 502
<212> TYPE: DNA
<213> ORGANISM: Klebsiella sp.

<400> SEQUENCE: 46

| | | | | | |
|---|---|---|---|---|---|
| tgttaaagcg | tgcgttctac | agcctgttag | tcctgctcgg | cctgctgctg | ttgaccgtgc | 60 |
| tgggccttga | ccgctggatg | agctggaaaa | ccgcgcccta | tatctatgat | gaactgcagg | 120 |
| acctgcccta | ccgtcaggtc | ggtgtggtgc | tgggcaccgc | caaatattac | cgcaccggcg | 180 |
| tcatcaatca | gtattaccgt | taccgcatcc | agggtgcgct | gaacgcctac | aacagcggca | 240 |
| aggtcaacta | tctcctgctg | agcggcgata | atgctctgca | aagctacaat | gaaccgatga | 300 |
| ccatgcgtcg | ggacctgatt | aaaggcggcg | tcgatcccgc | ggatatcgta | ctggactatg | 360 |
| ccggtttccg | taccctcgac | tcgatcgtcc | gtacccggaa | agtgttcgac | accaacgact | 420 |
| tcattatcat | cacccagcgc | ttccactgcg | aacgggcgct | gtttatcgcc | ctgcatatgg | 480 |
| ggatccaggc | ccagtgctac | gc | | | | 502 |

<210> SEQ ID NO 47
<211> LENGTH: 500
<212> TYPE: DNA
<213> ORGANISM: Klebsiella sp.

<400> SEQUENCE: 47

| | | | | | |
|---|---|---|---|---|---|
| cgctgaacct | cctcaaacaa | acgcaggccc | tgcacctgtc | ggctgcaggc | gaccagcgtg | 60 |
| gatccgctca | aacagctgca | ggccgagcac | cttctcaaag | cgcgccagct | cgcggctgac | 120 |
| cgtgggttgc | gaggtgtgca | gcatccgcgc | gcttcggtc | aggttgccgg | tggtcatcac | 180 |
| cgcgtgaaag | atttcgatat | gacgcaaatt | gacggctggc | atgcggtctc | cgtgaggctc | 240 |
| ggctggaacc | atatcatttt | tgcatagagt | cgcgataaaa | cgatattttt | tattcgtctg | 300 |
| tcactgtggc | gtaatcagaa | aaaacagcga | ccaacacacg | cactgcaccg | gagttcttat | 360 |
| gccacactcg | ctttacgcca | ccgatactga | cctgaccgcg | gacaacctgc | tgcgcctgcc | 420 |
| ggcggaattt | ggctgcccgg | tctgggtcta | tgatgcgcag | attattcgcc | gccagatagc | 480 |
| ccagctcagc | cagtttcgac | | | | | 500 |

<210> SEQ ID NO 48
<211> LENGTH: 229
<212> TYPE: DNA
<213> ORGANISM: Klebsiella sp.

<400> SEQUENCE: 48

| | | | | | |
|---|---|---|---|---|---|
| ggcttccacc | caaatcgctt | tgtcggcaac | gattttgct | aaaacggctt | tgcattcttt | 60 |
| accctcttgc | ccgctaagtg | cggtcactct | gtcataggcc | gcgccgctgc | tgcagcacat | 120 |
| ccagtacctg | ctgagcgtta | gctttcagat | cttcatgccc | gtgtaaacgc | atcaatatgg | 180 |
| cgacgttggc | ggcgacggcg | gcttcgtgag | cggcttcacc | tttaccttg | | 229 |

<210> SEQ ID NO 49
<211> LENGTH: 466
<212> TYPE: DNA
<213> ORGANISM: Klebsiella sp.

<400> SEQUENCE: 49

| | | | | | |
|---|---|---|---|---|---|
| tggctcaacg | ctgctcagtg | gtgcgaggtg | tcactttggt | gatcacatcg | gcgttgtctg | 60 |
| cacagtgaaa | tcagatccag | cgccgcgtcc | ggttttacgc | acgtagtccg | gattgtgggt | 120 |

-continued

```
gcctttctta acgatattca gccacggccc ttcgagatgc aggcccagcg cctggttcgg    180 atgttttttgc agatattcgc gcatcacgcg cacgccttgc ttcatcagat cgtcgctgga   240
ggtaatcagc gtcggcagga agctggtgca gcctgagcgt tcgttggcct tctgcatgat    300
ctccagcgtt tcgacagtga ccgcctctgg gctgtcgtta aactgcacgc cgccgcagcc    360
gttgagctgg acgtcgataa accgggggc gattattgcg ccgttgactg agcgctgctc     420
gatgtcagac ggcaaatctg ccagcggaca aagacgttcg ataaag                   466
```

<210> SEQ ID NO 50
<211> LENGTH: 450
<212> TYPE: DNA
<213> ORGANISM: Klebsiella sp.

<400> SEQUENCE: 50

```
ttaagcacca tatcgtaccg ctgctggcgc agcgtctgaa tgagctgcca ttgcatcttc    60
agctgatacc tttttccctg gcttttttcca gcggcgatcg agaccataaa tatggtggat   120
atcggggttg gctgcgagca tatcccgggt ctcttcatac aacaggacat ccacgctggc   180
ggcggggtac tgctgtttca gcgcgtgaat aagcggcgtg atcagcagca tgtcgccatg    240
atggcgcagc ttaatgacca ggatccgcgc cgggttcaac gggccgcggg agagggtttc    300
aggcgtcata ctctgttctt catccaggat aagggttccg attctagggg atcagacaga   360
ttgagagaag cgttgtattg ctctaccatg acccgatacg tatggcctga ggacgttttc    420
gtgcacaatc ccgcaatttc tcatcacgat                                      450
```

<210> SEQ ID NO 51
<211> LENGTH: 450
<212> TYPE: DNA
<213> ORGANISM: Klebsiella sp.

<400> SEQUENCE: 51

```
cactcaggct tgcctgtaac gcttgttcgc catcacgtaa ggtcgtatcg aaaataatga    60
cttgctggct catggtttgg atccttagtc tgtgtcctgg cgccttgttg acgagcataa   120
aaaaacccgc gccaaggcgc gggttttata gtcttgctgg aagatgactt aacgctgaac    180
gtcgcccaac agcctaccga gcaaatggca tgcgtttagt agtagtaggc tggtgatacg    240
agcggtgcga atcattgcgt caaactccag atgaaatcgt tatgctttta gagttactgg    300
atagccgttt taaagtcaac ccctggcatg gaaaaagcgt tttgggctga ctaaatgaat    360
tagcaaaatg tgctgatgta agccccattt tgccgaagat cctatttttgg accgaaggcg   420 gtttatcccc aatttgtttc atttgaaaaa                                      450
```

<210> SEQ ID NO 52
<211> LENGTH: 575
<212> TYPE: DNA
<213> ORGANISM: Klebsiella sp.

<400> SEQUENCE: 52

```
cgctgaaccg ctatccggag ccgcagccga agtgccgtga ttgagagcta cgcccgctac    60
gccgaggtca aaccggagca ggtgctggtc agccgcggcg ccgacgaagg catcgagctg   120
ctgatccgcg ccttctgtga gccggcgaa acgcggtgc tctactgccc gccgacctac    180
ggcatgtaca cgcgtcagcgc cgagaccatc ggcgtcgagt gccgcaccgt ccgacgctg    240 gccagctggc agctcgacct gccgggcatc gaagcgcggc tggacggcgt gaaggtggtg    300
```

```
tttgtctgca gcccgaacaa cccgaccggg cagattatcg acccgcagtc gatgcgcgac    360
ctgctggaga tgacccgcgg caaagccatc gtggtggccg acgaagccta tattgaattc    420
tgcccgcagg cgacgctcgc cggctggctc agcgactatc cgcacctggt ggtgctgcgc    480
acgctgtcca aagccttcgc cctcgccggc ctgcgctgcg gcttcaccct cgccaacgcc    540
gaggtgatta acgtgctgct gaaagtgatc gcccc                              575

<210> SEQ ID NO 53
<211> LENGTH: 375
<212> TYPE: DNA
<213> ORGANISM: Klebsiella sp.

<400> SEQUENCE: 53
cgtatatttc atcgtacaga aaccgtaaac acaggcattg gctgattttc agtgagtgaa     60
tttaaataga cttctgccgt tttcaatgct tcggcgatgg tcacatccat atcaaggtaa    120
cggtaggttc caagacgacc gacaaaagtg atgttggttt cattctcggc caatgacaaa    180
tatttttcaa gaagagccat ttctcccatc tggcgaatag gatagtaagg aatatcattt    240
tcttcacaag cacggctata ctctttataa caaacagagc cgtcgtgttg tcccaggga     300 gaaaaatatt tatgttcagt gatgcgagta tagggcacat ccacagaaca gtagttcatc    360
actgcgcatc cctgg                                                    375

<210> SEQ ID NO 54
<211> LENGTH: 400
<212> TYPE: DNA
<213> ORGANISM: Klebsiella sp.

<400> SEQUENCE: 54
gtacgccgat tttatatgcg tctgatatga ttccggaaaa atttagctgg ataattacct     60
acaatccgct agcgagtatg attcttagtt ggcgtgattt attcatgaat gggactctta    120
attttgagta tatttctata ctctatttta cgggaattat tttgacggtt gtcggtttgt    180
ctattttcaa taaattaaaa tatcgatttg cagagatcta aaagtgcgct ataagagcag    240
catgctaggc tatttatggt cagtagcaaa tccattgctt tttgccatga tttactattt    300
tatatttaag ctggtaatga gagtacaaat tccaaattat acagttttcc tcattaccgg    360
cttgtttccg tggcaatggt ttgccagttc ggccactaac                         400

<210> SEQ ID NO 55
<211> LENGTH: 413
<212> TYPE: DNA
<213> ORGANISM: Klebsiella sp.

<400> SEQUENCE: 55
cgagccaccc actgtagcgt atggatatcg cgcaagccgc cggggctgct tttcacgtcc     60
ggctcgaggt tatagctggt gccatgatag cgctgatgac ggacgttctg ctcttcgacc    120
ttggcggcga agaactttc cgatggccag aagccgtcgc taaaaatatg tttttgcagt    180
tcaaggaaca gcgcgacgtc gccgatcagc aggcgcgatt cgattaagtt ggtggcaacg    240
gtcagatccg agagaccttc cagcaggcac tcttcgaggg tgcgtacgct gtggcccacc    300
tccagcttga cgtcccacag cagggtgagc agttcgccga cttttttgcgc ctggtcgtcc    360 ggcagttttt tacgactgag gatcagcaga tcgacgtctg agagcgggtg cag           413

<210> SEQ ID NO 56
<211> LENGTH: 500
```

```
<212> TYPE: DNA
<213> ORGANISM: Klebsiella sp.

<400> SEQUENCE: 56
cttaacccgc acgctggcga aggcggccat atgggaacag aagagataga caccatcatt      60
ccggtgctgg aagagatgcg cgcaaagggg atgaacctca gcggtccgct gccggcagac     120
actctctttc agccgaaata tcttgatcat gccgatgcgg tactcgcgat gtaccacgat     180
cagggcctgc ccgtgctaaa ataccagggc tttggccgcg cgtgaacat  tacgctcggt     240 ttaccttta  ttcgtacctc cgtcgaccac ggcaccgcac tggaattagc gggccaggga     300
aaagcggacg tcggcagttt tatcacggcg cttaatctcg ccatcaaaat gattgttaat     360
acccaatgaa taatcgagtc catcaggggcc atttagcccg caaacgcttc gggcagaact    420
tcctcaacga tcagtttgtg atcgacagca tcgtctcggc gattaacccg cagaaaggcc    480
aggcgatggt tgaaatcggc                                                 500

<210> SEQ ID NO 57
<211> LENGTH: 473
<212> TYPE: DNA
<213> ORGANISM: Klebsiella sp.

<400> SEQUENCE: 57
gggtctgacc ccggttctgt gcatcggtga aaccgaagcc gaaaacgaag cgggcaaaac      60
ggaagaagtt tgcgcacgtc agatcgacgc cgtgctgaaa acccagggcg ctgccgcttt     120
cgaaggcgtg gttatcgctt acgaaccagt atgggctatc ggtaccggca atcagcgac     180 cccggctcag gcgcaggcgg tgcacaaatt catccgtgac cacattgcta aagctgacgc    240
caaaatcgct gagcaagtga tcatccagta cggcggttcc gttaacgctg caacgccgc     300 agagctgttc acccagccgg acatcgacgg cgcgctggtt ggcggcgcct ccctgaaagc    360
tgacgctttc gcggtgatcg ttaaagcagc agaagcagcg aaaaaagcgt aattcgcttt    420
tcccggtggc gacacgcgac cgggttgact gacaaaacgt gggagcccgg cct           473

<210> SEQ ID NO 58
<211> LENGTH: 463
<212> TYPE: DNA
<213> ORGANISM: Klebsiella sp.

<400> SEQUENCE: 58
ggtggcgcac cctggcgtcg tttgtgtaga aattatgaat attaatacca ggaaaattcc      60
taatttttgt gtacgctctg acgagcgcac aataaaacaa gacgaatttt tgaacaattg    120
tctttaaatt tgttaattga attgatctgt tgttgtttaa aggtatttga atttcttttg    180
tatagatatg taaattaaca ttgaaaagcc atttcaaaaa ttaaatatat ggcgaacata    240
gctattaact tatagttaac atcttcccgg gttgcctttt gatacttcgg gtaatatatt    300
tatttcgcac atcaaaataa ctcttttttc ttctgtttgt tattcatggc catctattgg    360
cgaaataagg cagagtagag ggggatgtgc ctaatatcct gcggaaggaa cgcaatgtac    420
atttacaggg aggagctgac gagccgtttc gcgatagctt tag                       463

<210> SEQ ID NO 59
<211> LENGTH: 526
<212> TYPE: DNA
<213> ORGANISM: Klebsiella sp.

<400> SEQUENCE: 59
```

```
ttggtggtgt gctcgcgaag aaatttaatc tgccggtcat cgtaagtttt gttgggcttg    60
gaagagtatt ttcttctgac agcatgcctt taaaattatt gcggcagttt actattgctg   120
catataaata tattgccagt aataagcgct gtatatttat gtttgaacat gaccgcgaca   180
gaaaaaaact ggctaagttg gttggactcg aagaacaaca gactattgtt attgatggtg   240
caggcattaa tccagagata tacaaatatt ctcttgaaca ggatcacgat gtccctgttg   300
tattgtttgc cagccgtatg ttgtggagta aaggactggg cgacttaatt gaagcgaaga   360
aaatattacg cagtaagaat attcacttta ctttgaatgt tgctggaatt ctggtcgaaa   420
atgataaaga tgcaatttcc cttcagggtc attgaaaatt ggcatcagca aggattaatt   480
aactggttag gtcgttcgaa taatgtttgc gatcttattg agcaat              526
```

<210> SEQ ID NO 60
<211> LENGTH: 473
<212> TYPE: DNA
<213> ORGANISM: Klebsiella sp.

<400> SEQUENCE: 60

```
ttacttgccc cttttgccg aactgaaaca aaggcccgtg ctggtgatcg gcggcggcga    60
gattgctgaa cgtaagatca agttcctgct gcgcgcccag gcgcaggtgc aggtggtcgc   120
tgaaacgctg tcaccggcgc tggccgatct ggctgcgcgc caggcactca gctggcgggc   180
gacggcattc agcgactcgc tggtggatga tgtctttctg gtgattgcgg ccaccgagga   240
tgaggcgctt aaccagcggg tgtttgcggc agctaacgcg cgctaccggt tggtcaacgt   300
ggtggataac caggcgctgt gctcgtttgt tttcccttct atcgtcgacc gttcgccgct   360
gctggtggcg atctcctcca gcggtaaagc gccggtgttg tcgcgcattc tgcgtgaaaa   420
aatcgaagcg ctgctgccga cgaatctcgg tcggctggcg gaatcagcaa gct         473
```

<210> SEQ ID NO 61
<211> LENGTH: 451
<212> TYPE: DNA
<213> ORGANISM: Klebsiella sp.

<400> SEQUENCE: 61

```
agcagggcaa tggtggtcgg tttcataaca tttcctgatg atgaaagtca tattaaccgg    60
cattctaaca gcagcattca gagggcaat gattttgggc aaccgattac gacgatcgcc   120
gcaaatgcta aaaagggag aggggattac cagctggcgg gcttttccgc gccgagatta   180
tccagcacgg cgcgcagcgc caggccgtca ggaaagtgaa ggtccggggc gatctcgaac   240
agcggccaga gcataaagcc gcggttttc atatcgtagt gcggaacggt caggcgctcg   300
ctgttaatga cagcatcgcc aaacagcatg atatcgaggt ccagcgtgcg cggccccag   360 cgttcggctt tgcgcactcg cccctgctgc agttcgatgc gctgagtatg atcgagcagc   420
gtctcggggg gcagggcggt ttccagcgca a                              451
```

<210> SEQ ID NO 62
<211> LENGTH: 525
<212> TYPE: DNA
<213> ORGANISM: Klebsiella sp.

<400> SEQUENCE: 62

```
ggcttaacgc cagctatgtc aacgctgcgg ttatgcggat ttttcatgcc tctgcggcta    60
acagaaaaaa gccttatgat agctatacta atgggctttt ttactccgtt ttgacccgat   120
tcctgaccgg cgtcagggtc aagtcacaaa aatcatcaca attttccgtc accggcgcta   180
```

```
caatcgaccg aagtcacaat ctcaaatcag aagagtattg ctaatgaaaa acatcaaccc      240
aacgcagacc tctgcctggc aggcattaca gaaacacttc gacgaaatga aagatgtcac      300
tatcagcgag cttttcgcca aagatagcga ccgttttcct aaattttccg cgacgttcga      360
cgatctgatg ctggtggact tctccaaaaa ccgcatcact gaagagacgc tggctaaact      420
gcaggatctg gcgaaagaga ctgacctggc gggcgctatc aagtcgatgt tctcaggtga      480
gaagatcaac cgcaccgaag accgcgcggt actgcacgtc gcgct                     525

<210> SEQ ID NO 63
<211> LENGTH: 475
<212> TYPE: DNA
<213> ORGANISM: Klebsiella sp.

<400> SEQUENCE: 63
tgcttcatcc gcatctcctt gaaatttatt tggtcttagg cggacggtag agcgctaata       60
gctcgtccac cttttacgc gtaccaccgt tgctgctgat gctgcgccgc accttcacaa      120
tatgcgtttc tgccgcgttt ttataccatt cctgcgtcag cggcgtgcgg tggttggaaa      180
tcagcaccgg gatgcgcttt ttcatcagcg attccgcctt ttgcgccagc agtacctgtt      240
gttccaggtt gaaactgttg gtgtggtagg cggtaaagtt cgccgtcgcc gttagcggcg      300
catagggcgg atcgcaatac accactgtgc ggctatccgc acgttgcatg cactcttcgt      360
aagattcgca gtaaaactcg gcgttttgcg ccttctcggc gaaatgatag agctcagctt      420
cggggaaata gggcttttta taacggccaa acggcacatt gaactcgccg cgcag         475

<210> SEQ ID NO 64
<211> LENGTH: 286
<212> TYPE: DNA
<213> ORGANISM: Klebsiella sp.

<400> SEQUENCE: 64
tgtcaatgcg caatttggtt aaatatgtcg gtattggcct gctggtgatg gggcttgccg       60
cctgcgataa cagcgattca aaagcgccaa ccgttggcgc agcagcggag agcaatgcca      120
gcggccaggc aatcagcctg ctggatggca agctgagctt caccctgcct gcgggcatgg      180
ccgaccagag cggcaaactg ggtacccagg cgaacaatat gcacgtctac tctgacgcta      240
ccggccagaa agcggtcatc gtcatcgtcg gcgacagcac caatga                   286
```

VIRULENCE GENES, PROTEINS, AND THEIR USE

FIELD OF THE INVENTION

This invention relates to virulence genes and proteins, and their use. More particularly, it relates to genes and proteins/peptides obtained from gram-negative bacteria, and their use in therapy and in screening for drugs.

BACKGROUND OF THE INVENTION

According to health care experts, infectious diseases caused by microbes are responsible for more deaths worldwide than any other single cause. The current estimate of the annual cost of medical care for treating infectious diseases in the United States alone is about $120 billion. While antibiotic treatment is effective for many microbial infections, antibiotic resistance among pathogenic bacteria is a growing health concern. Indeed, the American Medical Association has concluded that, "the global increase in resistance to antimicrobial drugs, including the emergence of bacterial strains that are resistant to all available antibacterial agents, has created a public health problem of potentially crisis proportions."

*Pseudomonas* and *Klebsiella* are two genuses of gram-negative bacteria that pose a significant health risk to infected host organisms, in part, due to their resistance to many antibiotics. These bacteria are noted for causing life-threatening infections, particularly in the lung. Cancer and burn patients also commonly suffer serious *Pseudomonas* infections, as do certain other individuals with immune system deficiencies. While *Klebsiella* sp. is responsible for many types of infections, outside of a medical setting, the most common infection caused by *Klebsiella* bacteria is pneumonia.

There is a need in the art for new antimicrobial therapeutic strategies.

SUMMARY OF THE INVENTION

The present invention is based, in part, on the discovery of 46 genes, when mutated lower the virulence of a gram-negative bacterium, and can be used in new antimicrobial therapeutic strategies. The invention provides attenuated bacterial mutants that are derived from pathogenic strains. These attenuated bacterial stains have a mutation in a VIRX gene identified herein as VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR39, VIR40, VIR41, VIR42, VIR43, VIR44, VIR45, and VIR46; and show reduced inhibition of *Dictyostelium* amoeba growth when compared to the growth observed in the presence of an isogenic bacterial strain. The term, "pathogenic," as used herein, is defined as an agent's ability to cause disease, damage or harm to a host organism. The term, "attenuated," as used herein, means an organism made less virulent relative to an isogenic pathogenic organism. The term, "mutant," as used herein, an organism carrying a specific mutation of a gene that is expressed in the organism's phenotype. A mutation may be insertional inactivation or deletion of a gene. It is preferred that the mutation be an insertional inactivation of a gene.

The invention also provides attenuated bacterial mutants that are derived from pathogenic gram-negative bacterial strains. These attenuated gram-negative bacterial strains have a mutation in a VIRX gene identified herein as VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR39, VIR40, VIR41, VIR42, VIR43, VIR44, VIR45, and VIR46; and show reduced inhibition of *Dictyostelium* amoeba growth when compared to the growth observed in the presence of an isogenic bacterial strain. A mutation may be insertional inactivation or deletion of a gene. It is preferred that the mutation be an insertional inactivation of a gene. It is also preferred that the attenuated gram-negative bacterial mutant be derived from a *Pseudomonas* or *Klebiella* spp. It is more preferred that the attenuated gram-negative bacterial mutant is a strain of *P. aeruginosa* or *K. pneumoniae*.

The invention additionally provides for a VIRX gene that may be part of an operon. The term, "operon," as used herein, is a unit of bacterial gene expression and regulation comprising several genes, usually with complementary functions. Insertion in a gene in an operon typically interferes with the function of this gene and of other genes located downstream or upstream in the operon. The function attributed to a gene refers to its function and/or that of any gene located downstream or upstream in the same operon. Accordingly, the invention also provides for a bacterial strain comprising an operon encoding a gene selected from the group consisting of VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR38, VIR39, VIR40, VIR41, VIR42, VIR44, VIR45, and VIR46, wherein the bacterial strain includes a mutation that reduces expression of the VIRX gene relative to an isogenic bacterial strain lacking the mutation. In one embodiment, the the mutation reduces inhibition of *Dictyostelium* amoeba growth when compared to the growth of *Dictyostelium* amoeba in the presence of an isogenic bacterial strain lacking the mutation.

The invention provides for one or more of the following attenuated *Pseudomonas* mutant strains: MUT1; MUT2; MUT3; MUT4; MUT5; MUT6; MUT7; MUT8; MUT9; MUT10; MUT11; MUT12; MUT13; MUT14; MUT15; MUT16; MUT17; MUT18; and MUT 19. The invention also provides for one or more of the following attenuated *Klebsiella* mutant strains: MUT20; MUT21; MUT22; MUT23; MUT24; MUT25; MUT26; MUT27; MUT28; MUT29; MUT30; MUT31; MUT32; MUT33; MUT34; MUT35; MUT36; MUT37; MUT38; MUT39; MUT40; MUT41; MUT42; MUT43; MUT44; MUT45; and MUT46.

The invention additionally provides a method for identifying an antimicrobial drug, wherein a candidate composition is contacted with at least one polypeptide encoded by a gene selected from the group consisting of VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR39, VIR40, VIR41, VIR42, VIR43, VIR44, VIR45 and VIR46. The biological activity of polypeptide in the presence of the candidate composition is compared with the biological activity of the polypeptide in the absence of the candidate composition. Alteration of the biological activity of the polypeptide indicates that the candidate composition is an antimicrobial drug. In some embodiments, the candidate composition contains at least two molecules. The candidate composition can contain at least one molecule less than about 500 Daltons or at least one molecule greater than about 500 Daltons. The candidate composition can be, e.g., an immunoglobulin, polysaccharide, lipid, nucleic acid, or combination thereof.

The invention additionally provides a method for identifying an antimicrobial drug, wherein a candidate composition is contacted with at least one polynucleotide encoded by a gene selected from the group consisting of VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR39, VIR40, VIR41, VIR42, VIR43, VIR44, VIR45, and VIR46. The expression of the polynucleotide in the presence of the candidate composition is compared with the expression of the polynucleotide in the absence of the candidate composition. Alteration of the expression of the polynucleotide indicates that the candidate composition is an antimicrobial drug. In some embodiments, the candidate composition contains at least two molecules. The candidate composition can contain at least one molecule less than about 500 Daltons or at least one molecule greater than about 500 Daltons. The candidate composition can be a polypeptide, polysaccharide, lipid, nucleic acid, e.g., ribonucleic acid, or combination thereof. In a preferred embodiment, the ribonucleic acid of the candidate composition is a small interfering ribonucleic acid.

The invention additionally provides a method for determining the degree of virulence of a pathogen present in a subject, comprising:

(a) measuring the level of expression of at least one polypeptide encoded by a gene selected from the group consisting of VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR39, VIR40, VIR41, VIR42, VIR43, VIR44, VIR45, and VIR46, in a sample from the first subject; and (b) comparing the amount of the polypeptide in the sample of step (a) to the amount of the polypeptide present in a control sample from a second subject known not to have the presence of the pathogen, wherein an alteration in the expression level of the polypeptide in the first subject as compared to the control sample indicates the degree of virulence of the pathogen.

In a preferred embodiment, the subject is a mammal. It is more preferred that the subject is a human.

The invention also provides a method for determining the degree of virulence of a pathogen present in a subject, comprising:

(a) measuring the level of expression of at least one polynucleotide encoded by a gene selected from the group consisting of VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR39, VIR40, VIR41, VIR42, VIR44, VIR45, and VIR46, in a sample from the first subject; and (b) comparing the amount of the polynucleotide in the sample of step (a) to the amount of the polynucleotide present in a control sample from a second subject known not to have the presence of the pathogen, wherein an alteration in the expression level of the polypeptide in the first subject as compared to the control sample indicates the degree of virulence of the pathogen.

In a preferred embodiment, the subject is a mammal. It is more preferred that the subject is a human.

The invention additionally provides attenuated bacterial strains that can be used as vaccines and as vectors for foreign antigens and for foreign DNA. These attenuated bacterial strains are useful for the preparation of vaccines effective against diseases associated with the corresponding bacterial strains. In a preferred embodiment, the attenuated bacterial strains are derived from *Pseudomonas* or *Klebsiella* spp.

The invention additionally provides attenuated bacterial strains that can be used as vectors for foreign genes cloned from other pathogens that will be expressed into proteins, and will raise protective immune responses against the pathogens from which they are derived. In a preferred embodiment, the attenuated bacterial strains used as the vectors are derived from *Pseudomonas* or *Klebsiella* spp.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention is based, in part, on the discovery of 46 genes when mutated lower the virulence of a gram-negative bacterium. Nineteen of these virulence genes were identified in *P. aeruginosa* PT894, while the remaining 27 genes were derived from mutagenesis of *Klebsiella*. These bacterial mutants have attenuated virulence relative to isogenic bacterial strains and are designated "MUTX." Provided herein are virulence genes affected in each novel, attenuated MUTX strain, as well as the nucleotides and polypeptides encoded thereby. The sequences encoded by the affected genes are collectively referred to as "VIRX nucleic acids" or "VIRX polynucleotides" and the corresponding encoded polypeptides are referred to as "VIRX polypeptides" or "VIRX proteins." Unless indicated otherwise, "VIRX" is meant to refer to any of the novel sequences disclosed herein.

The peptides and genes of the invention are useful for the preparation of therapeutic agents to treat infection because they attenuate the virulence of the wild-type pathogen. Therapy can be preventative or therapeutic. A subject receiving therapy can be, e.g. a human, a non-human primate (such as an ape, gorilla, or chimpanzee), cow, horse, pig, sheep, dog, cat, or rodent (including mouse or rat).

I. Identification of *Pseudomonas* and *Klebsiella* Genes Encoding Virulence Factors Genes encoding virulence factors (e.g., pathogens or toxins) to a host organism were identified by comparing the growth of *Dictyostelium discoideum*, in the presence and absence of test mutants of *Pseudomonas* and *Klebsiella* with an identifiable genetic alteration as detailed in Intentional Application PCT/IB02/03277, filed Jun. 7, 2002. *Dictyostelium* amoebae feed phagocytically upon bacteria such as *K. pneumoniae*. When *Dictyostelium* cells are plated with *K. pneumoniae* bacteria, each amoeba creates a plaque in the bacterial lawn in the region where bacteria have been phagocytosed. Addition of pathogenic bacteria, e.g., *P. aeruginosa* strain PT894 to the lawn of *K. pneumoniae* bacteria, inhibits the growth of the amoebae.

*Pseudomonas* test mutants were made by transposon insertion according to known methods in the art and tested for virulence in a *Dictyostelium* growth assay (see, PCT/IB02/03277, filed Jun. 7, 2002). *Klebsiella* mutants were also made by transposon insertion according to known methods in the art and tested for virulence in a *Dictyostelium* growth assay (see, PCT/IB02/03277, filed Jun. 7, 2002) using the PIIG1a mutant *Dictyostelium* strain (Cornillon et al., J. Biol. Chem., 275(44): 34287–92, 2000), a strain which was found to be particularly sensitive to virulent bacteria. Specifically, the *Klebsiella* mutants were obtained by standard bacteria electroporation technique using the plasposon pNKBOR (Genbank accession number: AF310136) and selected on solid LB medium containing 50 μg/ml kanamycin (Rossignol et al., Res. Microbiol., 152(5): 481–5, 2001).

Other mutagenesis methods known in the art, e.g., ultraviolet radiation exposure, treatment with intercalating agent or transducing phage, may also be used to generate mutants. Mutations yielding reduced virulence were identified where the growth of the *Dictyostelium* test host organism exposed to the mutant pathogen was greater than the *Dictyostelium* test host organism exposed to wild-type pathogen. Specific genetic mutations in pathogens displaying reduced virulence were subsequently identified and characterized by techniques well known in the art. Identification of specific gene mutations in *Klebsiella* mutants was performed by plasmid rescue and cloning of the genomic DNA at the insertion site mutant using the BglII or ApaI restriction enzyme according to (Rossignol et al., Res. Microbiol., 152(5): 481–5, 2001). Identification of specific gene mutations in *Pseudomonas* mutants was performed by subcloning the transposon and surrounding bacteria genomic DNA into an acceptor plamid. DNA sequencing was performed on amplified rescued plasmids, in order to identify the insertion site of the transposon. Rat mortality assays such as that described by Join-Lambert et al., Antimicrob. Agents Chemother., 45(2): 571–6, 2001, can be used to corroborate attenuated virulence activity in a mammalian host.

The 19 *Pseudomonas* attenuated MUTX organisms harboring the VIRX genes are summarized below in Table 1.

TABLE 1

| STRAIN | AFFECTED VIRULENCE GENE(S) | REFERENCE |
|---|---|---|
| MUT1 | anthranilate phosphoribosyltransferase (trpD; PA0650) | Essar et al., J. Bacteriol., 172: 853–66, 1990; Essar et al., J. Bacteriol., 172: 867–83, 1990. |
| MUT2 | ATP sulfurylase small subunit (CysD; PA4443) | Leyh et al., J. Biol. Chem., 263: 2409–16, 1988; Hummerjohann et al., Microbiology, 144 (Pt 5): 1375–86, 1998 |
| MUT3 | CysQ (PA5175) | Peng and Verma, J. Biol. Chem., 270: 29105–10, 1995; Neuwald et al., J. Bacteriol., 174: 415–25, 1992. |
| MUT4 | D-amino acid dehydrogenase, small subunit (dadA; PA5304) | Lobacka et al., J. Bacteriol., 176: 1500–10, 1994. |
| MUT5 | imidazoleglycerol-phosphate synthase, cyclase subunit (hisF1; PA5140) | Fani et al., Mol. Gen. Genet., 216: 224–9, 1989; Fani et al., Mol. Gen. Genet., 216: 224–9, 1989. |
| MUT6 | N-acetyl-γ-glutamyl-phosphate reductase (ArgC; PAO 0662) | Smith et al., Gene, 49: 53–60, 1986. |
| MUT7 | Dihydrolipoamide acetyltransferase (AceF; pyruvate dehydrogenase complex component E2; PA5016) | Rae et al., J. Bacteriol., 179: 3561–71, 1997. |
| MUT8 | NADH dehydrogenase I chain H (nuoH; PA2643) | Weidner et al., J. Mol. Biol., 5: 233: 109–22, 1993; Weidner et al., J. Mol. Biol., 233: 109–22, 1993. |
| MUT9 | pyoverdine synthetase D (PvdD; PA2399) | Rombel et al., Mol. Gen. Genet., 246: 519–28, 1995; Merriman et al., J. Bacteriol., 177: 252–8, 1995. |
| MUT10 | RND multidrug efflux transporter MexD (mexD; PA4598) | Poole et al., Mol. Microbiol., 21: 713–24, 1996; Poole et al., Mol. Microbiol., 21: 713–24, 1996. |
| MUT11 | PA3721 | Stover et al., Nature, 406: 959–964, 2000. |
| MUT12 | PA0596 | Tan et al., Proc. Natl. Acad. Sci. USA, 96: 2408–13, 1999. |
| MUT13 | PA5265 | Stover et al., Nature, 406: 959–964, 2000. |
| MUT14 | pyochelin biosynthetic protein pchC (PA4229) | Serino et al., Mol. Gen. Genet., 249: 217–28, 1995; Serino et al., J. Bactiol., 179: 248–57, 1997 |
| MUT15 | dihydroaeruginoic acid synthetase (pchE; PA4226) | Reimmann et al., Microbiology, 144: 3135–48, 1998. |
| MUT16 | Pyochelin synthetase (pchF; PA4225) | Reimmann et al., Microbiology, 144: 3135–48, 1998. |
| MUT17 | ATP-binding component of the ABC transporter (pchH; PA4223) | Featherston et al., Mol. Microbiol., 32(2): 289–99, 1999; Reimmann et al., J. Bacteriol., 183: 813–20, 2001. |

TABLE 1-continued

| STRAIN | AFFECTED VIRULENCE GENE(S) | REFERENCE |
|---|---|---|
| MUT18 | ATP-binding component of the ABC transporter (pchI; PA4222) | Reimmann et al., J. Bacteriol., 183: 813–20, 2001. |
| MUT19 | putative O-antigen biosynthesis gene cluster | Rocchetta et al., Microbiol. Mol. Biol. Rev. 63: 523–53, 1999. |

The 27 *Klebsiella* attenuated MUTX organisms harboring the VIRX genes disclosed in the present invention and assigned a new role in virulence are summarized below in Table 2.

TABLE 2

| STRAIN | AFFECTED VIRULENCE GENE(S) |
|---|---|
| MUT20 | hypothetical transcriptional regulator in met G-dld intergenic region |
| MUT21 | β-cystathionase |
| MUT22 | ribosome binding factor A |
| MUT23 | aspartokinase/homoserine dehydrogenase |
| MUT24 | cystathionine γ-synthase |
| MUT25 | Phophoribosylformylglycinamidine synthase |
| MUT26 | homoserine transsuccinylase |
| MUT27 | 3'-phosphoadenosine 5'-phosphosulfate reductase |
| MUT28 | Sfi protein |
| MUT29 | transcriptional activator protein LysR |
| MUT30 | TrpD |
| MUT31 | N-acetylglucosamine-6-phosphate deacetylase |
| MUT32 | WaaQ |
| MUT33 | 2-Isopropylmalate synthase |
| MUT34 | histidinol dehydrogenase |
| MUT35 | UDP-galactopyranose mutase |
| MUT36 | O-antigen export system permease protein rfba |
| MUT37 | uridyltransferase |
| MUT38 | pyridoxine phosphate biosynthetic protein PdxJ-PdxA |
| MUT39 | triose phosphate isomerase |
| MUT40 | aldehyde dehydrogenase |
| MUT41 | galactosyl transferase |
| MUT42 | siroheme synthetase |
| MUT43 | 7,8-dihydro-6-hydroxymethylpterin-pyrophosphokinase |
| MUT44 | glucose-6-phosphate isomerase |
| MUT45 | DNA methylase |
| MUT46 | putative inner membrane protein |

II. Attenuated Bacterial Mutants

A. Attenuated *Pseudomonas aeruginosa* Mutants

MUT1

A *Pseudomonas* bacterial mutant (MUT1) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding anthranilate phosphoribosyltransferase (PA0650). This gene encodes the VIR1 nucleic acid (SEQ ID NO:1) shown in Table 3A.

TABLE 3A

VIR1 Nucleotide Sequence (SEQ ID NO:1)

ATGGATATCAAGGGAGCCCTCAATCGCATCGTCAACCAGCTCGACCTGAC

CACCGAGGAAATGCAGGCGGTCATGCGCCAGATCATGACCGGGCAGTGCA

CCGACGCGCAGATCGGCGCCTTCCTGATGGGCATGCGGATGAAGAGCGAA

ACCATCGACGAGATCGTCGGCGCGGTGGCGGTGATGCGCGAACTGGCCGA

TABLE 3A-continued

VIR1 Nucleotide Sequence (SEQ ID NO:1)

CGGCGTGCAGTTGCCCTACGCTGAAGCATGTGGTCGACGTGGTCGGCACCG

GCGGCGATGGCGCGAACATCTTCAACGTGTCCTCGGCGGCGTCCTTCGTG

GTCGCCGCCGCTGGCGGCAAGGTCGCCAAACACGGTAACCGCGCGGTCTC

CGGCAAGAGCGGCAGCGCCGACTTGCTGGAAGCCGCCGGCATCTACCTGG

AGCTGACCTCCGAACAGGTGGCGCGTTGCATCGACACCGTCGGCGTCGGG

TTCATGTTCGCCCAGGTCCACCACAAGGCGATGAAGTACGCCGCCGGTCC

GCGCCGCGAGCTGGGCTTGCGGACTCTGTTCAACATGCTTGGCCCACTGA

CCAACCCGGCGGGAGTCAGGCACCAGGTGGTCGGGGTGTTCACCCAGGAA

CTGTGCAAGCCGCTGGCTGAAGTGCTCAAGCGTCTCGGCAGCGAGCATGT

GCTGGTGGTGCATTCGCGCGACGGGCTGGACGAGTTCAGTCTGGCCGCGG

CGACCCACATTGCCGAGTTGAAGGACGGCGAGGTACGCGAGTACGAAGTG

CGTCCCGAGGACTTCGGGATCAAGAGCCAGACCCTGATGGGGCTGGAGGT

CGACAGTCCGCAGGCCTCGCTGGAACTGATCCGCGACGCTTTGGGGCGGC

GCAAGACCGAGGCTGGGCAGAAGGCCGCCGAGCTGATCGTGATGAATGCC

GGCCCGGCACTGTACGCTGCCGATCTGGCGACCAGCCTGCACGAGGGCAT

TCAACTGGCCCACGATGCCCTGCACACCGGGCTGGCACGGGAGAAGATGG

ACGAACTGGTGGCCTTCACCGCCGTTTACAGAGAGGAGAACGCACAGTGA

The VIR1 protein (SEQ ID NO:2) encoded by SEQ ID NO:1 is presented using the one-letter amino acid code in Table 3B.

TABLE 3B

Encoded VIR1 protein sequence (SEQ ID NO:2)

MDIKGALNRIVNQLDLTTEEMQAVMRQIMTGQCTDAQIGAFLMGMRMKSE

TIDEIVGAVAVMRELADGVQLPTLKHVVDVVGTGGDGANIFNVSSAASFV

VAAAGGKVAKHGNRAVSGKSGSADLLEAAGIYLELTSEQVARCIDTVGVG

FMFAQVHHKAMKYAAGPRRELGLRTLFNMLGPLTNPAGVRHQVVGVFTQE

LCKPLAEVLKRLGSEHVLVVHSRDGLDEFSLAAATHIAELKDGEVREYEV

RPEDFGIKSQTLMGLEVDSPQASLELIRDALGRRKTEAGQKAAELIVMNA

GPALYAADLATSLHEGIQLAHDALHTGLAREKMDELVAFTAVYREENAQ

The role of VIR1 in virulence was confirmed using phage to retransduce this mutation into the wild-type PT894 strain where attenuated virulence was again observed in the *Dictyostelium* growth assay compared to an isogenic bacterial strain.

MUT2

A *Pseudomonas* bacterial mutant (MUT2) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding the ATP sulfurylase small subunit (CysD; PA4443). This gene encodes the VIR2 nucleic acid (SEQ ID NO:3) shown in Table 4A.

TABLE 4A

VIR2 Nucleotide Sequence (SEQ ID NO:3)

ATGGTCGACAAACTGACGCACCTGAAACAGCTGGAGGCGGAAAGCATCCA
CATCATCCGCGAGGTGGCCGCCGAGTTCGATAACCCGGTGATGCTGTACT
CGATCGGCAAGGATTCCGCGGTCATGCTGCACCTGGCCCGCAAGGCCTTC
TTCCCCGGCAAGCTGCCCTTCCCGGTGATGCACGTGGACACCCGCTGGAA
ATTCCAGGAGATGTACAGGTTCCGTGATCGGATGGTCGAGGAAATGGGCC
TGGATCTGATCACCCACGTCAACCCGGACGGCGTCGCCCAGGGCATCAAC
CCGTTCACCCACGGCAGCGCCAAGCACACCGACGTGATGAAGACCGAGGG
ACTCAAGCAGGCCCTGGACAAGTACGGTTTCGACGCTGCCTTCGGCGGTG
CGCGCCGCGACGAGGAGAAGTCGCGGGCCAAGGAACGGGTCTATTCGTTC
CGCGACAGCAAGCACCGCTGGGACCCGAAGAACCAGCGTCCCGAGCTGTG
GAACATCTACAACGGCAAGGTGAAGAAGGGCGAGTCGATCCGCGTCTTCC
CGCTGTCCAACTGGACCGAGCTGGACATCTGGCAATACATCTACCTGGAA
GGCATCCCGATCGTCCCGCTGTACTTCGCCGCCGAGCGCGAGGTCATCGA
GAAGAATGGCACATTGATCATGATCGACGACGAGCGCATCCTCGAGCATC
TCTCTGACGAAGAGAAAGCCCGCATCGAGAAGCGCATGGTGCGCTTCCGT
ACCCTCGGCTGCTACCCGCTCACCGGCGCGGTCGAGTCCAGCGCCACCAC
GCTGCCGGAAATCATCCAGGAAATGCTCCTGACGCGTACTTCCGAACGCC
AGGGCCGGGTCATCGACCATGACCAGGCCGGTTCGATGGAAGAAAAGAAA
CGTCAGGGCTATTTCTGA

The VIR2 protein (SEQ ID NO:4) encoded by SEQ ID NO:3 is presented using the one-letter amino acid code in Table 4B.

TABLE 4B

Encoded VIR2 protein sequence (SEQ ID NO:4)

MVDKLTHLKQLEAESIHIIREVAAEFDNPVMLYSIGKDSAVMLHLARKAF
FPGKLPFPVMHVDTRWKFQEMYRFRDRMVEEMGLDLITHVNPDGVAQGIN
PFTHGSAKHTDVMKTEGLKQALDKYGFDAAFGGARRDEEKSRAKERVYSF
RDSKHRWDPKNQRPELWNIYNGKVKKGESIRVFPLSNWTELDIWQYIYLE
GIPIVPLYFAAEREVIEKNGTLIMIDDERILEHLSDEEKARIEKRMVRFR
TLGCYPLTGAVESSATTLPEIIQEMLLTRTSERQGRVIDHDQAGSMEEKK
RQGYF

The role of VIR2 in virulence was confirmed using phage to retransduce this mutation into the wild-type PT894 strain where attenuated virulence was again observed in the *Dictyostelium* growth assay compared to an isogenic bacterial strain.

MUT3

A *Pseudomonas* bacterial mutant (MUT3) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding CysQ (PA5175). This gene encodes the VIR3 nucleic acid (SEQ ID NO:5) shown in Table 5A.

TABLE 5A

VIR3 Nucleotide Sequence (SEQ ID NO:5)

ATGAGGCCGGTGCCTTGGGGCGAATTGGTGGCGCTGGTGCGGCGCGCCGG
CGAGGCGATCCTGCCGCACTGGCGCGCCGACGTGGTGGTGCGCTCGAAGG
CCGACGAATCGCCGGTGACTGCCGCCGACCTGGCCGCGCACCATATATTG
GAGGCGGGATTGCGGGCGCTGGCGCCGGACATTCCGGTGCTTTCCGAAGA
GGATTGCGAGATACCGCTGAGCGAGCGCGGCCACTGGCGGCGCTGGTGGC
TGGTGGACCCGCTGGACGGCACCAAGGAGTTCATCTCCGGTAGCGAGGAG
TTCACCGTCAACGTGGCCCTGGTCGAGGATGGCCGGGTGCTGTTCGGCCT
GGTCGGCGTGCCGGTGAGCGGCCGCTGCTACTACGGTGGCGCCGGTCTCG
GTGCCTGGCGCGAGGAGGCCGATGGCCGCGCGCAACCGATCAGTGTGCGC
CTGGAGCCCGAGGAGGCCTTCACCGTGGTGGCCAGCAAGCGCCATGGCAG
CCCGGCCCAGGAGCGCCTGCTGGATGGCTTGAGCGAGCGCTTCGGCGACC
TGCGGCGAGCCAGCATCGGCAGTTCGCTGAAGTTCTGCCTGCTGGCCGAG
GGCGCTGCCGACTGCTATCCGCGCCTGACGCCAACCTCGCAATGGGACAC
GGCCGCCGCCCAGGGTGTGCTGGAAGGCGCCGGCGGCGAGGTGCTCGACC
TGCATGGTGCGCCATTCACCTACGAGCCGCGCGAGGATTACCTCAACGGC
TCCTTCCTGGCCCTGCCGCGCGCCGCCGAGTGGCGCAGCGAGCTGATCCA
ACTGGCGCGCGCGCTGCACTGA

The VIR3 protein (SEQ ID NO:6) encoded by SEQ ID NO:5 is presented using the one-letter amino acid code in Table 5B.

TABLE 5B

Encoded VIR3 protein sequence (SEQ ID NO:6)

MRPVPWGELVALVRRAGEAILPHWRADVVVRSKADESPVTAADLAAHHIL
EAGLRALAPDIPVLSEEDCEIPLSERGHWRRWWLVDPLDGTKEFISGSEE
FTVNVALVEDGRVLFGLVGVPVSGRCYYGGAGLGAWREEADGRAQPISVR
LEPEEAFTVVASKRHGSPAQERLLDGLSERFGDLRRASIGSSLKFCLLAE
GAADCYPRLTPTSQWDTAAAQGVLEGAGGEVLDLHGAPFTYEPREDYLNG
SFLALPRAAEWRSELIQLARALH

MUT4

A *Pseudomonas* bacterial mutant (MUT4) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding D-amino acid dehydrogenase, small subunit (dadA; PA5304). This gene encodes the VIR4 nucleic acid (SEQ ID NO:7) shown in Table 6A.

TABLE 6A

VIR4 Nucleotide Sequence (SEQ ID NO:7)

ATGCGAGTTCTGGTCCTTGGCAGCGGTGTCATCGGTACCGCCAGTGCGTA

TTACCTGGCCCGTGCCGGGTTCGAGGTGGTGGTGGTCGACCGTCAGGACG

GTCCCGCGCTGGAAACCAGCTTCGCCAACGCCGGCCAGGTGTCTCCCGGC

TACGCTTCGCCCTGGGCAGCCCCGGGCATTCCCCTGAAGGCCATGAAGTG

GCTGCTGGAAAAGCACGCGCCGCTGGCCATCAAGCTCACCTCCGATCCCA

GCCAGTACGCCTGGATGCTGCAGATGCTGCGCAACTGCACCGCCGAGCGC

TACGCCGTGAACAAGGAGCGCATGGTCCGCCTGTCCGAGTACAGCCGCGA

TTGCCTCGACGAACTGCGCGCCGAGACCGGCATCGCCTACGAGGGCCGCA

CCCTCGGCACCACCCAACTGTTCCGCACCCAGGCGCAGCTGGACGCCGCC

GGCAAGGACATCGCCGTGCTCGAGCGCTCCGGCGTGCCCTACGAGGTTCT

CGACCGCGACGGCATCGCCCGCGTAGAGCCGGCTTTGGCCAAGGTCGCCG

ACAAGCTGGTCGGCGCCTTGCGCCTGCCCAACGACCAGACCGGCGACTGC

CAGCTGTTCACCACCCGCCTGGCGGAAATGGCCAAGGGCCTGGGCGTGGA

GTTCCGCTTCGGCCAGAACATCGAGCGCCTGGACTTCGCCGGCGACCGCA

TCAACGGCGTGCTGGTCAACGGCGAATTGCTCACCGCCGACCACTACGTG

CTGGCCCTGGGCAGCTACTCGCCGCAACTGCTCAAGCCGCTGGGTATCAA

GGCTCCGGTCTATCCGCTGAAGGGTTATTCGCTGACCGTGCCGATCACCA

ACCCGGAGATGGCGCCGACCTCGACCATCCTCGACGAGACCTACAAGGTG

GCGATCACCCGCTTCGACCAGCGCATCCGCGTCGGCGGCATGGCGGAAAT

CGCCGGCTTCGACCTGTCGCTGAACCCGCGCCGCCGCGAGACCCTGGAAA

TGATCACCACCGACCTCTATCCCGAGGGCGGCGATATCAGCCAGGCGACC

TTCTGGACCGGCCTGCGCCCGGCGACCCCGGATGGCACCCCGATCGTCGG

CGCCACCCGCTACCGCAACCTGTTCCTCAATACCGGCCACGGCACCCTGG

GTTGGACCATGGCCTGCGGGTCGGGTCGCTACCTGGCCGACCTGATGGCG

AAGAAGCGCCCGCAGATCAGTACCGAAGGCCTGGATATTTCCCGCTACAG

CAATTCCCCGGAGAACGCCAAGAATGCCCATCCAGCGCCAGCACACTAA

The VIR4 protein (SEQ ID NO:8) encoded by SEQ ID NO:7 is presented using the one-letter amino acid code in Table 6B.

TABLE 6B

Encoded VIR4 protein sequence (SEQ ID NO:8)

MRVLVLGSGVIGTASAYYLARAGFEVVVVDRQDGPALETSFANAGQVSPG

YASPWAAPGIPLKAMKWLLEKHAPLAIKLTSDPSQYAWMLQMLRNCTAER

YAVNKERMVRLSEYSRDCLDELRAETGIAYEGRTLGTTQLFRTQAQLDAA

GKDIAVLERSGVPYEVLDRDGIARVEPALAKVADKLVGALRLPNDQTGDC

QLFTTRLAEMAKGLGVEFRFGQNIERLDFAGDRINGVLVNGELLTADHYV

TABLE 6B-continued

Encoded VIR4 protein sequence (SEQ ID NO:8)

LALGSYSPQLLKPLGIKAPVYPLKGYSLTVPITNPEMAPTSTILDETYKV

AITRFDQRIRVGGMAEIAGFDLSLNPRRRETLEMITTDLYPEGGDISQAT

FWTGLRPATPDGTPIVGATRYRNLFLNTGHGTLGWTMACGSGRYLADLMA

KKRPQISTEGLDISRYSNSPENAKNAHPAPAH

The role of VIR4 in virulence was confirmed using phage to retransduce this mutation into the wild-type PT894 strain where attenuated virulence was again observed in the *Dictyostelium* growth assay compared to an isogenic bacterial strain.

MUT5

A *Pseudomonas* bacterial mutant (MUT5) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding imidazoleglycerol-phosphate synthase, cyclase subunit (hisF; PA5140). This gene encodes the VIR5 nucleic acid (SEQ ID NO:9) shown in Table 7A.

TABLE 7A

VIR5 Nucleotide Sequence (SEQ ID NO:9)

ATGGCACTGGCAAAACGCATCATCCCCTGCCTCGACGTGGACAACGGCCG

AGTGGTCAAGGGCGTCAAGTTCGAGAACATCCGCGACGCCGGCGACCCGG

TCGAGATCGCTCGCCGCTACGACGAGCAGGGTGCCGACGAGATCACCTTC

CTCGATATCACCGCCAGCGTCGACGGGCGCGACACCACCCTGCATACCGT

CGAGCGCATGCCTAGCCAGGTGTTCATTCCGCTGACCGTGGGCGGCGGCG

TACGCAGCGTGCAGGACATCCGCAACCTGTTGAATGCCGGCGCGGACAAG

GTCTCGATCAACACCGCCGCGGTGTTCAACCCCGAGTTCGTCGGTGAGGC

CGCCGACCGCTTCGGCTCGCAGTGCATCGTGGTCGCCATCGACGCGAAGA

AGGTTTCCGCCCCGGGCGAGGCGCCGCGCTGGGAAATCTTCACCCATGGC

GGGCGCAAGCCCACCGGGCTGGATGCCGTGCTCTGGGCGAAGAAGATGGA

AGACTTGGGCGCTGGCGAGATTCTCCTGACCAGCATGGACCAGGACGGCG

TGAAGAGCGGTTACGACCTGGGCGTGACCCGCGCCATCAGCGAGGCGGTG

AACGTGCCGGTGATCGCTTCCGGCGGCGTCGGCAACCTGGAGCACCTGGC

CGCCGGCATCCTCGAGGGCAAGGCCGACGCGGTGCTCGCGGCGAGCATCT

TCCACTTCGGCGAGTACACCGTGCCGGAAGCCAAGGCCTACCTGGCCAGC

CGCGGTATCGTGGTGCGCTGA

The VIR5 protein (SEQ ID NO:10) encoded by SEQ ID NO:9 is presented using the one-letter amino acid code in Table 7B.

TABLE 7B

Encoded VIR5 protein sequence (SEQ ID NO:10)

MALAKRIIPCLDVDNGRVVKGVKFENIRDAGDPVEIARRYDEQGADEITF
LDITASVDGRDTTLHTVERMASQVFIPLTVGGGVRSVQDIRNLLNAGADK
VSINTAAVFNPEFVGEAADRFGSQCIVVAIDAKKVSAPGEAPRWEIFTHG
GRKPTGLDAVLWAKKMEDLGAGEILLTSMDQDGVKSGYDLGVTRAISEAV
NVPVIASGGVGNLEHLAAGILEGKADAVLAASIFHFGEYTVPEAKAYLAS
RGIVVR

MUT6

A *Pseudomonas* bacterial mutant (MUT6) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding N-acetyl-γ-glutamyl-phosphate reductase (ArgC; PA0662). This gene encodes the VIR6 nucleic acid (SEQ ID NO:11) shown in Table 8A.

TABLE 8A

VIR6 Nucleotide Sequence (SEQ ID NO:11)

ATGATCAAGGTCGGCATCGTTGGCGGTACGGGTTATACGGGCGTGGAACT
GCTGCGCCTGCTGGCGCAGCATCCGCAGGCCCGGGTGGAAGTGATCACTT
CGCGTTCCGAGGCGGGGGTGAAGGTCGCCGACATGTACCCGAACCTGCGA
GGTCATTATGACGACCTGCAGTTCAGCGTGCCGGACGCGCAGCGCCTCGG
CGCCTGCGACGTGGTGTTCTTCGCCACGCCGCACGGCGTGGCGCACGCGC
TGGCTGGCGAACTGCTGGACGCCGGGACCCGGGTCATCGATCTGTCCGCT
GACTTCCGCCTGGCGGACGCCGAGGAGTGGGCGCGCTGGTACGGCCAGCC
GCATGGCGCTCCGGCGCTGCTCGACGAGGCTGTCTACGGCCTGCCGGAAG
TGAACCGCGAGAAGATCCGCCAGGCCCGCCTGATCGCCGTGCCGGGCTGC
TACCCGACCGCGACCCAGCTGGGCCTGATCCCGCTGCTGGAAGCCGGCCT
GGCCGACGCCTCGCGGCTGATCGCCGATTGCAAGTCCGGGGTCAGCGGTG
CCGGTCGGGCGCCAAGGTTGGCTCGCTGTTCTGCGAGGCGGGCGAAAGC
ATGATGGCCTACGCGGTCAAAGGGCATCGGCATCTCCCGGAAATCAGCCA
GGGCCTGCGTCGGGCCTCCGGCGGCGACGTCGGGCTGACGTTCGTACCGC
ACCTGACGCCAATGATCCGCGGTATCCATGCAACCCTCTATGCCCATGTC
GCGGATCGCTCGGTCGACCTCCAGGCGTTGTTCGAGAAGCGCTACGCCGA
CGAACCCTTCGTCGACGTGATGCCGGCCGGCAGCCATCCGGAGACCCGCA
GCGTGCGTGGCGCCAATGTCTGCCGAATCGCCGTGCATCGCCCCAGGGC
GGCGACCTGGTGGTGGTGCTGTCGGTGATCGACAACCTGGTCAAGGGCGC
CTCGGGTCAGGCGCTCCAGAACATGAACATCCTGTTCGGGCTGGACGAGC
GCCTGGGCCTCTCGCATGCGGCCCTGCTCCCCTGA

The VIR6 protein (SEQ ID NO:12) encoded by SEQ ID NO:11 is presented using the one-letter amino acid code in Table 8B.

TABLE 8B

Encoded VIR6 protein sequence (SEQ ID NO:12)

MIKVGIVGGTGYTGVELLRLLAQHPQARVEVITSRSEAGVKVADMYPNLR
GHYDDLQFSVPDAQRLGACDVVFFATPHGVAHALAGELLDAGTRVIDLSA
DFRLADAEEWARWYGQPHGAPALLDEAVYGLPEVNREKIRQARLIAVPGC
YPTATQLGLIPLLEAGLADASRLIADCKSGVSGAGRGAKVGSLFCEAGES
MMAYAVKGHRHLPEISQGLRRASGGDVGLTFVPHLTPMIRGIHATLYAHV
ADRSVDLQALFEKRYADEPFVDVMPAGSHPETRSVRGANVCRIAVHRPQG
GDLVVVLSVIDNLVKGASGQALQNMNILFGLDERLGLSHAALLP

The role of VIR6 in virulence was confirmed using phage to retransduce this mutation into the wild-type PT894 strain where attenuated virulence was again observed in the *Dictyostelium* growth assay compared to an isogenic bacterial strain.

MUT7

A *Pseudomonas* bacterial mutant (MUT7) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding dihydrolipoamide acetyltransferase (AceF; PA5016). This gene encodes the VIR7 nucleic acid (SEQ ID NO:13) is shown in Table 9A.

TABLE 9A

VIR7 Nucleotide Sequence (SEQ ID NO:13)

GTGAGCGAACTCATTCGCGTACCCGACATCGGCAACGGTGAGGGTGAAGT
CATCGAGCTGCTGGTCAAGCCCGGCGACAAGGTCGAGGCCGATCAGAGCC
TGCTGACCCTGGAATCCGACAAGGCCAGCATGGAAATCCCCAGTCCCAAG
GCCGGGGTAGTGAAAAGCATCAAGGCGAAGGTCGGCGACACCTTGAAAGA
AGGTGACGAAATCCTCGAGCTGGAAGTGGAAGGCGGCGAACAGCCTGCCG
AAGCCAAGGCCGAGGCAGCGCCCGCCCAACCGGAAGCGCCCAAAGCCGAA
GCGCCTGCTCCCGCCCCGAGCGAGAGCAAGCCGGCCGCCCCCGCCGCGGC
CAGCGTCCAGGACATCAAGGTCCCGGACATCGGCTCGGCCGGCAAGGCCA
ACGTCATCGAAGTGATGGTCAAGGCCGGCGACACGGTCGAGGCCGACCAG
TCGCTGATCACCCTGGAATCCGACAAGGCCAGCATGGAGATCCCCTCGCC
GGCCTCCGGGGTGGTGGAAAGCGTCTCGATCAAGGTCGGTGACGAAGTCG
GCACCGGCGACCTGATCCTCAAGCTGAAGGTGGAAGGCGCCGCTCCGGCA
GCCGAAGAGCAACCGGCAGCCGCTCCGGCCCAGGCCGCGGCGCCCGCCGC
CGAGCAGAAGCCCGCCGCGGCGGCCCCTGCGCCAGCCAAGGCCGATACCC
CGGCTCCGGTCGGCGCACCCAGCCGCGACGGCGCCAAGGTCCACGCCGGC
CCGGCGGTGCGCATGCTGGCGCGCGAGTTCGGCGTCGAGCTGAGCGAAGT
GAAAGCCAGCGGTCCCAAGGGTCGCATCCTCAAGGAAGACGTCCAGGTCT
TCGTCAAGGAGCAACTGCAGCGCGCCAAGTCCGGCGGTGCCGGCGCCACC
GGCGGAGCCGGCATCCCGCCGATCCCGGAAGTCGACTTCAGCAAGTTCGG

TABLE 9A-continued

VIR7 Nucleotide Sequence (SEQ ID NO:13)

CGAAGTGGAAGAAGTGGCGATGACCCGCCTGATGCAGGTCGGCGCCGCCA

ACCTGCATCGCAGCTGGCTGAACGTGCCGCACGTGACCCAGTTCGACCAG

TCGGACATCACCGACATGGAAGCCTTCCGCGTTGCCCAGAAGGCCGCGGC

GGAGAAGGCCGGGGTCAAGCTGACCGTACTGCCGATCCTGCTCAAGGCCT

GCGCCCACCTGCTCAAGGAACTGCCGGACTTCAACAGTTCGCTGGCCCCC

AGCGGCAAGGCGCTGATCCGCAAGAAGTACGTACACATCGGCTTCGCCGT

GGACACTCCGGACGGCCTGCTGGTCCCGGTGATCCGCGATGTCGACCGGA

AGAGCCTCCTGCAACTGGCCGCCGAGGCCGCCGACCTGGCCGACAAGGCC

CGCAACAAGAAGCTCTCGGCCGATGCCATGCAGGGCGCCTGCTTCACCAT

CTCCAGTCTCGGCCACATCGGCGGCACCGGCTTCACGCCGATCGTCAACG

CGCCGGAAGTGGCGATCCTCGGTGTGTCCAAGGCGACCATGCAGCCGGTA

TGGGACGGCAAGGCCTTCCAGCCGCGCCTGATGCTGCCGCTGTCGCTGTC

CTACGACCATCGCGTGATCAACGGTGCCGCCGCGGCGCGCTTCACCAAGC

GCCTGGGCGAGCTGCTGGCGGACATCCGCACCCTGCTCCTGTAA

The VIR7 protein (SEQ ID NO: 14) encoded by SEQ ID NO: 13 is presented using the one-letter amino acid code in Table 9B.

TABLE 9B

Encoded VIR7 protein sequence (SEQ ID NO:14)

MSELIRVPDIGNGEGEVIELLVKPGDKVEADQSLLTLESDKASMEIPSPK

AGVVKSIKAKVGDTLKEGDEILELEVEGGEQPAEAKAEAAPAQPEAPKAE

APAPAPSESKPAAPAAASVQDIKVPDIGSAGKANVIEVMVKAGDTVEADQ

SLITLESDKASMEIPSPASGVVESVSIKVGDEVGTGDLILKLKVEGAAPA

AEEQPAAAPAQAAAPAAEQKPAAAAPAPAKADTPAPVGAPSRDGAKVHAG

PAVRMLAREFGVELSEVKASGPKGRILKEDVQVFVKEQLQRAKSGGAGAT

GGAGIPPIPEVDFSKFGEVEEVAMTRLMQVGAANLHRSWLNVPHVTQFDQ

SDITDMEAFRVAQKAAAEKAGVKLTVLPILLKACAHLLKELPDFNSSLAP

SGKALIRKKYVHIGFAVDTPDGLLVPVIRDVDRKSLLQLAAEAADLADKA

RNKKLSADAMQGACFTISSLGHIGGTGFTPIVNAPEVAILGVSKATMQPV

WDGKAFQPRLMLPLSLSYDHRVINGAAAARFTKRLGELLADIRTLLL

MUT8

A *Pseudomonas* bacterial mutant (MUT8) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding NADH dehydrogenase I chain H (nuoH; PA2643). This gene encodes the VIR8 nucleic acid (SEQ ID NO:15) shown in Table 10A.

TABLE 10A

VIR8 Nucleotide Sequence (SEQ ID NO:15)

ATGAGTTGGCTGACTCCCGCTCTGGTCACCATCATCCTCACCGTGGTCAA

GGCCATCGTGGTGCTGCTCGCCGTGGTCATCTGCGGCGCCCTGCTAAGCT

GGGTCGAGCGCCGCCTGCTCGGCCTCTGGCAGGACCGCTACGGCCCCAAC

CGGGTCGGTCCGTTCGGTGCGTTCCAGCTCGGCGCGGACATGGTCAAGAT

GTTCTTCAAGGAGGACTGGACCCCGCCGTTCGCCGACAAGATGATCTTCA

CCCTGGCCCCGGTAATCGCGATGGGCGCCCTGCTCGTCGCCTTCGCCATC

GTGCCGATCACCCCCACCTGGGGCGTGGCGGACCTGAACATCGGCATCCT

GTTCTTCTTCGCCATGGCCGGCCTGACGGTGTACGCCGTGCTGTTCGCCG

GCTGGTCGAGCAACAACAAGTTCGCCCTGCTCGGCAGCCTGCGCGCCTCG

GCCCAGACCATCTCCTACGAGGTGTTCCTGGCCCTGTCGCTGATGGGCAT

CGTCGCCCAGGTCGGCTCGTTCAACATGCGCGACATCGTCCAGTACCAGA

TCGACAACGTCTGGTTCATCATTCCGCAGTTCTTCGGCTTCTGCACCTTC

ATCATCGCCGGCGTCGCCGTGACCCACCGTCACCCGTTCGACCAGCCGGA

AGCGGAGCAGGAACTGGCGGACGGCTACCACATCGAGTACGCCGGGATGA

AATGGGGCATGTTCTTCGTCGGCGAGTACATCGGCATCGTACTGGTCTCG

GCGCTGCTGGCGACCCTGTTCTTCGGCGGCTGGCACGGTCCGTTCCTGGA

CACCCTGCCCTGGCTGTCGTTCTTCTACTTCGCCGCCAAGACCGGCTTCT

TCATCATGCTCTTCATCCTGATCCGCGCCTCGCTGCCGCGTCCGCGCTAT

GACCAGGTGATGGCGTTCAGCTGGAAGGTGTGCCTGCCGCTGACCCTGAT

CAACCTGCTGGTGACCGGCGCGCTCGTGCTGGCCGCGGCCCAGTAA

The VIR8 protein (SEQ ID NO: 16) encoded by SEQ ID NO:15 is presented using the one-letter amino acid code in Table 10B.

TABLE 10B

Encoded VIR8 protein sequence (SEQ ID NO:16)

MSWLTPALVTIILTVVKAIVVLLAVVICGALLSWVERRLLGLWQDRYGPN

RVGPFGAFQLGADMVKMFFKEDWTPPFADKMIFTLAPVIAMGALLVAFAI

VPITPTWGVADLNIGILFFFAMAGLTVYAVLFAGWSSNNKFALLGSLRAS

AQTISYEVFLALSLMGIVAQVGSFNMRDIVQYQIDNVWFIIPQFFGFCTF

IIAGVAVTHRHPFDQPEAEQELADGYHIEYAGMKWGMFFVGEYIGIVLVS

ALLATLFFGGWHGPFLDTLPWLSFFYFAAKTGFFIMLFILIRASLPRPRY

DQVMAFSWKVCLPLTLINLLVTGALVLAAAQ

MUT9

A *Pseudomonas* bacterial mutant (MUT9) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding pyoverdine synthase D (PvdD; PA2399). This gene encodes the VIR9 nucleic acid (SEQ ID NO:17) shown in Table 11A.

TABLE 11A

VIR9 Nucleotide Sequence (SEQ ID NO:17)

GTGCAAGCACTCATAGAGAAGGTGGGCTCCCTTTCCCCCCAGGAAAGGAA
GGCATTGGCTGTCCTGCTCAAGCAGCAAGGTGTCAATCTCTTCGAGATCG
CGCCAGTGTTCAAGCGCCAGGACGGCGAGCCCCTGCGGCTCTCCTATGCC
CAGGAGCGACAGTGGTTTCTCTGGCAACTGGAGCCGGAAAGCGCGGCCTA
CCATATCCCGAGTGTCTTGCGTCTACGTGGGCGGCTGGACCTGGATGCCC
TGCAACGCAGCTTCGACAGCCTGGTTGCGCGGCACGAGACCCTACGCACC
CGTTTTCGCCTCGACGGCGACGAGGCGCGCCAGGAGATCGCCGCATCCAT
GGCATTGCCGTTGGATATCGTCGCGTTGGGGCCGCTCGAGGAGGCGCCC
TCGCTCGGCAGGTCGAGACGACGATCGCGCGGCCGTTCGACCTGGAGCGT
GGGCCGCTGCTGCGGGTGAGCCTGTTGCGGCTGGCCGAGGACGACCATGT
GCTGGTGCTGGTCCAGCATCACATCGTGTCCGACGGTTGGTCGATGCAGG
TGATGGTCGAGGAACTGGTCCAGCTCTATGCCGCCTATAGTCGAGGGCTC
GAGGTAGCGCTGCCGGCTTTGCCGATCCAGTACGCGGACTACGCCCTGTG
GCAGCGCAGCTGGATGGAGGCCGGGGAAAAGGAGCGCCAGTTGGCGTACT
GGACCGGCCTGCTGGGCGGCGAGCAGCCGGTGCTGGAGTTGCCGTTCGAC
CGGCCGCGCCCCGTTCGGCAAAGCCATCGTGGTGCCCAGTTCATCCTGGA
ACTGGATATTGATCTGTCCCAGGCGCTCAGGCGCGTGGCCCAGCAGGAGG
GGGCTACTGCCTTCGCCCTGTTGCTGGCTTCGTTCCAGGCGCTGCTGTAT
CGCTACAGCGGGCAGGCGGATATCCGTGTCGGCGTGCCGATCGCCAATCG
CAACCGCGTGGAGACCGAGCGGCTGATCGGCTTCTTCGTCAACACCCAGG
TGCTCAAGGCCGACCTGGACGGTCGGATGGGCTTCGACGAGCTGCTGGCC
CAGGCCCGCCAACGCGCGCTGGAGGCCCAGGCGCACCAGGACCTGCCGTT
CGAGCAACTGGTGGAGGCCTTGCAGCCGGAGCGCAGTCTTAGCCACAACC
CGCTGTTCCAGGTGCTGTTCAACTACCAGAGCGAAGCCCGTGGCAACGGC
CAGGCATTCCGCTTCGACGAGTTACAGATGGAAAGCGTGCAGTTCGACAG
CCGGACGGCGCAGTTCGACTTGACGTTGGACCTGACGGACGAAGAGCAGC
GTTTTTGCGCCGTTTTCGACTACGCCACCGACCTGTTCGACGCCTCCACC
GTGGAACGCCTGGCCGGCCATTGGCGCAACCTGTTGCGCGGCATCGTCGC
CAACCCACGACAGCGGCTCGGCGAGTTGCCGCTGCTGGATGCGCCGGAGC
GCCGGCAGACCCTCTCCGAATGGAACCCGGCCCAGCGCGAGTGCGCGGTG
CAGGGCACCTTGCAGCAGCGTTTCGAGGAACAGGCGCGGCAACGGCCACA
GGCGGTTGCGCTGATCCTCGACGAACAACGGTTGAGCTACGGCGAACTGA
ATGCGCGGGCCAATCGCCTGGCGCACTGCCTGATCGCCCGTGGCGTTGGC
GCGGACGTGCCGGTCGGCTGGCGCTGGAGCGTTCGCTGGACATGCTGGT
CGGCTTGCTGGCGATCCTCAAGGCCGGCGGCGCCTACCTGCCGTTGGACC
CGGCGGCGCCAGAGGAGCGCCTGGCGCATATCCTCGACGACAGTGGGTA
CGGCTGCTGCTGACCCAGGGGCATCTGCTCGAGCGCCTGCCACGGCAGGC
GGGGGTGGAGGTGCTGGCCATCGACGGACTGGTGCTGGACGGCTACGCCG
AGAGCGATCCGCTCCCGACGCTATCGGCGGACAACCTGGCCTACGTGATC
TATACCTCGGGCTCGACCGGCAAGCCCAAGGGCACATTGCTCACCCACCG
CAACGCGCTGCGCCTGTTCAGCGCCACCGAGGCCTGGTTCGGCTTCGACG
AGCGGGACGTGTGGACATTGTTCCATTCCTACGCCTTCGATTTCTCGGTC
TGGGAAATCTTCGGCGCGCTGCTCTATGGCGGGTGCCTGGTGATTGTGCC
GCAATGGGTGAGCCGTTCGCCGGAAGACTTCTACCGTCTGCTGTGCCGCG
AAGGCGTGACGGTGCTCAACCAGACGCCGTCGGCGTTCAAGCAACTGATG
GCGGTGGCCTGTTCCGCCGACATGGCGACGCAGCAGCCGGCGCTGCGCTA
CGTGATCTTCGGTGGCGAGGCGCTGGATCTGCAGAGCCTGCGGCCGTGGT
TCCAGCGCTTCGGCGATCGCCAGCCGCAACTGGTGAACATGTACGGCATC
ACCGAGACCACGGTGCACGTAACCTACCGTCCGGTGAGCGAGGCCGACCT
GGAAGGTGGCCTGGTCAGTCCGATTGGCGGGACCATCCCGGACCTGTCCT
GGTACATCCTCGACCGTGACCTGAACCCGGTGCCGCGCGGCGCGGTGGGC
GAGCTGTACATCGGTCGCGCCGGGCTGGCGCGCGGCTACCTGAGGCGGCC
CGGGTTGAGTGCCACCCGCTTCGTGCCGAACCCGTTCCCCGGCGGCGCCG
GCGAGCGGCTGTACCGTACCGGCGACCTGGCACGGTTCCAGGCGGATGGC
AATATCGAGTACATCGGGCGTATCGACCACCAGGTGAAGGTTCGCGGCTT
CCGTATCGAACTGGGCGAGATCGAAGCGGCGCTCGCCGGTCTGGCCGGGG
TACGCGATGCCGTGGTGCTGGCCCATGACGGAGTCGGCGGCACGCAACTG
GTGGGATACGTGGTGGCGGACTCGGCGGAGGATGCCGAGCGTCTGCGGGA
GTCGCTGCGGGAGTCGCTGAAGCGGCACCTGCCGGACTACATGGTGCCGG
CGCACCTGATGCTGCTGGAGCGGATGCCGCTGACGGTCAATGGCAAGCTC
GACCGGCAGGCGTTGCCGCAACCGGATGCGAGCCTGTCGCAACAGGCCTA
TCGAGCGCCCGGTAGCGAGCTGGAGCAGCGCATCGCAGCGATCTGGTCGG
AGATCCTGGGAGTGGAACGGGTCGGCCTGGACGACAACTTCTTCGAACTG
GGCGGTCATTCGTTGCTGGCTACCCGGGTGATTTCTCGGGTTCGCCAGGA
GCAGCAGTTGGACGCAAGCCTGAAGGCGTTGTTCGAGCGGCCGGTTCTGG
AAGCGTTCGCCCAGGGATTGGAACGCACGACGGATGCGGTCTCGACGATA
CCGCTTGCCGATCGGCAGCAACCGTTGGCACTGTCCTTCGCTCAGGAGCG
TCAGTGGTTCCTCTGGCAACTGGAGCCGGAAAGCGCGGCCTACCATATTC
CGAGTGCCTTGCGCCTACGCGGGCGGCTGGACGTGGATGCCTTGCAACGC
AGCTTCGACAGCCTGGTCGCGCGGCATGAAACCTTGCGTACCCGCTTCCG
GCTGGAGGGAGGCGTTCGTACCAGCAGGTACAACCTGCGGTTAGCGTTT
CCATCGAGCGGGAACAGTTCGGTGAAGAAGGCCTGATCGAACGGATACAG
GCCATCGTTGTGCAGCCATTCGACCTGGAACGGGGCCGCTGCTGCGGGT
GAACCTGTTGCAACTGGCCGAGGACGACCATGTACTGGTGCTGGTCCAGC
ACCACATCGTGTCCGATGGTTGGTCGATGCAGGTGATGGTCGAGGAACTG
GTCCAGCTCTATGCCGCCTATAGCCAAGGGCTCGACGTGGTGTTGCCAGC
CCTGCCGATCCAGTACGCGGACTACGCCCTGTGGCAGCGCAGCTGGATGG

TABLE 11A-continued

VIR9 Nucleotide Sequence (SEQ ID NO:17)

AGGCGGGGAAAAGGAGCGCCAGTTGGCGTACTGGACCGGCCTGCTGGGC
GGCGAGCAGCCGGTGCTGGAGTTGCCGTTCGATCGGCCGCGTCCGGCCCG
GCAGAGCCATCGTGGCGCGCAGTTGGGTTTCGAGCTATCGCGGGAACTGG
TCGAGGCCGTGAGAGCCTTGGCCCAGCGTGAAGGCGCCAGTAGTTTCATG
CTGTTGCTGGCCTCGTTCCAGGCGCTGTTGTATCGCTACAGCGGGCAGGC
GGATATCCGTGTCGGTGTGCCGATCGCCAATCGCAACCGCGTGGAGACCG
AGCGGCTGATCGGCTTCTTCGTCAACACCCAGGTGCTCAAGGCCGACCTG
GACGGTCGGATGGGCTTCGACGAGCTGCTGGCCCAGGCCCGCCAACGCGC
GCTGGAGGCCCAGGCGCACCAGGACCTGCCGTTCGAGCAACTGGTGGAAG
CCTTGCAGCCGGAGCGCAATGCCAGCCACAACCCACTGTTCCAGGTGCTG
TTCAACCATCAGAGCGAGATACGCTCGGTGACGCCCGAGGTTCAGTTGGA
GGACCTGCGTCTGGAAGGCCTGGCCTGGGACGGCCAGACTGCGCAGTTCG
ACCTGACGCTGGATATTCAGGAAGACGAAAACGGCATCTGGGCCTCCTTC
GACTATGCCACCGATCTGTTCGACGCCTCCACCGTGGAACGCCTGGCCGC
CCATTGGCGCAACCTGTTGCGCGGCATCGTCGCCAACCCACGACAGCGGC
TCGGCGAGTTGCCGCTGCTGGATGCGCCGGAGCGCCGGCAGACCCTCTCC
GAATGGAACCCGGCCCAGCGCGAGTGCGCGGTGCAGGGCACCTTGCAGCA
GCGTTTCGAGGAGCAGGCGCGGCAACGGCCACAGGCGGTTGCGCTGATCC
TCGACGAACAACGGTTGAGCTACGGCGAACTGAATGCGCGGGCCAATCGC
CTGGCGCACTGCCTGATCGCTCGCGGCGTTGGCGCGGACGTGCCGGTCGG
GCTGGCGCTGGAGCGTTCGCTGGACATGCTGGTCGGCTTGCTGGCGATCC
TCAAGGCCGGCGGCGCCTACCTGCCGTTGGACCCGGCGGCGCCAGAGGAG
CGCCTGGCGCATATCCTCGACGACAGTGGGGTACGGCTGCTGCTGACCCA
GGGGCATCTGCTCGAGCGCCTGCCGCGGCAGGCGGGGGTGGAGGTGCTGG
CCATCGACGGACTGGTGCTGGACGGCTACGCCGAGAGCGATCCGCTCCCG
ACGCTATCGGCGGACAACCTGGCCTACGTGATCTATACCTCGGGCTCGAC
CGGCAAGCCCAAGGGCACGTTGCTCACCCACCGCAACGCGCTGCGCCTGT
TCAGCGCCACCGAGGCCTGGTTCGGCTTCGACGAGCGGGACGTGTGGACG
TTGTTCCATTCCTACGCCTTCGATTTCTCGGTCTCGGAAATCTTCGGCGC
GCTGCTCTATGCGGGCGCCTGGTGATCGTGCCGCAATGGGTGAGCCGTT
CGCCGGAAGACTTCTACCGTCTGCTGTGCCGCGAAGGCGTGACGGTGCTC
AACCAGACGCCGTCGGCGTTCAAGCAACTGATGGCGGTGGCCTGTTCCGC
CGACATGGCGACGCAGCAGCCGGCGCTGCGCTACGTGATCTTCGGTGGCG
AGGCGCTGGATCTGCAGAGCCTGCGGCCGTGGTTCCAGCGCTTTGGCGAT
CGCCAGCCGCAACTGGTGAACATGTACGGCATCACCGAGACCACGGTACA
CGTAACCTACCGTCCGGTGAGCGAAGCCGACCTGAAGGGTGGCCTGGTCA
GTCCGATCGGCGGGACCATCCCGGACCTGTCCTGGTACATCCTCGACCGT
GACCTGAACCCGGTGCCGCGCGGCGCGGTGGGCGAGCTGTACATCGGTCG
CGCCGGTCTGGCGCGCGGCTACCTGAGGCGGCCCGGGTTGAGTGCCACCC
GCTTCGTGCCGAACCCGTTCCCCGGCGGTCCCGGCGAGCGGCTGTACCGT
ACCGGCGACCTGGCACGGTTCCAGGCGGATGGCAATATCGAGTACATCGG
GCGTATCGACCACCAGGTGAAGGTTCGCGGCTTCCGTATCGAACTGGGTG
AGATCGAAGCGGCGCTCGCCGGTCTGGCCGGGGTACGCGATGCCGTGGTG
CTGGCCCATGACGGGTCGGCGGCACGCAACTGGTGGGATACGTGGTGGC
GGACTCGGCGGAGGATGCCGAGCGTCTGCGGGAGTCGCTGCGGGAGTCGC
TGAAGCGGCACCTGCCCGACTACATGGTGCCGGCGCACCTGATGCTGCTG
GAGCGGATGCCGCTGACGGTCAATGGCAAGCTCGACCGGCAGGCGTTGCC
GCAACCGGATGCGAGCTTGTCGCAGCAGGCCTATCGAGCGCCCGGTAGCG
AGCTGGAGCAGCGCATCGCAGCGATCTGGGCGGAGATCCTGGGAGTGGAA
CGGGTCGGCCTGGACGACAACTTCTTCGAACTGGGCGGTCACTCATTGTT
GCTGCTGATGCTCAAGGAGCGGATCGGCGATACCTGCCAGGCTACGCTGA
GCATCAGCCAACTGATGACCCATGCCAGCGTCGCGGAACAGGCGGCATGC
ATCGAGGGCAGGCGCGTGAGTCGTTGCTGGTGCCGCTCAACGGCAGGCG
CGAAGGTTCGCCGCTGTTCATGTTCCATCCGAGTTTCGGCTCTGTGCACT
GTTACAAGACCCTCGCCATGGCGCTGCGGGATCGTCATCCGGTCAAGGGT
GTTGTCTGCCGTGCCCTGCTGGGCGCTGGTCGCGAGGTGCCGGAGTGGGA
CGATATGGTTGCGGAATACGCCGAGCAATTGCTGCAGGAGCACCCCGAAG
GGGTTTTCAACCTGGCGGGATGGTCGCTCGGCGGCAACCTGGCGATGGAT
GTCGCGGCCCGGCTGGAGCAGCGTGGGCGGCAGGTGGCTTTCGTCGGCTG
GATCGATGCACCGGCACCGGTCAGGGTCGAAGCGTTCTGGAACGAGATCG
GGCCGACGCCGGAGGCAGTCCCGAACCTATCCGTGGGCGAGATGCGGGTG
GAACTGCTCGGTGTCATGTTTCCGGAGCGGGCCGAGCATATCGAACGGGC
CTGGTCATCGATCTGCTCCGCCACGACGGACGATGAGCAGCGCTGGACGA
GGATGAGCGACTGGGCGGAAGCGGAGATCGGCGCCGAGTTCGCGACACTG
CGCAGCGAAATCGCACAGAGCAACGAACTGGAAGTGTCCTGGGAGTTGAA
ACAGATCCTCGACGAGCGCCTGAAAGCGATGGATTACCCGCGTCTGACGG
CGAAGGTCAGCCTCTGGTGGGCCGCGCGCAGCACCAATGCCATCCAGCGG
AGCGCGGTGGAGCGCTCGATGGCCGAGGCGATCGGGGCTGAGCGTGTCGA
ACCGGTGCGGGTGCTGGATACCCGGCACGACAAGATCATCGACCACCCTG
AGTTTGTGCAGAGCTTCCGGGCCGCCCTGGAGCGTGCCGGGCGCTGA

The VIR9 protein (SEQ ID NO:18) encoded by SEQ ID NO:17 is presented using the one-letter amino acid code in Table 11B.

TABLE 11B

Encoded VIR9 protein sequence (SEQ ID NO:18)

MQALIEKVGSLSPQERKALAVLLKQQGVNLFEIAPVFKRQDGEPLRLSYA
QERQWFLWQLEPESAAYHIPSVLRLRGRLDLDALQRSFDSLVARHETLRT

TABLE 11B-continued

Encoded VIR9 protein sequence (SEQ ID NO:18)

RFRLDGDEARQEIAASMALPLDIVALGPLEEGALARQVETTIARPFDLER
GPLLRVSLLRLAEDDHVLVLVQHHIVSDGWSMQVMVEELVQLYAAYSRGL
EVALPALPIQYADYALWQRSWMEAGEKERQLAYWTGLLGGEQPVLELPFD
RPRPVRQSHRGAQFILELDIDLSQALRRVAQQEGATAFALLLASFQALLY
RYSGQADIRVGVPIANRNRVETERLIGFFVNTQVLKADLDGRMGFDELLA
QARQRALEAQAHQDLPFEQLVEALQPERSLSHNPLFQVLFNYQSEARGNG
QAFRFDELQMESVQFDSRTAQFDLTLDLTDEEQRFCAVFDYATDLFDAST
VERLAGHWRNLLRGIVANPRQRLGELPLLDAPERRQTLSEWNPAQRECAV
QGTLQQRFEEQARQRPQAVALILDEQRLSYGELNARANRLAHCLIARGVG
ADVPVGLALERSLDMLVGLLAILKAGGAYLPLDPAAPEERLAHILDDSGV
RLLLTQGHLLERLPRQAGVEVLAIDGLVLDGYAESDPLPTLSADNLAYVI
YTSGSTGKPKGTLLTHRNALRLFSATEAWFGFDERDVWTLFHSYAFDFSV
WEIFGALLYGGCLVIVPQWVSRSPEDFYRLLCREGVTVLNQTPSAFKQLM
AVACSADMATQQPALRYVIFGGEALDLQSLRPWFQRFGDRQPQLVNMYGI
TETTVHVTYRPVSEADLEGGLVSPIGGTIPDLSWYILDRDLNPVPRGAVG
ELYIGRAGLARGYLRRPGLSATRFVPNPFPGGAGERLYRTGDLARFQADG
NIEYIGRIDHQVKVRGFRIELGEIEAALAGLAGVRDAVVLAHDGVGGTQL
VGYVVADSAEDAERLRESLRESLKRHLPDYMVPAHLMLLERMPLTVNGKL
DRQALPQPDASLSQQAYRAPGSELEQRIAAIWSEILGVERVGLDDNFFEL
GGHSLLATRVISRVRQEQQLDASLKALFERPVLEAFAQGLERTTDAVSTI
PLADRQQPLALSFAQERQWFLWQLEPESAAYHIPSALRLRGRLDVDALQR
SFDSLVARHETLRTRFRLEGGRSYQQVQPAVSVSIEREQFGEEGLIERIQ
AIVVQPFDLERGPLLRVNLLQLAEDDHVLVLVQHHIVSDGWSMQVMVEEL
VQLYAAYSQGLDVVLPALPIQYADYALWQRSWMEAGEKERQLAYWTGLLG
GEQPVLELPFDRPRPARQSHRGAQLGFELSRELVEAVRALAQREGASSFM
LLLASFQALLYRYSGQADIRVGVPIANRNRVETERLIGFFVNTQVLKADL
DGRMGFDELLAQARQRALEAQAHQDLPFEQLVEALQPERNASHNPLFQVL
FNHQSEIRSVTPEVQLEDLRLEGLAWDGQTAQFDLTLDIQEDENGIWASF
DYATDLFDASTVERLAGHWRNLLRGIVANPRQRLGELPLLDAPERRQTLS
EWNPAQRECAVQGTLQQRFEEQARQRPQAVALILDEQRLSYGELNARANR
LAHCLIARGVGADVPVGLALERSLDMLVGLLAILKAGGAYLPLDPAAPEE
RLAHILDDSGVRLLLTQGHLLERLPRQAGVEVLAIDGLVLDGYAESDPLP
TLSADNLAYVIYTSGSTGKPKGTLLTHRNALRLFSATEAWFGFDERDVWT
LFHSYAFDFSVWEIFGALLYGGRLVIVPQWVSRSPEDFYRLLCREGVTVL
NQTPSAFKQLMAVACSADMATQQPALRYVIFGGEALDLQSLRPWFQRFGD
RQPQLVNMYGITETTVHVTYRPVSEADLKGGLVSPIGGTIPDLSWYILDR
DLNPVPRGAVGELYIGRAGLARGYLRRPGLSATRFVPNPFPGGAGERLYR
TGDLARFQADGNIEYIGRIDHQVKVRGFRIELGEIEAALAGLAGVRDAVV
LAHDGVGGTQLVGYVVADSAEDAERLRESLRESLKRHLPDYMVPAHLMLL

TABLE 11B-continued

Encoded VIR9 protein sequence (SEQ ID NO:18)

ERMPLTVNGKLDRQALPQPDASLSQQAYRAPGSELEQRIAAIWAEILGVE
RVGLDDNFFELGGHSLLLLMLKERIGDTCQATLSISQLMTHASVAEQAAC
IEGQARESLLVPLNGRREGSPLFMFHPSFGSVHCYKTLAMALRDRHPVKG
VVCRALLGAGREVPEWDDMVAEYAEQLLQEHPEGVFNLAGWSLGGNLAMD
VAARLEQRGRQVAFVGWIDAPAPVRVEAFWNEIGPTPEAVPNLSVGEMRV
ELLGVMFPERAEHIERAWSSICSATTDDEQRWTRMSDWAEAEIGAEFATL
RSEIAQSNELEVSWELKQILDERLKAMDYPRLTAKVSLWWAARSTNAIQR
SAVERSMAEAIGAERVEPVRVLDTRHDKIIDHPEFVQSFRAALERAGR

MUT10

A *Pseudomonas* bacterial mutant (MUT10) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding the RND multidrug efflux transporter MexD (mexD; PA4598). This gene encodes the VIR10 nucleic acid (SEQ ID NO:19) shown in Table 12A.

TABLE 12A

VIR10 Nucleotide Sequence (SEQ ID NO:19)

ATGTCCGAATTCTTCATCAAGCGGCCGAACTTCGCCTGGGTGGTGGCCCT
GTTCATCTCCCTGGCCGGCCTGCTGGTCATTTCCAAATTGCCGGTAGCGC
AGTACCCCAATGTCGCGCCGCCACAGATCACCATCACCGCCACCTATCCC
GGCGCCTCGGCGAAGGTGCTGGTGGACTCCGTCACCAGTGTGCTCGAGGA
GTCGCTGAACGGCGCCAAGGGCCTGCTCTACTTCGAGTCGACCAACAACT
CCAACGGCACCGCCGAGATCGTCGTCACCTTCGAGCCGGGCACCGATCCG
GACCTGGCCCAGGTGGACGTGCAGAACCGCCTGAAGAAAGCCGAGGCGCG
CATGCCGCAGGCGGTGCTGACCCAGGGCCTGCAGGTCGAGCAGACCAGCG
CCGGTTTCCTGCTGATCTATGCGCTCAGCTACAAGGAAGGCGCTCAGCGC
AGCGACACCACCGCCCTCGGCGACTACGCCGCGCGCAATATCAACAACGA
GCTGCGGCGCCTGCCGGGCGTCGGCAAGCTGCAATTCTTCTCTTCCGAGG
CGGCCATGCGGGTCTGGATCGATCCGCAGAAGCTGGTGGGCTTCGGCCTC
TCCATCGACGACGTGAGCAATGCCATCCGCGGGCAGAACGTGCAGGTGCC
GGCCGGCGCCTTCGGCAGCGCACCGGGCAGTTCCGCGCAGGAGCTGACGG
CGACCCTGGCGGTGAAGGGCACCCTGGACGATCCGCAGGAGTTCGGCCAG
GTAGTGCTGCGCGCCAACGAGGACGGCTCGCTGGTCCGGCTCGCCGATGT
CGCGCGCCTGGAACTCGGCAAGGAGAGCTACAACATTTCCTCGCGACTGA
ACGGCACGCCCACCGTGGGCGGGGCTATCCAGCTGTCGCCCGGGGCCAAC
GCGATCCAGACCGCTACCCTGGTGAAACAGCGTCTCGCCGAACTGTCGGC
GTTCTTCCCCGAGGACATGCAGTACAGCGTGCCCTACGACACCTCGCGCT
TCGTCGACGTGGCCATCGAGAAGGTGATCCACACCCTGATCGAAGCGATG

TABLE 12A-continued

VIR10 Nucleotide Sequence (SEQ ID NO:19)

GTCCTGGTGTTCCTGGTGATGTTCCTGTTCCTGCAGAACGTCCGCTACAC

CCTGATCCCGTCCATCGTGGTGCCGGTGTGCCTGCTGGGTACGCTGATGG

TGATGTACCTGCTGGGGTTCTCGGTGAACATGATGACCATGTTCGGCATG

GTCCTGGCGATCGGCATCCTGGTGGACGACGCCATCGTGGTGGTGGAGAA

CGTCGAGCGGATCATGGCGGAGGAGGGGATTTCCCCGGCCGAGGCCACGG

TCAAGGCGATGAAGCAGGTATCCGGCGCCATCGTCGGCATCACCCTGGTG

CTCTCGGCGGTGTTCCTGCCGCTGGCTTTCATGGCCGGTTCGGTGGGGGT

GATCTACCAGCAGTTCTCGGTGTCGCTGGCGGTCTCGATCCTGTTCTCCG

GCTTCCTCGCCCTGACCTTCACCCCGGCGCTGTGCGCCACGCTGCTCAAG

CCCATTCCCGAAGGGCACCACGAGAAGCGCGGCTTCTTCGGCGCCTTCAA

CCGTGGCTTCGCCCGCGTCACCGAGCGCTATTCGCTGCTCAACTCGAAGC

TGGTGGCGCGCGCCGGACGCTTCATGCTGGTGTACGCCGGCCTGGTGGCC

ATGCTCGGCTACTTCTACCTGCGCCTGCCGGAAGCCTTCGTGCCGGCGGA

AGACCTCGGCTACATGGTGGTCGACGTGCAACTGCCGCCTGGCGCTTCGC

GCGTGCGCACCGATGCCACCGGCGAGGAGCTCGAGCGCTTCCTCAAGTCC

CGCGAGGCGGTGGCTTCGGTGTTCCTGATCTCGGGCTTCAGCTTCTCCGG

CCAGGGCGACAATGCCGCGCTGGCCTTCCCAACCTTCAAGGACTGGTCCG

AGCGAGGCGCCGAGCAGTCGGCCGCCGCCGAGATCGCCGCGCTGAACGAG

CATTTCGCGCTGCCCGACGATGGCACGGTCATGGCCGTGTCGCCGCCACC

GATCAACGGTCTGGGTAACTCCGGCGGCTTCGCATTGCGCCTGATGGACC

GTAGCGGGGTCGGCCGCGAAGCGCTGCTGCAGGCTCGCGATACTCTTCTT

GGCGAGATCCAGACCAACCCGAAATTCCTTTACGCGATGATGGAAGGACT

GGCCGAAGCGCCGCAACTGCGCCTGTTGATCGACCGGGAGAAGGCCCGTG

CCCTGGGGGTGAGCTTCGAGACCATCAGCGGCACGCTGTCCGCTGCCTTC

GGCTCGGAGGTGATCAACGACTTCACCAATGCGGGGCGCCAACAGCGGGT

GGTGATCCAGGCCGAACAGGCCAACCGGATGACCCCGGAAAGCGTGCTCG

AGCTATACGTGCCTAACGCTGCTGGCAACCTGGTACCGCTCAGCGCCTTC

GTCAGCGTGAAATGGGAAGAGGGACCGGTGCAATTGGTGCGCTATAACGG

CTACCCGTCGATCCGCATCGTCGGTGACGCCGCGCCCGGCTTCAGTACCG

GCGAAGCCATGGCGGAAATGGAGCGCCTGGCCTCGCAGCTGCCGGCCGGC

ATCGGCTACGAGTGGACCGGCCTGTCCTATCAGGAGAAGGTCTCCGCCGG

GCAGGCCACCAGCCTGTTCGCCCTCGCCATCCTGGTGGTGTTCCTGTTGC

TGGTGGCGCTCTACGAGAGCTGGTCGATCCCGCTGTCGGTGATGCTGATC

GTGCCGATCGGCGCCATCGGCGCGGTGCTCGCGGTGATGGTCAGCGGTAT

GTCCAACGACGTGTATTTCAAGGTCGGCCTGATCACCATCATCGGTCTTT

CGGCGAAGAACGCGATCCTCATCGTCGAGTTCGCCAAGGAACTCTGGGAG

CAGGGGCATAGCCTGCGCGACGCCGCCATCGAGGCCGCGCGCCTGCGCTT

CCGGCCGATCATCATGACTTCCATGGCGTTCATCCTCGGCGTTGATACCCC

TGGCCCTGGCCCAGCGGTGCCGGCGCGGCGAGCCAGCGTGCCATCGGCACC

GGAGTGATCGGCGGGATGCTCAGCGCCACCTTCCTCGGCGTGCTGTTCGT

ACCTATCTGTTTCGTCTGGCTGCTGTCGCTGCTGCGCAGCAAGCCGCCAC

CCATCGAACAGGCCGCTTCGGCCGGGGAGTGA

The VIR10 protein (SEQ ID NO:20) encoded by SEQ ID NO: 19 is presented using the one-letter amino acid code in Table 12B.

TABLE 12B

Encoded VIR10 protein sequence (SEQ ID NO:20)

MSEFFIKRPNFAWVVALFISLAGLLVISKLPVAQYPNVAPPQITITATYP

GASAKVLVDSVTSVLEESLNGAKGLLYFESTNNSNGTAEIVVTFEPGTDP

DLAQVDVQNRLKKAEARMPQAVLTQGLQVEQTSAGFLLIYALSYKEGAQR

SDTTALGDYAARNINNELRRLPGVGKLQFFSSEAAMRVWIDPQKLVGFGL

SIDDVSNAIRGQNVQVPAGAFGSAPGSSAQELTATLAVKGTLDDPQEFGQ

VVLRANEDGSLVRLADVARLELGKESYNISSRLNGTPTVGGAIQLSPGAN

AIQTATLVKQRLAELSAFFPEDMQYSVPYDTSRFVDVAIEKVIHTLIEAM

VLVFLVMFLFLQNVRYTLIPSIVVPVCLLGTLMVMYLLGFSVNMMTMFGM

VLAIGILVDDAIVVVENVERIMAEEGISPAEATVKAMKQVSGAIVGITLV

LSAVFLPLAFMAGSVGVIYQQFSVSLAVSILFSGFLALTFTPALCATLLK

PIPEGHHEKRGFFGAFNRGFARVTERYSLLNSKLVARAGRFMLVYAGLVA

MLGYFYLRLPEAFVPAEDLGYMVVDVQLPPGASRVRTDATGEELERFLKS

REAVASVFLISGFSFSGQGDNAALAFPTFKDWSERGAEQSAAAEIAALNE

HFALPDDGTVMAVSPPPINGLGNSGGFALRLMDRSGVGREALLQARDTLL

GEIQTNPKFLYAMMEGLAEAPQLRLLIDREKARALGVSFETISGTLSAAF

GSEVINDFTNAGRQQRVVIQAEQGNRMTPESVLELYVPNAAGNLVPLSAF

VSVKWEEGPVQLVRYNGYPSIRIVGDAAPGFSTGEAMAEMERLASQLPAG

IGYEWTGLSYQEKVSAGQATSLFALAILVVFLLLVALYESWSIPLSVMLI

VPIGAIGAVLAVMVSGMSNDVYFKVGLITIIGLSAKNAILIVEFAKELWE

QGHSLRDAAIEAARLRFRPIIMTSMAFILGVIPLALASGAGAASQRAIGT

GVIGGMLSATFLGVLFVPICFVWLLSLLRSKPAPIEQAASAGE

MUT11

A *Pseudomonas* bacterial mutant (MUT11) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding PA3721. This gene encodes the VIR11 nucleic acid (SEQ ID NO:21) shown in Table 13A.

TABLE 13A

VIR11 Nucleotide Sequence (SEQ ID NO:21)

ATGAACGATGCTTCTCCCCGTCTGACCGAACGCGGCAGGCAACGCCGCCGCGCCATGCTCGACGCCG

CTACCCAGGCCTTTCTCGAACACGGTTTCGAAGGCACCACCCTGGACATGGTGATAGAACGGGCCGG

TGGTTCACGGGGGACCCTGTACAGCTCCTTCGGCGGCAACGAGGGCCTGTTCGCCGCGGTGATCGCC

CACATGATCGGGGAAATCTTCGACGACAGCGCCGATCAGCCGCGCCCCGCCGCCACGCTGAGCGCCA

CCCTCGAGCATTTCGGCCGGCGCTTTCTCACCAGCCTGCTCGATCCCCGCTGCCAGAGCCTCTATCG

CCTGGTGGTGGCGGAATCCCCGCGGTTTCCGGCGATCGGCAAGTCCTTCTACGAGCAGGGGCCGCAG

CAGAGCTATCTGCTGCTCAGCGAGCGACTGGCCGCGGTCGCTCCTCACATGGACGAGGAAACGCTCT

ACGCGGTGGCCTGCCAGTTTCTCGAGATGCTCAAGGCCGACCTGTTCCTCAAGGCCCTCAGCGTGGC

CGACTTCCAGCCGACCATGGCGCTGCTGGAAACCCGCCTCAAGCTGTCGGTGGACATCATCGCCTGC

TACCTGGAACACCTGTCGCAGAGCCCCGCGCAGGGCTGA

The VIR11 protein (SEQ ID NO:22) encoded by SEQ ID NO:21 is presented using the one-letter amino acid code in Table 13B.

TABLE 13B

Encoded VIR11 protein sequence (SEQ ID NO:22)

MNDASPRLTERGRQRRRAMLDAATQAFLEHGFEGTTLDMVIERAGGSRGTLYSSFGGKEGLFAAV

IAHMIGEIFDDSADQPRPAATLSATLEHFGRRFLTSLLDPRCQSLYRLVVAESPRFPAIGKSFYE

QGPQQSYLLLSERLAAVAPHMDEETLYAVACQFLEMLKADLFLKALSVADFQPTMALLETRLKLS

VDIIACYLEHLSQSPAQG

MUT12

A *Pseudomonas* bacterial mutant (MUT12) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding PA0596. This gene encodes the VIR12 nucleic acid (SEQ ID NO:23) shown in Table 14A.

TABLE 14A

VIR12 Nucleotide Sequence (SEQ ID NO:23)

ATGTCTGATGATGCCCGTTTCCAGCAGCTGAATTGCTGGTTGGACTCTTGTTTGCCCGAGTTGTTCG

TTGCCGAAGGTTGGGGGGAAGTGCCCCCCGCCGAACTGATCCCGGCCAGTAGCGACGCCAGCTTCCG

TCGTTATTTCCGCTGGCAGGGAGGGGACCGCAGCCTGGTGGTGATGGACGCGCCGCCGCCCCAGGAA

GACTGCCGACCGTTCGTCAAGGTCGCCGGACTGCTCGCCGGAGCCGGCGTGCATGTGCCGAGGATTC

TCGCCCAGGACCTGGAGAACGGTTTCCTGCTGCTCAGTGACCTGGGCCGGCAGACCTACCTCGACGT

GCTTCATCCCGGGAATGCCGACGAGCTGTTCGAACCGGCCCTGGATGCGCTGATCGCCTTCCAGAAG

GTCGATGTCGCCGGTGTCCTGCCTGCCTACGACGAAGCGGTGCTGCGCCGCGAGCTGCAGCTGTTCC

CCGACTGGTACCTGGCCCGCCACCTCGGCGTGGAGCTGGAGGGCGAGACGCTGGCCCGCTGGAAACG

GATCTGCGACCTGCTGGTACGCAGCGCGCTGGAGCAACCGCGGGTGTTCGTCCATCGCGACTATATG

CCGCGCAATCTGATGCTCAGCGAGCCCAACCCGGGCGTCCTCGACTTCCAGGACGCCCTGCACGGCC

CGGTCACCTACGATGTCACCTGCCTGTACAAGGACGCCTTCGTCAGTTGGCCGGAGCCGCGCGTGCA

TGCCGCGCTGAACCGTTACTGGAAGAAGGCGACCTGGGCCGGCATCCCGCTGCCGCCAAGCTTCGAA

TABLE 14A-continued

VIR12 Nucleotide Sequence (SEQ ID NO:23)

GACTTCCTCCGTGCCAGCGACCTGATGGGCGTGCAGCGCCACCTGAAGGTGATTGGCATCTTCGCCC

GTATCTGTCACCGCGACGGCAAGCCGCGCTACCTGGGTGACGTGCCGCGCTTCTTCCGTTATCTGGA

AACCGCCGTGGCGCGCCGTCCCGAGCTGGCCGAACTGGGCGAGCTGCTGGCCTCGCTGCCGCAGGGA

GCCGAGGCATGA

The VIR12 protein (SEQ ID NO:24) encoded by SEQ ID NO:23 is presented using the one-letter amino acid code in Table 14B.

TABLE 14B

Encoded VIR12 protein sequence (SEQ ID NO:24)

MSDDARFQQLNCWLDSCLPELFVAEGWGEVPPAELIPASSDASFRRYFRWQGGDRSLVVMDAPPP

QEDCRPFVKVAGLLAGAGVHVPRILAQDLENGFLLLSDLGRQTYLDVLHPGNADELFEPALDALI

AFQKVDVAGVLPAYDEAVLRRELQLFPDWYLARHLGVELEGETLARWKRICDLLVRSALEQPRVF

VHRDYMPRNLMLSEPNPGVLDFQDALHGPVTYDVTCLYKDAFVSWPEPRVHAALNRYWKKATWAG

IPLPPSFEDFLRASDLMGVQRHLKVIGIFARICHRDGKPRYLGDVPRFFRYLETAVARRPELAEL

GELLASLPQGAEA

MUT13

A *Pseudomonas* bacterial mutant (MUT13) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding PA5265. This gene encodes the VIR13 nucleic acid (SEQ ID NO:25) shown in Table 15A.

TABLE 15A

VIR13 Nucleotide Sequence (SEQ ID NO:25)

ATGAGCGGATTCCAGGACCAGAGTATCGACGAAGGCGTGCGCAAGCGCACCGCCTACCAGAACGATC

GGCGTGCACGACTGGCATTGAACGTCGAGCGACAGGACGGCGGTATCCTGCAGATTCCGGTGGCCAG

CGATATGCTCGGCCATGAGGAGCACGAGCGTATCCAGCAGAACACCTTCCTGGCTGTGATGCCGCTG

GTCCGCCTGCCAACGCTGGGCAAGGCCGGTTATGGCGACCAGCTGCCCGCCGGCGCGCTACCGCGGG

CGGGACGGATCTACCTGTTCCAGGACGGCAAGTTGTGGCGCGAACTGGAATGTGATGGCAAGGGCAA

CCTGTTCGAAGTCGATCTCCTGCAGGGGCGCAGCCAGCGTGCGGACAAGCGTCCGGCCTTAGGCAAG

ACACAAGCGCTGATCCTGGTGCCGGTGCTGGTCAAGGGGCAGTTCGTGATCCCACGCTACACCATGG

CCTATAGCGAAACTCCCTGGCCTTGGTCGTACATCGACTGGCTGGAGGAGGACCCGCAGCGGGTCAA

CCGGCGCTGCCAGCAGATGGCGTCCGCTTGGAACGCCTCGGTGGCCAACCAGCACTGGAAAGCCTCC

ATCCATCAACCCGCGCTGGTCATTGATCATCACGCCCAGGGTTTGCGACCTCGCGACTTCAACGTCG

AGAGCGCGCTGGAAGACCCGGCGGAATTCACACCTGAGTTCGCCGCCTTTCGCGAAGAGTCGCTGGT

GTGCCAGTTGCAGCGACGCCAGCAGGAATTGGCGCCCCTGCTGAAGCAGGCTCCGCCCTCTGCGCTA

CCTACTCTGGAAGCCGGAGAGGACGTACTGGAAACCCTCAAGCTGCGTGGCCATCCCAACCTCATCG

TABLE 15A-continued

VIR13 Nucleotide Sequence (SEQ ID NO:25)

```
GGCTGATGCTCGACGACTCGCTGTTCGCCTTGCGCCACGCTGCGGCGCAGGCGCGCCACTGCGCCGC
CTACTTGCGCAGCCTCAATGCACTGCTGCCGCACCGTCCCAACGGACGCTATGCACAGGTGCTGAGC
AACATGCTCGACGGCCCGCTCGCCAAGCTCAGGGGCGAGGTCGATCAGGCCGAACTGGACGAGGCGA
TCTTCGCCGAGGAGCGACAGTCTTGCCGAATCCACCTGACGCAGCAGGTCGAGCATCTGGTTGCCCT
GCTGGAAGGCCCCTTGCACCCGGTGTTGCAGGACTGGACCCACCAGTGCGACGAAGCCCTGCTGGAG
CCCTACAGCCTGATGAGCGAGGCACTGGCTGCGCTGAACCAGCTTCCCGACCGCTGCGACGCACTGT
ACAGCGGTACCGCCTACCGGGCGCTGGCGGCACATGTCGAGCGGGTGGTCAGCACGGTTCTGCAGGC
AAGCCACCCGCTTGGCGCCATGCTCCTGGCCAAGGACGAAGGACAACTTCCCGAGCCGGTTCGGCGC
CTGCAGGCGCTGCGCGATAGCCCGCGGACGCCGGACCCCGATGCAATGGGCCTCAGCACGCTGATGC
TGGGAGCCAGTCTGCTGGGCGAGGTCGACCAGCCCAGCGCCGGCAAGAGCCTCGCCTACTTCCTCGG
CGACCTGCTGGACGTGTTCGGCGCCAGCGTAGTCGAGCAACTCGGCCGGCTGTCCCAGGGCGCCACC
CAGATCCAGCTCGACCGCTTGTTCGCACCGACCTTCAATACTCTGAGCGCCCTCTCGGTGAAGATGA
AAGGTATCCGCCTGCTGCCCGACAGTCAGGTGCCGCTCGACATGGTTGTCGTCGGCGTGCGCGGAGC
CGGCCTGCGCAACGGTCTGACCGAGGTCGAGCGCCAGGAGCTGAGGCGCAAGAGCTATCGGCGCGCC
ATCGTTCAGGACGGTGCCGGCAATCCCCTGGCCGGCACCAGTCCCCGCGACACCGGCATGAGTCGCG
CCAACCTGCGCAACGTCATGGTGGTGGCGGTACCCAAGGATCACCCGGACCTGCTTGCCTACACGAA
ATTCCGTACGCAGTTAGGCACGTTGACCCAGGTGATGGAGAACACTCGCATCGTGCCGACGATGATG
CTGGGGTTTGCGATTTATAACTTGAATGTGCAGGTGCAGGCATACAGTGGCTTTGTAGACAGTGGAG
AAAAGCACAGAGGGACGATCGGGGCTGTCGGTGCAGTAATCGATTTAACAGCCGCTGGAGGAAGCCA
TGCAAAGCTGCTTTTCGGACCATCTACTGCAAAGTATCTAGAAACCCCACGTATATCGGTAGCCCAA
ATATCCCCTCGATGGGCCAGGAATCTAGAAGTTCAAACAGGCAGCCCTAAGTTAGGGTTGCTACGTG
GGCTTGGTGGCGCAGCCACACTATTCGGTGCAGGCATCAGTGTATGGGATGGCTACCGAGCTTTGAG
GCAGGGAGATAGCGATGCGGCTGCGGCCTACGGTGTGGCCGCAGTGGGTGGGGCCTTTGGGGTGCC
TACGTCCTAGGATGGATAGTAAACCCTTATGCTTTGCTGGCTGGTGCGGTTTTGGCGATCGGAGGCA
CTGTGGTCGCTAATCTACTGACTGACAGCGATGCGGAAACCATCGTAAAGAAAGGCCCCTTCGGCCG
GCAATTCGCCGAGGCTGGCCTGCTCGATTCGCTGATGGGCCAGGACCAGCGCTTCGCCCATCTGAAA
GACCCGCAAACGGCCTATCGCCAATTGCTGGGAGTCCTCGGCCATCCGCGGGTCTTTGTCCATCGCC
TGGAAGACTGGCGCAAATTGGCGCCGGCGGCGCATCGATCTGTCTTGCAGGAAGCGGAACGGGGTCG
CCAAGCGGTCAGCCGCACTGCGCTATCCTGCATCGACCCCAAGTTGCAGGCGCTGGAGGCAAACGAT
TGGGCCGTGGTGCTGAGTTCCCCGCTCCTGGCCATGTTCGAGAATGGCCAGAAGGCGTTCCGCCTGG
TGGCCCAGGAGTTTCTCAGCAGCTTGCCGATCGATCCGGGCACCCTGTTCGGCGTCAAGCGCTACCA
TCGGGTCCCCGCGGGCCCCGCCAAGCTCGAAGCCTTGCCGTTGGATGCTGCCAGCGTGCTCTATGTG
CTGCCGGCCAGCCTGCCGATTCCGCAGTTGTCTCCTCGGGCCCGCTATAGCATGCGCATGACCCAGG
GTTTGAAGATCAGCGCACAGTTCGAACTCAATGCCGACCAGCCTGAGCAGCGGCTTGTCCTGCCTCA
ACCCAGCCCGAAGAGTTGGAGTGCATTCACATCCGCCAATCGGTACCTTCCCCCGGACGACTTGGGC
CCCCATGCTGCGCCACCTTATTGGTTGATAGAGAACAGTGAGTTCAACGTATGA
```

The VIR13 protein (SEQ ID NO:26) encoded by SEQ ID NO:25 is presented using the one-letter amino acid code in Table 15B.

TABLE 15B

Encoded VIR13 protein sequence (SEQ ID NO:26)

MSGFQDQSIDEGVRKRTAYQNDRRARLALNVERQDGGILQIPVASDMLGHEEHERIQQNTFLAVM

PLVRLPTLGKAGYGDQLPAGALPRAGRIYLFQDGKLWRELECDGKGNLFEVDLLQGRSQRADKRP

ALGKTQALILVPVLVKGQFVIPRYTMAYSETPWPWSYIDWLEEDPQRVNRRCQQMASAWNASVAN

QHWKASIHQPALVIDHHAQGLRPRDFNVESALEDPAEFTPEFAAFREESLVCQLQRRQQELAPLL

KQAPPSALPTLEAGEDVLETLKLRGHPNLIGLMLDDSLFALRHAAAQARHCAAYLRSLNALLPHR

PNGRYAQVLSNMLDGPLAKLRGEVDQAELDEAIFAEERQSCRIHLTQQVEHLVALLEGPLHPVLQ

DWTHQCDEALLEPYSLMSEALAALNQLPDRCDALYSGTAYRALAAHVERVVSTVLQASHPLGAML

LAKDEGQLPEPVRRLQALRDSPRTPDPDAMGLSTLMLGASLLGEVDQPSAGKSLAYFLGDLLDVF

GASVVEQLGRLSQGATQIQLDRLFAPTFNTLSALSVKMKGIRLLPDSQVPLDMVVVGVRGAGLRN

GLTEVERQELRRKSYRRAIVQDGAGNPLAGTSPRDTGMSRANLRNVMVVAVPKDHPDLLAYTKFR

TQLGTLTQVMENTRIVPTMMLGFAIYNLNVQVQAYSGFVDSGEKHRGTIGAVGAVIDLTAAGGSH

AKLLFGPSTAKYLETPRISVAQISPRWARNLEVQTGSPKLGLLRGLGGAATLFGAGISVWDGYRA

LRQGDSDAAAAYGVAAVGGGLWGAYVLGWIVNPYALLAGAVLAIGGTVVANLLTDSDAETIVKKG

PFGRQFAEAGLLDSLMGQDQRFAHLKDPQTAYRQLLGVLGHPRVFVHRLEDWRKLAPAAHRSVLQ

EAERGRQAVSRTALSCIDPKLQALEANDWAVVLSSPLLAMFENGQKAFRLVAQEFLSSLPIDPGT

LFGVKRYHRVPAGPAKLEALPLDAASVLYVLPASLPIPQLSPRARYSMRMTQGLKISAQFELNAD

QPEQRLVLPQPSPKSWSAFTSANRYLPPDDLGPHAAPPYWLIENSEFNV

MUT14

A *Pseudomonas* bacterial mutant (MUT14) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding pyochelin biosynthetic protein pchC (PA4229). This gene encodes the VIR14 nucleic acid (SEQ ID NO:27) shown in Table 16A.

TABLE 16A

VIR14 Nucleotide Sequence (SEQ ID NO:27)

ATGAGCGCCGCCTGGGTCCGGCCGTTCCGCCTGACGCCGATGCCGCGCCTGCGCCTGGCCTGCTTCC

CCCATGCAGGCGGCAGCGCCAGCTTCTTCCGTAGCTGGAGCGAACGCCTGCCGCCAGACATCGACCT

GCTTGCCCTGCAGTACCCGGGTCGCGAGGACCGCTTCAACGAGGCGCCGGCCACCCGCCTGGAGGAC

CTCGCCGACGGCGCCGCCCTCGCCCTGCGCGATTTCGCCGACGCGCCCCTGGCGCTGTTCGGCCACA

GTCTCGGCGCGGCGCTGGCCTACGAAACCGCCCTGCGCCTGGAAAGCGCCGGCGCGCCGCTGCGCCA

CCTGTTCGTCTCCGCCCATCCGGCACCGCACCGGCAACGCGGCGGCGCGTTGCACCGCGGCGACGAG

GCGGCGCTGCTGGAGGACGTCCGCCGCCAGGGTGGCGCCAGCGAGCTACTCGAGGACGCCGACCTGC

GCGCGCTGTTCCTGCCGATCCTGCGCGCCGACTACCAGGCGATCGAGACCTACCGACGGGCGCAGCC

CATCGCCCTGGCCTGCGCCCTCGACGTCCTCCTCGGCGAGCACGACGAGGAAGTCAGCGCCGCCGAG

TABLE 16A-continued

VIR14 Nucleotide Sequence (SEQ ID NO:27)

GCGCAGGCCTGGAGCGACGCCAGCCGGACTCCCGCCAGGCTGCGGCGCTTTCCTGGCGGCCACTTCT

ACCTGAGCGAGGGGCGCGACGCGGTGATCGAGCACCTGCTGCGCCGCCTCGCACATCCCGACGCCCT

TTCCCGAGAGGTTGCATGA

The VIR14 protein (SEQ ID NO:28) encoded by SEQ ID NO:27 is presented using the one-letter amino acid code in Table 16B.

TABLE 16B

Encoded VIR14 protein sequence (SEQ ID NO:28)

MSAAWVRPFRLTPMPRLRLACFPHAGGSASFFRSWSERLPPDIDLLALQYPGREDRFNEAPATRLEDL

ADGAALALRDFADAPLALFGHSLGAALAYETALRLESAGAPLRHLFVSAHPAPHRQRGGALHRGDEAA

LLEDVRRQGGASELLEDADLRALFLPILRADYQAIETYRRAQPIALACALDVLLGEHDEEVSAAEAQA

WSDASRTPARLRRFPGGHFYLSEGRDAVIEHLLRRLAHPDALSREVA

MUT15

A *Pseudomonas* bacterial mutant (MUT15) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding dihydroaeruginoic acid synthetase pchE (PA4226). This gene encodes the VIR15 nucleic acid (SEQ ID NO:29) shown in Table 17A.

TABLE 17A

VIR15 Nucleotide Sequence (SEQ ID NO:29)

ATGGATCTGCCCCCCGATTCCCGTACCGCCCTGCGCGACTGGCTGACCGAGCAGCTCGCCGACCTGC

TCGGCGAACCGCTTGCTGACGTGCGCGCCCTGGCGGACGACGACGACCTGCTGGGCTGCGGCCTCGA

CTCGATCCGCCTGATGTACCTGCAGGAACGCCTGCGCGCGCGTGGCTCGACGCTGGACTTCGCCCAG

TTGGCGCAGCGCCCCTGCCTGGGGGCCTGGCTCGACCTGCTGGCCTGCGCGGACCGGCTGTCCGCCC

CGGCAACGGTCGCGCTGCCGACGGCGCAGGATCGCGATCAGCCGTTCGAGCTGTCTTCCGTGCAGCA

GGCCTACTGGCTGGGACGTGGCGCCGGCGAGGTGCTGGGCAACGTCAGCTGCCATGCCTTTCTGGAA

TTCCGCACGCGGGATGTCGACCCGCAGCGCCTGGCCGCGGCGGCGGAGTGCGTGCGTCAACGCCACC

CGATGTTGCGGGCGCGCTTCCTCGACGGTCGCCAGCAGATCCTTCCGACGCCGCCGCTGTCCTGCTT

CGACCTGCAGGACTGGCGCACCTTACAGGTGGACGAGGCCGAGCGCGACTGGCAGGCGCTGCGCGAC

TGGCGCGCCCATGAATGCCTGGCGGTGGAGCGCGGCCAGGTGTTCCTGCTCGGGCTGGTGCGCATGC

CGGGCGGCGAGGATCGCCTCTGGCTGAGTCTCGACCTGCTTGCCGCCGATGTCGAAAGCCTGCGCCT

GCTGCTGGCCGAACTGGGCGTTGCCTACCTGGCGCCGGAGCGCCTGGCGGAGCCGCCGGCGCTGCAT

TTCGCCGACTACCTGGCGCACCGTGCGGCGCAACGCGCCGAGGCCGCGGCGCGGGCCCGCGACTACT

GGCTGGAACGCCTGCCGCGCTTGCCGGACGCGCCGGCCCTGCCGTTGGCCTGCGCGCCGGAAAGCAT

CCGCCAGCCGCGCACCCGGCGCCTGGCATTCCAGCTTTCCGCCGGCGAGAGCCGGCGCCTGGAGCGT

TABLE 17A-continued

VIR15 Nucleotide Sequence (SEQ ID NO:29)

```
CTTGCCGCGCAGCATGGCGTGACCTTGTCCAGCGTGTTCGGCTGCGCCTTCGCGCTGGTCCTGGCGC
GCTGGAGCGAAAGCGCGGAATTTCTCCTCAACGTGCCGTTGTTCGATCGGCATGCCGACGACCCGCG
TATCGGCGAGGTGATCGCCGACTTCACCACCCTGTTGCTGCTGGAGTGCCGGATGCAGGCCGGGGTG
TCCTTCGCCGAGGCGGTGAAGAGCTTCCAGCGCAACCTCCACGGAGCCATCGACCACGCCGCATTCC
CCGCCCTGGAGGTGCTCCGCGAGGCGCGCCGGCAGGGCCAGCCACGCTCGGCGCCGGTGGTGTTCGC
CAGCAACCTGGGCGAGGAGGGCTTCGTCCCGGCGGCCTTCCGCGACGCTTTCGGCGATCTCCACGAC
ATGCTCTCGCAGACCCCGCAGGTCTGGCTCGACCACCAGCTCTACCGGGTGGGCGACGGTATCCTGC
TGGCCTGGGATAGCGTCGTCGGCCTGTTCCCCGAAGGTCTGCCGGAAACCATGTTCGAAGCCTACGT
GGGGCTGCTCCAGCGTCTCTGCGACAGCGCCTGGGGCAGCCCGCCGATCTGCCGTTGCCCTGGGCG
CAGCAGGCGCGCCGGGCCCTGCTCAACGGCCAGCCGGCATGCGCCACGGCGCGCACCCTGCATCGCG
ACTTCTTCCTTCGCGCCGCCGAGGCGCCGGATGCCGACGCGCTGCTCTATCGCGACCAACGTGTCAC
CCGCGGCGAACTGGCCGAGCGTGCGCTGCGCATCGCCGGCGGCCTGCGCGAAGCCGGGGTGCGCCCT
GGCGACGCGGTCGAGGTCAGCCTGCCGCGCGGACCGCAGCAGGTCGCGGCGGTATTCGGCGTGCTCG
CCGCAGGCGCCTGCTACGTGCCGCTGGACATCGACCAGCCGCCCGCACGGCGGCGCCTGATCGAAGA
GGCCGCCGGGGTATGCCTGGCGATCACCGAGGAGGACGATCCGCAGGCCTTGCCGCCGCGCCTGGAT
GTCCAGCGCCTGCTGCGCGGCCCGGCGCTGGCCGCCCCGTGCCGCTGGCGCCGCAGGCGAGTGCCT
ATGTGATCTACACCTCGGGCTCCACCGGGGTGCCCAAGGGCGTCGAGGTCAGCCACGCGGCGGCGAT
CAATACCATCGACGCGCTGCTCGACCTGCTGCGGGTGAACGCATCGGATCGCTTGCTGGCGGTCTCC
GCGCTGGACTTCGATCTGTCGGTCTTCGACCTGTTCGGCGGCCTCGGCGCCGGTGCCAGCCTGGTCC
TGCCGGCCCAGGAACAGGCGCGCGATGCCGCTGCCTGGGCGGAGGCTATCCAGCGGCATGCGGTGAG
CCTGTGGAACTCGGCGCCGGCCTTGCTGGAGATGGCCCTCAGCCTGCCGGCGAGCCAGGCCGACTAT
CGCAGTCTGCGGGCGGTGCTGCTGTCCGGCGACTGGGTGGCCCTGGACCTGCCCGGCCGCCTGCGCC
CACGTTGTGCCGAAGGCTGCCGCCTGCATGTGCTGGGTGGCGCTACCGAAGCGGGCATCTGGTCGAA
CCTGCAGAGCGTCGATACGGTGCCGCCGCACTGGCGTTCGATTCCCTACGGCCGGCCATTGCCGGGA
CAGGCCTACCGGGTGGTCGACACCCACGGGCGCGACGTGCCGGACCTGGTGGTCGGCGAGCTGTGGA
TCGGCGGCGCCAGCCTGGCCCGCGGCTATCGCAACGATCCCGAACTCAGCGCCCGGCGTTTCGTCCA
CGATGCCCAGGGCCGCTGGTATCGCACCGGCGATCGCGGTCGCTACTGGGGCGACGGTACCCTGGAA
TTCCTCGGTCGGGTCGACCAGCAGGTGAAAGTGCGCGGCCAGCGCATCGAGTTGGGCGAGGTGGAGG
CCGCGCTGTGCGCCCAGGCTGGCGTGGAGAGCGCCTGCGCGGCGGTGCTCGGCGGTGGCGTGGCGAG
CCTCGGCGCGGTGCTGGTACCGCGCCTGGCGCCACGGGCCGAAGGCTCCATGGATCTACCGGCCGCA
CAGCCCTTCGCCGGCCTGGCAGAGGCCGAGGCGGTACTCACCCGGGAAATCCTCGGCGCGCTGCTGG
AGGCGCCGCTGGAGCTAGACGACGGTTTGCGCCGGCGCTGGCTGGACTGGCTAGCGGACTCCGCCGC
CAGCGCGCTGCCGTCGCTCGACGAGGCGTTGCGCCGGCTCGGCTGGCAGGCCGCGGGGCTGACCGCG
ATGGGCAACGCTCTGCGCGGCCTGCTCGCCGGCGAACAGGCGCCGGCCGCGCTGCTCCTCGATCCCT
GGCTGGCGCCGCAGGCGGTGGCCGCGCGCCTGCCGGACGGCCGCGAGGCCCTGGCGCGCCTGCTCGA
AGCGCTGCCGACGCCGGCTGCCGGCGAACGCCTGCGGGTGGCGGTGCTGGATACCCGCGCCGGGCTC
TGGCTCGACCAGGGCATGGCCTCGCTGTTGCGCCCAGGGCTGGAACTGACCCTCTTCGAACGCAGCC
GCGTCCTCCTCGACGCCGCCGCCACCCGCTTGCCGGAACGGATCGTGGTGCAGGCGCTGGACGACGG
CCTGCTACCTGCCGAGCACCTCGGTCGCTACGACCGGGTGATCAGCTTCGCCGCGCTGCACGCCTAC
```

TABLE 17A-continued

VIR15 Nucleotide Sequence (SEQ ID NO:29)

GAGGCCAGCCGCGAAGGCCTGGCGCTGGCGGCGGCGCTGCTGCGCCCGCAGGGCCGCCTGTTGCTGG

TGGACCTGCTATGCGAGTCGCCACTGGCGCTGCTCGGTGCGGCCTTGCTCGACGACCGGCCGCTGCG

CCTGGCGGAGCTGCCGAGCCTGTTGGCCGATCTCGCCGCTGCGGGACTGGCGCCGCGTTGCCTGTGG

CGCAGCGAGCGGATCGCCCTGGTCGAGGCGCTGGCACCGGGACTCGGGCTCGACGCCGCCGCGCTCC

AGGCCGGCCTGGAGCAACGCCTGCCCCAGGCGATGCGGCCCGAACGCCTGTGGTGCCTGCCAAGCCT

GCCGTTGAACGGCAATGGCAAGGTCGATCGTCGCCGCCTGGCCGAGAGCATGACCCGCGCACTCGGC

GAGTGTCGTCACGAGCCCTCGGCGGAGGAGCCGCTGGAAGCCCATGAGCAAGCGCTGGCCGAGTGCT

GGGAAGCGGTTCTCAAACGCCCGGTCCGTCGTCGCGAGGCGAGCTTCTTCAGCCTCGGCGGCGACAG

CCTGCTGGCGACCCGCCTGCTGGCCGGCATACGTGAGCGTTTCGGCGTACGCCTGGGCATGGCCGAC

TTCTATCGCCAGCCGACCCTGGCCGGTCTTGCCCGCCACTTGCAGGTGCAGACCGTCGAAATCGAGG

AAACCCAACTGGAAGAGGGCGTGCTATGA

The VIR15 protein (SEQ ID NO:30) encoded by SEQ ID NO:29 is presented using the one-letter amino acid code in Table 17B.

TABLE 17B

Encoded VIR15 protein sequence (SEQ ID NO:30)

MDLPPDSRTALRDWLTEQLADLLGEPLADVRALADDDDLLGCGLDSIRLMYLQERLRARGSTLDFAQL

AQRPCLGAWLDLLACADRLSAPATVALPTAQDRDQPFELSSVQQAYWLGRGAGEVLGNVSCHAFLEFR

TRDVDPQRLAAAAECVRQRHPMLRARFLDGRQQILPTPPLSCFDLQDWRTLQVDEAERDWQALRDWRA

HECLAVERGQVFLLGLVRMPGGEDRLWLSLDLLAADVESLRLLLAELGVAYLAPERLAEPPALHFADY

LAHRAAQRAEAAARARDYWLERLPRLPDAPALPLACAPESIRQPRTRRLAFQLSAGESRRLERLAAQH

GVTLSSVFGCAFALVLARWSESAEFLLNVPLFDRHADDPRIGEVIADFTTLLLLECRMQAGVSFAEAV

KSFQRNLHGAIDHAAFPALEVLREARRQGQPRSAPVVFASNLGEEGFVPAAFRDAFGDLHDMLSQTPQ

VWLDHQLYRVGDGILLAWDSVVGLFPEGLPETMFEAYVGLLQRLCDSAWGQPADLPLPWAQQARRALL

NGQPACATARTLHRDFFLRAAEAPDADALLYRDQRVTRGELAERALRIAGGLREAGVRPGDAVEVSLP

RGPQQVAAVFGVLAAGACYVPLDIDQPPARRRLIEEAAGVCLAITEEDDPQALPPRLDVQRLLRGPAL

AAPVPLAPQASAYVIYTSGSTGVPKGVEVSHAAAINTIDALLDLLRVNASDRLLAVSALDFDLSVFDL

FGGLGAGASLVLPAQEQARDAAAWAEAIQRHAVSLWNSAPALLEMALSLPASQADYRSLRAVLLSGDW

VALDLPGRLRPRCAEGCRLHVLGGATEAGIWSNLQSVDTVPPHWRSIPYGRPLPGQAYRVVDTHGRDV

PDLVVGELWIGGASLARGYRNDPELSARRFVHDAQGRWYRTGDRGRYWGDGTLEFLGRVDQQVKVRGQ

RIELGEVEAALCAQAGVESACAAVLGGGVASLGAVLVPRLAPRAEGSMDLPAAQPFAGLAEAEAVLTR

EILGALLEAPLELDDGLRRRWLDWLADSAASALPSLDEALRRLGWQAAGLTAMGNALRGLLAGEQAPA

ALLLDPWLAPQAVAARLPDGREALARLLEALPTPAAGERLRVAVLDTRAGLWLDQGMASLLRPGLELT

LFERSRVLLDAAATRLPERIVVQALDDGLLPAEHLGRYDRVISFAALHAYEASREGLALAAALLRPQG

RLLLVDLLCESPLALLGAALLDDRPLRLAELPSLLADLAAAGLAPRCLWRSERIALVEALAPGLGLDA

AALQAGLEQRLPQAMRPERLWCLPSLPLNGNGKVDRRRLAESMTRALGECRHEPSAEEPLEAHEQALA

TABLE 17B-continued

Encoded VIR15 protein sequence (SEQ ID NO:30)

ECWEAVLKRPVRRREASFFSLGGDSLLATRLLAGIRERFGVRLGMADFYRQPTLAGLARHLQVQTVEI

EETQLEEGVL

MUT16

A *Pseudomonas* bacterial mutant (MUT16) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding pyochelin synthetase pchF (PA4225). This gene encodes the VIR16 nucleic acid (SEQ ID NO:31) shown in Table 18A.

TABLE 18A

VIR16 Nucleotide Sequence (SEQ ID NO:31)

ATGAGCCTCGGCGAACTGCTGGAAACCTGCCGCAGCCGGCGCATCGAACTCTGGAGCGAGGCGGGCC

GCCTGCGCTATCGCGCCCCCCAGGGTGCCCTCGACGCCGGCCTCGCCGAGCGCCTGCGGGCCGAGCG

CGAGGCCCTGCTGGAACACCTGGAAGGCGGCCCTGGCTGGCGCGCCGAACCCGACATGGCCCACCAG

CGCTTCCCGCTCACCCCGCTCCACCCCGCCTACGTGCTGGGCCGCCAGGCGGCCTTCGACTACGGCG

GTAACGCCTGCCAGCTGTACGCCGAGTACGACTGGCCGGCCGACACCGATCCGGCGCGCCTGGAGGC

GGCCTGGAACGCCATGGTCGAGCGCCACCCGATGCTGCGCGCGGTGATCCAGCACAACGCCTGGCAG

CGCGTGCTGCCCGAGGTGCCCTGGCAGCGGCTGACCGTGCATGCCTGCGCGGGGCTCGACGAGGCCG

CTTTCCAGGCGCACCTGGAGCGGGTCCGCGAACGCCTCGACCACGCCTGCGCGGCGCTCGACCAGTG

GCCGGTCCTGCGCCCCGAGCTGAGTATCGGCCGGGATGCCTGCGTACTGCACTGCTCGGTGGATTTC

ACCCTGGTCGACTACGCCAGCCTGCAATTGCTGCTTGGCGAATGGCGCCGCCGCTATCTCGATCCGC

AATGGACGGCGGAACCGCTGGAGGCGACCTTCCGCGACTATGTCGGCGTCGAGCAGCGCCGACGCCA

GTCGCCAGCCTGGCAGCGCGACCGCGACTGGTGGCTGGCGCGTCTCGACGCGCTACCCGGCCGTCCC

GACCTGCCGCTGCGGGTGCAGCCGGACACCCGGTCCACGCGCTTCCGGCACTTCCACGCGCGCCTCG

ACGACGCCGCCTGGCACCCGCTCGGCGCGCGCGCCGGCGAACACGGCCTGAGCGCTGCCGGCGTGGC

CTTGGCGGCCTTCGCCGAGACCATCGGTCGCTGGAGCCAGGCACCGGCGTTCTGTCTCAACCTGACG

GTACTCAACCGGCCGCCGCTGCATCCGCAGCTCGCGCAGGTGCTCGGTGACTTCACCGCGCTCAGCC

TGCTGGCAGTGGACAGCCGCCACGGCGACAGTTTCGTCGAGCCTCCCCGACGCATCGGCGAGCAGAT

GTTCGACGACCTCGACCACCCGACCTTCAGCGGCGTCGACCTGCTGCGCGAACTGGCGCGCCGGCGT

GGTCGCGGCGCCGATCTGATGCCGGTGGTGTTCACCAGTGGCATCGGCAGCGTGCAGCGCCTGCTCG

GCGATGGCGAGGCGCCGCGCGCGCCACGCTACATGATCAGCCAGACCCCGCAGGTCTGGCTGGACTG

CCAGGTCACCGACCAGTTCGGCGGCCTGGAGATCGGCTGGGACGTACGCCTCGGGTTGTTCCCCGAG

GGCCAGGCGGAAGCCATGTTCGACGACTTCGTCGGGCTGCTCCGGCGCCTGGCGCAGAGCCCGCGCG

CCTGGACCGACGGCGATGCCACGGAACCCGTCGAGGCGCCGCCGCAGGCGTTGCCCGGTAGTGCCCG

GAGCATCGCCGCCGGTTTCGCCGAGCGTGCCCTGCTGACCCCCGACGCCACGGCGATCCACGATGCC

CCCGGCAGCTACAGCTACCCCCAGGTCGCCCAGCACGCCAGCGCCCTGCGCCGCGTCCTGGAAGCGC

ACGGCGCGGGCCGTGGCCGGCGGGTCGCCGTGATGCTGCCGAAAAGCGCCGCGCAATTGGTCGCGGT

GATCGGCATCCTCCAGGCCGGCGCCGCCTATGTCCCGGTGGACATCCGCCAGCCTCCGCTGCGGCGC

CAGGCGATCCTCGCCAGCGCCGAAGTGGTCGCGCTGGTCTGCCTGGAAAGCGATGTCCCGGACGTCG

GCTGCGCCTGCGTGGCCATCGACCGGCTGGCCGCCGACAGCGCCTGGCCGCCACCGCCCGCGGCGGA

TABLE 18A-continued

VIR16 Nucleotide Sequence (SEQ ID NO:31)

```
GGTGGCGGCGGACGACCTCGCCTACGTGATCTACACCTCCGGCTCCACCGCCACGCCAAAGGGCGTG
ATGCTCAGCCATGCGGCGGTGAGCAACACGCTGCTCGACATCAACCAGCGCTACGCCGTCGACGCCA
ACGACCGCGTCCTCGGCCTCGCCGAGCTGAGCTTCGACCTCTCGGTCTACGACTTCTTCGGCGCCAC
CGCGGCGGGGGCCCAGGTGGTCCTCCCCGGACCCGGCGCGCGGCAGCGATCCATCGCACTGGGCGGAA
CTGCTGGAACGCCACGCCATCACCCTGTGGAACTCGGTGCCGGCCCAAGGCCAGATGCTCATCGATT
ACCTGGAGAGCGAGCCGCAACGTCACCTGCCGGGACCGCGCTGCGTGCTCTGGTCCGGTGACTGGAT
TCCGGTCAGCCTGCCGACCCGCTGGTGGCGGCGCTGGCCGGACAGCGCGCTGTTCACCCTGGCCGGC
CCCACCGAGGCGGCGATCTGGTCCATCGACCAGCCGATCCGCCCGCAGCACACCGAGCTGGCCAGCA
TCCCTTATGGCCGTGCCCTGCGCGGGCAGAGCGTGGAAGTCCTGGATGCCCGCGGGCGGCGCTGCCC
GCCGGGCGTGCGCGGCGAGATCCATATCGGCGGGGTGGGCCTGGCGCTCGGCTACGCCGGCGATCCG
CAGCGCACCGCCGAACGCTTCGTCCGTCACCCCGATGGCCGTCGCCTGTATCGCACCGGCGACCTCG
GCCGCTACCTGGCCGACGGCAGCATCGAGTTCCTCGGCCGCGAGGACGACCAGGTGAAGATTCGCGG
CCACCGCATCGAACTGGCCGAACTGGACGCCGCGCTGTGCGCTCATCCGCAGGTCAACCTGGCGGCC
ACCGTGGTGCTCGGCGAGACCCACGAGCGCAGCCTGGCCAGCTTCGTCACCCTGCATGCGCCGGTGG
AGGCTGGCGAGGATCCGCGTACGGCGCTCGACGCGGTGCGCCAGCGGGCGGCCCAGGCCTTGCGCCG
CGACTGGGGCAGCGAGGAGGGCATCTCCGCTGCGGTGGCCGCACTCGACCGTGCCTGCCTCGCCTCG
TTGGCCGCCTGGCTGGCCGGCAGCGGTCTGTTCGCCAGTGCGACGCCGCTGGACTTAGCCACCCTGT
GCCAGCGCCTGGGTATCGCCGAGGCGCGCCAGCGCCTGCTGCGCCACTGGTTGCGCCAACTGGAGGA
GGGCGGCTACCTGCGCGCCGAGGGCGAGGGCTGGCTGGGCTGCGCCGAGCGTCCCGCGCAGAGTCCG
GAGGACGCCTGGACGGCGTTCGCCGGCTGCGCGCCGGCGGCGCTCTGGCCGGCCGAGCTCGTCGCCT
ACCTGCGTGACAGCGCGCAATCCCTCGGCGAGCAACTGGCCGGGCGGATCAGCCCGGCGGCGCTGAT
GTTCCCGCAGGGCTCGGCGCGCATCGCCGAGGCCATGTACAGCCAGGGCCTGCATGCCCAGGCGCTG
CACGAGGCCATGGCCGAGGCCATCGCCGCCATCGTCGAGCGCCAGCCGCAACGGCGCTGGCGCCTGC
TGGAGCTTGGCGCCGGCACCGCCGCCGCCAGCCGCACGGTGATCGCCCCGTTGGCGCCGCTGGTGCA
GCGAGGGCGGAGGTGGACTACCTGTTCACCGACGTTTCCAGCTACTTCCTCGCCGCCGCCCGCGAG
CGCTTCGCCGACCAGCCGTGGGTACGCTTCGGCCGCTTCGACATGAACGGCGATCTTCTCGACCAGC
GCGTGGCGCCGCACTCGGTGGATATCCTGCTCAGCTCCGGGGCCTTGAACAACGCGCTGGACACCCC
CGCCCTGCTCGCCCGCCTGCGCGAGTTGCTCAGCGCCGACGCCTGGCTGGTGATCCAGGAACTGACG
CGCGAGCACAACGAGATCAGCGTCAGCCAGAGCCTGATGATCGAAAACCCGCGCGACCTCCGCGACG
AGCGCCGCCAACTGTTCGTCCACACCGGGCAATGGCTGGAGTGGCTGGCGGCACACGGTGGCGACCT
GGCTTGTGGGGTGTGCCGCCGGGCAGCGCTCTCGACCTGCTTGGCTACGATGTCCTGCTGGCTCGC
TGCAAGACCGACCCCCCCGCCTGGAGCCCGCCGAGCTGCTGGCCTTCGTCGAAGCGCGGGTGCCGC
GCTACATGCTCCCGGCGCAGTTGCGCGTGCTCGAACGCCTCCCGGTCACCGGCAACGGCAAGATCGA
CCGCAAGGCCCTGACCGGCTTTGCCCGCCAGCCCCAGGCGGACCTTCGGCATGGCGTCGCGCAGGCA
CCGGCCGACGAACTGGAGAATGCGCTGCTGGCACTCTGGCGGGAGGTGCTGGACAACCCGTCGCTGG
GCGTCGAGCAAGACTTCTTCGGGGCCGGCGGCGACTCGCTGTTGATCGCCCAGTTGATCGCCCGTTT
GCGCGAACGACTGGAAAGCGCCCGTCGCCATCCGTTCGATCGCCTGCTACGCTGGGCGCTCAGCCAG
CCGACGCCGCGCGGCCTGGCCGAACGCCTGCGCAGCGCGCCGGAAGAGGGCCGTGGGCCAGCCCTGG
```

TABLE 18A-continued

| VIR16 Nucleotide Sequence (SEQ ID NO:31) |
| --- |

CCGCGGCGCGCGGCGTCGCCCCGGCGCCGGCCGGCATGTCGCGCGCACCGCTCGCCCAGGGCGCGGT

GGCGCTCGACCCGCTGGTGCGCCTGGTGCCCGGCGAGGGCGTGCCGCGGGTGCTGGTCCACGAAGGC

CTCGGCACCCTACTGCCGTACCGCCCGCTGCTTCGCGCCCTGGGTGAGGGGCGGCCGTTGCTGGGGC

TGGCCGTGCATGACAGCGACGCCTACCTGGCGATCCCCGCCGAGCATCTCAACGCCTGCCTCGGCCG

CCGCTACGCCGAGGCGCTCCATCGCGCCGGGCTACGCGAGGTCGACCTGCTCGGCTACTGCTCCGGC

GGGCTGGTCGCCCTGGAGACCGCCAAGTCCCTGGTCCAGCGCGGGGTGCGCGTGCGCCAACTGGATA

TCGTCTCCAGCTACCGGATTCCCTACCGGGTGGACGACGAGCGCCTGCTGTTGTTCAGCTTCGCCCC

CACCCTCGCCCTGGATACCGCGGCGCTCGCCTTCCCCGCGCCGGAACGTCTCGGCCAGGCGGTGCAG

GCGGCGCTCGCGCAGACACCGGAGCGCCTGGTCGCCGACCCGCTGGCGGGGCTGCCGGGCCTGGCCG

ATCTCGTCGCCCTGCGCGGCCGCGTGCTACAGGCGGCCAGCGGTACCCCGACGCCGTCAGCGTCGA

ACGCGACACCCTCTACCGGCTGTTCTGTCACTCGGTGCGTGCCAGCCAGGCCGAGCCGCCCCACCCC

TACGTCGGCGCGCTGCGGCTGTTCGTGCCGGACGCCGGCAACCCATTGGTGCCGCGCTACGCCGAGG

CTCTGGAGACCCAATGGCGGGCCGCCGCGCTTGGCGCGTGCGGCATCCACGAGGTGCCCGGCGGGCA

CTTCGACTGCCTGGGCGAACCCCTGCCGCAATCCTTGTCGAAACCCATGCCAGAGGAGGCGAGCCGA

TGA

The VIR16 protein (SEQ ID NO:32) encoded by SEQ ID NO:31 is presented using the one-letter amino acid code in Table 18B.

TABLE 18B

| Encoded VIR16 protein sequence (SEQ ID NO:32) |
| --- |

MSLGELLETCRSRRIELWSEACRLRYRAPQGALDAGLAERLRAEREALLEHLEGGPGWRAEPDMA

HQRFPLTPVQAAYVLGRQAAFDYGGNACQLYAEYDWPADTDPARLEAAWNAMVERHPMLRAVIED

NAWQRVLPEVPWQRLTVHACAGLDEAAFQAHLERVRERLDHACAALDQWPVLRPELSIGRDACVL

HCSVDFTLVDYASLQLLLGEWRRRYLDPQWTAEPLEATFRDYVGVEQRRRQSPAWQRDRDWWLAR

LDALPGRPDLPLRVQPDTRSTRFRHFHARLDEAAWQALGARAGEHGLSAAGVALAAFAETIGRWS

QAPAFCLNLTVLNRPPLHPQLAQVLGDFTALSLLAVDSRHGDSFVERARRIGEQMFDDLDHPTFS

GVDLLRELARRRGRGADLMPVVFTSGIGSVQRLLGDGEAPRAPRYMISQTPQVWLDCQVTDQFGG

LEIGWDVRLGLFPEGQAEAMFDDFVGLLRRLAQSPRAWTDGDATEPVEAPPQALPGSARSIAAGF

AERALLTPDATAIHDAAGSYSYRQVAQHASALRRVLEAHGAGRGRRVAVMLPKSAAQLVAVIGTL

QAGAAYVPVDIRQPPLRRQAILASAEVVALVCLESDVPDVCCACVAIDRLAADSAWPPPPAAEVA

ADDLAYVIYTSGSTGTPKGVMLSHAAVSNTLLDINQRYGVDANDRVLGLAELSFDLSVYDFFGAT

AAGAQVVLPDPARGSDPSHWAELLERHAITLWNSVPAQGQMLIDYLESEPQRHLPGPRCVLWSGD

WIPVSLPTRWWRRWPDSALFSLGGATEAAIWSIEQPIRPQHTELASIPYGRALRGQSVEVLDARG

RRCPPGVRGEIHIGGVGLALGYAGDPQRTAERFVRHPDGRRLYRTGDLGRYLADGSIEFLGREDD

QVKIRGHRIELAELDAALCAHPQVNLAATVVLGETHERSLASFVTLHAPVEAGEDPRTALDAVRQ

RAAQALRRDWGSEEGIAAAVAALDRACLASLAAWLAGSGLFASATPLDLATLCQRLGIAEARQRL

LRHWLRQLEEGGYLRAEGEGWLGCAERPAQSPEDAWTAFAGCAPAALWPAELVAYLRDSAQSLGE

QLAGRISPAALMFPQGSARIAEAMYSQGLHAQALHEAMAEAIAAIVERQPQRRWRLLELGAGTAA

TABLE 18B-continued

Encoded VIR16 protein sequence (SEQ ID NO:32)

ASRTVIARLAPLVQRGAEVDYLFTDVSSYFLAAARERFADQPWVRFGRFDMNGDLLDQGVAPHSV

DILLSSGALNNALDTPALLAGLRELLSADAWLVIQELTREHNEISVSQSLMMENPRDLRDERRQL

FVHTGQWLEWLAAQGGDLACGVVPPGSALDLLGYDVLLARCKTDRARLEPAELLAFVEARVPRYM

LPAQLRVLERLPVTGNGKIDRKALTGFARQPQADLRHGVAQAPADELENALLALWREVLDNPSLG

VEQDFFGAGGDSLLIAQLIARLRERLESARRHPFDRLLRWALSQPTPRGLAERLRSAPEEGRGPA

LAAARGVAPAPAGMSRAPLAEGAVALDPLVRLVPGEGVPRVLVHEGLGTLLPYRPLLRALGEGRP

LLGLAVHDSDAYLAIPAEHLNACLGRRYAEALHRAGLREVDLLGYCSGGLVALETAKSLVQRGVR

VRQLDIVSSYRIPYRVDDERLLLFSFAATLGLDTAALGFPAPERLGQAVQAALAQTPERLVAEAL

AGLPGLADLVALRGRVLQAASGSADAVSVERDTLYRLFCHSVRASQAEAPEPYVGALRLFVPDAG

NPLVPRYAEALETQWRAAALGACGIHEVPGGHFDCLGEALAQSLSKPMPEEASR

MUT17

A *Pseudomonas* bacterial mutant (MUT 17) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding putative ATP-binding component of the ABC transporter, pchH (PA4223). This gene encodes the VIR17 nucleic acid (SEQ ID NO:33) shown in Table 19A.

TABLE 19A

VIR17 Nucleotide Sequence (SEQ ID NO:33)

GTGACCCCGGTGCTGTGGCGCCTGCTGCGCACCTATCGCTGGCGGCTGGCGGCGGCCATGCGGTTGC

AGGCCCTGGCCGGGCTCTGCTCGCTGTTGCCCTGGATGCTTCTCGCCTGGCTCGCCGAGCCGCTGGC

GCGCGGCCAGGCGCAGCCGGCCCTGCTGGCCCTGGTGCTGCTGGCGGTGCTGGCCTGGCTGGGCTGC

CAGGCGCTGGCCGCGCACCTGGCCCACCGGGTCGACGCGGACCTCTGCAACGACCTGCGCCTGCGCC

TGCTGGCCCACCTGCAACGGCTGCCGCTGGACTGGTTCGGTCGCCAGGGCCCGGACGGCGTGGCGCG

CCTCGTGGAGCAGGACGTGCGGGCCCTGCACCAACTGATCGCGCACGCTCCCAACGATCTCAGCAAC

CTGTTGGTGGTGCCGCTCGTCGCGTTGCTCTGGCTGGCCTGGCTGCACCCCTGGCTGCTGCTGTTCT

GCCTGCTGCCGCTGGTGCTGGCCGCCGCCGGCTTCCTGCTGCTGCGCTCGGCGCGCTACCGCGACCT

GGTGCTGCGGCGCAACGCCGCGCTGGAAAGGCTCTCGGCGGACTATGGCGAATTCGCCCACAACCTG

CTGCTGGCCCGACAGTACCCCGGCGCCGGCATACAACAGGGCGCCGAGGCGTCGGCGGCGGCCTTCG

GCGAAGCGTTCGGCGCCTGGGTGAAGCGGGTCGGCCACCTCGCCGCGCTGGTCTACGTGCAGTTGTC

GACGCCCTGGCTGCTGGCCTGGGTCCTGCTCGGCGCGCTGGCCCTGGATGCCCTCGGCGTGCCGCTG

GCGCTCGGCCAGGCCTGTGCCTTCCTGCTCCTGCTGCGGGCCTTGGCTGCCCCGGTGCAGGCGCTCG

GCCACGGCGGCGACGCGCTGCTGGGCGCGCGCCGCCGCCGAGCGCCTGCAGCAGGTGTTCGACCA

GGCGCCGCTGGCCGAGGGCCGCTCGACCCGCGAGCCGGTCGATGGCGCGGTGGCGCTGCACGGCCTG

GGCCATGCCTATGAAGGCGTGGAGGTCCTGGCCGATATCGATCTGGAGCTGGAGGATGGCAGCCTGG

TGCCCCTGGTCGGTCCCTCGGGCTCCGGCAAGAGCACCCTGCTGCACCTGCTGGCGCGCTACATGGA

CGCGCAGCGCGGCGAACTGGAGGTTGGCGGCCTGGCACTGAAGGACATGCCTGATGCCGTGCGCCAT

CGGCATATCGCGCTGGTCGGCCAGCAGGCGGCCGCGCTGGAGATATCCCTGGCCGACAACATTGCCC

TGTTCCGCCCCGATGCCGATCTCCAGGAGATTCGCCAGGCGGCCCGTGACGCCTGCCTCGACGAGCG

CATCATGGCCCTGCCGCGTGGCTACGACAGCGTGCCGGGACGCGACCTGCAACTGTCCGGCGCCGAA

TABLE 19A-continued

VIR17 Nucleotide Sequence (SEQ ID NO:33)

CTGCAACGACTGGCCCTGGCCCGTGCGCTGCTATCGCCGGCGAGCCTGTTGCTGCTCGACGAGCCAA

CCTCGGCGCTCGATCCGCACACCGCCCGGCAGGTCCTGCGCAACCTGCGCGAACCCCGCGGTGGCCG

GACCCGGGTGATCGTCGCCCATCGTCTGGCCGAAGTCAGCGATGCCGACCTGATCCTGGTGCTGGTC

GCTGGCCGTCTGGTCGAACGCGGCGAGCACGCGGCGCTGTTGGCGGCGGACGGCGCCTATGCGCGCT

TGTGGCGTGAACAGAACGGCGCGGAGGTGGCGGCATGA

The VIR17 protein (SEQ ID NO:34) encoded by SEQ ID NO:33 is presented using the one-letter amino acid code in Table 19B.

TABLE 19B

Encoded VIR10 protein sequence (SEQ ID NO:34)

MTPVLWRLLRTYRWRLAAAMGLQALAGLCSLLPWMLLAWLAEPLARGQAQPALLALVLLAVLAWL

GCQALAAHLAHRVDADLCNDLRLRLLAHLQRLPLDWFGRQGPDGVARLVEQDVRALHQLIAHAPN

DLSNLLVVPLVALLWLAWLHPWLLLFCLLPLVLAAAGFLLLRSARYRDLVLRRNAALERLSADYG

EFAHNLLLARQYPGAGIQQGAEASAAAFGEAFGAWVKRVGHLAALVYVQLSTPWLLAWVLLGALA

LDALGVPLALGQACAFLLLLRALAAPVQALGHGGDALLGARAAAERLQQVFDQAPLAEGRSTREP

VDGAVALHCLGHAYEGVEVLADIDLELEDGSLVALVGPSGSGKSTLLHLLARYMDAQRGELEVGG

LALKDMPDAVRHRHIALVGQQAAALEISLADNIALFRPDADLQEIRQAARDACLDERIMALPRGY

DSVPGRDLQLSGGELQRLALARALLSPASLLLLDEPTSALDPQTARQVLRNLRERGGGRTRVIVA

HRLAEVSDADLILVLVAGRLVERGEHAALLAADGAYARLWREQNGAEVAA

The role of VIR17 in virulence was confirmed using phage to retransduce this mutation into the wild-type PT894 strain where attenuated virulence was again observed in the *Dictyostelium* growth assay compared to an isogenic bacterial strain.

MUT18

A *Pseudomonas* bacterial mutant (MUT18) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as the gene encoding the putative ATP-binding component of ABC transporter, pchI (PA4222). This gene encodes the VIR18 nucleic acid (SEQ ID NO:35) shown in Table 20A.

TABLE 20A

VIR18 Nucleotide Sequence (SEQ ID NO:35)

ATGACCCTGTTCGAACGAATGCGTGCGCTGCCCGAAGACTGCCGTGCCGCGTTGCGCCGGGCGAGCG

CCTGCGCGGTCCTGGCGGCGCTGCTGGACGCCGCTTGCGGCGTATTGCTGGTGCCGTTGGTCGAGGC

CTGGTTCGCCGAAGGCGCGTTGCCCTGGCGCTGGGTCGCCGCGTTGCTCGGCTTGAGCCTGGCGCAG

GCGCTGTTGCAGTACCTGGCCCTGCGTCGCGGTTTCGCCGCCGGCGGCTCGCTGGCGGCTGGACTGG

TGCGCAGCCTGGTGGCGCGCTTGCCGCGCCTGGCGCCGCCGGCGCTGCGCCGGGTCGCGCCGGCCGA

TABLE 20A-continued

VIR18 Nucleotide Sequence (SEQ ID NO:35)

AGGCCTGCTGCGCGGCCCGGTGATGCAGGCGATGGGCATTCCGGCGCACCTGCTGGGGCCGCTGATC

GCCGCGTTGGTGACGCCGCTCGGGGTGATCCTCGGGCTGTTCCTGATCGACCCGTCCATCGCCCTCG

GCCTGCTCCTTGCTGGTGCCTTCCTCGCCGCGCTGTTGCGCTGGAGCGGGCGGCGCAATCTGGCGGC

GGAGGATGCCCGGCTGGCCGCCGAGCGCGACGCCGCACGGCAGTTGCAGGCGTTCGCCGAACCCCAC

CCACTGCTGCGCGCGGCGCAGCGCGAAAGCGTCGCCCGCCAGGGGCTGGAAGAGGCCTTGCGCAGTC

TCCACCGCAGCACCCTGGATCTGTTGCGGCGCAGCCTCCCCAGCGGCCTCGGCTTCGCCCTGGCGGT

GCAGGCGGCGTTCGCCTTCGCCCTGCTCGGCGGCGCCTGGGCGGTGGAGCGGCAATGGCTGGACGGC

GCTCGGCTGGTGGCCGTGCTGGTGCTGCTGGTGCGCTTCATCGAGCCGCTGGCCCAGCTCACCCATC

TCGACCAGGCGTTGCGCGGCGCCTGGCAGGCGCTGGATACCCTGCTGCGGGTTTTCGCCCTGGCTCC

GCTGCGCAGCCCCGAGCCGGGCGAGCGGCCGCACGACGCCAGCCTGGCGGCCGAGGCCGTGGAATTG

CCCCTGGAAGATGGCCGCGCCTTGCTCGAGGACATTTCCCTGAGGCTGGAGCCGGGTTCGCTGAACG

TCCTCGTCGGACCCTCCGGGGCCGGCAAGAGCAGCCTGCTGGCGCTGCTCGGGCGGCTCTACGACGT

CGATGCCGGGCGTGTCCTGCTGGGTGGCGTGGATATCCGCCGGTTGAGCGAAACGACCCTCGCCGCC

AGTCGTAACCTGGTGTTCCAGGACAACGGCCTGTTCCGCGGCAGCGTTGCCTGGAACCTGCGCATGG

CGCGAGCGGACGCCGATCTCGAAGCGCTGCGCGAGGCGGCGCGGGCGGTTGGCCTGCTGGAAGAGAT

CGAGGCCTGGCCGCAGGGCTGGGACAGCGACGTCGGTCCCGGCGGCGCGCTGCTGTCCGGCGGCCAG

CGGCAACGCCTGTGCCTGGCTCGCGGGCTGCTCTCGACGCCGCCGTTGCTGCTGCTCGACGAGCCCA

CCGCCAGCCTCGACGCCGCCAGCGAGGCGCAGGTGCTGCGCAGCCTGCTCGGGTTGCGCGGCCGGCG

CACCCTGCTGGTAGTGACCCACCGCCCGGCGCTGGCGCGTCAGGCCGACCAGGTACTGCTGCTGCAG

GAGGGGCGCCTGCGCCTCAGCGGACTTCACGCCGATCTGCTCGTCCGGGACGACTGGTATGCCGGTT

TCGTCGGGCTGGCGGGCGAGGAAAGTTCCGCGACGGTCGTGGATCGATAG

40

The VIR18 protein (SEQ ID NO:36) encoded by SEQ ID NO:37 is presented using the one-letter amino acid code in Table 20B.

TABLE 20B

Encoded VIR18 protein sequence (SEQ ID NO:36)

MTLFERMRALPEDCRAALRRASAWAVLAALLDAACGVLLVPLVEAWFAEGALPWRWVAALLGLSL

AQALLQYLALRRGFAAGGSLAAGLVRSLVARLPRLAPPALRRVAPAEGLLRGPVMQAMGIPAHLL

GPLIAALVTPLGVILGLFLIDPSIALGLLLAGAFLAALLRWSGRRNLAAEDARLAAERDAARQLQ

AFAERQPLLRAAQRESVARQGLEEALRSLHRSTLDLLRRSLPSGLCFALAVQAAFAFALLGGAWA

VERQWLDGARLVAVLVLLVRFIEPLAQLTHLDQALRGAWQALDTLLRVFALAPLRSPEPGERPHD

ASLAAEAVELRLEDGRALLEDISLRLEPGSLNVLVGPSGAGKSSLLALLGRLYDVDAGRVLLGGV

DIRRLSETTLAASRNLVFQDNGLFRGSVAWNLRMARADADLEALREAARAVGLLEEIEAWPQGWD

SDVCPGGALLSGGQRQRLCLARGLLSTAPLLLLDEPTASLDAASEAQVLRSLLCLRGRRTLLVVT

HRPALARQADQVLLLEEGRLRLSGLHADLLVRDDWYAGFVGLAGEESSATVVDR

The role of VIR18 in virulence was confirmed using phage to retransduce this mutation into the wild-type PT894 strain where attenuated virulence was again observed in the *Dictyostelium* growth assay compared to an isogenic bacterial strain.

MUT19

A *Pseudomonas* bacterial mutant (MUT19) was made by transposon insertion in a *P. aeruginosa* wild-type strain PT894. In the *Dictyostelium* growth assay, the mutated microorganism was less virulent compared to an isogenic bacterial strain. The nucleotide sequence immediately following the transposon insertion was cloned and identified as a gene cluster encoding the *P. aeruginosa* serotype 09 putative O-antigen biosynthesis pathway (VIR19). The insertion site nucleic acid sequence identifying the VIR19 gene in MUT19 is shown in Table 21.

TABLE 21

MUT19 Transposon Insertion Site (SEQ ID NO:37)

CTCTTTCAGCCGCACGCGGCGCACCTCGTGTGTGATCAGTGAGTGGTTTGCAACTGCGGGTCAAG

GATCTGGATTTCCCTCACANGTNCGATCATCGTGCGGGAGGGCAAGGGCTCCAAGGATCGGGCCT

TGATGTTACCCGAGAGCTTGGCACCCACCCTGCGCCAGCAGCGNNAATTGATCCGGTGGATGACC

TTTTGAATGACCTTTAATAGATTATATTACTAATTAATTGGGGACCCTANAGCTCCCCTTTTTA

TTTTAAAAATTTTTTCACAAAACGGTTTATTTNCATAAAGCTTGCTCAATCAATCACCNTATCCN

CCGGAATTCGGCCTAGGCGGCCAGATCTGATCAAGAGACAGACCTCCAGCTTTGCATCCGGAGCG

ACCACACGAGCGAGGTCAGTCACTTTCATCGAAGGAATTTTCTTGACATAGATCTCACCACCTTC

CATGTCCTCAAAGGCATGCCACACTAACTCGACGCCCTCCTCCAAAGAAATCATGAACCGGGTCA

TCCGCTCATCAGTGATAGGCAAGACGCCCTTGTCCTTG

The role of this cluster in virulence was confirmed using phage to retransduce this mutation into the wild-type PT894 strain where attenuated virulence was again observed in the *Dictyostelium* growth assay compared to an isogenic bacterial strain.

B. Attenuated *Klebsiella* Mutants

MUT20

A *Klebsiella* bacterial mutant (MUT20) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding a hypothetical transcriptional regulator in met G-dld intergenic region (VIR20). The insertion site nucleic acid sequence identifying the VIR20 gene in MUT20 is shown in Table 22.

TABLE 22

MUT20 Transposon Insertion Site (SEQ ID NO:38)

ACGCAGGATATCTTCTTCATCAAATTGTCGATGCCCGCCTTCGCTACGCTGCGGTTTCAGTAGACCG

TAACGACGCTGCCAGGCGCGCAGTGTGACCGGATTGATTCCGCAACGTTCGGCGACTTCACCGATAC

TGTAAAACGCCATAGCAGCCTCACATCAACCTGATACCTTAATACCTAAACTAACGAATTCAGGCAT

CCTGTACAACTCTATTTTCTTGTACAGATAAAGATATCAGGTTGCGGCTCACAGCGCCCGGGAAAAA

AGATGAAAAAATGTTTAGCTGATTTCGCGGTGGTTCATTTTTTCTCCGGCCATGCGACGGCGGGTAG

GCCCCCCAGGCGCGCGCTGGCGAACAAATTGCCCTGAAACTGTGAAATACCGGCTGATTCCAGCCAC

ATCCACTCTTCAGCACGCTCAACGCCGACGGCTGAGACCGCAATCTCCAGACAAGTACAGCATTTGA

TAATCGCCTG

MUT21

A *Klebsiella* bacterial mutant (MUT2 1) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding β-cystathionase (VIR21). The insertion site nucleic acid sequence identifying the VIR21 gene in MUT21 is shown in Table 23.

TABLE 23

MUT21 Transposon Insertion Site (SEQ ID NO:39)

GACCATGTGCTGATGACCAATACCGCCTATGAGCCAAGCCAGGACTTTTGTACCAAAATTCTCGCCA

AACTCGGCGTCACCACCAGCTGGTTCGATCCCTTAATCGGCGCCGATATCGCCCGTCTGGTTCGCCC

TGAGACCCGCGTGGTGTTCCTCGAATCGCCCGGCTCGATCACCATGGAAGTGCACGATGTGCCGGCG

ATAGTCGCCGCCGTGCGTCAGGTCGCCCCGGAAGCGATTATCATGATCGATAACACCTGGGCGGCGG

GGATCCTGTTTAAAGCCCTGGATTTTGGCATTGATATTTCCATTCAGGCAGGCACCAAATACCTGAT

CGGCCATTCCGACGCCATGGTGGGCACCGCGGTGGCGAACGCGCGCTCCTGGCCGCAGCTGCGTGAA

AATGCCTACCTGATGGGGCAAATGCTGGACGCCGATACTGCCTATATGACCAGCCGCGGCCTGCGAA

CCCTGGGCGTGCGCCTGCGTCAGCATCATGAAAGCAGCCTGCGCATC

MUT22

A *Klebsiella* bacterial mutant (MUT22) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as ribosome binding factor A (VIR22). The insertion site nucleic acid sequence identifying the VIR22 gene in MUT22 is shown in Table 24.

TABLE 24

MUT22 Transposon Insertion Site (SEQ ID NO:40)

CTTTTGGCCCCTTTTTTGTCTTTATTCTGGAGAACTTATTATGGCGAAAGAATTTGGTCGCCCGCAG

CGTGTGGCCCAGGAGATGCAAAAAGAGATTGCCATCATCCTGCAGCGTGAAATTAAAGATCCGCGTC

TGGGCATGATGACCACCGTTTCCGGTGTGGAAATGTCCCGTGACCTGGCCTATGCCAAGGTGTATGT

CACCTTCCTTAACGACAAACATGAAGCCGCGCTGAAACCCGGCATCAAAGCGCTGCAGGAAGCTTCT

GGCTTTATCCGCTCTCTGCTGGGGAAAGCGATGCGTCTGCGCATCGTACCGGAACTGACTTTCTTCT

ACGACAACTCACTGGTGGAAGGGATGCGTATGTCCAACCTGG

MUT23

A *Klebsiella* bacterial mutant (MUT23) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding aspartokinase/homoserine dehydrogenase (VIR23). The insertion site nucleic acid sequence identifying the VIR23 gene in MUT23 is shown in Table 25.

TABLE 25

MUT23 Transposon Insertion Site (SEQ ID NO:41)

GCCCAGCCCGCTTTCCCGCTTGCCCAGTTAAAAGCCTTCGTGGAGCAGGAATTTGCTCAGATTAAGC

ATGTTCTGCACGGCATCAGCCTGCTGGGTCAGTGCCCGGACAGCGTCAATGCCGCGCTGATCTGCCG

CGGCGAAAAGCTCTCCATCGCCATCATGGCGGGTCTGCTGGAAGCCCGTGGACACAAAGTCAGTGTC

ATTAACCCGGTCGAAAAACTGCTCGCCGTGGGTCACTATCTGGAATCCACCGTCGATATCGCCGAAT

CCACCCGCCGCATTGCCGCCAGCCAGATCCCGGCAGACCATATGATCCTGATGGCCGGGTTTACCGC

CGGCAATGAGAAAGGCGAGCTGGTGGTGCTGGGGCGTAACGGCTCCGACTACTCGGCTGCGGTACTG

GCCGCCTGCCTGCGCGCTGACTGCTGCGAAATCTGGACCGATGTCGACGGAGTGTACACCTGCGATC

CGCGTCAGGTGCCGGATGCGCGCCTGCTGAAATCGATGTCTTATCAGGAGGCGATGGAGCTCTCCTA

CTTTGGCGCGAAAGTGCTGCACCCGCGCACCATTGCCCCTATCGCCCAGTTCCAAATCCCATGCCTG

ATTAAAAATACCGGCAACCCCC

MUT24

A *Klebsiella* bacterial mutant (MUT24) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding cystathione γ-synthetase (VIR24). The insertion site nucleic acid sequence identifying the VIR24 gene in MUT24 is shown in Table 26.

TABLE 26

MUT24 Transposon Insertion Site (SEQ ID NO:42)

GGCGCAGCGTCTGCTCGTCACCGTCAAGCTCGAAGCTTAACATTGCGCCAAAACCTTTTTGCTGACG

CGCCGCAATTTCATGCCCCTGGTTTTCCGGCAGCGATGGATGATACAGCTTTTTCACCAGCGGCTGG

GTTTTCAGATACTCAACGATCGCCAGGGCATTTCGCTGCGCCACTTCCATCCGTGGAGACAGCGTCC

GCAGCCCGCGCAACAGCAGATAGCTGTCGAAGGCGCTGCCGGTGACGCCAATATTATTCGCCCACCA

TGCCAGTTCGGTGACAGTTGCCGGATCTTTGGCAATCACCACCCCGGCCACCACATCGGAGTGACCA

TTGAGGTATTTGGTACAGGA

MUT25

A *Klebsiella* bacterial mutant (MUT25) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding phosphoribosylformylglycinamidine synthase (VIR25). The insertion site nucleic acid sequence identifying the VIR25 gene in MUT25 is shown in Table 27.

TABLE 27

MUT25 Transposon Insertion Site (SEQ ID NO:43)

GTTGCGTCCCAGGCGGGTAAACGCATCCTGCAGGTAGTCAATTTCGTCGTCGGCCAGCGCCAGACCC

AGACGGAGGTTGGCGTCAATCAGCGCCTGACGCCCTTCGCCCAGCAGGTCGACGCTGGTGACCGGCG

TCGGCTGATGGTGAGCGAACAGCTTCTCGCCCGCTTCCAGCTCGTCGAAGACGCTCTCCATCATGCG

GTCATGCAGCTCCGCCGCCACCGCGGCCCACTGCGCTTCGGTCAGGGTTGAGGCTTCAACGTAATAC

GCCACGCCGCGCTCAAGACGCACAACCTGCGCCAGACCGCAGTTGTGAGCGATATCGGTAGCTTTAG

TABLE 27-continued

MUT25 Transposon Insertion Site (SEQ ID NO:43)

AAGACCAGGGAGAGATGGTGCCAGGGCGAGGGGTCACGAGCAGTAATTTACCGGTCGGGGTATGGCT

GCTTAAGCTCGGGCCATACTGAAGCAGTCGCGCCAGGCGCTCGCGATCGTCAGCGCTCAGCGGGCG

TTCAGATCGGCAAAATGAATATATTCGGCAT

MUT26

A *Klebsiella* bacterial mutant (MUT26) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding homoserine transsuccinylase (VIR26). The insertion site nucleic acid sequence identifying the VIR26 gene in MUT26 is shown in Table 28.

TABLE 28

MUT26 Transposon Insertion Site (SEQ ID NO:44)

GTATTGGCATCGTACTCCTGGGCTGGCCGGTGACAAAGGCGATGCGCTTATCTTTGCTGGCGAACAA

ATACGCATCGCCCTCTTCCGTCTCCGCGAGGATCTCGAGATCGGTATAGTCGCGAATAAGTCCGGCC

GGAAAATCAGCATAGCGTGAGTGCGGGGCCAGGAAAGAGTCGTCGAAACCGCGGGTCAGTAAGGCGT

GCGGATGAAGAATATGGTGTTCATAGACGCCGGAAATCTTTTCGGCGCGGGTCTGCTTGGGAATGCC

GTACAGAATGTTCAGCGCGGCCTGAACCGCCCAACAGACGAACAGCGTCGAAGTGACGTGATCCTTG

GCCCACTCCAGCACCTGTTTGATCTGCGGCCAGTAAGCAACATCGTTAAACTCAACCAGGCCTAAAG

GAGCGCCGGTAACAATCAGGCCGTCAAAGTTCTGATC

MUT27

A *Klebsiella* bacterial mutant (MUT27) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding 3'-phosphoadenosine 5'-phosphosulfate reductase (VIR27). The insertion site nucleic acid sequence identifying the VIR27 gene in MUT27 is shown in Table 29.

TABLE 29

MUT27 Transposon Insertion Site (SEQ ID NO:45)

GAGGTTCATATGTCCGTACTCGATCTAAACGCGCTTAATGCATTGCCGAAAGTGGAACGCATTCTGG

CACTCGCGGAAACCAACGCCCAACTGGAAAAGCTTGACGCCGAAGGGCGTGTGGCGTGGGCGCTGGA

AAATCTGCCGGGAAACTATGTGCTGTCGTCGAGCTTTGGCATTCAGGCGGCGGTAAGTTTGCATCTG

GTGAATCAGATCCGCCCGGACATTCCGGTGATCCTCACCGATACCGGCTACCTGTTCCCGGAAACCT

ATCAGTTTATTGACGAGCTGACGGACAAG

MUT28

A *Klebsiella* bacterial mutant (MUT28) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding Sfi protein (VIR28). The insertion site nucleic acid sequence identifying the VIR28 gene in MUT28 is shown in Table 30.

TABLE 30

MUT28 Transposon Insertion Site (SEQ ID NO:46)

TGTTAAAGCGTGCGTTCTACAGCCTGTTAGTCCTGCTCGGCCTGCTGCTGTTGACCGTGCTGGGCCT

TGACCGCTGGATGAGCTGGAAAACCGCGCCCTATATCTATGATGAACTGCAGGACCTGCCCTACCGT

CAGGTCGGTGTGGTGCTGGGCACCGCCAAATATTACCGCACCGGCGTCATCAATCAGTATTACCGTT

ACCGCATCCAGGGTGCGCTGAACGCCTACAACAGCGGCAAGGTCAACTATCTCCTGCTGAGCGGCGA

TAATGCTCTGCAAAGCTACAATGAACCGATGACCATGCGTCGGGACCTGATTAAAGGCGGCGTCGAT

CCCGCGGATATCGTACTGGACTATGCCGGTTTCCGTACCCTCGACTCGATCGTCCGTACCCGGAAAG

TGTTCGACACCAACGACTTCATTATCATCACCCAGCGCTTCCACTGCGAACGGGCGCTGTTTATCGC

CCTGCATATGGGGATCCAGGCCCAGTGCTACGC

MUT29

A *Klebsiella* bacterial mutant (MUT29) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding transcriptional activator protein LysR (VIR29). The insertion site nucleic acid sequence identifying the VIR29 gene in MUT29 is shown in Table 31.

TABLE 31

MUT29 Transposon Insertion Site (SEQ ID NO:47)

CGCTGAACCTCCTCAAACAAACGCAGGCCCTGCACCTGTCGGCTGCAGGCGACCAGCGTGGATCCGC

TCAAACAGCTGCAGGCCGAGCACCTTCTCAAAGCGCGCCAGCTCGCGGCTGACCGTGGGTTGCGAGG

TGTGCAGCATCCGCGCCGCTTCGGTCAGGTTGCCGGTGGTCATCACCGCGTGAAAGATTTCGATATG

ACGCAAATTGACGGCTGGCATGCGGTCTCCGTGAGGCTCGGCTGGAACCATATCATTTTTGCATAGA

GTCGCGATAAAACGATATTTTTTATTCGTCTGTCACTGTGGCGTAATCAGAAAAAACAGCGACCAAC

ACACGCACTGCACCGGAGTTCTTATGCCACACTCGCTTTACGCCACCGATACTGACCTGACCGCGGA

CAACCTGCTGCGCCTGCCGGCGGAATTTGGCTGCCCGGTCTGGGTCTATGATGCGCAGATTATTCGC

CGCCAGATAGCCCAGCTCAGCCAGTTTCGAC

MUT30

A *Klebsiella* bacterial mutant (MUT30) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding TrpD (VIR30). The insertion site nucleic acid sequence identifying the VIR30 gene in MUT30 is shown in Table 32.

TABLE 32

MUT30 Transposon Insertion Site (SEQ ID NO:48)

GGCTTCCACCCAAATCGCTTTGTCGGCAACGATTTTTGCTAAAACGGCTTTGCATTCTTTACCCTCT

TGCCCGCTAAGTGCGGTCACTCTGTCATAGGCCGCGCCGCTGCTGCAGCACATCCAGTACCTGCTGA

GCGTTAGCTTTCAGATCTTCATGCCCGTGTAAACGCATCAATATGGCGACGTTGGCGGCGACGGCGG

CTTCGTGAGCGGCTTCACCTTTACCTTG

MUT31

A *Klebsiella* bacterial mutant (MUT31) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding N-acetylglucosamine-6-phosphate deacetylase (VIR31). The insertion site nucleic acid sequence identifying the VIR31 gene in MUT31 is shown in Table 33.

MUT33

A *Klebsiella* bacterial mutant (MUT33) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding 2-isopropylmalate synthase (VIR33). The insertion site nucleic acid sequence identifying the VIR33 gene in MUT33 is shown in Table 35.

TABLE 33

MUT31 Transposon Insertion Site (SEQ ID NO:49)

TGGCTCAACGCTGCTCAGTGGTGCGAGGTGTCACTTTGGTGATCACATCGGCGTTGTCTGCACAGTG

AAATCAGATCCAGCGCCGCGTCCGGTTTTACGCACGTAGTCCGGATTGTGGGTGCCTTTCTTAACGA

TATTCAGCCACGGCCCTTCGAGATGCAGGCCCAGCGCCTGGTTCGGATGTTTTTGCAGATATTCGCG

CATCACGCGCACGCCTTGCTTCATCAGATCGTCGCTGGAGGTAATCAGCGTCGGCAGGAAGCTGGTG

CAGCCTGAGCGTTCGTTGGCCTTCTGCATGATCTCCAGCGTTTCGACAGTGACCGCCTCTGGGCTGT

CGTTAAACTGCACGCCGCCGCAGCCGTTGAGCTGGACGTCGATAAAACCGGGGGCGATTATTGCGCC

GTTGACTGAGCGCTGCTCGATGTCAGACGGCAAATCTGCCAGCGGACAAAGACGTTCGATAAAG

MUT32

A *Klebsiella* bacterial mutant (MUT32) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding WaaQ (VIR32; Regué et al. J. Bacteriol. 183(12): 3564–73, 2001). The insertion site nucleic acid sequence identifying the VIR32 gene in MUT32 is shown in Table 34.

TABLE 34

MUT32 Transposon Insertion Site (SEQ ID NO:50)

TTAAGCACCATATCGTACCGCTGCTGGCGCAGCGTCTGAATGAGCTGCCATTGCATCTTCAGCTGAT

ACCTTTTTCCCTGGCTTTTTCCAGCGGCGATCGAGACCATAAATATGGTGGATATCGGGGTTGGCTG

CGAGCATATCCCGGGTCTCTTCATACAACAGGACATCCACGCTGGCGGCGGGGTACTGCTGTTTCAG

CGCGTGAATAAGCGGCGTGATCAGCAGCATGTCGCCATGATGGCGCAGCTTAATGACCAGGATCCGC

GCCGGGTTCAACGGGCCGCGGGAGAGCGTTTCAGGCGTCATACTCTGTTCTTCATCCAGGATAAGGG

TTCCGATTCTAGGGGATCAGACAGATTGAGAGAAGCGTTGTATTGCTCTACCATGACCCGATACGTA

TGGCCTGAGGACGTTTTCGTGCACAATCCCGCAATTTCTCATCACGAT

TABLE 35

MUT33 Transposon Insertion Site (SEQ ID NO:51)

CACTCAGGCTTGCCTGTAACGCTTGTTCGCCATCACGTAAGGTCGTATCGAAAATAATGACTTGCTG

GCTCATGGTTTGGATCCTTAGTCTGTGTCCTGGCGCCTTGTTGACGAGCATAAAAAAACCCGCGCCA

AGGCGCGGGTTTTATAGTCTTGCTGGAAGATGACTTAACGCTGAACGTCGCCCAACAGCCTACCGAG

CAAATGGCATGCGTTTAGTAGTAGTAGGCTGGTGATACGAGCGGTGCGAATCATTGCGTCAAACTCC

AGATGAAATCGTTATGCTTTTAGAGTTACTGGATAGCCGTTTTAAAGTCAACCCCTGGCATGGAAAA

AGCGTTTTGGGCTGACTAAATGAATTAGCAAAATGTGCTGATGTAAGCCCCATTTTGCCGAAGATCC

TATTTTGGACCGAAGGCGGTTTATCCCCAATTTGTTTCATTTGAAAAA

MUT34

A *Klebsiella* bacterial mutant (MUT34) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding histidinol dehydrogenase (VIR34). The insertion site nucleic acid sequence identifying the VIR34 gene in MUT34 is shown in Table 36.

TABLE 36

MUT34 Transposon Insertion Site (SEQ ID NO:52)

CGCTGAACCGCTATCCGGAGCCGCAGCCGAAGTGCCGTGATTGAGAGCTACGCCCGCTACGCCGAGG

TCAAACCGGAGCAGGTGCTGGTCAGCCGCGGCGCCGACGAAGGCATCGAGCTGCTGATCCGCGCCTT

CTGTGAGCCCGGCGAAGACGCGGTGCTCTACTGCCCGCCGACCTACGGCATGTACAGCGTCAGCGCC

GAGACCATCGGCGTCGAGTGCCGCACCGTGCCGACGCTGGCCAGCTGGCAGCTCGACCTGCCGGGCA

TCGAAGCGCGGCTGGACGGCGTGAAGGTGGTGTTTGTCTGCAGCCCGAACAACCCGACCGGGCAGAT

TATCGACCCGCAGTCGATGCGCGACCTGCTGGAGATGACCCGCGGCAAAGCCATCGTGGTGGCCGAC

GAAGCCTATATTGAATTCTGCCCGCAGGCGACGCTCGCCGGCTGGCTCAGCGACTATCCGCACCTGG

TGGTGCTGCGCACGCTGTCCAAAGCCTTCGCCCTCGCCGGCCTGCGCTGCGGCTTCACCCTCGCCAA

CGCCGAGGTGATTAACGTGCTGCTGAAAGTGATCGCCCC

MUT35

A *Klebsiella* bacterial mutant (MUT35) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding UDP-galactopyranose mutase (VIR35; Clarke et al., J. Bacteriol., 177: 5411–18, 1995). The insertion site nucleic acid sequence identifying the VIR35 gene in MUT35 is shown in Table 37.

TABLE 37

MUT35 Transposon Insertion Site (SEQ ID NO:53)

CGTATATTTCATCGTACAGAAACCGTAAACACAGGCATTGGCTGATTTTCAGTGAGTGAATTTAAAT

AGACTTCTGCCGTTTTCAATGCTTCGGCGATGGTCACATCCATATCAAGGTAACGGTAGGTTCCAAG

ACGACCGACAAAAGTGATGTTGGTTTCATTCTCGGCCAATGACAAATATTTTTCAAGAAGAGCCATT

TCTCCCATCTGGCGAATAGGATAGTAAGGAATATCATTTTCTTCACAAGCACGGCTATACTCTTTAT

TABLE 37-continued

| MUT35 Transposon Insertion Site (SEQ ID NO:53) |
|---|
| AACAAACAGAGCCGTCGTGTTGTTCCCAGGGAGAAAAATATTTATGTTCAGTGATGCGAGTATAGGG |
| CACATCCACAGAACAGTAGTTCATCACTGCGCATCCCTGG |

MUT36

A *Klebsiella* bacterial mutant (MUT36) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding O-antigen export system permease protein rfba (VIR36; Bronner et al., Mol. Microbiol., 14: 505–19, 1994). The insertion site nucleic acid sequence identifying the VIR36 gene in MUT36 is shown in Table 38.

TABLE 38

| MUT36 Transposon Insertion Site (SEQ ID NO:54) |
|---|
| GTACGCCGATTTTATATGCGTCTGATATGATTCCGGAAAAATTTAGCTGGATAATTACCTACAATCC |
| GCTAGCGAGTATGATTCTTAGTTGGCGTGATTTATTCATGAATGGGACTCTTAATTTTGAGTATATT |
| TCTATACTCTATTTTACGGGAATTATTTTGACGGTTGTCGGTTTGTCTATTTTCAATAAATTAAAAT |
| ATCGATTTGCAGAGATCTAAAAGTGCGCTATAAGAGCAGCATGCTAGGCTATTTATGGTCAGTAGCA |
| AATCCATTGCTTTTTGCCATGATTTACTATTTTATATTTAAGCTGGTAATGAGAGTACAAATTCCAA |
| ATTATACAGTTTTCCTCATTACCGGCTTGTTTCCGTGGCAATGGTTTGCCAGTTCGGCCACTAAC |

MUT37

A *Klebsiella* bacterial mutant (MUT37) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding uridyltransferase (VIR37). The insertion site nucleic acid sequence identifying the VIR37 gene in MUT37 is shown in Table 39.

TABLE 39

| MUT37 Transposon Insertion Site (SEQ ID NO:55) |
|---|
| CGAGCCACCCACTGTAGCGTATGGATATCGCGCAAGCCGCCGGGGCTGCTTTTCACGTCCGGCTCGA |
| GGTTATAGCTGGTGCCATGATAGCGCTGATGACGGACGTTCTGCTCTTCGACCTTGGCGGCGAAGAA |
| CTTTTCCGATGGCCAGAAGCCGTCGCTAAAAATATGTTTTTGCAGTTCAAGGAACAGCGCGACGTCG |
| CCGATCAGCAGGCGCGATTCGATTAAGTTGGTGGCAACGGTCAGATCCGAGAGACCTTCCAGCAGGC |
| ACTCTTCGAGGGTGCGTACGCTGTGGCCCACCTCCAGCTTGACGTCCCACAGCAGGGTGAGCAGTTC |
| GCCGACTTTTTGCGCCTGGTCGTCCGGCAGTTTTTTACGACTGAGGATCAGCAGATCGACGTCTGAG |
| AGCGGGTGCAG |

MUT38

A *Klebsiella* bacterial mutant (MUT3 8) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding pyridoxine phosphate biosynthetic protein PdxJ-PdxA (VIR38). The insertion site nucleic acid sequence identifying the VIR38 gene in MUT38 is shown in Table 40.

TABLE 40

| MUT38 Transposon Insertion Site (SEQ ID NO:56) |
| --- |
| CTTAACCCGCACGCTGGCGAAGGCGGCCATATGGGAACAGAAGAGATAGACACCATCATTCCGGTGC |
| TGGAAGAGATGCGCGCAAAGGGGATGAACCTCAGCGGTCCGCTGCCGGCAGACACTCTCTTTCAGCC |
| GAAATATCTTGATCATGCCGATGCGGTACTCGCGATGTACCACGATCAGCCCCTGCCCGTGCTAAAA |
| TACCAGGGCTTTGGCCGCGGCGTGAACATTACGCTCGGTTTACCTTTTATTCGTACCTCCGTCGACC |
| ACGGCACCGCACTGGAATTAGCGGGCCAGGGAAAAGCGGACGTCGGCAGTTTTATCACGGCGCTTAA |
| TCTCCCCATCAAAATGATTGTTAATACCCAATGAATAATCGAGTCCATCAGGGCCATTTAGCCCGCA |
| AACGCTTCGGGCAGAACTTCCTCAACGATCAGTTTGTCATCGACAGCATCGTCTCGGCGATTAACCC |
| GCAGAAAGGCCAGGCGATGGTTGAAATCGGC |

MUT39

A *Klebsiella* bacterial mutant (MUT39) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding triose phosphate isomerase (VIR39). The insertion site nucleic acid sequence identifying the VIR39 gene in MUT39 is shown in Table 41.

TABLE 41

| MUT39 Transposon Insertion Site (SEQ ID NO:57) |
| --- |
| GGGTCTGACCCCGGTTCTGTGCATCGGTGAAACCGAAGCCGAAAACGAAGCGGGCAAAACGGAAGAA |
| GTTTCCGCACGTCAGATCGACGCCGTGCTGAAAACCCAGGGCGCTGCCGCTTTCGAAGGCGTGGTTA |
| TCGCTTACGAACCAGTATGGGCTATCGGTACCGGCAAATCAGCGACCCCGGCTCAGGCGCAGCCGGT |
| GCACAAATTCATCCGTGACCACATTGCTAAACCTCACCCCAAAATCGCTGACCAACTGATCATCCAG |
| TACGGCGGTTCCGTTAACGCTGGCAACCCCGCAGAGCTGTTCACCCACCCCGACATCGACGGCGCGC |
| TGGTTGGCGGCGCCTCCCTGAAAGCTGACGCTTTCGCGGTGATCGTTAAAGCAGCAGAAGCAGCGAA |
| AAAAGCGTAATTCGCTTTTCCCGGTGGCGACACGCGACCGGGTTGACTGACAAAACGTGGGAGCCCG |
| GCCT |

MUT40

A *Klebsiella* bacterial mutant (MUT40) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding aldehyde dehydrogenase (VIR40). The insertion site nucleic acid sequence identifying the VIR40 gene in MUT40 is shown in Table 42.

TABLE 42

MUT40 Transposon Insertion Site (SEQ ID NO:58)

GGTGGCGCACCCTGGCGTCGTTTGTGTAGAAATTATGAATATTAATACCAGGAAAATTCCTAATTTT

TGTGTACGCTCTGACGAGCGCACAATAAAACAAGACGAATTTTTGAACAATTGTCTTTAAATTTGTT

AATTGAATTGATCTGTTGTTGTTTAAAGGTATTTGAATTTCTTTTGTATAGATATGTAAATTAACAT

TGAAAAGCCATTTCAAAAATTAAATATATGGCCAACATAGCTATTAACTTATAGTTAACATCTTCCC

GGGTTGCCTTTTGATACTTCGGGTAATATATTTATTTCGCACATCAAAATAACTCTTTTTTCTTCTG

TTTGTTATTCATGGCCATCTATTGGCGAAATAAGGCAGAGTAGAGGGGGATGTGCCTAATATCCTGC

CCAAGGAACGCAATGTACATTTACAGGGAGGAGCTGACGAGCCGTTTCGCGATAGCTTTAG

MUT41

A *Klebsiella* bacterial mutant (MUT41) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding galacosyl transferase (VIR41; Clarke et al., J. Bacteriol., 177 : 5411–18, 1995). The insertion site nucleic acid sequence identifying the VIR41 gene in MUT41 is shown in Table 43.

TABLE 43

MUT41 Transposon Insertion Site (SEQ ID NO:59)

TTGGTGGTGTGCTCGCGAAGAAATTTAATCTGCCGGTCATCGTAAGTTTTGTTGGGCTTGGAAGAGT

ATTTTCTTCTGACAGCATGCCTTTAAAATTATTGCGGCAGTTTACTATTCCTGCATATAAATATATT

GCCAGTAATAAGCGCTGTATATTTATGTTTGAACATGACCGCGACAGAAAAAAACTGGCTAAGTTGG

TTGGACTCGAAGAACAACAGACTATTGTTATTGATGGTGCAGGCATTAATCCAGAGATATACAAATA

TTCTCTTGAACAGCATCACGATGTCCCTGTTGTATTGTTTGCCAGCCGTATGTTGTGGAGTAAAGGA

CTGGGCGACTTAATTGAAGCGAAGAAAATATTACGCAGTAAGAATATTCACTTTACTTTGAATGTTG

CTGGAATTCTGGTCGAAAATGATAAAGATGCAATTTCCCTTCAGGGTCATTGAAAATTGGCATCAGC

AAGGATTAATTAACTGGTTAGGTCGTTCGAATAATGTTTGCGATCTTATTGAGCAAT

MUT42

A *Klebsiella* bacterial mutant (MUT42) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding siroheme synthetase (VIR42; Kolko et al., J. Bacteriol., 183: 328–35, 2001).

The insertion site nucleic acid sequence identifying the VIR42 gene in MUT42 is shown in Table 44.

TABLE 44

MUT42 Transposon Insertion Site (SEQ ID NO:60)

TTACTTGCCCCTTTTTGCCGAACTGAAACAAAGGCCCGTGCTGGTGATCGGCGGCGGCGAGATTGCT

GAACGTAAGATCAAGTTCCTGCTGCGCGCCCAGGCGCAGGTGCAGGTGGTCGCTGAAACGCTGTCAC

CGGCGCTGGCCGATCTGGCTGCGCGCCAGGCACTCAGCTGGCGGGCGACGGCATTCAGCGACTCGCT

GGTGGATGATGTCTTTCTGGTGATTGCGGCCACCGAGGATGAGGCGCTTAACCAGCGGGTGTTTGCG

GCAGCTAACGCGCGCTACCGGTTGGTCAACCTGGTGGATAACCAGGCGCTGTGCTCGTTTGTTTTCC

CTTCTATCGTCGACCGTTCGCCGCTGCTGGTGGCGATCTCCTCCAGCGGTAAAGCGCCGGTGTTGTC

TABLE 44-continued

MUT42 Transposon Insertion Site (SEQ ID NO:60)

GCGCATTCTGCGTGAAAAAATCGAAGCGCTGCTGCCGACGAATCTCGGTCGGCTGGCGCAATCAGCA

AGCT

MUT43

A *Klebsiella* bacterial mutant (MUT43) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding 7,8-dihydro-6-hydroxymethylpterin-pyrophosphokinase (VIR43). The insertion site nucleic acid sequence identifying the VIR43 gene in MUT43 is shown in Table 45.

TABLE 45

MUT43 Transposon Insertion Site (SEQ ID NO:61)

AGCAGGGCAATGGTGGTCGGTTTCATAACATTTCCTGATGATGAAAGTCATATTAACCGGCATTCTA

ACAGCAGCATTCAGAGGGGCAATGATTTTGGGCAACCGATTACGACGATCGCCGCAAATGCTAAAAA

AGGGAGAGGGGATTACCAGCTGGCGGGCTTTTCCGCGCCGAGATTATCCAGCACGGCGCGCAGCGCC

AGGCCGTCAGGAAAGTGAAGGTCCGGGGCGATCTCGAACAGCGGCCAGAGCATAAAGCCGCGGTTTT

TCATATCGTAGTGCGGAACGGTCAGGCGCTCGCTGTTAATGACAGCATCGCCAAACAGCATGATATC

GAGGTCCAGCGTGCGCGGCCCCCAGCGTTCGGCTTTGCGCACTCGCCCCTGCTGCAGTTCGATGCGC

TGAGTATGATCGAGCAGCGTCTCGGGGGGCAGGGCGGTTTCCAGCGCAA

MUT44

A *Klebsiella* bacterial mutant (MUT44) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding glucose-6-phosphate isomerase (VIR44). The insertion site nucleic acid sequence identifying the VIR44 gene in MUT44 is shown in Table 46.

TABLE 46

MUT44 Transposon Insertion Site (SEQ ID NO:62)

GGCTTAACGCCAGCTATGTCAACGCTGCGGTTATGCGGATTTTTCATGCCTCTGCGGCTAACAGAAA

AAAGCCTTATGATAGCTATACTAATGGGGCTTTTTACTCCGTTTTGACCCGATTCCTGACCGGCGTC

AGGGTCAAGTCACAAAAATCATCACAATTTTCCGTCACCGGCGCTACAATCGACCGAAGTCACAATC

TCAAATCAGAAGAGTATTGCTAATGAAAAACATCAACCCAACGCAGACCTCTGCCTGGCAGGCATTA

CAGAAACACTTCGACGAAATGAAAGATGTCACTATCAGCGAGCTTTTCGCCAAAGATAGCGACCGTT

TTTCTAAATTTTCCGCGACGTTCGACGATCTGATGCTGGTGGACTTCTCCAAAAACCGCATCACTGA

AGAGACGCTGGCTAAACTGCAGGATCTGGCGAAAGAGACTGACCTGGCGGGCGCTATCAAGTCGATG

TTCTCAGGTGAGAAGATCAACCGCACCGAAGACCGCGCGGTACTGCACGTCGCGCT

MUT45

A *Klebsiella* bacterial mutant (MUT45) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding DNA methylase (VIR45). The insertion site nucleic acid sequence identifying the VIR45 gene in MUT45 is shown in Table 47.

TABLE 47

MUT45 Transposon Insertion Site (SEQ ID NO:63)

TGCTTCATCCGCATCTCCTTGAAATTTATTTGGTCTTAGGCGGACGGTAGAGCGCTAATAGCTCGTC

CACCTTTTTACGCGTACCACCGTTGCTGCTGATGCTGCGCCGCACCTTCACAATATGCGTTTCTGCC

GCGTTTTTATACCATTCCTGCGTCAGCGGCGTGCGGTGGTTGGAAATCAGCACCGGGATGCGCTTTT

TCATCAGCGATTCCGCCTTTTGCGCCAGCAGTACCTGTTGTTCCAGGTTGAAACTGTTGGTGTGGTA

GGCGGTAAAGTTCGCCGTCGCCGTTAGCGGCGCATAGGGCGGATCGCAATACACCACTGTGCGGCTA

TCCGCACGTTGCATGCACTCTTCGTAAGATTCGCAGTAAAACTCGGCGTTTTGCGCCTTCTCGGCGA

AATGATAGAGCTCAGCTTCGGGGAAATAGGGCTTTTTATAACGGCCAAACGGCACATTGAACTCGCC

GCGCAG

MUT46

A *Klebsiella* bacterial mutant (MUT46) was made by transposon insertion in a *Klebsiella* sp. wild-type strain. In the *Dictyostelium* growth assay, the mutated microorganism was less virulent compared to an isogenic bacterial strain. The nucleotide sequence immediately following the transposon insertion was cloned and identified as the gene encoding a putative inner membrane protein (VIR46). The insertion site nucleic acid sequence identifying the VIR46 gene in MUT46 is shown in Table 48.

TABLE 48

MUT46 Transposon Insertion Site (SEQ ID NO:64)

TGTCAATGCGCAATTTGGTTAAATATGTCGGTATTGGCCTGCTGGTGATGGGGCTTGCCGCCTGCGA

TAACAGCGATTCAAAAGCGCCAACCGTTGGCGCAGCAGCGGAGAGCAATGCCAGCGGCCAGGCAATC

AGCCTGCTGGATGGCAAGCTGAGCTTCACCCTGCCTGCGGGCATGGCCGACCAGAGCGGCAAACTGG

GTACCCAGGCGAACAATATGCACGTCTACTCTGACGCTACCGGCCAGAAAGCGGTCATCGTCATCGT

CGGCGACAGCACCAATGA

IV. Suitable Target Pathogens

Other *Pseudomonas* sp. and *Klebsiella* sp. and many other microbes, including gram-negative bacterial strains, are likely to include virulence genes encoding VIRX-related peptides or proteins having amino acid sequence identity or similarity to those identified herein. Suitable bacterial pathogens may include, but are not limited to, Pneumococci sp., *Klebsiella*, sp., *Pseudomonas* , e.g., *P. aeruginosa, Salmonella*, e.g., *Salmonella typhimurium, Legionella*, e.g., *Legionella pneumophilia, Escherichia*, e.g., *Escherichia coli, Listeria*, e.g., *Listeria monocytogenes, Staphylococcus*, e.g., *Staphylococcus aureus*, Streptococci sp., *Vibrio*, e.g., *Vibrio cholerae*. Pathogenic mycobacteria of the present invention may include e.g., *Mycobacterium tuberculosis*. Pathogenic fungi of the present invention may include, e.g., *Candida albicans*. Pathogenic unicellular eukaryotic organisms of the present invention may include, e.g., *Leishmania donovani*.

Having identified VIRX genes according to the invention, it is possible to use the gene sequence to search for related genes or peptides in other microorganisms. This may be carried out by searching in existing databases, e.g., EMBL or GenBank. The levels of identity between gene sequences and levels of identity or similarity between, amino acid sequences can be calculated using known methods. In relation to the present invention, publicly available computer based methods for determining identity and similarity include the BLASTP, BLASTN and FASTA (Atschul et al., J. Molec. Biol., 1990; 215:403–410), the BLASTX program available from NCBI, and the Gap program from Genetics Computer Group, Madison Wis.

Preferably, the peptides that may be useful in the various aspects of the invention have greater than a 40% similarity with the peptides identified herein. More preferably, the peptides have greater than 60% sequence similarity. Most preferably, the peptides have greater than 80% sequence similarity, e.g., 95% similarity. With regard to the polynucleotide sequences identified herein, related polynucleotides that may be useful in the various aspects of the invention may have greater than 40% identity with the sequences identified herein. More preferably, the polynucleotide sequences have greater than 60% sequence identity. Most preferably, the polynucleotide sequences have greater than 80% sequence identity, e.g., 95% identity.

In addition to related molecules from other microorganisms, the invention encompasses modifications made to the peptides and polynucleotides identified herein which do not significantly alter the biological function. It will be apparent to the artisan that the degeneracy of the genetic code can result in polynucleotides with minor base changes from those specified herein, but which nevertheless encode the same peptides. Complementary polynucleotides are also within the invention. Conservative replacements at the amino acid level are also envisaged, i.e., different acidic or basic amino acids may be substituted without substantial loss of function.

It is recognized in the art that highly refined mechanisms that regulate transcription have evolved and are present in bacteria. Most bacterial genes are organized into operons, which are groups of genes coding for related proteins. Operons can either be repressed or induced thus regulating those genes. An operon consists of an operator, promoter, regulator, and structural genes. The regulator gene codes for a repressor protein that binds to the operator, obstructing the promoter (thus, transcription) of the structural genes. The regulator does not have to be adjacent to other genes in the operon. If the repressor protein is removed, transcription may occur.

Transposon mutagenesis usually inactivates the gene in which the transposon is inserted, as well as any gene downstream in the same operon. If the VIRX gene is a structural gene in an operon, inactivation of the VIRX gene disrupts the expression of other structural genes in the same operon and positioned downstream of the inactivated VIRX gene. For example, an insertion in pchE gene also inactivates pchF, pchG, pchH, and pchI genes because they all reside within the pchEFGHI operon and are downstream of the inactivated pchE gene. Accordingly, the present invention includes attenuation of virulence due to alteration of a VIRX gene residing in an operon as well as alterations to nucleic acid yielding loss of expression of structural genes located in the same operon and located downstream of the VIRX gene. In one embodiment, the present invention is an alteration inactivating the first gene of an operon carrying a VIRX gene of the invention. The alteration of nucleic acids of VIRX genes and VIRX-containing operons may be insertional inactivation or gene deletion. It is preferred that the alteration of nucleic acids of VIRX genes and VIRX-containing operons be insertional inactivation.

The present invention also provides for a bacterial strain comprising an operon encoding a gene selected from the group consisting of VIR1, VIR2, VIR3, VIR4, VIR5, VIR6, VIR7, VIR8, VIR9, VIR10, VIR11, VIR12, VIR13, VIR14, VIR15, VIR16, VIR17, VIR18, VIR19, VIR20, VIR21, VIR22, VIR23, VIR24, VIR25, VIR26, VIR27, VIR28, VIR29, VIR30, VIR31, VIR32, VIR33, VIR34, VIR35, VIR36, VIR37, VIR38, VIR39, VIR40, VIR41, VIR42, VIR44, VIR45, and VIR46, wherein the bacterial strain includes a mutation that reduces expression of the VIRX gene relative to an isogenic bacterial strain lacking the mutation. In one embodiment, the mutation reduces inhibition of *Dictyostelium* amoeba growth when compared to the growth of *Dictyostelium* amoeba in the presence of an isogenic bacterial strain lacking the mutation. In another embodiment, the attenuated bacterial strain has more than one mutation of an operon containing a VIRX gene when compared to an isogenic bacterial strain.

V. VIRX Nucleic Acids and Polypeptides can be Used to Identify Antimicrobial Drugs A. Screening In a separate embodiment, the VIRX genes, or their polynucleotide or polypeptide products disclosed herein is used in screening assays for the identification of potential antimicrobial drugs. Routine screening assays are known to those skilled in the art, and can be adapted using the VIRX products of the invention in the appropriate way. For example, the products of the invention can be used as the target for a potential drug, with the ability of the drug to inactivate or bind to the target indicating its potential antimicrobial activity. In the methods of the present invention, one or more test compounds may be present or produced in the assay mixture. Preferably one compound is present, or produced, in the assay mixture.

B. Character of Antimicrobial Candidate Compositions

VIRX nucleic acids and polypeptides may be used to identify drugs or therapeutics in a candidate composition useful in the prevention or treatment of pathogen-associated disease or infection. A candidate composition can include one or more molecules for analysis in a screening assay and can be a synthetic or semi-synthetic molecules. Such molecules include inorganic as well as organic chemical molecules. The molecules may be less than about 500 Daltons or more than 500 Daltons. The molecules may be naturally occurring. Naturally occurring molecules may include, e.g., saccharides, lipids, peptides, proteins, nucleic acids, or combinations thereof, e.g., aminoglycosides, glycolipids, lipopolysaccharides, or macrolides. Proteins may be immunoglobulins, e.g., polyclonal or monoclonal antibodies. Nucleic acids may be DNA or RNA, e.g., small interfering RNA (siRNA). The precise source of the molecule is not critical to the method of the present invention. The molecule might be derived from e.g., synthetic compounds libraries that are commercially available, e.g., Sigma-Aldrich (Milwaukee, Wis.), or libraries of natural occurring molecules in the form of bacterial, fungal, plant, and animal extracts such as those available from Xenova (Slough, UK). The synthetic (or semi-synthetic) or natural occurring molecules might be modified using standard chemical, physical, or biochemical methods known in the art.

VI. VIRX Nucleic Acids and Polypeptides can be Used to Detect the Degree of Virulence of Pathogens A diagnostic test can assist physicians in determining the type of disease and appropriate associated therapy. As such, a separate embodiment of this invention provides for the use of VIRX genes or their polynucleotides or nucleic acid products as virulence markers for detecting the presence of a pathogen, a pathogen-associated disease, or the virulence of a pathogen. There are many diagnostic assay approaches known to the artisan. Generally, the diagnostic method used would comprise the steps of (a) obtaining a sample from a potentially diseased subject or a diseased subject; (b) measuring the level of at least one polypeptide or polynucleotide virulence marker in the sample; and (c) comparing the amount of the virulence marker in the sample of step (a) to the amount of the virulence marker present in a control sample from a second subject known not to have the presence of the pathogen, where an alteration in the expression level of the virulence marker in the first subject as compared to the control sample indicates the presence of a pathogen, a pathogen-associated disease, or the virulence of a pathogen. Preferably, the subject is a mammal. More preferred is that the subject is a human. The person of skill will recognize that diagnostic tests may be performed in an array-type format wherein, e.g., the presence of two or more VIRX genes or gene products indicate the presence of a pathogen, a pathogen-associated disease, or the virulence of a pathogen.

VII. Attenuated Organisms of the Present Invention can be Used in Vaccine Preparation In another embodiment, the invention provides for the use of the attenuated organisms described herein in vaccine preparation. The preparation of vaccines based on attenuated microorganisms is known to those skilled in the art. Vaccine compositions can be formulated with suitable carriers or adjuvants, e.g., alum, as necessary or desired, to provide effective immunization against infection. The preparation of vaccine formulations will be apparent to the artisan. The attenuated microorganisms may be prepared with a mutation that disrupts the expression of any of the VIRX genes identified herein. The artisan will be aware of methods for disrupting expression of particular VIRX genes. Techniques that may be used include, but are not limited to, insertional inactivation, or gene deletion techniques. Attenuated microorganisms according to the invention may also comprise additional mutations in other genes, for example in a second gene identified herein or in a separate gene required for growth of the microorganism, e.g., an Aro mutation. Attenuated microorganisms may also be used as carrier systems for the delivery of heterologous antigens, therapeutic proteins or nucleic acids (DNA or RNA). In this embodiment, the attenuated microorganisms are used to deliver a heterologous antigen, protein or nucleic acid to a particular site in vivo. Introduction of a heterologous antigen, peptide or nucleic acid into an attenuated microorganism can be carried out by conventional techniques, including the use of recombinant constructs, e.g., vectors, which comprise polynucleotides that express the heterologous antigen or therapeutic protein, and also include suitable promoter sequences. Alternatively, the gene that encodes the heterologous antigen or protein may be incorporated into the genome of the organism and the endogenous promoters used to control expression. In the vaccines of the present invention, the pharmaceutically effective dosage of the mutants of the present invention to be administered may vary depending on the age, weight and sex of the subject, and the mode of administration. The subject can be, e.g., a human, a non-human primate (such as an ape, gorilla, or chimpanzee), cow, horse, pig, sheep, dog, cat, or rodent (including mouse or rat).

VIII. Definitions

As used herein, each of the following terms has the meaning associated with it in this section.

The term "pathogen," as used herein, is intended to include an agent that causes disease, especially a living microorganism such as a bacterium or fungus. The terms "agent" and "factor" are used interchangeably herein to describe pathogens or toxins useful in the methods of the present invention. Pathogens may include any bacteria, mycobacteria, fungi and unicellular eukaryotic organism, including wild types and mutants thereof, which causes disease or brings about damage or harm to a host organism. Pathogens may also be a poisonous substance, e.g., toxin, which is produced by living cells or organisms and is capable of causing disease when introduced to a host.

The term, "pathogenic," as used herein, is defined as an agent's ability to cause disease, damage or harm to a host organism.

The term, "attenuated," as used herein, means an organism made less virulent relative to an isogenic pathogenic organism.

The term, "virulence," as used herein, is a measure of the degree of pathogenicity of an agent to a host organism. Virulence is usually expressed as the dose of an agent or cell number of a pathogen that will elicit a pathological response in the host organism within a given time period. "Reducing the virulence" as used herein is defined as the ability of a compound to attenuate, diminish, decrease, suppress, or arrest the development of, or the progression of disease, damage or harm to a host organism mediated by a pathogen.

The term, "host organism," as used herein, is intended to include any living organism. Preferably the host organism is a eukaryote, e.g., vertebrate. More preferably the host organism is a mammal. It is most preferred that the host organism be a human.

The term, "mutant," as used herein, an organism carrying a specific mutation of a gene that is expressed in the organism's phenotype.

The term, "mutation," as used herein, is an alteration of one or more nucleic acids of a polynucleotide sequence encoding a gene. A mutation may include the insertion of additional nucleic acids to a polynucleotide sequence encoding a gene, e.g., insertional inactivation of a gene. Alternatively, a mutation may include, but is not limited to, deletion of one or more nulceic acids of a polynucleotide sequence encoding a gene.

The term, "operon," as used herein, is a unit of bacterial gene expression and regulation comprising several genes usually with complementary functions. Typically an operon includes nucleic acid and control elements in the nucleic acid that may be recognized by regulators of gene products. Insertion in a gene in an operon interferes with the function of this gene and of other genes located downstream or upstream in the operon. It is understood herein that the function attributed to a gene refers to its function and/or that of any gene located downstream or upstream in the same operon.

The term, "pharmaceutically effective dosage," as used herein, means that amount necessary at least partly to attain the desired effect, or to delay the onset of, inhibit the progression of, or halt altogether, the onset or progression of the particular condition being treated.

The terms "similarity" and "identity" are known in the art. The use of the term "identity" refers to a sequence comparison based on identical matches between correspondingly identical positions in the sequences being compared. The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

EQUIVALENTS

From the foregoing detailed description of the specific embodiments of the invention, it should be apparent that bacterial genes have been identified and assigned a new role in virulence. Further, these genes and their products are useful in the identification of antimicrobial agents, the diagnosis of pathogen-associated disease or infection as well as the preparation of vaccines. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims. For instance, the choice of the particular pathogen, or combination of pathogens selected for assay or vaccination, the test conditions used in diagnostic assays utilizing the pathogens of this invention, or the method of mutagenesis used to derive the attenuated mutants

EXAMPLES

This Example is provided for the purpose of illustration only and the invention should in no way be construed as being limited to these Example, but rather should be construed to encompass any and all variations which become evident as a result of the teaching provided.

Example 1

Strains and Culture Conditions Used to Screen for Attenuated Viurlence in Test Bacterial Mutants The *D. discoideum* wild-type strain DH1–10 used in these studies is a subclone of DH1 (Cornillon et al., J. Biol. Chem., 275(44):34287–92, 2000). Cells were grown at 21° C. in HL5 medium (14.3 g/l peptone (Oxoid), 7.15 g/l yeast extract, 18 g/l maltose, 0.64 g/l $Na_2HPO_4.2H_2O$, 0.49 g/l $KH_2PO_4$, pH 6.7) (Cornillon et al., J. Cell. Sci., 107 (Pt 10):2691–704, 1994) and subcultured twice a week.

Bacteria were grown overnight at 37° C. on Luria-Bertani (LB) agar. Single colonies were inoculated into 5 ml PB (2% (wt/vol) peptone, 0.3% (wt/vol) $MgCl_2.6H_2O$, 1% (wt/vol) $K_2SO_4$) (Essar et al., J. Bacteriol., 172(2):884–900,1990) in a 50 ml flask and grown at 37° C. for 8 hr prior to use. The growth of various strains was tested in rich medium (PB) by measuring the optical density (600 nm) of a culture at different times after inoculation and was found to be comparable for all strains used. Under these conditions, similar $OD_{600s}$ were obtained for each strain and the induction of quorum sensing was maximal. Minimal Inhibitory Concentrations (MICs) were determined in Mueller-Hinton broth by the microdilution method (Thornsberry et al., NCCLS, 3: 48–56, 1983). Mutations yielding reduced virulence were identified where the growth of the *Dictyostelium* test host organism exposed to the mutant pathogen was greater than the *Dictyostelium* test host organism exposed to wild-type pathogen. Specific genetic mutations in pathogens displaying reduced virulence were identified and characterized by techniques well know in the art.

What is claimed is:

1. A method for identifying an antimicrobial drug, said method comprising:
   (a) contacting a candidate composition that is a test antimicrobial drug with a polypeptide encoded by the VIR5 gene from *Pseudomonas aeruginosa*
   (b) measuring the imidazoleglycerol-phosphate synthase activity of said VTR5 polypeotide in the presence and absence of said candidate composition; and
   (c) comparing the imidazoleglycerol-phosphate synthase activity of said VTR5 polypeptide in the presence and absence of said candidate composition, wherein a decrease in the imidazoleglycerol-phosphate synthase activity of said VTR5 polypeptide in the presence of said candidate composition indicates that said candidate composition is an antimicrobial drug, where such an alteration causes a reduction in the inhibition of growth in a *Dictyostelium* growth assay.

2. The method of claim 1, wherein said candidate composition comprises a molecule less than 500 Daltons.

3. The method of claim 1, wherein said candidate composition comprises a molecule greater than 500 Daltons.

4. The method of claim 1, wherein said candidate composition selected from a group consisting of a polypeptide, polysaccharide, lipid, nucleic acid, or combination thereof.

5. The method of claim 4, wherein said polypeptide is an immunoglobulin. immunoglobulin.

6. The method of claim 1, wherein said change comprises an increase in imidazoleglycerol-phosphate synthase activity.

7. The method of claim 1, wherein said change comprises a decrease in imidazoleglycerol-phosphate synthase activity.

8. The method of claim 4, wherein said nucleic acid is a small interfering RNA (siRNA).

9. The method of claim 5, wherein said immunoglobulin is a monoclonal antibody or a polyclonal antibody.

* * * * *